(12) United States Patent
Aoyagi-Scharber et al.

(10) Patent No.: US 9,376,480 B2
(45) Date of Patent: Jun. 28, 2016

(54) TARGETED THERAPEUTIC LYSOSOMAL ENZYME FUSION PROTEINS AND USES THEREOF

(71) Applicant: BioMarin Pharmaceutical Inc., Novato, CA (US)

(72) Inventors: Mika Aoyagi-Scharber, Mill Valley, CA (US); Teresa Margaret Christianson, Rohnert Park, CA (US); Melita Dvorak-Ewell, Berkeley, CA (US); Daniel J. Wendt, Walnut Creek, CA (US); Shinong Long, San Ramon, CA (US); Jonathan LeBowitz, Novato, CA (US); Daniel Solomon Gold, San Francisco, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 172 days.

(21) Appl. No.: 14/092,336

(22) Filed: Nov. 27, 2013

(65) Prior Publication Data

US 2014/0161788 A1 Jun. 12, 2014

Related U.S. Application Data

(60) Provisional application No. 61/788,968, filed on Mar. 15, 2013, provisional application No. 61/730,378, filed on Nov. 27, 2012.

(51) Int. Cl.
| | |
|---|---|
| *C07K 14/65* | (2006.01) |
| *C12N 9/24* | (2006.01) |
| *C07K 19/00* | (2006.01) |
| *A61K 38/00* | (2006.01) |
| *A61K 38/47* | (2006.01) |

(52) U.S. Cl.
CPC .............. *C07K 14/65* (2013.01); *C12N 9/2402* (2013.01); *C12Y 302/0105* (2013.01); *A61K 38/00* (2013.01); *A61K 38/47* (2013.01); *C07K 2319/06* (2013.01)

(58) Field of Classification Search
CPC .... A61K 38/00; C07K 14/65; C07K 2319/06; C12N 15/62; C12N 9/2402; C12Y 302/0105
See application file for complete search history.

(56) References Cited

U.S. PATENT DOCUMENTS

| | | | |
|---|---|---|---|
| 5,364,934 | A | 11/1994 | Drayna et al. |
| 6,255,096 | B1 | 7/2001 | Hopwood et al. |
| 7,442,372 | B2 | 10/2008 | Kakkis |
| 7,485,314 | B2 | 2/2009 | Kakkis et al. |
| 2003/0072761 | A1 | 4/2003 | LeBowitz |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2005/0244400 | A1 | 11/2005 | LeBowitz et al. |
| 2005/0281805 | A1 | 12/2005 | LeBowitz et al. |
| 2011/0223147 | A1 | 9/2011 | Lebowitz et al. |
| 2012/0213762 | A1 | 8/2012 | LeBowitz et al. |
| 2012/0232021 | A1 | 9/2012 | Martini et al. |
| 2014/0080178 | A1* | 3/2014 | Schnorr ............... C12N 9/0071 435/69.1 |

FOREIGN PATENT DOCUMENTS

| | | |
|---|---|---|
| WO | WO-02087510 A2 | 11/2002 |
| WO | WO-03/032727 A1 | 4/2003 |
| WO | WO-03/032913 A2 | 4/2003 |
| WO | WO-03102583 A1 | 12/2003 |
| WO | WO-2005078077 A2 | 8/2005 |
| WO | WO-2009/137721 A2 | 11/2009 |
| WO | WO-2010/078511 A2 | 7/2010 |
| WO | WO-2010/148253 A2 | 12/2010 |
| WO | WO-2012/088461 A2 | 6/2012 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Volpato et al. , J. Mol. Biol. 373(3):599-611, 2007.*
Sadowski et al., Current Opinion in Structural Biology 19:357-362, 2009.*
Bach et al., Binding of mutants of human insulin-like growth factor II to insulin-like growth factor binding proteins 1-6, J. Biol. Chem., 268(13):9246-54 (1993).
Baxter, Insulin-like growth factor (IGF)-binding proteins: interactions with IGFs and intrinsic bioactivities, *Am. J. Physiol Endocrinol Metab.*, 278(6):967-76 (2000).
Carter et al., Improved oligonucleotide site-directed rautagenesis using M13 vectors, *Nucl. Acids Res.*, 13:4331 (1986).
Chothia, The nature of the accessible and buried surfaces in proteins, *J. Mol. Biol.*, 150:1 (1976).
Deakin et al., A simplified and sensitive fluorescent method for disaccharide analysis of both heparan sulfate and chondroitin/dermatan sulfates from biological samples, *Glycobiology*, 18:483 (2008).
Genbank Accession No. NM_000263, "Homo sapiens N-acetylglucosaminidase, alpha (NAGLU), mRNA," dated Mar. 24, 1999.
Gordon et al., A role for PACE4 in the proteolytic activation of anthrax toxin protective antigen, *Infection and Immunity*, 65(8):3370-5(1997).
Graham et al., Characteristics of a human cell line transformed by DNA from human adenovirus type 5, *J. Gen Virol.*, 36:59 (1977).

(Continued)

*Primary Examiner* — Delia Ramirez
(74) *Attorney, Agent, or Firm* — Marshall, Gerstein & Borun LLP

(57) ABSTRACT

The present invention relates in general to therapeutic fusion proteins useful to treat lysosomal storage diseases and methods for treating such diseases. Exemplary therapeutic fusion proteins comprise a lysosomal enzyme, a lysosomal targeting moiety, e.g., an IGF-II peptide, and a spacer peptide. Also provided are compositions and methods for treating Mucopolysaccharidosis Type IIIB (Sanfilippo B Syndrome), comprising a targeted therapeutic fusion protein comprising alpha-N-acetylglucosaminidase (Naglu), a lysosomal targeting moiety, e.g., an IGF-II peptide, and a spacer peptide.

21 Claims, 5 Drawing Sheets

(56) References Cited

OTHER PUBLICATIONS

Hashimoto et al., N-terminal deletion mutants of insulin-like growth factor-II (IGF-II) show Thr7 and Leu8 important for binding to insulin and IGF-I receptors and Leu8 critical for all IGF-II functions, *J. Biol. Chem.*, 270(30):18013-8 (1995).

Kakkis et al., Enzyme-replacement therapy in mucopolysaccharidosis I, *N. Engl. J. Med.*, 344(3):182-8 (2001).

Lawrence et al., Disease-specific non-reducing end carbohydrate biomarkers for mucopolysaccharidoses, *Nat. Chem. Biol.*, 8:197 (2012).

Lawrence et al., Evolutionary differences in glycosaminoglycan fine structure detected by quantitative glycan reductive isotope labeling, *J. Biol. Chem.*, 283:33674 (2008).

Li et al., Mouse model of Sanfilippo syndrome type B produced by targeted disruption of the gene encoding alpha-N-acetylglucosaminidase, *Proc. Natl. Acad. Sci. USA*, 96:14505-10 (1999).

Magee et al., Insulin-like growth factor I and its binding proteins: a study of the binding interface using B-domain analogues, *Biochemistry*, 38(48):15863-70 (1999).

Mather et al., Culture of testicular cells in hormone-supplemented serum-free medium, *Annals N.Y. Acad. Sci.*, 383:44-68 (1982).

Mather, Establishment and characterization of two distinct mouse testicular epitheliar cell lines, *Biol. Reprod.*, 23:243-251 (1980).

Moehring et al., Strains of CHO-K1 cells resistant to *Pseudomonas* exotoxin A and cross-resistant to diphtheria toxin and viruses, *Infection and Immunity*, 41(3):998-1009 (1983).

Nischt et al., Recombinant expression and properties of the human calcium-binding extracellular matrix protein BM-40, *Eur. J. Biochem.*, 200:529-36 (1991).

Ohmi et al., Defects in the medial entorhinal cortex and dentate gyrus in the mouse model of Sanfilippo syndrome type B, *PLoS One*, 6:e27461 (2011).

Roth et al., Mutants of human insulin-like growth factor II: expression and characterization of analogs with a substitution of TYR27 and/or a deletion of residues 62-67, *Biochem. Biophys. Res. Commun.*, 181(2):907-14 (1991).

Ryazantsev et al., Lysosomal accumulation of SCMAS (subunit c of mitochondrial ATP synthase) in neurons of the mouse model of mucopolysaccharidosis III B, *Mol. Genet. Metab.*, 90(4):393-401 (2007).

Schellenberger et al., A recombinant polypeptide extends the in vivo half-life of peptides and proteins in a tunable manner, *Nat. Biotech.*, 27:1186-90 (2009).

Terasawa et al., Solution structure of human insulin-like growth factor II; recognition sites for receptors and binding proteins, *EMBO J.*, 13(23):5590-7 (1994).

Torres et al., Solution structure of human insulin-like growth factor II. Relationship to receptor and binding protein interactions., *J. Mol. Biol.*, 248(2):385-401 (1995).

Trinh et al., Optimization of codon pair use within the (GGGGS)3 linker sequence results in enhanced protein expression, *Mol. Immunol.*, 40:717-22 (2004).

Urlaub et al., Isolation of Chinese hamster cell mutants deficient in dihydrofolate reductase activity, *Proc. Natl. Acad. Sci. USA*, 77:4216 (1980).

Vitry et al., Storage vesicles in neurons are related to Golgi complex alterations in mucopolysaccharidosis IIIB, *Am. J. Pathol.*, 177(6):2984-99 (2010).

Walkley et al., GM2 ganglioside as a regulator of pyramidal neuron dendritogenesis, *Ann. NY Acad. Sci.*, 845:188-99 (1998).

Wang et al., The insulin A and B chains contain sufficient structural information to form the native molecule, *Trends Biochem. Sci.*, 279-81(1991).

Weber et al., The insulin A and B chains contain sufficient structural information to form the native molecule, *Hum. Mol. Genet.*, 5:771-7 (1996).

Wells et al., Cassette mutagenesis: an efficient method for generation of multiple mutations at defined sites, *Gene*, 34:315 (1985).

Wells et al., Importance of hydrogen-bone formation in stablilizing the transition state of subtilisin, *Philos. Trans. R. Soc. London Ser A*, 317:415 (1986).

Zoller et al., Oligonucleotide-directed mutagenesis using M13-derived vectors: an efficient and general procedure for the production of point mutations in any fragment of DNA., *Nucl. Acids Res.*, 10:6487 (1987).

International Search Report and Written Opinion, International Application No. PCT/US2013/072287, mailed Feb. 17, 2014.

\* cited by examiner

Figure 1

A. Naglu amino acid sequence (signal sequence underlined) (SEQ ID NO: 1)

```
M E A V A V A A A V G V L L L A G A G G A A
G D E A R E A A A V R A L V A R L L G P G P
A A D F S V S V E R A L A A K P G L D T Y S
L G G G G A A R V R V R G S T G V A A A A G
L H R Y L R D F C G C H V A W S G S Q L R L
P R P L P A V P G E L T E A T P N R Y R Y Y
Q N V C T Q S Y S F V W W D W A R W E R E I
D W M A L N G I N L A L A W S G Q E A I W Q
R V Y L A L G L T Q A E I N E F F T G P A F
L A W G R M G N L H T W D G P L P P S W H I
K Q L Y L Q H R V L D Q M R S F G M T P V L
P A F A G H V P E A V T R V F P Q V N V T K
M G S W G H F N C S Y S C S F L L A P E D P
I F P I I G S L F L R E L I K E F G T D H I
Y G A D T F N E M Q P P S S E P S Y L A A A
T T A V Y E A M T A V D T E A V W L L Q G W
L F Q H Q P Q F W G P A Q I R A V L G A V P
R G R L L V L D L F A E S Q P V Y T R T A S
F Q G Q P F I W C M L H N F G G N H G L F G
A L E A V N G G P E A A R L F P N S T M V G
T G M A P E G I S Q N E V V Y S L M A E L G
W R K D P V P D L A A W V T S F A A R R Y G
V S H P D A G A A W R L L L R S V Y N C S G
E A C R G H N R S P L V R R P S L Q M N T S
I W Y N R S D V F E A W R L L L T S A P S L
A T S P A F R Y D L L D L T R Q A V Q E L V
S L Y Y E E A R S A Y L S K E L A S L L R A
G G V L A Y E L L P A L D E V L A S D S R F
L L G S W L E Q A R A A V S E A E A D F Y
E Q N S R Y Q L T L W G P E G N I L D Y A N
K Q L A G L V A N Y Y T P R W R L F L E A L
V D S V A Q G I P F Q Q H Q F D K N V F Q L
E Q A F V L S K Q R Y P S Q P R G D T V D L
A K K I F L K Y Y P R W V A G S W
```

B. IGFII 8-67 R37A amino acid sequence (SEQ ID NO: 2)

A. Naglu nucleotide sequence (signal sequence underlined) (SEQ ID NO: 3)

```
ATGGAGGCGGTGGCGGTGGCCGCGGCGGTGGGGGTCCTTCTCCTGGCCGGGGCCGGGGGCGCGG
CAGGCGACGAGGCCCGGGAGGCGGCGGCCGTGCGGGCGCTCGTGGCCCGGCTGCTGGGGCCAGG
CCCCGCGGCCGACTTCTCCGTGTCGGTGGAGCGCGCTCTGGCTGCCAAGCCGGGCTTGGACACC
TACAGCCTGGGCGGCGGCGGCGCGGCGCGCGTGCGGGTGCGCGGCTCCACGGGCGTGGCGGCCG
CCGCGGGGCTGCACCGCTACCTGCGCGACTTCTGTGGCTGCCACGTGGCCTGGTCCGGCTCTCA
GCTGCGCCTGCCGCGGCCACTGCCAGCCGTGCCGGGGGAGCTGACCGAGGCCACGCCCAACAGG
TACCGCTATTACCAGAATGTGTGCACGCAAAGCTACTCTTTCGTGTGGTGGGACTGGGCCCGCT
GGGAGCGAGAGATAGACTGGATGGCGCTGAATGGCATCAACCTGGCACTGGCCTGGAGCGGCCA
GGAGGCCATCTGGCAGCGGGTGTACCTGGCCTTGGGCCTGACCCAGGCAGAGATCAATGAGTTC
TTTACTGGTCCTGCCTTCCTGGCCTGGGGCGAATGGGCAACCTGCACACCTGGGATGGCCCCC
TGCCCCCCTCCTGGCACATCAAGCAGCTTTACCTGCAGCACCGGGTCCTGGACCAGATGCGCTC
CTTCGGCATGACCCCAGTGCTGCCTGCATTCGCGGGGCATGTTCCCGAGGCTGTCACCAGGGTG
TTCCCTCAGGTCAATGTCACGAAGATGGGCAGTTGGGGCCACTTTAACTGTTCCTACTCCTGCT
CCTTCCTTCTGGCTCCGGAAGACCCCATATTCCCCATCATCGGGAGCCTCTTCCTGCGAGAGCT
GATCAAAGAGTTTGGCACAGACCACATCTATGGGGCCGACACTTTCAATGAGATGCAGCCACCT
TCCTCAGAGCCCTCCTACCTTGCCGCAGCCACCACTGCCGTCTATGAGGCCATGACTGCAGTGG
ATACTGAGGCTGTGTGGCTGCTCCAAGGCTGGCTCTTCCAGCACCAGCCGCAGTTCTGGGGGCC
CGCCCAGATCAGGGCTGTGCTGGGAGCTGTGCCCCGTGGCCGCCTCCTGGTTCTGGACCTGTTT
GCTGAGAGCCAGCCTGTGTATACCCGCACTGCCTCCTTCCAGGGCCAGCCCTTCATCTGGTGCA
TGCTGCACAACTTTGGGGGAAACCATGGTCTTTTGGAGCCCTAGAGGCTGTGAACGGAGGCCC
AGAAGCTGCCCGCCTCTTCCCCAACTCCACCATGGTAGGCACGGGCATGGCCCCGAGGGCATC
AGCCAGAACGAAGTGGTCTATTCCCTCATGGCTGAGCTGGGCTGGCGAAAGGACCCAGTGCCAG
ATTTGGCAGCCTGGGTGACCAGCTTTGCCGCCCGGCGGTATGGGGTCTCCCACCCGGACGCAGG
GGCAGCGTGGAGGCTACTGCTCCGGAGTGTGTACAACTGCTCCGGGGAGGCCTGCAGGGGCCAC
AATCGTAGCCCGCTGGTCAGGCGGCCGTCCCTACAGATGAATACCAGCATCTGGTACAACCGAT
CTGATGTGTTTGAGGCCTGGCGGCTGCTGCTCACATCTGCTCCCTCCCTGGCCACCAGCCCCGC
CTTCCGCTACGACCTGCTGGACCTCACTCGGCAGGCAGTGCAGGAGCTGGTCAGCTTGTACTAT
GAGGAGGCAAGAAGCGCCTACCTGAGCAAGGAGCTGGCCTCCCTGTTGAGGGCTGGAGGCGTCC
TGGCCTATGAGCTGCTGCCGGCACTGGACGAGGTGCTGGCTAGTGACAGCCGCTTCTTGCTGGG
CAGCTGGCTAGAGCAGGCCCGAGCAGCGGCAGTCAGTGAGGCCGAGGCCGATTTCTACGAGCAG
AACAGCCGCTACCAGCTGACCTTGTGGGGGCCAGAAGGCAACATCCTGGACTATGCCAACAAGC
AGCTGGCGGGGTTGGTGGCCAACTACTACACCCCTCGCTGGCGGCTTTTCCTGGAGGCGCTGGT
TGACAGTGTGGCCCAGGGCATCCCTTTCCAACAGCACCAGTTTGACAAAAATGTCTTCCAACTG
GAGCAGGCCTTCGTTCTCAGCAAGCAGAGGTACCCCAGCCAGCCGCGAGGAGACACTGTGGACC
TGGCCAAGAAGATCTTCCTCAAATATTACCCCGCTGGGTGGCCGGCTCTTGG
```

B. IGFII 8-67 R37A nucleotide sequence (SEQ ID NO: 4)

```
CTGTGCGGCGGGGAGCTGGTGGACACCCTCCAGTTCGTCTGTGGGGACCGCGGCTTCTACTTCA
GCAGGCCCGCAAGCCGTGTGAGCGCTCGCAGCCGTGGCATCGTTGAGGAGTGCTGTTTCCGCAG
CTGTGACCTGGCCCTCCTGGAGACGTACTGTGCTACCCCCGCCAAGTCCGAG
```

Figure 3

EFGGGGSTR (SEQ ID NO: 22)
GAP (SEQ ID NO: 9)
GGGGS (SEQ ID NO: 12)
GPSGSPG (SEQ ID NO: 23)
GPSGSPGT (SEQ ID NO: 24)
GPSGSPGH (SEQ ID NO: 25)
GGGGSGGGGSGGGGSGGGGSGGGPST (SEQ ID NO: 26)
GGGGSGGGGSGGGGSGGGGSGGGPSH (SEQ ID NO: 27)
GGGGSGGGGSGGGGSGGGGSGGGPSGGGGSGGGPS (SEQ ID NO: 28)
GAPGGGSGGGGSGGGGSGGGGSGGGPSGGGGSGGGPSGAP (SEQ ID NO: 29)
GGGGSGGGGSGGGGSGGGGSGGGPSGGGGSGGGGSGGGGSGGGGSGGGPS (SEQ ID NO: 30)
GAPGGGSGGGGSGGGGSGGGGSGGGPSGGGGSGGGGSGGGGSGGGGSGGGPSGAP (SEQ ID NO: 31)
GGGGSGGGGSGGGGSGGGPSGGGGSGGGGSGGGPS (SEQ ID NO: 32)
GAPGGGSGGGGSGGGGSGGGPSGGGGSGGGGSGGGPSGAP (SEQ ID NO: 33)
GGGGSGGGGSGGGGSGGGPSGGGGSGGGGSGGGPSGGGGSGGGGSGGGPS (SEQ ID NO: 34)
GAPGGGSGGGGSGGGGSGGGPSGGGGSGGGGSGGGPSGGGGSGGGGSGGGPSGAP (SEQ ID NO: 35)
GGGGSGGGGSGGGGSGGGGSGGGPS (SEQ ID NO: 36)
GAPGGGSGGGGSGGGGSGGGGSGGGPSGAP (SEQ ID NO: 37)
GGGGSGGGGSAAAASGGGGSGGGPS (SEQ ID NO: 38)
GAPGGGSGGGGSAAAASGGGGSGGGPSGAP (SEQ ID NO: 39)
GGGGSGGGGSAAAASGGGGSGGGGSAAAASGGGGSGGGGSAAAASGGGPS (SEQ ID NO: 40)
GAPGGGSGGGGSAAAASGGGGSGGGGSAAAASGGGGSGGGGSAAAASGGGPSGAP (SEQ ID NO: 41)
GGGGSGGGGSAAAASGGGPSGGGGSAAAASGGGPSGGGGSAAAASGGGPS (SEQ ID NO: 42)
GAPGGGSGGGGSAAAASGGGPSGGGGSAAAASGGGPSGGGGSAAAASGGGPSGAP (SEQ ID NO: 43)
GGSPAGSPTSTEEGTSESATPESGPGTSTEPSEGSAPGSPAGSPGPS (SEQ ID NO: 44)
GAPGGSPAGSPTSTEEGTSESATPESGPGTSTEPSEGSAPGSPAGSPGPSGAP (SEQ ID NO: 45)
GGSPAGSPTSTEEGTSESATPESGPGTSTEPSEGSAPGSPAGSPTSTGPS (SEQ ID NO: 46)
GAPGGSPAGSPTSTEEGTSESATPESGPGTSTEPSEGSAPGSPAGSPTSTGPSGAP (SEQ ID NO: 47)
GGGSPAPTPTPAPTPAPTPAGGGPS (SEQ ID NO: 48)
GAPGGGSPAPTPTPAPTPAPTPAGGGPSGAP (SEQ ID NO: 49)
GGGSPAPAPTPAPAPTPAPAGGGPS (SEQ ID NO: 50)
GAPGGGSPAPAPTPAPAPTPAPAGGGPSGAP (SEQ ID NO: 51)
GGGSAEAAAKEAAAKEAAAKAGGPS (SEQ ID NO: 52)
GAPGGGSAEAAAKEAAAKEAAAKAGGPSGAP (SEQ ID NO: 53)
GGGSPAEAAAKEAAAKEAAAKEAAAKEAAAKAPSGGG (SEQ ID NO: 54)

(Figure 3 continued)

GAPGGGSPAEAAAKEAAAKEAAAKEAAAKEAAAKAPSGGGGAP (SEQ ID NO: 55)
GGGGSGGGGSGGGGS (SEQ ID NO: 56)
GAPGGGGSGGGGSGGGGSGAP (SEQ ID NO: 57)
GGGGSGGGGSGGGGSGGGGS (SEQ ID NO: 58)
GAPGGGGSGGGGSGGGGSGGGGSGAP (SEQ ID NO: 59)
GGGGA (SEQ ID NO: 60)
GGGGAGGGGAGGGGAGGGGAGGGPST (SEQ ID NO: 61)
GGGGAGGGGAGGGGAGGGGAGGGPSH (SEQ ID NO: 62)
GGGGAGGGGAGGGGAGGGGAGGGPSGGGGAGGGPS (SEQ ID NO: 63)
GAPGGGGAGGGGAGGGGAGGGGAGGGPSGGGGAGGGPSGAP (SEQ ID NO: 64)
GGGGAGGGGAGGGGAGGGGAGGGPSGGGAGGGGAGGGGAGGGGAGGGPS (SEQ ID NO: 65)
GAPGGGGAGGGGAGGGGAGGGGAGGGPSGGGGAGGGGAGGGGAGGGGAGGGPSGAP (SEQ ID NO:66)
GGGGAGGGGAGGGGAGGGPSGGGGAGGGGAGGGPS (SEQ ID NO: 67)
GAPGGGGAGGGGAGGGGAGGGPSGGGGAGGGGAGGGPSGAP (SEQ ID NO: 68)
GGGGAGGGGAGGGGAGGGPSGGGGAGGGGAGGGPSGGGGAGGGGAGGGPS (SEQ ID NO: 69)
GAPGGGGAGGGGAGGGGAGGGPSGGGGAGGGGAGGGPSGGGGAGGGGAGGGPSGAP (SEQ ID NO: 70)
GGGGAGGGGAGGGGAGGGGAGGGPS (SEQ ID NO: 71)
GAPGGGGAGGGGAGGGGAGGGGAGGGPSGAP (SEQ ID NO: 72)
GGGGAGGGGAAAAASGGGGAGGGPS (SEQ ID NO: 73)
GAPGGGGAGGGGAAAAASGGGGAGGGPSGAP (SEQ ID NO: 74)
GGGGAGGGGAAAAASGGGGAGGGGAAAAASGGGGAGGGGAAAAASGGGPS (SEQ ID NO: 75)
GAPGGGGAGGGGAAAAASGGGGAGGGGAAAAASGGGGAGGGGAAAAASGGGPSGAP (SEQ ID NO: 76)
GGGGAGGGGAAAAASGGGPSGGGGAAAAASGGGPSGGGGAAAAASGGGPS (SEQ ID NO: 77)
GAPGGGGAGGGGAAAAASGGGPSGGGGAAAAASGGGPSGGGGAAAAASGGGPSGAP (SEQ ID NO: 78)
GGGGAGGGGAGGGGA (SEQ ID NO: 79)
GAPGGGGAGGGGAGGGGAGAP (SEQ ID NO: 80)
GGGGAGGGGAGGGGAGGGGA (SEQ ID NO: 81)
GAPGGGGAGGGGAGGGGAGGGGAGAP (SEQ ID NO: 82)
GGGGAGGGGAGGGGAGGGGAGGGGAGGGGAGGGGAGGGGAGGGPS [or (GGGGA)$_8$GGGPS] (SEQ ID NO: 83)
GGGGAGGGGAGGGGAGGGGAGGGGAGGGGAGGGGAGGGGAGGGPSH [or (GGGGA)$_8$GGGPSH] (SEQ ID NO: 84)
GGGGAGGGGAGGGGAGGGGAGGGGAGGGGAGGGGAGGGGAGGGGAGGGPS [or (GGGGA)$_9$GGGPS] (SEQ ID NO: 85)
 GGGGAGGGGAGGGGAGGGGAGGGGAGGGGAGGGGAGGGGAGGGGAGGGPSH [or (GGGGA)$_9$GGGPSH] (SEQ ID NO: 86)

(Figure 3 continued)

GGGGPAPGPGPAPGPAPGPAGGGPS (SEQ ID NO: 87)
GAPGGGGPAPGPGPAPGPAPGPAGGGPGGAP (SEQ ID NO: 88)
GGGGPAPAPGPAPAPGPAPAGGGPS (SEQ ID NO: 89)
GAPGGGGPAPAPGPAPAPGPAPAGGGPGGAP (SEQ ID NO: 90)
(GGGGS)$_n$ (SEQ ID NOs: 12, 56, 58, 91-94)
(GGGGS)$_n$-GGGPS (SEQ ID NOs: 36, 95-100)
GAP-(GGGGS)$_n$-GGGPS (SEQ ID NOs: 101-107)
GAP-(GGGGS)$_n$-GGGPS-GAP (SEQ ID NOs: 37, 108-113)
GAP-(GGGGS)$_n$-GGGPS-(GGGGS)$_n$-GAP (SEQ ID NOs: 114-162)
GAP-GGGPS-(GGGGS)$_n$-GAP (SEQ ID NOs: 163-169)
GAP-(GGGGS)$_n$-AAAAS-GGGPS-(GGGGS)$_n$-AAAA-GAP (SEQ ID NOs: 170-218)
GAP-(GGGGS)$_n$-PAPAP-(Xaa)n-GAP (SEQ ID NOs: 219-267)
GAP-(GGGGS)$_n$-PAPAPT-(Xaa)n-GAP (SEQ ID NOs: 268-316)
GAP-(GGGGS)$_n$-(Xaa)n-PAPAP-(Xaa)n-(AAAKE)n-(Xaa)n-(GGGGS)$_n$-GAP (SEQ ID NOs: 544-551)
(GGGGA)$_n$ (SEQ ID NOs: 60, 79, 81, 317-320)
(GGGGA)$_n$-GGGPS (SEQ ID NOs: 71, 321-326)
GAP-(GGGGA)$_n$-GGGPS, (SEQ ID NOs: 327-333)
GAP-(GGGGA)$_n$-GGGPS-GAP (SEQ ID NOs: 334-340)
GAP-(GGGGA)$_n$-GGGPS-(GGGGA)$_n$-GAP (SEQ ID NOs: 341-389)
GAP-GGGPS-(GGGGA)$_n$-GAP (SEQ ID NOs: 390-396)
GAP-(GGGGA)$_n$-AAAAS-GGGPS-(GGGGA)$_n$-AAAA-GAP (SEQ ID NOs: 397-445)
GAP-(GGGGA)$_n$-PAPAP-(Xaa)$_n$-GAP (SEQ ID NOs: 446-494)
GAP-(GGGGA)$_n$-PAPAPT-(Xaa)$_n$-GAP (SEQ ID NOs: 495-543)
GAP-(GGGGA)$_n$-(Xaa)$_n$-PAPAP-(Xaa)$_n$-(AAAKE)n-(Xaa)$_n$-(GGGGA)$_n$-GAP (SEQ ID NOs: 552-559)

SEQUENCE LISTING

```
<160> NUMBER OF SEQ ID NOS: 571

<210> SEQ ID NO 1
<211> LENGTH: 743
<212> TYPE: PRT
<213> ORGANISM: Homo sapiens
<220> FEATURE:
<221> NAME/KEY: SIGNAL
<222> LOCATION: (1)..(23)

<400> SEQUENCE: 1

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
```

-continued

```
               100                 105                 110
Pro Leu Pro Ala Val Pro Gly Glu Leu Thr Glu Ala Thr Pro Asn Arg
            115                 120                 125
Tyr Arg Tyr Tyr Gln Asn Val Cys Thr Gln Ser Tyr Ser Phe Val Trp
        130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
            180                 185                 190
Phe Thr Gly Pro Ala Phe Leu Ala Trp Gly Arg Met Gly Asn Leu His
        195                 200                 205
Thr Trp Asp Gly Pro Leu Pro Ser Trp His Ile Lys Gln Leu Tyr
210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
        275                 280                 285
Pro Ile Ile Gly Ser Leu Phe Leu Arg Glu Leu Ile Lys Glu Phe Gly
        290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
        355                 360                 365
Val Leu Gly Ala Val Pro Arg Gly Arg Leu Leu Val Leu Asp Leu Phe
        370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
        435                 440                 445
Ser Gln Asn Glu Val Val Tyr Ser Leu Met Ala Glu Leu Gly Trp Arg
        450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
        515                 520                 525
```

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 2
<211> LENGTH: 60
<212> TYPE: PRT
<213> ORGANISM: Homo sapiens

<400> SEQUENCE: 2

Leu Cys Gly Gly Glu Leu Val Asp Thr Leu Gln Phe Val Cys Gly Asp
1               5                   10                  15

Arg Gly Phe Tyr Phe Ser Arg Pro Ala Ser Arg Val Ser Ala Arg Ser
            20                  25                  30

Arg Gly Ile Val Glu Glu Cys Cys Phe Arg Ser Cys Asp Leu Ala Leu
        35                  40                  45

Leu Glu Thr Tyr Cys Ala Thr Pro Ala Lys Ser Glu
    50                  55                  60

<210> SEQ ID NO 3
<211> LENGTH: 2298
<212> TYPE: DNA
<213> ORGANISM: Homo sapiens
<220> FEATURE:
<221> NAME/KEY: misc_signal
<222> LOCATION: (1)..(69)
<223> OTHER INFORMATION: Signal sequence

<400> SEQUENCE: 3
atggaggcgg tggcggtggc cgcggcggtg ggggtccttc tcctggccgg ggccgggggc     60
gcggcaggca tggaggcggt ggcggtggcc gcggcggtgg gggtccttct cctggccggg    120

```
gccgggggcg cggcaggcga cgaggcccgg gaggcggcgg ccgtgcgggc gctcgtggcc      180
cggctgctgg ggccaggccc cgcggccgac ttctccgtgt cggtggagcg cgctctggct      240
gccaagccgg gcttggacac ctacagcctg ggcggcggcg gcgcggcgcg cgtgcgggtg      300
cgcggctcca cgggcgtggc ggccgccgcg gggctgcacc gctacctgcg cgacttctgt      360
ggctgccacg tggcctggtc cggctctcag ctgcgcctgc cgcggccact gccagccgtg      420 ccggggagc tgaccgaggc cacgcccaac aggtaccgct attaccagaa tgtgtgcacg       480
caaagctact ctttcgtgtg gtgggactgg gcccgctggg agcgagagat agactggatg      540
gcgctgaatg gcatcaacct ggcactggcc tggagcggcc aggaggccat ctggcagcgg      600
gtgtacctgg ccttgggcct gacccaggca gagatcaatg agttctttac tggtcctgcc      660
ttcctggcct gggggcgaat gggcaacctg cacacctggg atggccccct gccccctcc      720 tggcacatca agcagcttta cctgcagcac cgggtcctgg accagatgcg ctccttcggc      780
atgaccccag tgctgcctgc attcgcgggg catgttcccg aggctgtcac cagggtgttc      840
cctcaggtca atgtcacgaa gatgggcagt tgggccact ttaactgttc ctactcctgc      900
tccttccttc tggctccgga agaccccata ttccccatca tcgggagcct cttcctgcga      960
gagctgatca aagagtttgg cacagaccac atctatgggg ccgacacttt caatgagatg     1020
cagccacctt cctcagagcc ctcctacctt gccgcagcca ccactgccgt ctatgaggcc     1080
atgactgcag tggatactga ggctgtgtgg ctgctcaag gctggctctt ccagcaccag      1140
ccgcagttct gggggcccgc ccagatcagg gctgtgctgg gagctgtgcc ccgtggccgc     1200
ctcctggttc tggacctgtt tgctgagagc cagcctgtgt atacccgcac tgcctccttc     1260
cagggccagc ccttcatctg gtgcatgctg cacaactttg ggggaaaacca tggtcttttt     1320 ggagccctag aggctgtgaa cggaggccca gaagctgccc gcctcttccc caactccacc     1380
atggtaggca cgggcatggc ccccgagggc atcagccaga acgaagtggt ctattccctc     1440
atggctgagc tgggctggcg aaaggaccca gtgccagatt tggcagcctg ggtgaccagc     1500
tttgccgccc ggcggtatgg ggtctcccac ccggacgcag ggcagcgtg gaggctactg      1560 ctccggagtg tgtacaactg ctccggggag gcctgcaggg gccacaatcg tagcccgctg     1620
gtcaggcggc cgtccctaca gatgaatacc agcatctggt acaaccgatc tgatgtgttt     1680
gaggcctggc ggctgctgct cacatctgct ccctccctgg ccaccagccc cgccttccgc     1740
tacgacctgc tggacctcac tcggcaggca gtgcaggagc tggtcagctt gtactatgag     1800
gaggcaagaa gcgcctacct gagcaaggag ctggcctccc tgttgagggc tggaggcgtc     1860
ctggcctatg agctgctgcc ggcactggac gaggtgctgg ctagtgacag ccgcttcttg     1920
ctgggcagct ggctagagca ggcccgagca gcggcagtca gtgaggccga ggccgatttc     1980
tacgagcaga acagccgcta ccagctgacc ttgtgggggc cagaaggcaa catcctggac     2040
tatgccaaca agcagctggc ggggttggtg gccaactact acacccctcg ctggcggctt      2100
ttcctggagg cgctggttga cagtgtggcc cagggcatcc ctttccaaca gcaccagttt     2160
gacaaaaatg tcttccaact ggagcaggcc ttcgttctca gcaagcagag gtaccccagc     2220
cagccgcgag gagacactgt ggacctggcc aagaagatct cctcaaaata ttaccccgc      2280 tgggtggccg gctcttgg                                                    2298

<210> SEQ ID NO 4
<211> LENGTH: 180
<212> TYPE: DNA
<213> ORGANISM: Homo sapiens
```

<400> SEQUENCE: 4
ctgtgcggcg gggagctggt ggacaccctc cagttcgtct gtggggaccg cggcttctac    60
ttcagcaggc ccgcaagccg tgtgagcgct cgcagccgtg gcatcgttga ggagtgctgt   120
ttccgcagct gtgacctggc cctcctggag acgtactgtg ctaccccgc caagtccgag   180

<210> SEQ ID NO 5
<211> LENGTH: 67
<212> TYPE: PRT
<213> ORGANISM: Homo sapiens

<400> SEQUENCE: 5

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 6

Arg Xaa Xaa Arg
1

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)

```
<223> OTHER INFORMATION: Xaa is Lys or Arg

<400> SEQUENCE: 7

Xaa Xaa Xaa Xaa Xaa Arg
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Met Arg Ala Trp Ile Phe Phe Leu Leu Cys Leu Ala Gly Arg Ala Leu
1               5                   10                  15

Ala

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide

<400> SEQUENCE: 9

Gly Ala Pro
1

<210> SEQ ID NO 10
<211> LENGTH: 3
<212> TYPE: PRT
<213> ORGANISM: Artificial Sequence
<220> FEATURE:
<223> OTHER INFORMATION: Synthetic peptide

<400> SEQUENCE: 10

Gly Pro Ser
1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide

<400> SEQUENCE: 11

Gly Gly Ser
1

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Gly Gly Gly Gly Ser
1               5

<210> SEQ ID NO 13
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 13

Gly Gly Gly Gly Gly Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Gly Gly Gly Pro Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Gly Gly Gly Ser Pro
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Gly Gly Gly Ser
1

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Ala Ala Ala Ala Ser
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide

<400> SEQUENCE: 18

Ala Ala Ala Ser
1

<210> SEQ ID NO 19
<211> LENGTH: 4
<212> TYPE: PRT
<213> ORGANISM: Artificial Sequence
<220> FEATURE:
```

```
<223> OTHER INFORMATION: Synthetic peptide

<400> SEQUENCE: 19

Pro Ala Pro Ala
1

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Thr Pro Ala Pro Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Ala Ala Ala Lys Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Glu Phe Gly Gly Gly Gly Ser Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Gly Pro Ser Gly Ser Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Gly Pro Ser Gly Ser Pro Gly Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 25

Gly Pro Ser Gly Ser Pro Gly His
1               5

<210> SEQ ID NO 26
<211> LENGTH: 26
<212> TYPE: PRT
<213> ORGANISM: Artificial Sequence
<220> FEATURE:
<223> OTHER INFORMATION: Synthetic peptide

<400> SEQUENCE: 26

Gly Gly Gly Gly Ser Gly Gly Gly Ser Gly Gly Gly Ser Gly
1               5                   10                  15

Gly Gly Gly Ser Gly Gly Gly Pro Ser Thr
            20                  25

<210> SEQ ID NO 27
<211> LENGTH: 26
<212> TYPE: PRT
<213> ORGANISM: Artificial Sequence
<220> FEATURE:
<223> OTHER INFORMATION: Synthetic peptide

<400> SEQUENCE: 27

Gly Gly Gly Gly Ser Gly Gly Gly Ser Gly Gly Gly Ser Gly
1               5                   10                  15

Gly Gly Gly Ser Gly Gly Gly Pro Ser His
            20                  25

<210> SEQ ID NO 28
<211> LENGTH: 35
<212> TYPE: PRT
<213> ORGANISM: Artificial Sequence
<220> FEATURE:
<223> OTHER INFORMATION: Synthetic peptide

<400> SEQUENCE: 28

Gly Gly Gly Gly Ser Gly Gly Gly Ser Gly Gly Gly Ser Gly
1               5                   10                  15

Gly Gly Gly Ser Gly Gly Gly Pro Ser Gly Gly Gly Ser Gly Gly
            20                  25                  30

Gly Pro Ser
        35

<210> SEQ ID NO 29
<211> LENGTH: 41
<212> TYPE: PRT
<213> ORGANISM: Artificial Sequence
<220> FEATURE:
<223> OTHER INFORMATION: Synthetic peptide

<400> SEQUENCE: 29

Gly Ala Pro Gly Gly Gly Gly Ser Gly Gly Gly Ser Gly Gly Gly
1               5                   10                  15

Gly Ser Gly Gly Gly Gly Ser Gly Gly Gly Pro Ser Gly Gly Gly Gly
            20                  25                  30

Ser Gly Gly Gly Pro Ser Gly Ala Pro
        35                  40

<210> SEQ ID NO 30
<211> LENGTH: 50
```

```
<212> TYPE: PRT
<213> ORGANISM: Artificial Sequence
<220> FEATURE:
<223> OTHER INFORMATION: Synthetic peptide

<400> SEQUENCE: 30

Gly Gly Gly Gly Ser Gly Gly Gly Ser Gly Gly Gly Ser Gly
 1               5                  10                  15

Gly Gly Gly Ser Gly Gly Gly Pro Ser Gly Gly Gly Ser Gly Gly
                20                  25                  30

Gly Gly Ser Gly Gly Gly Gly Ser Gly Gly Gly Ser Gly Gly Gly
            35                  40                  45

Pro Ser
    50

<210> SEQ ID NO 31
<211> LENGTH: 56
<212> TYPE: PRT
<213> ORGANISM: Artificial Sequence
<220> FEATURE:
<223> OTHER INFORMATION: Synthetic peptide

<400> SEQUENCE: 31

Gly Ala Pro Gly Gly Gly Gly Ser Gly Gly Gly Ser Gly Gly Gly
 1               5                  10                  15

Gly Ser Gly Gly Gly Gly Ser Gly Gly Gly Pro Ser Gly Gly Gly
                20                  25                  30

Ser Gly Gly Gly Gly Ser Gly Gly Gly Gly Ser Gly Gly Gly Ser
            35                  40                  45

Gly Gly Gly Pro Ser Gly Ala Pro
    50                  55

<210> SEQ ID NO 32
<211> LENGTH: 35
<212> TYPE: PRT
<213> ORGANISM: Artificial Sequence
<220> FEATURE:
<223> OTHER INFORMATION: Synthetic peptide

<400> SEQUENCE: 32

Gly Gly Gly Gly Ser Gly Gly Gly Gly Ser Gly Gly Gly Ser Gly
 1               5                  10                  15

Gly Gly Pro Ser Gly Gly Gly Gly Ser Gly Gly Gly Ser Gly Gly
                20                  25                  30

Gly Pro Ser
        35

<210> SEQ ID NO 33
<211> LENGTH: 41
<212> TYPE: PRT
<213> ORGANISM: Artificial Sequence
<220> FEATURE:
<223> OTHER INFORMATION: Synthetic peptide

<400> SEQUENCE: 33

Gly Ala Pro Gly Gly Gly Gly Ser Gly Gly Gly Gly Ser Gly Gly
 1               5                  10                  15

Gly Ser Gly Gly Gly Pro Ser Gly Gly Gly Ser Gly Gly Gly Gly
                20                  25                  30

Ser Gly Gly Gly Pro Ser Gly Ala Pro
            35                  40
```

```
<210> SEQ ID NO 34
<211> LENGTH: 50
<212> TYPE: PRT
<213> ORGANISM: Artificial Sequence
<220> FEATURE:
<223> OTHER INFORMATION: Synthetic peptide

<400> SEQUENCE: 34

Gly Gly Gly Gly Ser Gly Gly Gly Ser Gly Gly Gly Ser Gly
1               5                   10                  15

Gly Gly Pro Ser Gly Gly Gly Ser Gly Gly Gly Ser Gly Gly
            20                  25                  30

Gly Pro Ser Gly Gly Gly Ser Gly Gly Gly Ser Gly Gly Gly
        35                  40                  45

Pro Ser
    50

<210> SEQ ID NO 35
<211> LENGTH: 56
<212> TYPE: PRT
<213> ORGANISM: Artificial Sequence
<220> FEATURE:
<223> OTHER INFORMATION: Synthetic peptide

<400> SEQUENCE: 35

Gly Ala Pro Gly Gly Gly Ser Gly Gly Gly Ser Gly Gly Gly
1               5                   10                  15

Gly Ser Gly Gly Gly Pro Ser Gly Gly Gly Ser Gly Gly Gly
            20                  25                  30

Ser Gly Gly Gly Pro Ser Gly Gly Gly Ser Gly Gly Gly Ser
        35                  40                  45

Gly Gly Gly Pro Ser Gly Ala Pro
    50                  55

<210> SEQ ID NO 36
<211> LENGTH: 25
<212> TYPE: PRT
<213> ORGANISM: Artificial Sequence
<220> FEATURE:
<223> OTHER INFORMATION: Synthetic peptide

<400> SEQUENCE: 36

Gly Gly Gly Gly Ser Gly Gly Gly Ser Gly Gly Gly Ser Gly
1               5                   10                  15

Gly Gly Gly Ser Gly Gly Gly Pro Ser
            20                  25

<210> SEQ ID NO 37
<211> LENGTH: 31
<212> TYPE: PRT
<213> ORGANISM: Artificial Sequence
<220> FEATURE:
<223> OTHER INFORMATION: Synthetic peptide

<400> SEQUENCE: 37

Gly Ala Pro Gly Gly Gly Ser Gly Gly Gly Ser Gly Gly Gly
1               5                   10                  15

Gly Ser Gly Gly Gly Gly Ser Gly Gly Gly Pro Ser Gly Ala Pro
            20                  25                  30

<210> SEQ ID NO 38
<211> LENGTH: 25
```

```
<212> TYPE: PRT
<213> ORGANISM: Artificial Sequence
<220> FEATURE:
<223> OTHER INFORMATION: Synthetic peptide

<400> SEQUENCE: 38

Gly Gly Gly Gly Ser Gly Gly Gly Ser Ala Ala Ala Ser Gly
1               5                   10                  15

Gly Gly Gly Ser Gly Gly Gly Pro Ser
            20                  25

<210> SEQ ID NO 39
<211> LENGTH: 31
<212> TYPE: PRT
<213> ORGANISM: Artificial Sequence
<220> FEATURE:
<223> OTHER INFORMATION: Synthetic peptide

<400> SEQUENCE: 39

Gly Ala Pro Gly Gly Gly Gly Ser Gly Gly Gly Gly Ser Ala Ala Ala
1               5                   10                  15

Ala Ser Gly Gly Gly Gly Ser Gly Gly Gly Pro Ser Gly Ala Pro
            20                  25                  30

<210> SEQ ID NO 40
<211> LENGTH: 50
<212> TYPE: PRT
<213> ORGANISM: Artificial Sequence
<220> FEATURE:
<223> OTHER INFORMATION: Synthetic peptide

<400> SEQUENCE: 40

Gly Gly Gly Gly Ser Gly Gly Gly Ser Ala Ala Ala Ala Ser Gly
1               5                   10                  15

Gly Gly Gly Ser Gly Gly Gly Ser Ala Ala Ala Ala Ser Gly Gly
            20                  25                  30

Gly Gly Ser Gly Gly Gly Ser Ala Ala Ala Ala Ser Gly Gly Gly
        35                  40                  45

Pro Ser
    50

<210> SEQ ID NO 41
<211> LENGTH: 56
<212> TYPE: PRT
<213> ORGANISM: Artificial Sequence
<220> FEATURE:
<223> OTHER INFORMATION: Synthetic peptide

<400> SEQUENCE: 41

Gly Ala Pro Gly Gly Gly Gly Ser Gly Gly Gly Gly Ser Ala Ala Ala
1               5                   10                  15

Ala Ser Gly Gly Gly Gly Ser Gly Gly Gly Gly Ser Ala Ala Ala Ala
            20                  25                  30

Ser Gly Gly Gly Gly Ser Gly Gly Gly Gly Ser Ala Ala Ala Ala Ser
        35                  40                  45

Gly Gly Gly Pro Ser Gly Ala Pro
    50                  55

<210> SEQ ID NO 42
<211> LENGTH: 50
<212> TYPE: PRT
<213> ORGANISM: Artificial Sequence
<220> FEATURE:
```

<223> OTHER INFORMATION: Synthetic peptide

<400> SEQUENCE: 42

Gly Gly Gly Gly Ser Gly Gly Gly Ser Ala Ala Ala Ser Gly
1               5                   10                  15

Gly Gly Pro Ser Gly Gly Gly Ser Ala Ala Ala Ser Gly Gly
            20                  25                  30

Gly Pro Ser Gly Gly Gly Ser Ala Ala Ala Ser Gly Gly Gly
        35                  40                  45

Pro Ser
    50

<210> SEQ ID NO 43
<211> LENGTH: 56
<212> TYPE: PRT
<213> ORGANISM: Artificial Sequence
<220> FEATURE:
<223> OTHER INFORMATION: Synthetic peptide

<400> SEQUENCE: 43

Gly Ala Pro Gly Gly Gly Ser Gly Gly Gly Ser Ala Ala Ala
1               5                   10                  15

Ala Ser Gly Gly Gly Pro Ser Gly Gly Gly Ser Ala Ala Ala
            20                  25                  30

Ser Gly Gly Gly Pro Ser Gly Gly Gly Ser Ala Ala Ala Ser
        35                  40                  45

Gly Gly Gly Pro Ser Gly Ala Pro
    50                  55

<210> SEQ ID NO 44
<211> LENGTH: 47
<212> TYPE: PRT
<213> ORGANISM: Artificial Sequence
<220> FEATURE:
<223> OTHER INFORMATION: Synthetic peptide

<400> SEQUENCE: 44

Gly Gly Ser Pro Ala Gly Ser Pro Thr Ser Thr Glu Glu Gly Thr Ser
1               5                   10                  15

Glu Ser Ala Thr Pro Glu Ser Gly Pro Gly Thr Ser Thr Glu Pro Ser
            20                  25                  30

Glu Gly Ser Ala Pro Gly Ser Pro Ala Gly Ser Pro Gly Pro Ser
        35                  40                  45

<210> SEQ ID NO 45
<211> LENGTH: 53
<212> TYPE: PRT
<213> ORGANISM: Artificial Sequence
<220> FEATURE:
<223> OTHER INFORMATION: Synthetic peptide

<400> SEQUENCE: 45

Gly Ala Pro Gly Gly Ser Pro Ala Gly Ser Pro Thr Ser Thr Glu Glu
1               5                   10                  15

Gly Thr Ser Glu Ser Ala Thr Pro Glu Ser Gly Pro Gly Thr Ser Thr
            20                  25                  30

Glu Pro Ser Glu Gly Ser Ala Pro Gly Ser Pro Ala Gly Ser Pro Gly
        35                  40                  45

Pro Ser Gly Ala Pro
    50

<210> SEQ ID NO 46
<211> LENGTH: 50
<212> TYPE: PRT
<213> ORGANISM: Artificial Sequence
<220> FEATURE:
<223> OTHER INFORMATION: Synthetic peptide

<400> SEQUENCE: 46

Gly Gly Ser Pro Ala Gly Ser Pro Thr Ser Thr Glu Glu Gly Thr Ser
1               5                   10                  15

Glu Ser Ala Thr Pro Glu Ser Gly Pro Gly Thr Ser Thr Glu Pro Ser
            20                  25                  30

Glu Gly Ser Ala Pro Gly Ser Pro Ala Gly Ser Pro Thr Ser Thr Gly
        35                  40                  45

Pro Ser
    50

<210> SEQ ID NO 47
<211> LENGTH: 56
<212> TYPE: PRT
<213> ORGANISM: Artificial Sequence
<220> FEATURE:
<223> OTHER INFORMATION: Synthetic peptide

<400> SEQUENCE: 47

Gly Ala Pro Gly Gly Ser Pro Ala Gly Ser Pro Thr Ser Thr Glu Glu
1               5                   10                  15

Gly Thr Ser Glu Ser Ala Thr Pro Glu Ser Gly Pro Gly Thr Ser Thr
            20                  25                  30

Glu Pro Ser Glu Gly Ser Ala Pro Gly Ser Pro Ala Gly Ser Pro Thr
        35                  40                  45

Ser Thr Gly Pro Ser Gly Ala Pro
    50                  55

<210> SEQ ID NO 48
<211> LENGTH: 25
<212> TYPE: PRT
<213> ORGANISM: Artificial Sequence
<220> FEATURE:
<223> OTHER INFORMATION: Synthetic peptide

<400> SEQUENCE: 48

Gly Gly Gly Ser Pro Ala Pro Thr Pro Thr Pro Ala Pro Thr Pro Ala
1               5                   10                  15

Pro Thr Pro Ala Gly Gly Gly Pro Ser
            20                  25

<210> SEQ ID NO 49
<211> LENGTH: 31
<212> TYPE: PRT
<213> ORGANISM: Artificial Sequence
<220> FEATURE:
<223> OTHER INFORMATION: Synthetic peptide

<400> SEQUENCE: 49

Gly Ala Pro Gly Gly Gly Ser Pro Ala Pro Thr Pro Thr Pro Ala Pro
1               5                   10                  15

Thr Pro Ala Pro Thr Pro Ala Gly Gly Gly Pro Ser Gly Ala Pro
            20                  25                  30

<210> SEQ ID NO 50
<211> LENGTH: 25

```
<212> TYPE: PRT
<213> ORGANISM: Artificial Sequence
<220> FEATURE:
<223> OTHER INFORMATION: Synthetic peptide

<400> SEQUENCE: 50

Gly Gly Gly Ser Pro Ala Pro Ala Pro Thr Pro Ala Pro Ala Pro Thr
1               5                   10                  15

Pro Ala Pro Ala Gly Gly Gly Pro Ser
            20                  25

<210> SEQ ID NO 51
<211> LENGTH: 31
<212> TYPE: PRT
<213> ORGANISM: Artificial Sequence
<220> FEATURE:
<223> OTHER INFORMATION: Synthetic peptide

<400> SEQUENCE: 51

Gly Ala Pro Gly Gly Gly Ser Pro Ala Pro Ala Pro Thr Pro Ala Pro
1               5                   10                  15

Ala Pro Thr Pro Ala Pro Ala Gly Gly Gly Pro Ser Gly Ala Pro
            20                  25                  30

<210> SEQ ID NO 52
<211> LENGTH: 25
<212> TYPE: PRT
<213> ORGANISM: Artificial Sequence
<220> FEATURE:
<223> OTHER INFORMATION: Synthetic peptide

<400> SEQUENCE: 52

Gly Gly Gly Ser Ala Glu Ala Ala Ala Lys Glu Ala Ala Ala Lys Glu
1               5                   10                  15

Ala Ala Ala Lys Ala Gly Gly Pro Ser
            20                  25

<210> SEQ ID NO 53
<211> LENGTH: 31
<212> TYPE: PRT
<213> ORGANISM: Artificial Sequence
<220> FEATURE:
<223> OTHER INFORMATION: Synthetic peptide

<400> SEQUENCE: 53

Gly Ala Pro Gly Gly Gly Ser Ala Glu Ala Ala Ala Lys Glu Ala Ala
1               5                   10                  15

Ala Lys Glu Ala Ala Ala Lys Ala Gly Gly Pro Ser Gly Ala Pro
            20                  25                  30

<210> SEQ ID NO 54
<211> LENGTH: 37
<212> TYPE: PRT
<213> ORGANISM: Artificial Sequence
<220> FEATURE:
<223> OTHER INFORMATION: Synthetic peptide

<400> SEQUENCE: 54

Gly Gly Gly Ser Pro Ala Glu Ala Ala Ala Lys Glu Ala Ala Ala Lys
1               5                   10                  15

Glu Ala Ala Ala Lys Glu Ala Ala Ala Lys Glu Ala Ala Ala Lys Ala
            20                  25                  30

Pro Ser Gly Gly Gly
            35
```

<210> SEQ ID NO 55
<211> LENGTH: 43
<212> TYPE: PRT
<213> ORGANISM: Artificial Sequence
<220> FEATURE:
<223> OTHER INFORMATION: Synthetic peptide

<400> SEQUENCE: 55

Gly Ala Pro Gly Gly Gly Ser Pro Ala Glu Ala Ala Lys Glu Ala
1               5                   10                  15

Ala Ala Lys Glu Ala Ala Ala Lys Glu Ala Ala Ala Lys Glu Ala Ala
            20                  25                  30

Ala Lys Ala Pro Ser Gly Gly Gly Gly Ala Pro
        35                  40

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 21
<212> TYPE: PRT
<213> ORGANISM: Artificial Sequence
<220> FEATURE:
<223> OTHER INFORMATION: Synthetic peptide

<400> SEQUENCE: 57

Gly Ala Pro Gly Gly Gly Gly Ser Gly Gly Gly Gly Ser Gly Gly
1               5                   10                  15

Gly Ser Gly Ala Pro
        20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Gly Gly Gly Gly Ser Gly Gly Gly Gly Ser Gly Gly Gly Gly Ser Gly
1               5                   10                  15

Gly Gly Gly Ser
        20

<210> SEQ ID NO 59
<211> LENGTH: 26
<212> TYPE: PRT
<213> ORGANISM: Artificial Sequence
<220> FEATURE:
<223> OTHER INFORMATION: Synthetic peptide

<400> SEQUENCE: 59

Gly Ala Pro Gly Gly Gly Gly Ser Gly Gly Gly Gly Ser Gly Gly
1               5                   10                  15

Gly Ser Gly Gly Gly Gly Ser Gly Ala Pro

```
            20                  25

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide

<400> SEQUENCE: 60

Gly Gly Gly Gly Ala
1               5

<210> SEQ ID NO 61
<211> LENGTH: 26
<212> TYPE: PRT
<213> ORGANISM: Artificial Sequence
<220> FEATURE:
<223> OTHER INFORMATION: Synthetic peptide

<400> SEQUENCE: 61

Gly Gly Gly Gly Ala Gly Gly Gly Ala Gly Gly Gly Gly Ala Gly
1               5                   10                  15

Gly Gly Gly Ala Gly Gly Gly Pro Ser Thr
            20                  25

<210> SEQ ID NO 62
<211> LENGTH: 26
<212> TYPE: PRT
<213> ORGANISM: Artificial Sequence
<220> FEATURE:
<223> OTHER INFORMATION: Synthetic peptide

<400> SEQUENCE: 62

Gly Gly Gly Gly Ala Gly Gly Gly Ala Gly Gly Gly Gly Ala Gly
1               5                   10                  15

Gly Gly Gly Ala Gly Gly Gly Pro Ser His
            20                  25

<210> SEQ ID NO 63
<211> LENGTH: 35
<212> TYPE: PRT
<213> ORGANISM: Artificial Sequence
<220> FEATURE:
<223> OTHER INFORMATION: Synthetic peptide

<400> SEQUENCE: 63

Gly Gly Gly Gly Ala Gly Gly Gly Ala Gly Gly Gly Gly Ala Gly
1               5                   10                  15

Gly Gly Gly Ala Gly Gly Gly Pro Ser Gly Gly Gly Gly Ala Gly
            20                  25                  30

Gly Pro Ser
        35

<210> SEQ ID NO 64
<211> LENGTH: 41
<212> TYPE: PRT
<213> ORGANISM: Artificial Sequence
<220> FEATURE:
<223> OTHER INFORMATION: Synthetic peptide

<400> SEQUENCE: 64

Gly Ala Pro Gly Gly Gly Gly Ala Gly Gly Gly Gly Ala Gly Gly
1               5                   10                  15
```

Gly Ala Gly Gly Gly Ala Gly Gly Pro Ser Gly Gly Gly
            20                  25                  30

Ala Gly Gly Gly Pro Ser Gly Ala Pro
        35                  40

<210> SEQ ID NO 65
<211> LENGTH: 50
<212> TYPE: PRT
<213> ORGANISM: Artificial Sequence
<220> FEATURE:
<223> OTHER INFORMATION: Synthetic peptide

<400> SEQUENCE: 65

Gly Gly Gly Gly Ala Gly Gly Gly Ala Gly Gly Gly Ala Gly
1               5                   10                  15

Gly Gly Gly Ala Gly Gly Gly Pro Ser Gly Gly Gly Ala Gly Gly
            20                  25                  30

Gly Gly Ala Gly Gly Gly Gly Ala Gly Gly Gly Ala Gly Gly Gly
        35                  40                  45

Pro Ser
    50

<210> SEQ ID NO 66
<211> LENGTH: 56
<212> TYPE: PRT
<213> ORGANISM: Artificial Sequence
<220> FEATURE:
<223> OTHER INFORMATION: Synthetic peptide

<400> SEQUENCE: 66

Gly Ala Pro Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Gly Gly Gly Ala Gly Gly Gly Gly Ala Gly Gly Gly Ala
        35                  40                  45

Gly Gly Gly Pro Ser Gly Ala Pro
    50                  55

<210> SEQ ID NO 67
<211> LENGTH: 35
<212> TYPE: PRT
<213> ORGANISM: Artificial Sequence
<220> FEATURE:
<223> OTHER INFORMATION: Synthetic peptide

<400> SEQUENCE: 67

Gly Gly Gly Gly Ala Gly Gly Gly Ala Gly Gly Gly Ala Gly
1               5                   10                  15

Gly Gly Pro Ser Gly Gly Gly Gly Ala Gly Gly Gly Ala Gly Gly
            20                  25                  30

Gly Pro Ser
    35

<210> SEQ ID NO 68
<211> LENGTH: 41
<212> TYPE: PRT
<213> ORGANISM: Artificial Sequence
<220> FEATURE:
<223> OTHER INFORMATION: Synthetic peptide

<400> SEQUENCE: 68

```
Gly Ala Pro Gly Gly Gly Ala Gly Gly Gly Ala Gly Gly Gly
1               5                   10                  15
Gly Ala Gly Gly Gly Pro Ser Gly Gly Gly Ala Gly Gly Gly
                20              25                  30
Ala Gly Gly Gly Pro Ser Gly Ala Pro
            35              40

<210> SEQ ID NO 69
<211> LENGTH: 50
<212> TYPE: PRT
<213> ORGANISM: Artificial Sequence
<220> FEATURE:
<223> OTHER INFORMATION: Synthetic peptide

<400> SEQUENCE: 69

Gly Gly Gly Gly Ala Gly Gly Gly Ala Gly Gly Gly Ala Gly
1               5                   10                  15
Gly Gly Pro Ser Gly Gly Gly Ala Gly Gly Gly Ala Gly Gly
                20              25                  30
Gly Pro Ser Gly Gly Gly Ala Gly Gly Gly Ala Gly Gly Gly
            35              40              45
Pro Ser
    50

<210> SEQ ID NO 70
<211> LENGTH: 56
<212> TYPE: PRT
<213> ORGANISM: Artificial Sequence
<220> FEATURE:
<223> OTHER INFORMATION: Synthetic peptide

<400> SEQUENCE: 70

Gly Ala Pro Gly Gly Gly Ala Gly Gly Gly Ala Gly Gly Gly
1               5                   10                  15
Gly Ala Gly Gly Gly Pro Ser Gly Gly Gly Ala Gly Gly Gly
                20              25                  30
Ala Gly Gly Gly Pro Ser Gly Gly Gly Ala Gly Gly Gly Ala
            35              40              45
Gly Gly Gly Pro Ser Gly Ala Pro
        50              55

<210> SEQ ID NO 71
<211> LENGTH: 25
<212> TYPE: PRT
<213> ORGANISM: Artificial Sequence
<220> FEATURE:
<223> OTHER INFORMATION: Synthetic peptide

<400> SEQUENCE: 71

Gly Gly Gly Gly Ala Gly Gly Gly Ala Gly Gly Gly Ala Gly
1               5                   10                  15
Gly Gly Gly Ala Gly Gly Gly Pro Ser
            20              25

<210> SEQ ID NO 72
<211> LENGTH: 31
<212> TYPE: PRT
<213> ORGANISM: Artificial Sequence
<220> FEATURE:
<223> OTHER INFORMATION: Synthetic peptide

<400> SEQUENCE: 72
```

```
Gly Ala Pro Gly Gly Gly Ala Gly Gly Gly Ala Gly Gly Gly
1               5                   10                  15

Gly Ala Gly Gly Gly Gly Ala Gly Gly Gly Pro Ser Gly Ala Pro
                20                  25                  30
```

<210> SEQ ID NO 73
<211> LENGTH: 25
<212> TYPE: PRT
<213> ORGANISM: Artificial Sequence
<220> FEATURE:
<223> OTHER INFORMATION: Synthetic peptide

<400> SEQUENCE: 73

```
Gly Gly Gly Gly Ala Gly Gly Gly Ala Ala Ala Ala Ala Ser Gly
1               5                   10                  15

Gly Gly Gly Ala Gly Gly Gly Pro Ser
                20                  25
```

<210> SEQ ID NO 74
<211> LENGTH: 31
<212> TYPE: PRT
<213> ORGANISM: Artificial Sequence
<220> FEATURE:
<223> OTHER INFORMATION: Synthetic peptide

<400> SEQUENCE: 74

```
Gly Ala Pro Gly Gly Gly Gly Ala Gly Gly Gly Ala Ala Ala Ala
1               5                   10                  15

Ala Ser Gly Gly Gly Gly Ala Gly Gly Gly Pro Ser Gly Ala Pro
                20                  25                  30
```

<210> SEQ ID NO 75
<211> LENGTH: 50
<212> TYPE: PRT
<213> ORGANISM: Artificial Sequence
<220> FEATURE:
<223> OTHER INFORMATION: Synthetic peptide

<400> SEQUENCE: 75

```
Gly Gly Gly Gly Ala Gly Gly Gly Ala Ala Ala Ala Ala Ser Gly
1               5                   10                  15

Gly Gly Ala Gly Gly Gly Gly Ala Ala Ala Ala Ala Ser Gly Gly
                20                  25                  30

Gly Ala Gly Gly Gly Gly Ala Ala Ala Ala Ala Ser Gly Gly Gly
        35                  40                  45

Pro Ser
    50
```

<210> SEQ ID NO 76
<211> LENGTH: 56
<212> TYPE: PRT
<213> ORGANISM: Artificial Sequence
<220> FEATURE:
<223> OTHER INFORMATION: Synthetic peptide

<400> SEQUENCE: 76

```
Gly Ala Pro Gly Gly Gly Gly Ala Gly Gly Gly Gly Ala Ala Ala Ala
1               5                   10                  15

Ala Ser Gly Gly Gly Gly Ala Gly Gly Gly Gly Ala Ala Ala Ala Ala
                20                  25                  30

Ser Gly Gly Gly Gly Ala Gly Gly Gly Gly Ala Ala Ala Ala Ala Ser
        35                  40                  45
```

```
Gly Gly Gly Pro Ser Gly Ala Pro
    50              55

<210> SEQ ID NO 77
<211> LENGTH: 50
<212> TYPE: PRT
<213> ORGANISM: Artificial Sequence
<220> FEATURE:
<223> OTHER INFORMATION: Synthetic peptide

<400> SEQUENCE: 77

Gly Gly Gly Gly Ala Gly Gly Gly Ala Ala Ala Ala Ser Gly
1               5                   10                  15

Gly Gly Pro Ser Gly Gly Gly Ala Ala Ala Ala Ser Gly Gly
            20                  25                  30

Gly Pro Ser Gly Gly Gly Ala Ala Ala Ala Ser Gly Gly Gly
        35                  40                  45

Pro Ser
    50

<210> SEQ ID NO 78
<211> LENGTH: 56
<212> TYPE: PRT
<213> ORGANISM: Artificial Sequence
<220> FEATURE:
<223> OTHER INFORMATION: Synthetic peptide

<400> SEQUENCE: 78

Gly Ala Pro Gly Gly Gly Ala Gly Gly Gly Ala Ala Ala Ala
1               5                   10                  15

Ala Ser Gly Gly Gly Pro Ser Gly Gly Gly Ala Ala Ala Ala
            20                  25                  30

Ser Gly Gly Gly Pro Ser Gly Gly Gly Ala Ala Ala Ala Ser
        35                  40                  45

Gly Gly Gly Pro Ser Gly Ala Pro
    50              55

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide

<400> SEQUENCE: 79

Gly Gly Gly Gly Ala Gly Gly Gly Ala Gly Gly Gly Ala
1               5                   10                  15

<210> SEQ ID NO 80
<211> LENGTH: 21
<212> TYPE: PRT
<213> ORGANISM: Artificial Sequence
<220> FEATURE:
<223> OTHER INFORMATION: Synthetic peptide

<400> SEQUENCE: 80

Gly Ala Pro Gly Gly Gly Ala Gly Gly Gly Ala Gly Gly Gly
1               5                   10                  15

Gly Ala Gly Ala Pro
            20

<210> SEQ ID NO 81
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 81

Gly Gly Gly Gly Ala Gly Gly Gly Ala Gly Gly Gly Ala Gly
1               5                   10                  15

Gly Gly Gly Ala
            20

<210> SEQ ID NO 82
<211> LENGTH: 26
<212> TYPE: PRT
<213> ORGANISM: Artificial Sequence
<220> FEATURE:
<223> OTHER INFORMATION: Synthetic peptide

<400> SEQUENCE: 82

Gly Ala Pro Gly Gly Gly Gly Ala Gly Gly Gly Ala Gly Gly
1               5                   10                  15

Gly Ala Gly Gly Gly Gly Ala Gly Ala Pro
            20                  25

<210> SEQ ID NO 83
<211> LENGTH: 45
<212> TYPE: PRT
<213> ORGANISM: Artificial Sequence
<220> FEATURE:
<223> OTHER INFORMATION: Synthetic peptide

<400> SEQUENCE: 83

Gly Gly Gly Gly Ala Gly Gly Gly Ala Gly Gly Gly Ala Gly
1               5                   10                  15

Gly Gly Ala Gly Gly Gly Ala Gly Gly Gly Ala Gly Gly Gly
            20                  25                  30

Gly Gly Ala Gly Gly Gly Ala Gly Gly Gly Pro Ser
        35                  40                  45

<210> SEQ ID NO 84
<211> LENGTH: 46
<212> TYPE: PRT
<213> ORGANISM: Artificial Sequence
<220> FEATURE:
<223> OTHER INFORMATION: Synthetic peptide

<400> SEQUENCE: 84

Gly Gly Gly Gly Ala Gly Gly Gly Ala Gly Gly Gly Ala Gly
1               5                   10                  15

Gly Gly Ala Gly Gly Gly Ala Gly Gly Gly Ala Gly Gly Gly
            20                  25                  30

Gly Gly Ala Gly Gly Gly Ala Gly Gly Gly Pro Ser His
        35                  40                  45

<210> SEQ ID NO 85
<211> LENGTH: 50
<212> TYPE: PRT
<213> ORGANISM: Artificial Sequence
<220> FEATURE:
<223> OTHER INFORMATION: Synthetic peptide

<400> SEQUENCE: 85

Gly Gly Gly Gly Ala Gly Gly Gly Ala Gly Gly Gly Ala Gly
1               5                   10                  15
```

Gly Gly Gly Ala Gly Gly Gly Ala Gly Gly Gly Ala Gly Gly
            20              25              30

Gly Gly Ala Gly Gly Gly Ala Gly Gly Gly Ala Gly Gly Gly
        35              40              45

Pro Ser
    50

<210> SEQ ID NO 86
<211> LENGTH: 51
<212> TYPE: PRT
<213> ORGANISM: Artificial Sequence
<220> FEATURE:
<223> OTHER INFORMATION: Synthetic peptide

<400> SEQUENCE: 86

Gly Gly Gly Gly Ala Gly Gly Gly Ala Gly Gly Gly Ala Gly
1               5                   10                  15

Gly Gly Ala Gly Gly Gly Ala Gly Gly Gly Ala Gly Gly Gly
            20              25              30

Gly Gly Ala Gly Gly Gly Ala Gly Gly Gly Ala Gly Gly Gly
        35              40              45

Pro Ser His
    50

<210> SEQ ID NO 87
<211> LENGTH: 25
<212> TYPE: PRT
<213> ORGANISM: Artificial Sequence
<220> FEATURE:
<223> OTHER INFORMATION: Synthetic peptide

<400> SEQUENCE: 87

Gly Gly Gly Gly Pro Ala Pro Gly Pro Gly Pro Ala Pro Gly Pro Ala
1               5                   10                  15

Pro Gly Pro Ala Gly Gly Gly Pro Ser
            20              25

<210> SEQ ID NO 88
<211> LENGTH: 31
<212> TYPE: PRT
<213> ORGANISM: Artificial Sequence
<220> FEATURE:
<223> OTHER INFORMATION: Synthetic peptide

<400> SEQUENCE: 88

Gly Ala Pro Gly Gly Gly Pro Ala Pro Gly Pro Gly Pro Ala Pro
1               5                   10                  15

Gly Pro Ala Pro Gly Pro Ala Gly Gly Gly Pro Gly Gly Ala Pro
            20              25              30

<210> SEQ ID NO 89
<211> LENGTH: 25
<212> TYPE: PRT
<213> ORGANISM: Artificial Sequence
<220> FEATURE:
<223> OTHER INFORMATION: Synthetic peptide

<400> SEQUENCE: 89

Gly Gly Gly Gly Pro Ala Pro Ala Pro Gly Pro Ala Pro Ala Pro Gly
1               5                   10                  15

Pro Ala Pro Ala Gly Gly Gly Pro Ser
            20              25

```
<210> SEQ ID NO 90
<211> LENGTH: 31
<212> TYPE: PRT
<213> ORGANISM: Artificial Sequence
<220> FEATURE:
<223> OTHER INFORMATION: Synthetic peptide

<400> SEQUENCE: 90

Gly Ala Pro Gly Gly Gly Pro Ala Pro Ala Pro Gly Pro Ala Pro
1               5                   10                  15

Ala Pro Gly Pro Ala Pro Ala Gly Gly Pro Gly Gly Ala Pro
            20                  25                  30

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide

<400> SEQUENCE: 91

Gly Gly Gly Gly Ser Gly Gly Gly Gly Ser
1               5                   10

<210> SEQ ID NO 92
<211> LENGTH: 25
<212> TYPE: PRT
<213> ORGANISM: Artificial Sequence
<220> FEATURE:
<223> OTHER INFORMATION: Synthetic peptide

<400> SEQUENCE: 92

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 93
<211> LENGTH: 30
<212> TYPE: PRT
<213> ORGANISM: Artificial Sequence
<220> FEATURE:
<223> OTHER INFORMATION: Synthetic peptide

<400> SEQUENCE: 93

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 94
<211> LENGTH: 35
<212> TYPE: PRT
<213> ORGANISM: Artificial Sequence
<220> FEATURE:
<223> OTHER INFORMATION: Synthetic peptide

<400> SEQUENCE: 94

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
```

35

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Gly Gly Gly Gly Ser Gly Gly Gly Pro Ser
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Synthetic peptide

<400> SEQUENCE: 96

Gly Gly Gly Gly Ser Gly Gly Gly Gly Ser Gly Gly Gly Pro Ser
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Gly Gly Gly Gly Ser Gly Gly Gly Gly Ser Gly Gly Gly Gly Ser Gly
1               5                   10                  15

Gly Gly Pro Ser
            20

<210> SEQ ID NO 98
<211> LENGTH: 30
<212> TYPE: PRT
<213> ORGANISM: Artificial Sequence
<220> FEATURE:
<223> OTHER INFORMATION: Synthetic peptide

<400> SEQUENCE: 98

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Pro Ser
            20                  25                  30

<210> SEQ ID NO 99
<211> LENGTH: 35
<212> TYPE: PRT
<213> ORGANISM: Artificial Sequence
<220> FEATURE:
<223> OTHER INFORMATION: Synthetic peptide

<400> SEQUENCE: 99

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Pro Ser
        35

```
<210> SEQ ID NO 100
<211> LENGTH: 40
<212> TYPE: PRT
<213> ORGANISM: Artificial Sequence
<220> FEATURE:
<223> OTHER INFORMATION: Synthetic peptide

<400> SEQUENCE: 100

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Pro Ser
        35                  40

<210> SEQ ID NO 101
<211> LENGTH: 13
<212> TYPE: PRT
<213> ORGANISM: Artificial Sequence
<220> FEATURE:
<223> OTHER INFORMATION: Synthetic peptide

<400> SEQUENCE: 101

Gly Ala Pro Gly Gly Gly Gly Ser Gly Gly Gly Pro Ser
1               5                   10

<210> SEQ ID NO 102
<211> LENGTH: 18
<212> TYPE: PRT
<213> ORGANISM: Artificial Sequence
<220> FEATURE:
<223> OTHER INFORMATION: Synthetic peptide

<400> SEQUENCE: 102

Gly Ala Pro Gly Gly Gly Gly Ser Gly Gly Gly Ser Gly Gly
1               5                   10                  15

Pro Ser

<210> SEQ ID NO 103
<211> LENGTH: 23
<212> TYPE: PRT
<213> ORGANISM: Artificial Sequence
<220> FEATURE:
<223> OTHER INFORMATION: Synthetic peptide

<400> SEQUENCE: 103

Gly Ala Pro Gly Gly Gly Gly Ser Gly Gly Gly Ser Gly Gly
1               5                   10                  15

Gly Ser Gly Gly Gly Pro Ser
            20

<210> SEQ ID NO 104
<211> LENGTH: 28
<212> TYPE: PRT
<213> ORGANISM: Artificial Sequence
<220> FEATURE:
<223> OTHER INFORMATION: Synthetic peptide

<400> SEQUENCE: 104

Gly Ala Pro Gly Gly Gly Gly Ser Gly Gly Gly Ser Gly Gly
1               5                   10                  15

Gly Ser Gly Gly Gly Gly Ser Gly Gly Gly Pro Ser
            20                  25
```

<210> SEQ ID NO 105
<211> LENGTH: 33
<212> TYPE: PRT
<213> ORGANISM: Artificial Sequence
<220> FEATURE:
<223> OTHER INFORMATION: Synthetic peptide

<400> SEQUENCE: 105

Gly Ala Pro Gly Gly Gly Gly Ser Gly Gly Gly Gly Ser Gly Gly
1               5                   10                  15

Gly Ser Gly Gly Gly Gly Ser Gly Gly Gly Gly Ser Gly Gly Gly Pro
            20                  25                  30

Ser

<210> SEQ ID NO 106
<211> LENGTH: 38
<212> TYPE: PRT
<213> ORGANISM: Artificial Sequence
<220> FEATURE:
<223> OTHER INFORMATION: Synthetic peptide

<400> SEQUENCE: 106

Gly Ala Pro Gly Gly Gly Gly Ser Gly Gly Gly Gly Ser Gly Gly
1               5                   10                  15

Gly Ser Gly Gly Gly Gly Ser Gly Gly Gly Gly Ser Gly Gly Gly Gly
            20                  25                  30

Ser Gly Gly Gly Pro Ser
        35

<210> SEQ ID NO 107
<211> LENGTH: 43
<212> TYPE: PRT
<213> ORGANISM: Artificial Sequence
<220> FEATURE:
<223> OTHER INFORMATION: Synthetic peptide

<400> SEQUENCE: 107

Gly Ala Pro Gly Gly Gly Gly Ser Gly Gly Gly Gly Ser Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Pro Ser
        35                  40

<210> SEQ ID NO 108
<211> LENGTH: 16
<212> TYPE: PRT
<213> ORGANISM: Artificial Sequence
<220> FEATURE:
<223> OTHER INFORMATION: Synthetic peptide

<400> SEQUENCE: 108

Gly Ala Pro Gly Gly Gly Gly Ser Gly Gly Gly Pro Ser Gly Ala Pro
1               5                   10                  15

<210> SEQ ID NO 109
<211> LENGTH: 21
<212> TYPE: PRT
<213> ORGANISM: Artificial Sequence
<220> FEATURE:
<223> OTHER INFORMATION: Synthetic peptide

<400> SEQUENCE: 109

```
Gly Ala Pro Gly Gly Gly Gly Ser Gly Gly Gly Ser Gly Gly
1               5                   10                  15

Pro Ser Gly Ala Pro
        20
```

<210> SEQ ID NO 110
<211> LENGTH: 26
<212> TYPE: PRT
<213> ORGANISM: Artificial Sequence
<220> FEATURE:
<223> OTHER INFORMATION: Synthetic peptide

<400> SEQUENCE: 110

```
Gly Ala Pro Gly Gly Gly Gly Ser Gly Gly Gly Ser Gly Gly
1               5                   10                  15

Gly Ser Gly Gly Gly Pro Ser Gly Ala Pro
            20                  25
```

<210> SEQ ID NO 111
<211> LENGTH: 36
<212> TYPE: PRT
<213> ORGANISM: Artificial Sequence
<220> FEATURE:
<223> OTHER INFORMATION: Synthetic peptide

<400> SEQUENCE: 111

```
Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly Pro
            20                  25                  30

Ser Gly Ala Pro
        35
```

<210> SEQ ID NO 112
<211> LENGTH: 41
<212> TYPE: PRT
<213> ORGANISM: Artificial Sequence
<220> FEATURE:
<223> OTHER INFORMATION: Synthetic peptide

<400> SEQUENCE: 112

```
Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly
            20                  25                  30

Ser Gly Gly Gly Pro Ser Gly Ala Pro
        35                  40
```

<210> SEQ ID NO 113
<211> LENGTH: 46
<212> TYPE: PRT
<213> ORGANISM: Artificial Sequence
<220> FEATURE:
<223> OTHER INFORMATION: Synthetic peptide

<400> SEQUENCE: 113

```
Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly
            20                  25                  30

Ser Gly Gly Gly Gly Ser Gly Gly Gly Pro Ser Gly Ala Pro
        35                  40                  45
```

<210> SEQ ID NO 114
<211> LENGTH: 21
<212> TYPE: PRT
<213> ORGANISM: Artificial Sequence
<220> FEATURE:
<223> OTHER INFORMATION: Synthetic peptide

<400> SEQUENCE: 114

Gly Ala Pro Gly Gly Gly Gly Ser Gly Gly Gly Pro Ser Gly Gly Gly
1               5                   10                  15

Gly Ser Gly Ala Pro
            20

<210> SEQ ID NO 115
<211> LENGTH: 26
<212> TYPE: PRT
<213> ORGANISM: Artificial Sequence
<220> FEATURE:
<223> OTHER INFORMATION: Synthetic peptide

<400> SEQUENCE: 115

Gly Ala Pro Gly Gly Gly Gly Ser Gly Gly Gly Pro Ser Gly Gly Gly
1               5                   10                  15

Gly Ser Gly Gly Gly Gly Ser Gly Ala Pro
            20                  25

<210> SEQ ID NO 116
<211> LENGTH: 31
<212> TYPE: PRT
<213> ORGANISM: Artificial Sequence
<220> FEATURE:
<223> OTHER INFORMATION: Synthetic peptide

<400> SEQUENCE: 116

Gly Ala Pro Gly Gly Gly Gly Ser Gly Gly Gly Pro Ser Gly Gly Gly
1               5                   10                  15

Gly Ser Gly Gly Gly Gly Ser Gly Gly Gly Gly Ser Gly Ala Pro
            20                  25                  30

<210> SEQ ID NO 117
<211> LENGTH: 36
<212> TYPE: PRT
<213> ORGANISM: Artificial Sequence
<220> FEATURE:
<223> OTHER INFORMATION: Synthetic peptide

<400> SEQUENCE: 117

Gly Ala Pro Gly Gly Gly Gly Ser Gly Gly Gly Pro Ser Gly Gly Gly
1               5                   10                  15

Gly Ser Gly Gly Gly Gly Ser Gly Gly Gly Ser Gly Gly Gly Gly
            20                  25                  30

Ser Gly Ala Pro
        35

<210> SEQ ID NO 118
<211> LENGTH: 41
<212> TYPE: PRT
<213> ORGANISM: Artificial Sequence
<220> FEATURE:
<223> OTHER INFORMATION: Synthetic peptide

<400> SEQUENCE: 118

Gly Ala Pro Gly Gly Gly Gly Ser Gly Gly Gly Pro Ser Gly Gly Gly
1               5                   10                  15

Gly Ser Gly Gly Gly Ser Gly Gly Gly Ser Gly Gly Gly Gly
        20                  25                  30

Ser Gly Gly Gly Gly Ser Gly Ala Pro
        35                  40

<210> SEQ ID NO 119
<211> LENGTH: 46
<212> TYPE: PRT
<213> ORGANISM: Artificial Sequence
<220> FEATURE:
<223> OTHER INFORMATION: Synthetic peptide

<400> SEQUENCE: 119

Gly Ala Pro Gly Gly Gly Ser Gly Gly Pro Ser Gly Gly Gly
1               5                   10                  15

Gly Ser Gly Gly Gly Gly Ser Gly Gly Gly Ser Gly Gly Gly Gly
        20                  25                  30

Ser Gly Gly Gly Gly Ser Gly Gly Gly Ser Gly Ala Pro
        35                  40                  45

<210> SEQ ID NO 120
<211> LENGTH: 51
<212> TYPE: PRT
<213> ORGANISM: Artificial Sequence
<220> FEATURE:
<223> OTHER INFORMATION: Synthetic peptide

<400> SEQUENCE: 120

Gly Ala Pro Gly Gly Gly Gly Ser Gly Gly Pro Ser Gly Gly Gly
1               5                   10                  15

Gly Ser Gly Gly Gly Gly Ser Gly Gly Gly Ser Gly Gly Gly Gly
        20                  25                  30

Ser Gly Gly Gly Gly Ser Gly Gly Gly Ser Gly Gly Gly Gly Ser
        35                  40                  45

Gly Ala Pro
        50

<210> SEQ ID NO 121
<211> LENGTH: 26
<212> TYPE: PRT
<213> ORGANISM: Artificial Sequence
<220> FEATURE:
<223> OTHER INFORMATION: Synthetic peptide

<400> SEQUENCE: 121

Gly Ala Pro Gly Gly Gly Gly Ser Gly Gly Gly Ser Gly Gly Gly
1               5                   10                  15

Pro Ser Gly Gly Gly Gly Ser Gly Ala Pro
        20                  25

<210> SEQ ID NO 122
<211> LENGTH: 31
<212> TYPE: PRT
<213> ORGANISM: Artificial Sequence
<220> FEATURE:
<223> OTHER INFORMATION: Synthetic peptide

<400> SEQUENCE: 122

Gly Ala Pro Gly Gly Gly Gly Ser Gly Gly Gly Gly Ser Gly Gly Gly
1               5                   10                  15

Pro Ser Gly Gly Gly Gly Ser Gly Gly Gly Gly Ser Gly Ala Pro
        20                  25                  30

<210> SEQ ID NO 123
<211> LENGTH: 36
<212> TYPE: PRT
<213> ORGANISM: Artificial Sequence
<220> FEATURE:
<223> OTHER INFORMATION: Synthetic peptide

<400> SEQUENCE: 123

Gly Ala Pro Gly Gly Gly Gly Ser Gly Gly Gly Gly Ser Gly Gly Gly
1               5                   10                  15

Pro Ser Gly Gly Gly Gly Ser Gly Gly Gly Gly Ser Gly Gly Gly Gly
            20                  25                  30

Ser Gly Ala Pro
        35

<210> SEQ ID NO 124
<211> LENGTH: 41
<212> TYPE: PRT
<213> ORGANISM: Artificial Sequence
<220> FEATURE:
<223> OTHER INFORMATION: Synthetic peptide

<400> SEQUENCE: 124

Gly Ala Pro Gly Gly Gly Gly Ser Gly Gly Gly Gly Ser Gly Gly Gly
1               5                   10                  15

Pro Ser Gly Gly Gly Gly Ser Gly Gly Gly Gly Ser Gly Gly Gly Gly
            20                  25                  30

Ser Gly Gly Gly Gly Ser Gly Ala Pro
        35                  40

<210> SEQ ID NO 125
<211> LENGTH: 46
<212> TYPE: PRT
<213> ORGANISM: Artificial Sequence
<220> FEATURE:
<223> OTHER INFORMATION: Synthetic peptide

<400> SEQUENCE: 125

Gly Ala Pro Gly Gly Gly Gly Ser Gly Gly Gly Gly Ser Gly Gly Gly
1               5                   10                  15

Pro Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Ala Pro
        35                  40                  45

<210> SEQ ID NO 126
<211> LENGTH: 51
<212> TYPE: PRT
<213> ORGANISM: Artificial Sequence
<220> FEATURE:
<223> OTHER INFORMATION: Synthetic peptide

<400> SEQUENCE: 126

Gly Ala Pro Gly Gly Gly Gly Ser Gly Gly Gly Gly Ser Gly Gly Gly
1               5                   10                  15

Pro Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Ala Pro
    50

<210> SEQ ID NO 127
<211> LENGTH: 56
<212> TYPE: PRT
<213> ORGANISM: Artificial Sequence
<220> FEATURE:
<223> OTHER INFORMATION: Synthetic peptide

<400> SEQUENCE: 127

Gly Ala Pro Gly Gly Gly Ser Gly Gly Gly Ser Gly Gly
1               5                   10                  15

Pro Ser Gly Gly Gly Gly Ser Gly Gly Gly Gly Ser Gly Gly Gly Gly
                20                  25                  30

Ser Gly Gly Gly Gly Ser Gly Gly Gly Ser Gly Gly Gly Ser
        35                  40                  45

Gly Gly Gly Gly Ser Gly Ala Pro
    50                  55

<210> SEQ ID NO 128
<211> LENGTH: 31
<212> TYPE: PRT
<213> ORGANISM: Artificial Sequence
<220> FEATURE:
<223> OTHER INFORMATION: Synthetic peptide

<400> SEQUENCE: 128

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Ala Pro
                20                  25                  30

<210> SEQ ID NO 129
<211> LENGTH: 36
<212> TYPE: PRT
<213> ORGANISM: Artificial Sequence
<220> FEATURE:
<223> OTHER INFORMATION: Synthetic peptide

<400> SEQUENCE: 129

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Ala Pro
        35

<210> SEQ ID NO 130
<211> LENGTH: 41
<212> TYPE: PRT
<213> ORGANISM: Artificial Sequence
<220> FEATURE:
<223> OTHER INFORMATION: Synthetic peptide

<400> SEQUENCE: 130

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Gly Gly Gly Ser Gly Ala Pro
        35                  40

<210> SEQ ID NO 131

```
<211> LENGTH: 46
<212> TYPE: PRT
<213> ORGANISM: Artificial Sequence
<220> FEATURE:
<223> OTHER INFORMATION: Synthetic peptide

<400> SEQUENCE: 131

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Gly Gly Gly Ser Gly Gly Gly Gly Ser Gly Ala Pro
        35                  40                  45

<210> SEQ ID NO 132
<211> LENGTH: 51
<212> TYPE: PRT
<213> ORGANISM: Artificial Sequence
<220> FEATURE:
<223> OTHER INFORMATION: Synthetic peptide

<400> SEQUENCE: 132

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Gly Gly Gly Ser Gly Gly Gly Gly Ser Gly Gly Gly Ser
        35                  40                  45

Gly Ala Pro
    50

<210> SEQ ID NO 133
<211> LENGTH: 56
<212> TYPE: PRT
<213> ORGANISM: Artificial Sequence
<220> FEATURE:
<223> OTHER INFORMATION: Synthetic peptide

<400> SEQUENCE: 133

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Gly Gly Gly Ser Gly Gly Gly Gly Ser Gly Gly Gly Ser
        35                  40                  45

Gly Gly Gly Gly Ser Gly Ala Pro
    50                  55

<210> SEQ ID NO 134
<211> LENGTH: 61
<212> TYPE: PRT
<213> ORGANISM: Artificial Sequence
<220> FEATURE:
<223> OTHER INFORMATION: Synthetic peptide

<400> SEQUENCE: 134

Gly Ala Pro Gly Gly Gly Gly Ser Gly Gly Gly Ser Gly Gly Gly
1               5                   10                  15

Gly Ser Gly Gly Gly Pro Ser Gly Gly Gly Ser Gly Gly Gly Gly
                20                  25                  30

Ser Gly Gly Gly Gly Ser Gly Gly Gly Gly Ser Gly Gly Gly Ser
        35                  40                  45
```

Gly Gly Gly Gly Ser Gly Gly Gly Ser Gly Ala Pro
            50                  55                  60

<210> SEQ ID NO 135
<211> LENGTH: 36
<212> TYPE: PRT
<213> ORGANISM: Artificial Sequence
<220> FEATURE:
<223> OTHER INFORMATION: Synthetic peptide

<400> SEQUENCE: 135

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
            20                  25                  30

Ser Gly Ala Pro
        35

<210> SEQ ID NO 136
<211> LENGTH: 41
<212> TYPE: PRT
<213> ORGANISM: Artificial Sequence
<220> FEATURE:
<223> OTHER INFORMATION: Synthetic peptide

<400> SEQUENCE: 136

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
            20                  25                  30

Ser Gly Gly Gly Gly Ser Gly Ala Pro
        35                  40

<210> SEQ ID NO 137
<211> LENGTH: 46
<212> TYPE: PRT
<213> ORGANISM: Artificial Sequence
<220> FEATURE:
<223> OTHER INFORMATION: Synthetic peptide

<400> SEQUENCE: 137

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
            20                  25                  30

Ser Gly Gly Gly Gly Ser Gly Gly Gly Gly Ser Gly Ala Pro
        35                  40                  45

<210> SEQ ID NO 138
<211> LENGTH: 51
<212> TYPE: PRT
<213> ORGANISM: Artificial Sequence
<220> FEATURE:
<223> OTHER INFORMATION: Synthetic peptide

<400> SEQUENCE: 138

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
            20                  25                  30

Ser Gly Gly Gly Gly Ser Gly Gly Gly Gly Ser Gly Gly Gly Gly Ser
        35                  40                  45

```
Gly Ala Pro
    50

<210> SEQ ID NO 139
<211> LENGTH: 56
<212> TYPE: PRT
<213> ORGANISM: Artificial Sequence
<220> FEATURE:
<223> OTHER INFORMATION: Synthetic peptide

<400> SEQUENCE: 139

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
                20                  25                  30

Ser Gly Gly Gly Gly Ser Gly Gly Gly Ser Gly Gly Gly Gly Ser
        35                  40                  45

Gly Gly Gly Gly Ser Gly Ala Pro
    50                  55

<210> SEQ ID NO 140
<211> LENGTH: 61
<212> TYPE: PRT
<213> ORGANISM: Artificial Sequence
<220> FEATURE:
<223> OTHER INFORMATION: Synthetic peptide

<400> SEQUENCE: 140

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
                20                  25                  30

Ser Gly Gly Gly Gly Ser Gly Gly Gly Gly Ser Gly Gly Gly Gly Ser
        35                  40                  45

Gly Gly Gly Gly Ser Gly Gly Gly Gly Ser Gly Ala Pro
    50                  55                  60

<210> SEQ ID NO 141
<211> LENGTH: 66
<212> TYPE: PRT
<213> ORGANISM: Artificial Sequence
<220> FEATURE:
<223> OTHER INFORMATION: Synthetic peptide

<400> SEQUENCE: 141

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Pro Ser Gly Gly Gly Gly
                20                  25                  30

Ser Gly Gly Gly Gly Ser Gly Gly Gly Gly Ser Gly Gly Gly Gly Ser
        35                  40                  45

Gly Gly Gly Gly Ser Gly Gly Gly Gly Ser Gly Gly Gly Gly Ser Gly
    50                  55                  60

Ala Pro
65

<210> SEQ ID NO 142
<211> LENGTH: 41
<212> TYPE: PRT
<213> ORGANISM: Artificial Sequence
<220> FEATURE:
```

<223> OTHER INFORMATION: Synthetic peptide

<400> SEQUENCE: 142

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Pro
            20                  25                  30

Ser Gly Gly Gly Gly Ser Gly Ala Pro
        35                  40

<210> SEQ ID NO 143
<211> LENGTH: 46
<212> TYPE: PRT
<213> ORGANISM: Artificial Sequence
<220> FEATURE:
<223> OTHER INFORMATION: Synthetic peptide

<400> SEQUENCE: 143

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Pro
            20                  25                  30

Ser Gly Gly Gly Gly Ser Gly Gly Gly Ser Gly Ala Pro
        35                  40                  45

<210> SEQ ID NO 144
<211> LENGTH: 51
<212> TYPE: PRT
<213> ORGANISM: Artificial Sequence
<220> FEATURE:
<223> OTHER INFORMATION: Synthetic peptide

<400> SEQUENCE: 144

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Pro
            20                  25                  30

Ser Gly Gly Gly Gly Ser Gly Gly Gly Ser Gly Gly Gly Gly Ser
        35                  40                  45

Gly Ala Pro
    50

<210> SEQ ID NO 145
<211> LENGTH: 56
<212> TYPE: PRT
<213> ORGANISM: Artificial Sequence
<220> FEATURE:
<223> OTHER INFORMATION: Synthetic peptide

<400> SEQUENCE: 145

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Pro
            20                  25                  30

Ser Gly Gly Gly Gly Ser Gly Gly Gly Ser Gly Gly Gly Gly Ser
        35                  40                  45

Gly Gly Gly Gly Ser Gly Ala Pro
    50                  55

<210> SEQ ID NO 146
<211> LENGTH: 61

```
<212> TYPE: PRT
<213> ORGANISM: Artificial Sequence
<220> FEATURE:
<223> OTHER INFORMATION: Synthetic peptide

<400> SEQUENCE: 146

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Pro
            20                  25                  30

Ser Gly Gly Gly Ser Gly Gly Gly Ser Gly Gly Gly Ser
        35                  40                  45

Gly Gly Gly Gly Ser Gly Gly Gly Ser Gly Ala Pro
    50                  55                  60

<210> SEQ ID NO 147
<211> LENGTH: 66
<212> TYPE: PRT
<213> ORGANISM: Artificial Sequence
<220> FEATURE:
<223> OTHER INFORMATION: Synthetic peptide

<400> SEQUENCE: 147

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Pro
            20                  25                  30

Ser Gly Gly Gly Ser Gly Gly Gly Ser Gly Gly Gly Ser
        35                  40                  45

Gly Gly Gly Gly Ser Gly Gly Gly Ser Gly Gly Gly Ser Gly
    50                  55                  60

Ala Pro
65

<210> SEQ ID NO 148
<211> LENGTH: 71
<212> TYPE: PRT
<213> ORGANISM: Artificial Sequence
<220> FEATURE:
<223> OTHER INFORMATION: Synthetic peptide

<400> SEQUENCE: 148

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Pro
            20                  25                  30

Ser Gly Gly Gly Ser Gly Gly Gly Ser Gly Gly Gly Ser
        35                  40                  45

Gly Gly Gly Gly Ser Gly Gly Gly Ser Gly Gly Gly Ser Gly
    50                  55                  60

Gly Gly Gly Ser Gly Ala Pro
65                  70

<210> SEQ ID NO 149
<211> LENGTH: 46
<212> TYPE: PRT
<213> ORGANISM: Artificial Sequence
<220> FEATURE:
<223> OTHER INFORMATION: Synthetic peptide

<400> SEQUENCE: 149
```

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Gly Gly Gly Pro Ser Gly Gly Gly Ser Gly Ala Pro
        35                  40                  45

<210> SEQ ID NO 150
<211> LENGTH: 51
<212> TYPE: PRT
<213> ORGANISM: Artificial Sequence
<220> FEATURE:
<223> OTHER INFORMATION: Synthetic peptide

<400> SEQUENCE: 150

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Gly Gly Gly Pro Ser Gly Gly Gly Ser Gly Gly Gly Ser
        35                  40                  45

Gly Ala Pro
    50

<210> SEQ ID NO 151
<211> LENGTH: 56
<212> TYPE: PRT
<213> ORGANISM: Artificial Sequence
<220> FEATURE:
<223> OTHER INFORMATION: Synthetic peptide

<400> SEQUENCE: 151

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Gly Gly Gly Pro Ser Gly Gly Gly Ser Gly Gly Gly Ser
        35                  40                  45

Gly Gly Gly Gly Ser Gly Ala Pro
    50                  55

<210> SEQ ID NO 152
<211> LENGTH: 61
<212> TYPE: PRT
<213> ORGANISM: Artificial Sequence
<220> FEATURE:
<223> OTHER INFORMATION: Synthetic peptide

<400> SEQUENCE: 152

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Gly Gly Gly Pro Ser Gly Gly Gly Ser Gly Gly Gly Ser
        35                  40                  45

Gly Gly Gly Gly Ser Gly Gly Gly Ser Gly Ala Pro
    50                  55                  60

<210> SEQ ID NO 153
<211> LENGTH: 66
<212> TYPE: PRT

<213> ORGANISM: Artificial Sequence
<220> FEATURE:
<223> OTHER INFORMATION: Synthetic peptide

<400> SEQUENCE: 153

Gly Ala Pro Gly Gly Gly Gly Ser Gly Gly Gly Gly Ser Gly Gly
1               5                   10                  15

Gly Ser Gly Gly Gly Gly Ser Gly Gly Gly Ser Gly Gly Gly Gly
                20                  25                  30

Ser Gly Gly Gly Pro Ser Gly Gly Gly Ser Gly Gly Gly Gly Ser
            35                  40                  45

Gly Gly Gly Gly Ser Gly Gly Gly Ser Gly Gly Gly Ser Gly
    50                  55                  60

Ala Pro
65

<210> SEQ ID NO 154
<211> LENGTH: 71
<212> TYPE: PRT
<213> ORGANISM: Artificial Sequence
<220> FEATURE:
<223> OTHER INFORMATION: Synthetic peptide

<400> SEQUENCE: 154

Gly Ala Pro Gly Gly Gly Gly Ser Gly Gly Gly Gly Ser Gly Gly
1               5                   10                  15

Gly Ser Gly Gly Gly Gly Ser Gly Gly Gly Ser Gly Gly Gly Gly
                20                  25                  30

Ser Gly Gly Gly Pro Ser Gly Gly Gly Ser Gly Gly Gly Gly Ser
            35                  40                  45

Gly Gly Gly Gly Ser Gly Gly Gly Ser Gly Gly Gly Ser Gly
    50                  55                  60

Gly Gly Gly Ser Gly Ala Pro
65                  70

<210> SEQ ID NO 155
<211> LENGTH: 76
<212> TYPE: PRT
<213> ORGANISM: Artificial Sequence
<220> FEATURE:
<223> OTHER INFORMATION: Synthetic peptide

<400> SEQUENCE: 155

Gly Ala Pro Gly Gly Gly Gly Ser Gly Gly Gly Gly Ser Gly Gly
1               5                   10                  15

Gly Ser Gly Gly Gly Gly Ser Gly Gly Gly Ser Gly Gly Gly Gly
                20                  25                  30

Ser Gly Gly Gly Pro Ser Gly Gly Gly Ser Gly Gly Gly Gly Ser
            35                  40                  45

Gly Gly Gly Gly Ser Gly Gly Gly Ser Gly Gly Gly Ser Gly
    50                  55                  60

Gly Gly Gly Ser Gly Gly Gly Gly Ser Gly Ala Pro
65                  70                  75

<210> SEQ ID NO 156
<211> LENGTH: 51
<212> TYPE: PRT
<213> ORGANISM: Artificial Sequence
<220> FEATURE:
<223> OTHER INFORMATION: Synthetic peptide

```
<400> SEQUENCE: 156

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Pro Ser Gly Gly Gly Gly Ser
        35                  40                  45

Gly Ala Pro
    50

<210> SEQ ID NO 157
<211> LENGTH: 56
<212> TYPE: PRT
<213> ORGANISM: Artificial Sequence
<220> FEATURE:
<223> OTHER INFORMATION: Synthetic peptide

<400> SEQUENCE: 157

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Pro Ser Gly Gly Gly Gly Ser
        35                  40                  45

Gly Gly Gly Gly Ser Gly Ala Pro
    50                  55

<210> SEQ ID NO 158
<211> LENGTH: 61
<212> TYPE: PRT
<213> ORGANISM: Artificial Sequence
<220> FEATURE:
<223> OTHER INFORMATION: Synthetic peptide

<400> SEQUENCE: 158

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Pro Ser Gly Gly Gly Gly Ser
        35                  40                  45

Gly Gly Gly Gly Ser Gly Gly Gly Ser Gly Ala Pro
    50                  55                  60

<210> SEQ ID NO 159
<211> LENGTH: 66
<212> TYPE: PRT
<213> ORGANISM: Artificial Sequence
<220> FEATURE:
<223> OTHER INFORMATION: Synthetic peptide

<400> SEQUENCE: 159

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Pro Ser Gly Gly Gly Gly Ser
        35                  40                  45

Gly Gly Gly Gly Ser Gly Gly Gly Gly Ser Gly Gly Gly Ser Gly
    50                  55                  60
```

Ala Pro
65

<210> SEQ ID NO 160
<211> LENGTH: 71
<212> TYPE: PRT
<213> ORGANISM: Artificial Sequence
<220> FEATURE:
<223> OTHER INFORMATION: Synthetic peptide

<400> SEQUENCE: 160

Gly Ala Pro Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Gly Gly Gly Pro Ser Gly Gly Gly Ser
            35                  40                  45

Gly Gly Gly Gly Ser Gly Gly Gly Ser Gly Gly Gly Ser Gly
    50                  55                  60

Gly Gly Gly Ser Gly Ala Pro
65                  70

<210> SEQ ID NO 161
<211> LENGTH: 76
<212> TYPE: PRT
<213> ORGANISM: Artificial Sequence
<220> FEATURE:
<223> OTHER INFORMATION: Synthetic peptide

<400> SEQUENCE: 161

Gly Ala Pro Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Gly Gly Gly Pro Ser Gly Gly Gly Ser
            35                  40                  45

Gly Gly Gly Gly Ser Gly Gly Gly Ser Gly Gly Gly Ser Gly
    50                  55                  60

Gly Gly Gly Ser Gly Gly Gly Ser Gly Ala Pro
65                  70                  75

<210> SEQ ID NO 162
<211> LENGTH: 81
<212> TYPE: PRT
<213> ORGANISM: Artificial Sequence
<220> FEATURE:
<223> OTHER INFORMATION: Synthetic peptide

<400> SEQUENCE: 162

Gly Ala Pro Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Gly Gly Gly Pro Ser Gly Gly Gly Ser
            35                  40                  45

Gly Gly Gly Gly Ser Gly Gly Gly Ser Gly Gly Gly Ser Gly
    50                  55                  60

Gly Gly Gly Ser Gly Gly Gly Gly Ser Gly Gly Gly Ser Gly Ala
65                  70                  75                  80

Pro

<210> SEQ ID NO 163
<211> LENGTH: 16
<212> TYPE: PRT
<213> ORGANISM: Artificial Sequence
<220> FEATURE:
<223> OTHER INFORMATION: Synthetic peptide

<400> SEQUENCE: 163

Gly Ala Pro Gly Gly Gly Pro Ser Gly Gly Gly Ser Gly Ala Pro
1               5                   10                  15

<210> SEQ ID NO 164
<211> LENGTH: 21
<212> TYPE: PRT
<213> ORGANISM: Artificial Sequence
<220> FEATURE:
<223> OTHER INFORMATION: Synthetic peptide

<400> SEQUENCE: 164

Gly Ala Pro Gly Gly Gly Pro Ser Gly Gly Gly Ser Gly Gly
1               5                   10                  15

Gly Ser Gly Ala Pro
            20

<210> SEQ ID NO 165
<211> LENGTH: 26
<212> TYPE: PRT
<213> ORGANISM: Artificial Sequence
<220> FEATURE:
<223> OTHER INFORMATION: Synthetic peptide

<400> SEQUENCE: 165

Gly Ala Pro Gly Gly Gly Pro Ser Gly Gly Gly Ser Gly Gly
1               5                   10                  15

Gly Ser Gly Gly Gly Gly Ser Gly Ala Pro
            20                  25

<210> SEQ ID NO 166
<211> LENGTH: 31
<212> TYPE: PRT
<213> ORGANISM: Artificial Sequence
<220> FEATURE:
<223> OTHER INFORMATION: Synthetic peptide

<400> SEQUENCE: 166

Gly Ala Pro Gly Gly Gly Pro Ser Gly Gly Gly Ser Gly Gly
1               5                   10                  15

Gly Ser Gly Gly Gly Gly Ser Gly Gly Gly Gly Ser Gly Ala Pro
            20                  25                  30

<210> SEQ ID NO 167
<211> LENGTH: 36
<212> TYPE: PRT
<213> ORGANISM: Artificial Sequence
<220> FEATURE:
<223> OTHER INFORMATION: Synthetic peptide

<400> SEQUENCE: 167

Gly Ala Pro Gly Gly Gly Pro Ser Gly Gly Gly Ser Gly Gly
1               5                   10                  15

Gly Ser Gly Gly Gly Gly Ser Gly Gly Gly Gly Ser Gly Gly Gly Gly
            20                  25                  30

Ser Gly Ala Pro
        35

<210> SEQ ID NO 168
<211> LENGTH: 41
<212> TYPE: PRT
<213> ORGANISM: Artificial Sequence
<220> FEATURE:
<223> OTHER INFORMATION: Synthetic peptide

<400> SEQUENCE: 168

Gly Ala Pro Gly Gly Gly Pro Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Gly Gly Gly Gly Ser Gly Ala Pro
        35                  40

<210> SEQ ID NO 169
<211> LENGTH: 46
<212> TYPE: PRT
<213> ORGANISM: Artificial Sequence
<220> FEATURE:
<223> OTHER INFORMATION: Synthetic peptide

<400> SEQUENCE: 169

Gly Ala Pro Gly Gly Gly Pro Ser Gly Gly Gly Gly Ser Gly Gly
1               5                   10                  15

Gly Ser Gly Gly Gly Gly Ser Gly Gly Gly Ser Gly Gly Gly
            20                  25                  30

Ser Gly Gly Gly Gly Ser Gly Gly Gly Gly Ser Gly Ala Pro
        35                  40                  45

<210> SEQ ID NO 170
<211> LENGTH: 30
<212> TYPE: PRT
<213> ORGANISM: Artificial Sequence
<220> FEATURE:
<223> OTHER INFORMATION: Synthetic peptide

<400> SEQUENCE: 170

Gly Ala Pro Gly Gly Gly Gly Ser Ala Ala Ala Ala Ser Gly Gly
1               5                   10                  15

Pro Ser Gly Gly Gly Gly Ser Ala Ala Ala Ala Gly Ala Pro
            20                  25                  30

<210> SEQ ID NO 171
<211> LENGTH: 35
<212> TYPE: PRT
<213> ORGANISM: Artificial Sequence
<220> FEATURE:
<223> OTHER INFORMATION: Synthetic peptide

<400> SEQUENCE: 171

Gly Ala Pro Gly Gly Gly Gly Ser Ala Ala Ala Ala Ser Gly Gly
1               5                   10                  15

Pro Ser Gly Gly Gly Gly Ser Gly Gly Gly Gly Ser Ala Ala Ala Ala
            20                  25                  30

Gly Ala Pro
        35

<210> SEQ ID NO 172
<211> LENGTH: 40

```
<212> TYPE: PRT
<213> ORGANISM: Artificial Sequence
<220> FEATURE:
<223> OTHER INFORMATION: Synthetic peptide

<400> SEQUENCE: 172

Gly Ala Pro Gly Gly Gly Gly Ser Ala Ala Ala Ala Ser Gly Gly Gly
1               5                   10                  15
Pro Ser Gly Gly Gly Gly Ser Gly Gly Gly Gly Ser Gly Gly Gly Gly
            20                  25                  30
Ser Ala Ala Ala Ala Gly Ala Pro
        35                  40

<210> SEQ ID NO 173
<211> LENGTH: 45
<212> TYPE: PRT
<213> ORGANISM: Artificial Sequence
<220> FEATURE:
<223> OTHER INFORMATION: Synthetic peptide

<400> SEQUENCE: 173

Gly Ala Pro Gly Gly Gly Gly Ser Ala Ala Ala Ala Ser Gly Gly Gly
1               5                   10                  15
Pro Ser Gly Gly Gly Gly Ser Gly Gly Gly Gly Ser Gly Gly Gly Gly
            20                  25                  30
Ser Gly Gly Gly Gly Ser Ala Ala Ala Ala Gly Ala Pro
        35                  40                  45

<210> SEQ ID NO 174
<211> LENGTH: 50
<212> TYPE: PRT
<213> ORGANISM: Artificial Sequence
<220> FEATURE:
<223> OTHER INFORMATION: Synthetic peptide

<400> SEQUENCE: 174

Gly Ala Pro Gly Gly Gly Gly Ser Ala Ala Ala Ala Ser Gly Gly Gly
1               5                   10                  15
Pro Ser Gly Gly Gly Gly Ser Gly Gly Gly Gly Ser Gly Gly Gly Gly
            20                  25                  30
Ser Gly Gly Gly Gly Ser Gly Gly Gly Gly Ser Ala Ala Ala Ala Gly
        35                  40                  45
Ala Pro
    50

<210> SEQ ID NO 175
<211> LENGTH: 55
<212> TYPE: PRT
<213> ORGANISM: Artificial Sequence
<220> FEATURE:
<223> OTHER INFORMATION: Synthetic peptide

<400> SEQUENCE: 175

Gly Ala Pro Gly Gly Gly Gly Ser Ala Ala Ala Ala Ser Gly Gly Gly
1               5                   10                  15
Pro Ser Gly Gly Gly Gly Ser Gly Gly Gly Gly Ser Gly Gly Gly Gly
            20                  25                  30
Ser Gly Gly Gly Gly Ser Gly Gly Gly Gly Ser Gly Gly Gly Gly Ser
        35                  40                  45
Ala Ala Ala Ala Gly Ala Pro
    50                  55
```

<210> SEQ ID NO 176
<211> LENGTH: 60
<212> TYPE: PRT
<213> ORGANISM: Artificial Sequence
<220> FEATURE:
<223> OTHER INFORMATION: Synthetic peptide

<400> SEQUENCE: 176

Gly Ala Pro Gly Gly Gly Gly Ser Ala Ala Ala Ser Gly Gly
1               5                   10                  15

Pro Ser Gly Gly Gly Gly Ser Gly Gly Gly Gly Ser Gly Gly Gly Gly
                20                  25                  30

Ser Gly Gly Gly Gly Ser Gly Gly Gly Gly Ser Gly Gly Gly Ser
        35                  40                  45

Gly Gly Gly Gly Ser Ala Ala Ala Ala Gly Ala Pro
    50                  55                  60

<210> SEQ ID NO 177
<211> LENGTH: 35
<212> TYPE: PRT
<213> ORGANISM: Artificial Sequence
<220> FEATURE:
<223> OTHER INFORMATION: Synthetic peptide

<400> SEQUENCE: 177

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Gly Ser Ala Ala Ala Ala
                20                  25                  30

Gly Ala Pro
        35

<210> SEQ ID NO 178
<211> LENGTH: 40
<212> TYPE: PRT
<213> ORGANISM: Artificial Sequence
<220> FEATURE:
<223> OTHER INFORMATION: Synthetic peptide

<400> SEQUENCE: 178

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Gly Ser Gly Gly Gly Gly
                20                  25                  30

Ser Ala Ala Ala Ala Gly Ala Pro
        35                  40

<210> SEQ ID NO 179
<211> LENGTH: 45
<212> TYPE: PRT
<213> ORGANISM: Artificial Sequence
<220> FEATURE:
<223> OTHER INFORMATION: Synthetic peptide

<400> SEQUENCE: 179

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Gly Ser Gly Gly Gly Gly
                20                  25                  30

Ser Gly Gly Gly Gly Ser Ala Ala Ala Ala Gly Ala Pro
        35                  40                  45

<210> SEQ ID NO 180
<211> LENGTH: 50
<212> TYPE: PRT
<213> ORGANISM: Artificial Sequence
<220> FEATURE:
<223> OTHER INFORMATION: Synthetic peptide

<400> SEQUENCE: 180

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Ser Gly Gly Gly Gly
            20                  25                  30

Ser Gly Gly Gly Gly Ser Gly Gly Gly Gly Ser Ala Ala Ala Ala Gly
        35                  40                  45

Ala Pro
    50

<210> SEQ ID NO 181
<211> LENGTH: 55
<212> TYPE: PRT
<213> ORGANISM: Artificial Sequence
<220> FEATURE:
<223> OTHER INFORMATION: Synthetic peptide

<400> SEQUENCE: 181

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Ser Gly Gly Gly Gly
            20                  25                  30

Ser Gly Gly Gly Gly Ser Gly Gly Gly Gly Ser Gly Gly Gly Ser
        35                  40                  45

Ala Ala Ala Ala Gly Ala Pro
    50                  55

<210> SEQ ID NO 182
<211> LENGTH: 60
<212> TYPE: PRT
<213> ORGANISM: Artificial Sequence
<220> FEATURE:
<223> OTHER INFORMATION: Synthetic peptide

<400> SEQUENCE: 182

Gly Ala Pro Gly Gly Gly Gly Ser Gly Gly Gly Gly Ser Ala Ala Ala
1               5                   10                  15

Ala Ser Gly Gly Gly Pro Ser Gly Gly Gly Ser Gly Gly Gly Gly
            20                  25                  30

Ser Gly Gly Gly Gly Ser Gly Gly Gly Gly Ser Gly Gly Gly Ser
        35                  40                  45

Gly Gly Gly Gly Ser Ala Ala Ala Ala Gly Ala Pro
    50                  55                  60

<210> SEQ ID NO 183
<211> LENGTH: 65
<212> TYPE: PRT
<213> ORGANISM: Artificial Sequence
<220> FEATURE:
<223> OTHER INFORMATION: Synthetic peptide

<400> SEQUENCE: 183

Gly Ala Pro Gly Gly Gly Gly Ser Gly Gly Gly Gly Ser Ala Ala Ala
1               5                   10                  15

```
Ala Ser Gly Gly Gly Pro Ser Gly Gly Gly Ser Gly Gly Gly
        20                  25                  30

Ser Gly Gly Gly Gly Ser Gly Gly Gly Ser Gly Gly Gly Ser
        35                  40                  45

Gly Gly Gly Gly Ser Gly Gly Gly Ser Ala Ala Ala Gly Ala
    50                  55                  60

Pro
65

<210> SEQ ID NO 184
<211> LENGTH: 40
<212> TYPE: PRT
<213> ORGANISM: Artificial Sequence
<220> FEATURE:
<223> OTHER INFORMATION: Synthetic peptide

<400> SEQUENCE: 184

Gly Ala Pro Gly Gly Gly Gly Ser Gly Gly Gly Gly Ser Gly Gly Gly
1               5                   10                  15

Gly Ser Ala Ala Ala Ala Ser Gly Gly Gly Pro Ser Gly Gly Gly
            20                  25                  30

Ser Ala Ala Ala Ala Gly Ala Pro
        35                  40

<210> SEQ ID NO 185
<211> LENGTH: 45
<212> TYPE: PRT
<213> ORGANISM: Artificial Sequence
<220> FEATURE:
<223> OTHER INFORMATION: Synthetic peptide

<400> SEQUENCE: 185

Gly Ala Pro Gly Gly Gly Gly Ser Gly Gly Gly Gly Ser Gly Gly Gly
1               5                   10                  15

Gly Ser Ala Ala Ala Ala Ser Gly Gly Gly Pro Ser Gly Gly Gly Gly
            20                  25                  30

Ser Gly Gly Gly Gly Ser Ala Ala Ala Ala Gly Ala Pro
        35                  40                  45

<210> SEQ ID NO 186
<211> LENGTH: 50
<212> TYPE: PRT
<213> ORGANISM: Artificial Sequence
<220> FEATURE:
<223> OTHER INFORMATION: Synthetic peptide

<400> SEQUENCE: 186

Gly Ala Pro Gly Gly Gly Gly Ser Gly Gly Gly Gly Ser Gly Gly Gly
1               5                   10                  15

Gly Ser Ala Ala Ala Ala Ser Gly Gly Gly Pro Ser Gly Gly Gly Gly
            20                  25                  30

Ser Gly Gly Gly Gly Ser Gly Gly Gly Gly Ser Ala Ala Ala Ala Gly
        35                  40                  45

Ala Pro
    50

<210> SEQ ID NO 187
<211> LENGTH: 55
<212> TYPE: PRT
<213> ORGANISM: Artificial Sequence
<220> FEATURE:
<223> OTHER INFORMATION: Synthetic peptide
```

<400> SEQUENCE: 187

Gly Ala Pro Gly Gly Gly Ser Gly Gly Gly Ser Gly Gly Gly
1               5                   10                  15

Gly Ser Ala Ala Ala Ala Ser Gly Gly Pro Ser Gly Gly Gly
            20                  25                  30

Ser Gly Gly Gly Gly Ser Gly Gly Gly Ser Gly Gly Gly Ser
        35                  40                  45

Ala Ala Ala Ala Gly Ala Pro
    50                  55

<210> SEQ ID NO 188
<211> LENGTH: 60
<212> TYPE: PRT
<213> ORGANISM: Artificial Sequence
<220> FEATURE:
<223> OTHER INFORMATION: Synthetic peptide

<400> SEQUENCE: 188

Gly Ala Pro Gly Gly Gly Ser Gly Gly Gly Ser Gly Gly Gly
1               5                   10                  15

Gly Ser Ala Ala Ala Ala Ser Gly Gly Pro Ser Gly Gly Gly
            20                  25                  30

Ser Gly Gly Gly Gly Ser Gly Gly Gly Ser Gly Gly Gly Ser
        35                  40                  45

Gly Gly Gly Gly Ser Ala Ala Ala Ala Gly Ala Pro
    50                  55                  60

<210> SEQ ID NO 189
<211> LENGTH: 65
<212> TYPE: PRT
<213> ORGANISM: Artificial Sequence
<220> FEATURE:
<223> OTHER INFORMATION: Synthetic peptide

<400> SEQUENCE: 189

Gly Ala Pro Gly Gly Gly Ser Gly Gly Gly Ser Gly Gly Gly
1               5                   10                  15

Gly Ser Ala Ala Ala Ala Ser Gly Gly Pro Ser Gly Gly Gly
            20                  25                  30

Ser Gly Gly Gly Gly Ser Gly Gly Gly Ser Gly Gly Gly Ser
        35                  40                  45

Gly Gly Gly Gly Ser Gly Gly Gly Ser Ala Ala Ala Gly Ala
    50                  55                  60

Pro
65

<210> SEQ ID NO 190
<211> LENGTH: 70
<212> TYPE: PRT
<213> ORGANISM: Artificial Sequence
<220> FEATURE:
<223> OTHER INFORMATION: Synthetic peptide

<400> SEQUENCE: 190

Gly Ala Pro Gly Gly Gly Ser Gly Gly Gly Ser Gly Gly Gly
1               5                   10                  15

Gly Ser Ala Ala Ala Ala Ser Gly Gly Pro Ser Gly Gly Gly
            20                  25                  30

Ser Gly Gly Gly Gly Ser Gly Gly Gly Gly Ser Gly Gly Gly Gly Ser 35                  40                  45

Gly Gly Gly Gly Ser Gly Gly Gly Ser Gly Gly Gly Ser Ala
    50                  55                  60

Ala Ala Ala Gly Ala Pro
65                  70

<210> SEQ ID NO 191
<211> LENGTH: 45
<212> TYPE: PRT
<213> ORGANISM: Artificial Sequence
<220> FEATURE:
<223> OTHER INFORMATION: Synthetic peptide

<400> SEQUENCE: 191

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Ala Ala Ala Gly Ala Pro
        35                  40                  45

<210> SEQ ID NO 192
<211> LENGTH: 50
<212> TYPE: PRT
<213> ORGANISM: Artificial Sequence
<220> FEATURE:
<223> OTHER INFORMATION: Synthetic peptide

<400> SEQUENCE: 192

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Gly Gly Gly Ser Ala Ala Ala Gly
        35                  40                  45

Ala Pro
    50

<210> SEQ ID NO 193
<211> LENGTH: 55
<212> TYPE: PRT
<213> ORGANISM: Artificial Sequence
<220> FEATURE:
<223> OTHER INFORMATION: Synthetic peptide

<400> SEQUENCE: 193

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Gly Gly Gly Gly Ser Gly Gly Gly Ser
        35                  40                  45

Ala Ala Ala Ala Gly Ala Pro
    50                  55

<210> SEQ ID NO 194
<211> LENGTH: 60
<212> TYPE: PRT
<213> ORGANISM: Artificial Sequence
<220> FEATURE:
<223> OTHER INFORMATION: Synthetic peptide -continued

```
<400> SEQUENCE: 194

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Gly Gly Gly Ser Gly Gly Gly Ser
        35                  40                  45

Gly Gly Gly Gly Ser Ala Ala Ala Ala Gly Ala Pro
    50                  55                  60

<210> SEQ ID NO 195
<211> LENGTH: 65
<212> TYPE: PRT
<213> ORGANISM: Artificial Sequence
<220> FEATURE:
<223> OTHER INFORMATION: Synthetic peptide

<400> SEQUENCE: 195

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Gly Gly Gly Ser Gly Gly Gly Ser
        35                  40                  45

Gly Gly Gly Gly Ser Gly Gly Gly Ser Ala Ala Ala Ala Gly Ala
    50                  55                  60

Pro
65

<210> SEQ ID NO 196
<211> LENGTH: 70
<212> TYPE: PRT
<213> ORGANISM: Artificial Sequence
<220> FEATURE:
<223> OTHER INFORMATION: Synthetic peptide

<400> SEQUENCE: 196

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30

Ser Gly Gly Gly Gly Ser Gly Gly Gly Ser Gly Gly Gly Ser
        35                  40                  45

Gly Gly Gly Gly Ser Gly Gly Gly Gly Ser Gly Gly Gly Ser Ala
    50                  55                  60

Ala Ala Ala Gly Ala Pro
65                  70

<210> SEQ ID NO 197
<211> LENGTH: 75
<212> TYPE: PRT
<213> ORGANISM: Artificial Sequence
<220> FEATURE:
<223> OTHER INFORMATION: Synthetic peptide

<400> SEQUENCE: 197

Gly Ala Pro Gly Gly Gly Ser Gly Gly Gly Ser Gly Gly Gly
1               5                   10                  15

Gly Ser Gly Gly Gly Gly Ser Ala Ala Ala Ala Ser Gly Gly Pro
            20                  25                  30
```

Ser Gly Gly Gly Gly Ser Gly Gly Gly Ser Gly Gly Gly Ser
        35                  40                  45

Gly Gly Gly Gly Ser Gly Gly Gly Ser Gly Gly Gly Ser Gly
    50                  55                  60

Gly Gly Gly Ser Ala Ala Ala Ala Gly Ala Pro
65                  70                  75

<210> SEQ ID NO 198
<211> LENGTH: 50
<212> TYPE: PRT
<213> ORGANISM: Artificial Sequence
<220> FEATURE:
<223> OTHER INFORMATION: Synthetic peptide

<400> SEQUENCE: 198

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Ala Ala Ala Ala
        20                  25                  30

Ser Gly Gly Gly Pro Ser Gly Gly Gly Ser Ala Ala Ala Ala Gly
        35                  40                  45

Ala Pro
    50

<210> SEQ ID NO 199
<211> LENGTH: 55
<212> TYPE: PRT
<213> ORGANISM: Artificial Sequence
<220> FEATURE:
<223> OTHER INFORMATION: Synthetic peptide

<400> SEQUENCE: 199

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Ala Ala Ala Ala
        20                  25                  30

Ser Gly Gly Gly Pro Ser Gly Gly Gly Ser Gly Gly Gly Gly Ser
        35                  40                  45

Ala Ala Ala Ala Gly Ala Pro
    50                  55

<210> SEQ ID NO 200
<211> LENGTH: 60
<212> TYPE: PRT
<213> ORGANISM: Artificial Sequence
<220> FEATURE:
<223> OTHER INFORMATION: Synthetic peptide

<400> SEQUENCE: 200

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Ala Ala Ala Ala
        20                  25                  30

Ser Gly Gly Gly Pro Ser Gly Gly Gly Ser Gly Gly Gly Gly Ser
        35                  40                  45

Gly Gly Gly Ser Ala Ala Ala Ala Gly Ala Pro
    50                  55                  60

<210> SEQ ID NO 201
<211> LENGTH: 65

<212> TYPE: PRT
<213> ORGANISM: Artificial Sequence
<220> FEATURE:
<223> OTHER INFORMATION: Synthetic peptide

<400> SEQUENCE: 201

Gly Ala Pro Gly Gly Gly Ser Gly Gly Gly Ser Gly Gly Gly
1               5                   10                  15

Gly Ser Gly Gly Gly Gly Ser Gly Gly Gly Gly Ser Ala Ala Ala Ala
            20                  25                  30

Ser Gly Gly Gly Pro Ser Gly Gly Gly Ser Gly Gly Gly Ser
        35                  40                  45

Gly Gly Gly Gly Ser Gly Gly Gly Ser Ala Ala Ala Ala Gly Ala
    50                  55                  60

Pro
65

<210> SEQ ID NO 202
<211> LENGTH: 70
<212> TYPE: PRT
<213> ORGANISM: Artificial Sequence
<220> FEATURE:
<223> OTHER INFORMATION: Synthetic peptide

<400> SEQUENCE: 202

Gly Ala Pro Gly Gly Gly Ser Gly Gly Gly Ser Gly Gly Gly
1               5                   10                  15

Gly Ser Gly Gly Gly Gly Ser Gly Gly Gly Ser Ala Ala Ala Ala
            20                  25                  30

Ser Gly Gly Gly Pro Ser Gly Gly Gly Ser Gly Gly Gly Ser
        35                  40                  45

Gly Gly Gly Gly Ser Gly Gly Gly Ser Gly Gly Gly Gly Ser Ala
    50                  55                  60

Ala Ala Ala Gly Ala Pro
65                  70

<210> SEQ ID NO 203
<211> LENGTH: 75
<212> TYPE: PRT
<213> ORGANISM: Artificial Sequence
<220> FEATURE:
<223> OTHER INFORMATION: Synthetic peptide

<400> SEQUENCE: 203

Gly Ala Pro Gly Gly Gly Ser Gly Gly Gly Ser Gly Gly Gly
1               5                   10                  15

Gly Ser Gly Gly Gly Gly Ser Gly Gly Gly Ser Ala Ala Ala Ala
            20                  25                  30

Ser Gly Gly Gly Pro Ser Gly Gly Gly Ser Gly Gly Gly Ser
        35                  40                  45

Gly Gly Gly Gly Ser Gly Gly Gly Ser Gly Gly Gly Gly Ser Gly
    50                  55                  60

Gly Gly Ser Ala Ala Ala Ala Gly Ala Pro
65                  70                  75

<210> SEQ ID NO 204
<211> LENGTH: 80
<212> TYPE: PRT
<213> ORGANISM: Artificial Sequence
<220> FEATURE:
<223> OTHER INFORMATION: Synthetic peptide

```
<400> SEQUENCE: 204

Gly Ala Pro Gly Gly Gly Ser Gly Gly Gly Ser Gly Gly Gly
1               5                   10                  15

Gly Ser Gly Gly Gly Ser Gly Gly Gly Ser Ala Ala Ala Ala
            20                  25                  30

Ser Gly Gly Pro Ser Gly Gly Gly Ser Gly Gly Gly Ser
        35                  40                  45

Gly Gly Gly Gly Ser Gly Gly Gly Ser Gly Gly Ser Gly
    50                  55                  60

Gly Gly Gly Ser Gly Gly Gly Ser Ala Ala Ala Gly Ala Pro
65                  70                  75                  80

<210> SEQ ID NO 205
<211> LENGTH: 55
<212> TYPE: PRT
<213> ORGANISM: Artificial Sequence
<220> FEATURE:
<223> OTHER INFORMATION: Synthetic peptide

<400> SEQUENCE: 205

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Gly
            20                  25                  30

Ser Ala Ala Ala Ala Ser Gly Gly Pro Ser Gly Gly Gly Ser
        35                  40                  45

Ala Ala Ala Ala Gly Ala Pro
        50              55

<210> SEQ ID NO 206
<211> LENGTH: 60
<212> TYPE: PRT
<213> ORGANISM: Artificial Sequence
<220> FEATURE:
<223> OTHER INFORMATION: Synthetic peptide

<400> SEQUENCE: 206

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Gly Gly
            20                  25                  30

Ser Ala Ala Ala Ala Ser Gly Gly Pro Ser Gly Gly Gly Ser
        35                  40                  45

Gly Gly Gly Gly Ser Ala Ala Ala Ala Gly Ala Pro
    50                  55                  60

<210> SEQ ID NO 207
<211> LENGTH: 65
<212> TYPE: PRT
<213> ORGANISM: Artificial Sequence
<220> FEATURE:
<223> OTHER INFORMATION: Synthetic peptide

<400> SEQUENCE: 207

Gly Ala Pro Gly Gly Gly Ser Gly Gly Gly Ser Gly Gly Gly
1               5                   10                  15

Gly Ser Gly Gly Gly Ser Gly Gly Gly Ser Gly Gly Gly Gly
            20                  25                  30

Ser Ala Ala Ala Ala Ser Gly Gly Gly Pro Ser Gly Gly Gly Ser
```

```
                35                  40                  45
Gly Gly Gly Gly Ser Gly Gly Gly Ser Ala Ala Ala Gly Ala
    50                  55                  60
Pro
65
```

<210> SEQ ID NO 208
<211> LENGTH: 70
<212> TYPE: PRT
<213> ORGANISM: Artificial Sequence
<220> FEATURE:
<223> OTHER INFORMATION: Synthetic peptide

<400> SEQUENCE: 208

```
Gly Ala Pro Gly Gly Gly Gly Ser Gly Gly Gly Gly Ser Gly Gly Gly
1               5                   10                  15
Gly Ser Gly Gly Gly Gly Ser Gly Gly Gly Gly Ser Gly Gly Gly Gly
                20                  25                  30
Ser Ala Ala Ala Ala Ser Gly Gly Gly Pro Ser Gly Gly Gly Gly Ser
            35                  40                  45
Gly Gly Gly Gly Ser Gly Gly Gly Ser Gly Gly Gly Gly Ser Ala
    50                  55                  60
Ala Ala Ala Gly Ala Pro
65                  70
```

<210> SEQ ID NO 209
<211> LENGTH: 75
<212> TYPE: PRT
<213> ORGANISM: Artificial Sequence
<220> FEATURE:
<223> OTHER INFORMATION: Synthetic peptide

<400> SEQUENCE: 209

```
Gly Ala Pro Gly Gly Gly Gly Ser Gly Gly Gly Gly Ser Gly Gly Gly
1               5                   10                  15
Gly Ser Gly Gly Gly Gly Ser Gly Gly Gly Gly Ser Gly Gly Gly Gly
                20                  25                  30
Ser Ala Ala Ala Ala Ser Gly Gly Gly Pro Ser Gly Gly Gly Gly Ser
            35                  40                  45
Gly Gly Gly Gly Ser Gly Gly Gly Gly Ser Gly Gly Gly Gly Ser Gly
    50                  55                  60
Gly Gly Gly Ser Ala Ala Ala Ala Gly Ala Pro
65                  70                  75
```

<210> SEQ ID NO 210
<211> LENGTH: 80
<212> TYPE: PRT
<213> ORGANISM: Artificial Sequence
<220> FEATURE:
<223> OTHER INFORMATION: Synthetic peptide

<400> SEQUENCE: 210

```
Gly Ala Pro Gly Gly Gly Gly Ser Gly Gly Gly Gly Ser Gly Gly Gly
1               5                   10                  15
Gly Ser Gly Gly Gly Gly Ser Gly Gly Gly Gly Ser Gly Gly Gly Gly
                20                  25                  30
Ser Ala Ala Ala Ala Ser Gly Gly Gly Pro Ser Gly Gly Gly Gly Ser
            35                  40                  45
Gly Gly Gly Gly Ser Gly Gly Gly Gly Ser Gly Gly Gly Gly Ser Gly
    50                  55                  60
```

Gly Gly Gly Ser Gly Gly Gly Ser Ala Ala Ala Gly Ala Pro
65                  70                  75                  80

<210> SEQ ID NO 211
<211> LENGTH: 85
<212> TYPE: PRT
<213> ORGANISM: Artificial Sequence
<220> FEATURE:
<223> OTHER INFORMATION: Synthetic peptide

<400> SEQUENCE: 211

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Ala Ala Ala Ala Ser Gly Gly Gly Pro Ser Gly Gly Gly Gly Ser
            35                  40                  45

Gly Gly Gly Gly Ser Gly Gly Gly Ser Gly Gly Gly Ser Gly
        50                  55                  60

Gly Gly Gly Ser Gly Gly Gly Ser Gly Gly Gly Ser Ala Ala
65                  70                  75                  80

Ala Ala Gly Ala Pro
                85

<210> SEQ ID NO 212
<211> LENGTH: 60
<212> TYPE: PRT
<213> ORGANISM: Artificial Sequence
<220> FEATURE:
<223> OTHER INFORMATION: Synthetic peptide

<400> SEQUENCE: 212

Gly Ala Pro Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Ala Ala Ala Ala Ser Gly Gly Gly Pro Ser
            35                  40                  45

Gly Gly Gly Gly Ser Ala Ala Ala Ala Gly Ala Pro
        50                  55                  60

<210> SEQ ID NO 213
<211> LENGTH: 65
<212> TYPE: PRT
<213> ORGANISM: Artificial Sequence
<220> FEATURE:
<223> OTHER INFORMATION: Synthetic peptide

<400> SEQUENCE: 213

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly
            20                  25                  30

Ser Gly Gly Gly Gly Ser Ala Ala Ala Ala Ser Gly Gly Gly Pro Ser
            35                  40                  45

Gly Gly Gly Gly Ser Gly Gly Gly Ser Ala Ala Ala Ala Gly Ala
        50                  55                  60

Pro
65

<210> SEQ ID NO 214
<211> LENGTH: 70
<212> TYPE: PRT
<213> ORGANISM: Artificial Sequence
<220> FEATURE:
<223> OTHER INFORMATION: Synthetic peptide

<400> SEQUENCE: 214

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Ala Ala Ala Ala Ser Gly Gly Gly Pro Ser
        35                  40                  45

Gly Gly Gly Gly Ser Gly Gly Gly Ser Gly Gly Gly Ser Ala
    50                  55                  60

Ala Ala Ala Gly Ala Pro
65                  70

<210> SEQ ID NO 215
<211> LENGTH: 75
<212> TYPE: PRT
<213> ORGANISM: Artificial Sequence
<220> FEATURE:
<223> OTHER INFORMATION: Synthetic peptide

<400> SEQUENCE: 215

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Ala Ala Ala Ala Ser Gly Gly Gly Pro Ser
        35                  40                  45

Gly Gly Gly Gly Ser Gly Gly Gly Ser Gly Gly Gly Ser Gly
    50                  55                  60

Gly Gly Gly Ser Ala Ala Ala Ala Gly Ala Pro
65                  70                  75

<210> SEQ ID NO 216
<211> LENGTH: 80
<212> TYPE: PRT
<213> ORGANISM: Artificial Sequence
<220> FEATURE:
<223> OTHER INFORMATION: Synthetic peptide

<400> SEQUENCE: 216

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Ala Ala Ala Ala Ser Gly Gly Gly Pro Ser
        35                  40                  45

Gly Gly Gly Gly Ser Gly Gly Gly Ser Gly Gly Gly Ser Gly
    50                  55                  60

Gly Gly Gly Ser Gly Gly Gly Ser Ala Ala Ala Ala Gly Ala Pro
65                  70                  75                  80

<210> SEQ ID NO 217
<211> LENGTH: 85
<212> TYPE: PRT

<213> ORGANISM: Artificial Sequence
<220> FEATURE:
<223> OTHER INFORMATION: Synthetic peptide

<400> SEQUENCE: 217

Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Ala Ala Ala Ala Ser Gly Gly Pro Ser
            35                  40                  45

Gly Gly Gly Gly Ser Gly Gly Gly Ser Gly Gly Gly Gly Ser Gly
        50                  55                  60

Gly Gly Gly Ser Gly Gly Gly Ser Gly Gly Gly Gly Ser Ala Ala
65                  70                  75                  80

Ala Ala Gly Ala Pro
            85

<210> SEQ ID NO 218
<211> LENGTH: 90
<212> TYPE: PRT
<213> ORGANISM: Artificial Sequence
<220> FEATURE:
<223> OTHER INFORMATION: Synthetic peptide

<400> SEQUENCE: 218

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Ala Ala Ala Ala Ser Gly Gly Pro Ser
            35                  40                  45

Gly Gly Gly Gly Ser Gly Gly Gly Ser Gly Gly Gly Gly Ser Gly
        50                  55                  60

Gly Gly Gly Ser Gly Gly Gly Ser Gly Gly Gly Gly Ser Gly Gly
65                  70                  75                  80

Gly Gly Ser Ala Ala Ala Ala Gly Ala Pro
            85                  90

<210> SEQ ID NO 219
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(14)
<223> OTHER INFORMATION: Xaa can be any naturally occurring amino acid

<400> SEQUENCE: 219

Gly Ala Pro Gly Gly Gly Gly Ser Pro Ala Pro Ala Pro Xaa Gly Ala
1               5                   10                  15

Pro

<210> SEQ ID NO 220
<211> LENGTH: 18
<212> TYPE: PRT
<213> ORGANISM: Artificial Sequence
<220> FEATURE:
<223> OTHER INFORMATION: Synthetic peptide
<220> FEATURE:

```
<221> NAME/KEY: misc_feature
<222> LOCATION: (14)..(15)
<223> OTHER INFORMATION: Xaa can be any naturally occurring amino acid

<400> SEQUENCE: 220

Gly Ala Pro Gly Gly Gly Gly Ser Pro Ala Pro Ala Pro Xaa Xaa Gly
1               5                   10                  15

Ala Pro

<210> SEQ ID NO 221
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(16)
<223> OTHER INFORMATION: Xaa can be any naturally occurring amino acid

<400> SEQUENCE: 221

Gly Ala Pro Gly Gly Gly Gly Ser Pro Ala Pro Ala Pro Xaa Xaa Xaa
1               5                   10                  15

Gly Ala Pro

<210> SEQ ID NO 222
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(17)
<223> OTHER INFORMATION: Xaa can be any naturally occurring amino acid

<400> SEQUENCE: 222

Gly Ala Pro Gly Gly Gly Gly Ser Pro Ala Pro Ala Pro Xaa Xaa Xaa
1               5                   10                  15

Xaa Gly Ala Pro
            20

<210> SEQ ID NO 223
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(18)
<223> OTHER INFORMATION: Xaa can be any naturally occurring amino acid

<400> SEQUENCE: 223

Gly Ala Pro Gly Gly Gly Gly Ser Pro Ala Pro Ala Pro Xaa Xaa Xaa
1               5                   10                  15

Xaa Xaa Gly Ala Pro
            20

<210> SEQ ID NO 224
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (14)..(19)
<223> OTHER INFORMATION: Xaa can be any naturally occurring amino acid

<400> SEQUENCE: 224

Gly Ala Pro Gly Gly Gly Ser Pro Ala Pro Ala Pro Xaa Xaa Xaa
1               5                   10                  15

Xaa Xaa Xaa Gly Ala Pro
            20

<210> SEQ ID NO 225
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(20)
<223> OTHER INFORMATION: Xaa can be any naturally occurring amino acid

<400> SEQUENCE: 225

Gly Ala Pro Gly Gly Gly Ser Pro Ala Pro Ala Pro Xaa Xaa Xaa
1               5                   10                  15

Xaa Xaa Xaa Xaa Gly Ala Pro
            20

<210> SEQ ID NO 226
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(19)
<223> OTHER INFORMATION: Xaa can be any naturally occurring amino acid

<400> SEQUENCE: 226

Gly Ala Pro Gly Gly Gly Gly Ser Gly Gly Gly Gly Ser Pro Ala Pro
1               5                   10                  15

Ala Pro Xaa Gly Ala Pro
            20

<210> SEQ ID NO 227
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(20)
<223> OTHER INFORMATION: Xaa can be any naturally occurring amino acid

<400> SEQUENCE: 227

Gly Ala Pro Gly Gly Gly Gly Ser Gly Gly Gly Gly Ser Pro Ala Pro
1               5                   10                  15

Ala Pro Xaa Xaa Gly Ala Pro
            20

<210> SEQ ID NO 228
<211> LENGTH: 24
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (19)..(21)
<223> OTHER INFORMATION: Xaa can be any naturally occurring amino acid

<400> SEQUENCE: 228

Gly Ala Pro Gly Gly Gly Gly Ser Gly Gly Gly Gly Ser Pro Ala Pro
1               5                   10                  15

Ala Pro Xaa Xaa Xaa Gly Ala Pro
            20

<210> SEQ ID NO 229
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(22)
<223> OTHER INFORMATION: Xaa can be any naturally occurring amino acid

<400> SEQUENCE: 229

Gly Ala Pro Gly Gly Gly Gly Ser Gly Gly Gly Gly Ser Pro Ala Pro
1               5                   10                  15

Ala Pro Xaa Xaa Xaa Xaa Gly Ala Pro
            20                  25

<210> SEQ ID NO 230
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(23)
<223> OTHER INFORMATION: Xaa can be any naturally occurring amino acid

<400> SEQUENCE: 230

Gly Ala Pro Gly Gly Gly Gly Ser Gly Gly Gly Gly Ser Pro Ala Pro
1               5                   10                  15

Ala Pro Xaa Xaa Xaa Xaa Xaa Gly Ala Pro
            20                  25

<210> SEQ ID NO 231
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(24)
<223> OTHER INFORMATION: Xaa can be any naturally occurring amino acid

<400> SEQUENCE: 231

Gly Ala Pro Gly Gly Gly Gly Ser Gly Gly Gly Gly Ser Pro Ala Pro
1               5                   10                  15

Ala Pro Xaa Xaa Xaa Xaa Xaa Xaa Gly Ala Pro
            20                  25

<210> SEQ ID NO 232
<211> LENGTH: 28
<212> TYPE: PRT
<213> ORGANISM: Artificial Sequence
<220> FEATURE:
<223> OTHER INFORMATION: Synthetic peptide
```

-continued

```
<220> FEATURE:
<221> NAME/KEY: misc_feature
<222> LOCATION: (19)..(25)
<223> OTHER INFORMATION: Xaa can be any naturally occurring amino acid

<400> SEQUENCE: 232

Gly Ala Pro Gly Gly Gly Gly Ser Gly Gly Gly Gly Ser Pro Ala Pro
1               5                   10                  15

Ala Pro Xaa Xaa Xaa Xaa Xaa Xaa Xaa Gly Ala Pro
            20                  25

<210> SEQ ID NO 233
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 233

Gly Ala Pro Gly Gly Gly Gly Ser Gly Gly Gly Gly Ser Gly Gly Gly
1               5                   10                  15

Gly Ser Pro Ala Pro Ala Pro Xaa Gly Ala Pro
            20                  25

<210> SEQ ID NO 234
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(25)
<223> OTHER INFORMATION: Xaa can be any naturally occurring amino acid

<400> SEQUENCE: 234

Gly Ala Pro Gly Gly Gly Gly Ser Gly Gly Gly Gly Ser Gly Gly Gly
1               5                   10                  15

Gly Ser Pro Ala Pro Ala Pro Xaa Xaa Gly Ala Pro
            20                  25

<210> SEQ ID NO 235
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(26)
<223> OTHER INFORMATION: Xaa can be any naturally occurring amino acid

<400> SEQUENCE: 235

Gly Ala Pro Gly Gly Gly Gly Ser Gly Gly Gly Gly Ser Gly Gly Gly
1               5                   10                  15

Gly Ser Pro Ala Pro Ala Pro Xaa Xaa Xaa Gly Ala Pro
            20                  25

<210> SEQ ID NO 236
<211> LENGTH: 30
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (24)..(27)
<223> OTHER INFORMATION: Xaa can be any naturally occurring amino acid

<400> SEQUENCE: 236

Gly Ala Pro Gly Gly Gly Gly Ser Gly Gly Gly Ser Gly Gly Gly
1               5                   10                  15
Gly Ser Pro Ala Pro Ala Pro Xaa Xaa Xaa Xaa Gly Ala Pro
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(28)
<223> OTHER INFORMATION: Xaa can be any naturally occurring amino acid

<400> SEQUENCE: 237

Gly Ala Pro Gly Gly Gly Gly Ser Gly Gly Gly Ser Gly Gly Gly
1               5                   10                  15
Gly Ser Pro Ala Pro Ala Pro Xaa Xaa Xaa Xaa Xaa Gly Ala Pro
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(29)
<223> OTHER INFORMATION: Xaa can be any naturally occurring amino acid

<400> SEQUENCE: 238

Gly Ala Pro Gly Gly Gly Gly Ser Gly Gly Gly Ser Gly Gly Gly
1               5                   10                  15
Gly Ser Pro Ala Pro Ala Pro Xaa Xaa Xaa Xaa Xaa Xaa Gly Ala Pro
            20                  25                  30

<210> SEQ ID NO 239
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(30)
<223> OTHER INFORMATION: Xaa can be any naturally occurring amino acid

<400> SEQUENCE: 239

Gly Ala Pro Gly Gly Gly Gly Ser Gly Gly Gly Ser Gly Gly Gly
1               5                   10                  15
Gly Ser Pro Ala Pro Ala Pro Xaa Xaa Xaa Xaa Xaa Xaa Xaa Gly Ala
            20                  25                  30
Pro

<210> SEQ ID NO 240
<211> LENGTH: 32
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(29)
<223> OTHER INFORMATION: Xaa can be any naturally occurring amino acid

<400> SEQUENCE: 240

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Gly Ala Pro
            20                  25                  30

<210> SEQ ID NO 241
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(30)
<223> OTHER INFORMATION: Xaa can be any naturally occurring amino acid

<400> SEQUENCE: 241

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Gly Ala
            20                  25                  30

Pro

<210> SEQ ID NO 242
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(31)
<223> OTHER INFORMATION: Xaa can be any naturally occurring amino acid

<400> SEQUENCE: 242

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Xaa Gly
            20                  25                  30

Ala Pro

<210> SEQ ID NO 243
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(32)
<223> OTHER INFORMATION: Xaa can be any naturally occurring amino acid

<400> SEQUENCE: 243

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Xaa Xaa
```

Gly Ala Pro
35

<210> SEQ ID NO 244
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(33)
<223> OTHER INFORMATION: Xaa can be any naturally occurring amino acid

<400> SEQUENCE: 244

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Xaa Xaa
            20                  25                  30

Xaa Gly Ala Pro
        35

<210> SEQ ID NO 245
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(34)
<223> OTHER INFORMATION: Xaa can be any naturally occurring amino acid

<400> SEQUENCE: 245

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Xaa Xaa
            20                  25                  30

Xaa Xaa Gly Ala Pro
        35

<210> SEQ ID NO 246
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(35)
<223> OTHER INFORMATION: Xaa can be any naturally occurring amino acid

<400> SEQUENCE: 246

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Xaa Xaa Xaa Xaa
            20                  25                  30

Xaa Xaa Xaa Gly Ala Pro
        35

<210> SEQ ID NO 247
<211> LENGTH: 37
<212> TYPE: PRT
<213> ORGANISM: Artificial Sequence

```
<220> FEATURE:
<223> OTHER INFORMATION: Synthetic peptide
<220> FEATURE:
<221> NAME/KEY: misc_feature
<222> LOCATION: (34)..(34)
<223> OTHER INFORMATION: Xaa can be any naturally occurring amino acid

<400> SEQUENCE: 247

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Xaa Gly Ala Pro
        35

<210> SEQ ID NO 248
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(35)
<223> OTHER INFORMATION: Xaa can be any naturally occurring amino acid

<400> SEQUENCE: 248

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Xaa Xaa Gly Ala Pro
        35

<210> SEQ ID NO 249
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(36)
<223> OTHER INFORMATION: Xaa can be any naturally occurring amino acid

<400> SEQUENCE: 249

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Xaa Xaa Xaa Gly Ala Pro
        35

<210> SEQ ID NO 250
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(37)
<223> OTHER INFORMATION: Xaa can be any naturally occurring amino acid

<400> SEQUENCE: 250

Gly Ala Pro Gly Gly Gly Gly Ser Gly Gly Gly Ser Gly Gly Gly
```

```
                1               5                  10                  15
Gly Ser Gly Gly Gly Gly Ser Gly Gly Gly Ser Pro Ala Pro Ala
                20                  25                  30

Pro Xaa Xaa Xaa Xaa Gly Ala Pro
        35                  40
```

<210> SEQ ID NO 251
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(38)
<223> OTHER INFORMATION: Xaa can be any naturally occurring amino acid

<400> SEQUENCE: 251

```
Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Ser Pro Ala Pro Ala
                20                  25                  30

Pro Xaa Xaa Xaa Xaa Xaa Gly Ala Pro
        35                  40
```

<210> SEQ ID NO 252
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(39)
<223> OTHER INFORMATION: Xaa can be any naturally occurring amino acid

<400> SEQUENCE: 252

```
Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Ser Pro Ala Pro Ala
                20                  25                  30

Pro Xaa Xaa Xaa Xaa Xaa Xaa Gly Ala Pro
        35                  40
```

<210> SEQ ID NO 253
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(40)
<223> OTHER INFORMATION: Xaa can be any naturally occurring amino acid

<400> SEQUENCE: 253

```
Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Ser Pro Ala Pro Ala
                20                  25                  30

Pro Xaa Xaa Xaa Xaa Xaa Xaa Xaa Gly Ala Pro
        35                  40
```

<210> SEQ ID NO 254

-continued

```
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(39)
<223> OTHER INFORMATION: Xaa can be any naturally occurring amino acid

<400> SEQUENCE: 254

Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Gly Ser Gly Gly Gly Gly
            20                  25                  30

Ser Pro Ala Pro Ala Pro Xaa Gly Ala Pro
        35                  40

<210> SEQ ID NO 255
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(40)
<223> OTHER INFORMATION: Xaa can be any naturally occurring amino acid

<400> SEQUENCE: 255

Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Gly Ser Gly Gly Gly Gly
            20                  25                  30

Ser Pro Ala Pro Ala Pro Xaa Xaa Gly Ala Pro
        35                  40

<210> SEQ ID NO 256
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(41)
<223> OTHER INFORMATION: Xaa can be any naturally occurring amino acid

<400> SEQUENCE: 256

Gly Ala Pro Gly Gly Gly Gly Ser Gly Gly Gly Gly Ser Gly Gly Gly
1               5                  10                  15

Gly Ser Gly Gly Gly Gly Ser Gly Gly Gly Gly Ser Gly Gly Gly Gly
            20                  25                  30

Ser Pro Ala Pro Ala Pro Xaa Xaa Xaa Gly Ala Pro
        35                  40

<210> SEQ ID NO 257
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(42)
<223> OTHER INFORMATION: Xaa can be any naturally occurring amino acid
```

```
<400> SEQUENCE: 257

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Pro Ala Pro Ala Pro Xaa Xaa Xaa Xaa Gly Ala Pro
        35                  40                  45

<210> SEQ ID NO 258
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(43)
<223> OTHER INFORMATION: Xaa can be any naturally occurring amino acid

<400> SEQUENCE: 258

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Pro Ala Pro Ala Pro Xaa Xaa Xaa Xaa Xaa Gly Ala Pro
        35                  40                  45

<210> SEQ ID NO 259
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(44)
<223> OTHER INFORMATION: Xaa can be any naturally occurring amino acid

<400> SEQUENCE: 259

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Pro Ala Pro Ala Pro Xaa Xaa Xaa Xaa Xaa Xaa Gly Ala Pro
        35                  40                  45

<210> SEQ ID NO 260
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(45)
<223> OTHER INFORMATION: Xaa can be any naturally occurring amino acid

<400> SEQUENCE: 260

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly
            20                  25                  30

Ser Pro Ala Pro Ala Pro Xaa Xaa Xaa Xaa Xaa Xaa Xaa Gly Ala Pro
        35                  40                  45
```

```
<210> SEQ ID NO 261
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(44)
<223> OTHER INFORMATION: Xaa can be any naturally occurring amino acid

<400> SEQUENCE: 261

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Pro Ala Pro Ala Pro Xaa Gly Ala Pro
        35                  40                  45

<210> SEQ ID NO 262
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(45)
<223> OTHER INFORMATION: Xaa can be any naturally occurring amino acid

<400> SEQUENCE: 262

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Pro Ala Pro Ala Pro Xaa Xaa Gly Ala Pro
        35                  40                  45

<210> SEQ ID NO 263
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(46)
<223> OTHER INFORMATION: Xaa can be any naturally occurring amino acid

<400> SEQUENCE: 263

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Pro Ala Pro Ala Pro Xaa Xaa Xaa Gly Ala
        35                  40                  45

Pro

<210> SEQ ID NO 264
<211> LENGTH: 50
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (44)..(47)
<223> OTHER INFORMATION: Xaa can be any naturally occurring amino acid

<400> SEQUENCE: 264

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Xaa Xaa Xaa Xaa Gly
        35                  40                  45

Ala Pro
    50

<210> SEQ ID NO 265
<211> LENGTH: 51
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(48)
<223> OTHER INFORMATION: Xaa can be any naturally occurring amino acid

<400> SEQUENCE: 265

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Xaa Xaa Xaa Xaa Xaa
        35                  40                  45

Gly Ala Pro
    50

<210> SEQ ID NO 266
<211> LENGTH: 52
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(49)
<223> OTHER INFORMATION: Xaa can be any naturally occurring amino acid

<400> SEQUENCE: 266

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Xaa Xaa Xaa Xaa Xaa
        35                  40                  45

Xaa Gly Ala Pro
    50

<210> SEQ ID NO 267
<211> LENGTH: 53
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (44)..(50)
<223> OTHER INFORMATION: Xaa can be any naturally occurring amino acid

<400> SEQUENCE: 267

Gly Ala Pro Gly Gly Gly Ser Gly Gly Gly Ser Gly Gly
1               5                   10                  15

Gly Ser Gly Gly Gly Ser Gly Gly Gly Ser Gly Gly Gly
                20                  25                  30

Ser Gly Gly Gly Ser Pro Ala Pro Ala Pro Xaa Xaa Xaa Xaa
        35                  40                  45

Xaa Xaa Gly Ala Pro
    50

<210> SEQ ID NO 268
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(15)
<223> OTHER INFORMATION: Xaa can be any naturally occurring amino acid

<400> SEQUENCE: 268

Gly Ala Pro Gly Gly Gly Gly Ser Pro Ala Pro Ala Pro Thr Xaa Gly
1               5                   10                  15

Ala Pro

<210> SEQ ID NO 269
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(16)
<223> OTHER INFORMATION: Xaa can be any naturally occurring amino acid

<400> SEQUENCE: 269

Gly Ala Pro Gly Gly Gly Gly Ser Pro Ala Pro Ala Pro Thr Xaa Xaa
1               5                   10                  15

Gly Ala Pro

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(17)
<223> OTHER INFORMATION: Xaa can be any naturally occurring amino acid

<400> SEQUENCE: 270

Gly Ala Pro Gly Gly Gly Gly Ser Pro Ala Pro Ala Pro Thr Xaa Xaa
1               5                   10                  15

Xaa Gly Ala Pro
        20

<210> SEQ ID NO 271
<211> LENGTH: 21
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(18)
<223> OTHER INFORMATION: Xaa can be any naturally occurring amino acid

<400> SEQUENCE: 271

Gly Ala Pro Gly Gly Gly Gly Ser Pro Ala Pro Ala Pro Thr Xaa Xaa
1               5                   10                  15

Xaa Xaa Gly Ala Pro
            20

<210> SEQ ID NO 272
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(19)
<223> OTHER INFORMATION: Xaa can be any naturally occurring amino acid

<400> SEQUENCE: 272

Gly Ala Pro Gly Gly Gly Gly Ser Pro Ala Pro Ala Pro Thr Xaa Xaa
1               5                   10                  15

Xaa Xaa Xaa Gly Ala Pro
            20

<210> SEQ ID NO 273
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(20)
<223> OTHER INFORMATION: Xaa can be any naturally occurring amino acid

<400> SEQUENCE: 273

Gly Ala Pro Gly Gly Gly Gly Ser Pro Ala Pro Ala Pro Thr Xaa Xaa
1               5                   10                  15

Xaa Xaa Xaa Xaa Gly Ala Pro
            20

<210> SEQ ID NO 274
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(21)
<223> OTHER INFORMATION: Xaa can be any naturally occurring amino acid

<400> SEQUENCE: 274

Gly Ala Pro Gly Gly Gly Gly Ser Pro Ala Pro Ala Pro Thr Xaa Xaa
1               5                   10                  15

Xaa Xaa Xaa Xaa Xaa Gly Ala Pro
            20

<210> SEQ ID NO 275
```

```
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: Xaa can be any naturally occurring amino acid

<400> SEQUENCE: 275

Gly Ala Pro Gly Gly Gly Gly Ser Gly Gly Gly Ser Pro Ala Pro
1               5                   10                  15

Ala Pro Thr Xaa Gly Ala Pro
            20

<210> SEQ ID NO 276
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(21)
<223> OTHER INFORMATION: Xaa can be any naturally occurring amino acid

<400> SEQUENCE: 276

Gly Ala Pro Gly Gly Gly Gly Ser Gly Gly Gly Ser Pro Ala Pro
1               5                   10                  15

Ala Pro Thr Xaa Xaa Gly Ala Pro
            20

<210> SEQ ID NO 277
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(22)
<223> OTHER INFORMATION: Xaa can be any naturally occurring amino acid

<400> SEQUENCE: 277

Gly Ala Pro Gly Gly Gly Gly Ser Gly Gly Gly Ser Pro Ala Pro
1               5                   10                  15

Ala Pro Thr Xaa Xaa Xaa Gly Ala Pro
            20                  25

<210> SEQ ID NO 278
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(23)
<223> OTHER INFORMATION: Xaa can be any naturally occurring amino acid

<400> SEQUENCE: 278

Gly Ala Pro Gly Gly Gly Gly Ser Gly Gly Gly Ser Pro Ala Pro
1               5                   10                  15

Ala Pro Thr Xaa Xaa Xaa Xaa Gly Ala Pro
            20                  25
```

```
<210> SEQ ID NO 279
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(24)
<223> OTHER INFORMATION: Xaa can be any naturally occurring amino acid

<400> SEQUENCE: 279

Gly Ala Pro Gly Gly Gly Gly Ser Gly Gly Gly Ser Pro Ala Pro
1               5                   10                  15

Ala Pro Thr Xaa Xaa Xaa Xaa Xaa Gly Ala Pro
            20                  25

<210> SEQ ID NO 280
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(25)
<223> OTHER INFORMATION: Xaa can be any naturally occurring amino acid

<400> SEQUENCE: 280

Gly Ala Pro Gly Gly Gly Gly Ser Gly Gly Gly Ser Pro Ala Pro
1               5                   10                  15

Ala Pro Thr Xaa Xaa Xaa Xaa Xaa Xaa Gly Ala Pro
            20                  25

<210> SEQ ID NO 281
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(26)
<223> OTHER INFORMATION: Xaa can be any naturally occurring amino acid

<400> SEQUENCE: 281

Gly Ala Pro Gly Gly Gly Gly Ser Gly Gly Gly Ser Pro Ala Pro
1               5                   10                  15

Ala Pro Thr Xaa Xaa Xaa Xaa Xaa Xaa Xaa Gly Ala Pro
            20                  25

<210> SEQ ID NO 282
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 282

Gly Ala Pro Gly Gly Gly Gly Ser Gly Gly Gly Ser Gly Gly Gly
1               5                   10                  15

Gly Ser Pro Ala Pro Ala Pro Thr Xaa Gly Ala Pro
            20                  25
```

```
<210> SEQ ID NO 283
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(26)
<223> OTHER INFORMATION: Xaa can be any naturally occurring amino acid

<400> SEQUENCE: 283

Gly Ala Pro Gly Gly Gly Gly Ser Gly Gly Gly Gly Ser Gly Gly Gly
1               5                   10                  15

Gly Ser Pro Ala Pro Ala Pro Thr Xaa Xaa Gly Ala Pro
            20                  25

<210> SEQ ID NO 284
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(27)
<223> OTHER INFORMATION: Xaa can be any naturally occurring amino acid

<400> SEQUENCE: 284

Gly Ala Pro Gly Gly Gly Gly Ser Gly Gly Gly Gly Ser Gly Gly Gly
1               5                   10                  15

Gly Ser Pro Ala Pro Ala Pro Thr Xaa Xaa Xaa Gly Ala Pro
            20                  25                  30

<210> SEQ ID NO 285
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(28)
<223> OTHER INFORMATION: Xaa can be any naturally occurring amino acid

<400> SEQUENCE: 285

Gly Ala Pro Gly Gly Gly Gly Ser Gly Gly Gly Gly Ser Gly Gly Gly
1               5                   10                  15

Gly Ser Pro Ala Pro Ala Pro Thr Xaa Xaa Xaa Xaa Gly Ala Pro
            20                  25                  30

<210> SEQ ID NO 286
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(29)
<223> OTHER INFORMATION: Xaa can be any naturally occurring amino acid

<400> SEQUENCE: 286

Gly Ala Pro Gly Gly Gly Gly Ser Gly Gly Gly Gly Ser Gly Gly Gly
1               5                   10                  15

Gly Ser Pro Ala Pro Ala Pro Thr Xaa Xaa Xaa Xaa Xaa Gly Ala Pro
            20                  25                  30
```

<210> SEQ ID NO 287
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(30)
<223> OTHER INFORMATION: Xaa can be any naturally occurring amino acid

<400> SEQUENCE: 287

Gly Ala Pro Gly Gly Gly Gly Ser Gly Gly Gly Ser Gly Gly Gly
1               5                   10                  15

Gly Ser Pro Ala Pro Ala Pro Thr Xaa Xaa Xaa Xaa Xaa Xaa Gly Ala
            20                  25                  30

Pro

<210> SEQ ID NO 288
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(31)
<223> OTHER INFORMATION: Xaa can be any naturally occurring amino acid

<400> SEQUENCE: 288

Gly Ala Pro Gly Gly Gly Gly Ser Gly Gly Gly Ser Gly Gly Gly
1               5                   10                  15

Gly Ser Pro Ala Pro Ala Pro Thr Xaa Xaa Xaa Xaa Xaa Xaa Xaa Gly
            20                  25                  30

Ala Pro

<210> SEQ ID NO 289
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(30)
<223> OTHER INFORMATION: Xaa can be any naturally occurring amino acid

<400> SEQUENCE: 289

Gly Ala Pro Gly Gly Gly Gly Ser Gly Gly Gly Ser Gly Gly Gly
1               5                   10                  15

Gly Ser Gly Gly Gly Gly Ser Pro Ala Pro Ala Pro Thr Xaa Gly Ala
            20                  25                  30

Pro

<210> SEQ ID NO 290
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(31)
<223> OTHER INFORMATION: Xaa can be any naturally occurring amino acid

```
<400> SEQUENCE: 290

Gly Ala Pro Gly Gly Gly Gly Ser Gly Gly Gly Ser Gly Gly
1               5                   10                  15

Gly Ser Gly Gly Gly Gly Ser Pro Ala Pro Ala Pro Thr Xaa Xaa Gly
            20                  25                  30

Ala Pro

<210> SEQ ID NO 291
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(32)
<223> OTHER INFORMATION: Xaa can be any naturally occurring amino acid

<400> SEQUENCE: 291

Gly Ala Pro Gly Gly Gly Gly Ser Gly Gly Gly Ser Gly Gly
1               5                   10                  15

Gly Ser Gly Gly Gly Gly Ser Pro Ala Pro Ala Pro Thr Xaa Xaa Xaa
            20                  25                  30

Gly Ala Pro
        35

<210> SEQ ID NO 292
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(33)
<223> OTHER INFORMATION: Xaa can be any naturally occurring amino acid

<400> SEQUENCE: 292

Gly Ala Pro Gly Gly Gly Gly Ser Gly Gly Gly Ser Gly Gly
1               5                   10                  15

Gly Ser Gly Gly Gly Gly Ser Pro Ala Pro Ala Pro Thr Xaa Xaa Xaa
            20                  25                  30

Xaa Gly Ala Pro
        35

<210> SEQ ID NO 293
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(34)
<223> OTHER INFORMATION: Xaa can be any naturally occurring amino acid

<400> SEQUENCE: 293

Gly Ala Pro Gly Gly Gly Gly Ser Gly Gly Gly Ser Gly Gly
1               5                   10                  15

Gly Ser Gly Gly Gly Gly Ser Pro Ala Pro Ala Pro Thr Xaa Xaa Xaa
            20                  25                  30

Xaa Xaa Gly Ala Pro
        35
```

<210> SEQ ID NO 294
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(35)
<223> OTHER INFORMATION: Xaa can be any naturally occurring amino acid

<400> SEQUENCE: 294

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Thr Xaa Xaa Xaa
                20                  25                  30

Xaa Xaa Xaa Gly Ala Pro
        35

<210> SEQ ID NO 295
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(36)
<223> OTHER INFORMATION: Xaa can be any naturally occurring amino acid

<400> SEQUENCE: 295

Gly Ala Pro Gly Gly Gly Gly Ser Gly Gly Gly Gly Ser Gly Gly Gly
1               5                   10                  15

Gly Ser Gly Gly Gly Gly Ser Pro Ala Pro Ala Pro Thr Xaa Xaa Xaa
                20                  25                  30

Xaa Xaa Xaa Xaa Gly Ala Pro
        35

<210> SEQ ID NO 296
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(35)
<223> OTHER INFORMATION: Xaa can be any naturally occurring amino acid

<400> SEQUENCE: 296

Gly Ala Pro Gly Gly Gly Gly Ser Gly Gly Gly Gly Ser Gly Gly Gly
1               5                   10                  15

Gly Ser Gly Gly Gly Gly Ser Gly Gly Gly Gly Ser Pro Ala Pro Ala
                20                  25                  30

Pro Thr Xaa Gly Ala Pro
        35

<210> SEQ ID NO 297
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(36)

```
<223> OTHER INFORMATION: Xaa can be any naturally occurring amino acid

<400> SEQUENCE: 297

Gly Ala Pro Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Thr Xaa Xaa Gly Ala Pro
        35

<210> SEQ ID NO 298
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(37)
<223> OTHER INFORMATION: Xaa can be any naturally occurring amino acid

<400> SEQUENCE: 298

Gly Ala Pro Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Thr Xaa Xaa Xaa Gly Ala Pro
        35                  40

<210> SEQ ID NO 299
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(38)
<223> OTHER INFORMATION: Xaa can be any naturally occurring amino acid

<400> SEQUENCE: 299

Gly Ala Pro Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30

Pro Thr Xaa Xaa Xaa Xaa Gly Ala Pro
        35                  40

<210> SEQ ID NO 300
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(39)
<223> OTHER INFORMATION: Xaa can be any naturally occurring amino acid

<400> SEQUENCE: 300

Gly Ala Pro Gly Gly Gly Ser Gly Gly Gly Ser Gly Gly Gly
1               5                   10                  15

Gly Ser Gly Gly Gly Gly Ser Gly Gly Gly Ser Pro Ala Pro Ala
            20                  25                  30
```

```
Pro Thr Xaa Xaa Xaa Xaa Xaa Gly Ala Pro
        35                  40

<210> SEQ ID NO 301
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(40)
<223> OTHER INFORMATION: Xaa can be any naturally occurring amino acid

<400> SEQUENCE: 301

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Pro Ala Pro Ala
                20                  25                  30

Pro Thr Xaa Xaa Xaa Xaa Xaa Xaa Gly Ala Pro
        35                  40

<210> SEQ ID NO 302
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(41)
<223> OTHER INFORMATION: Xaa can be any naturally occurring amino acid

<400> SEQUENCE: 302

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Pro Ala Pro Ala
                20                  25                  30

Pro Thr Xaa Xaa Xaa Xaa Xaa Xaa Xaa Gly Ala Pro
        35                  40

<210> SEQ ID NO 303
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(40)
<223> OTHER INFORMATION: Xaa can be any naturally occurring amino acid

<400> SEQUENCE: 303

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Gly Gly Gly
                20                  25                  30

Ser Pro Ala Pro Ala Pro Thr Xaa Gly Ala Pro
        35                  40

<210> SEQ ID NO 304
<211> LENGTH: 44
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (40)..(41)
<223> OTHER INFORMATION: Xaa can be any naturally occurring amino acid

<400> SEQUENCE: 304

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Gly Gly Gly
                20                  25                  30

Ser Pro Ala Pro Ala Pro Thr Xaa Xaa Gly Ala Pro
                35                  40

<210> SEQ ID NO 305
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(42)
<223> OTHER INFORMATION: Xaa can be any naturally occurring amino acid

<400> SEQUENCE: 305

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Gly Gly Gly
                20                  25                  30

Ser Pro Ala Pro Ala Pro Thr Xaa Xaa Xaa Gly Ala Pro
                35                  40                  45

<210> SEQ ID NO 306
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(43)
<223> OTHER INFORMATION: Xaa can be any naturally occurring amino acid

<400> SEQUENCE: 306

Gly Ala Pro Gly Gly Gly Gly Ser Gly Gly Gly Ser Gly Gly Gly
1               5                   10                  15

Gly Ser Gly Gly Gly Gly Ser Gly Gly Gly Gly Ser Gly Gly Gly
                20                  25                  30

Ser Pro Ala Pro Ala Pro Thr Xaa Xaa Xaa Xaa Gly Ala Pro
                35                  40                  45

<210> SEQ ID NO 307
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(44)
<223> OTHER INFORMATION: Xaa can be any naturally occurring amino acid

<400> SEQUENCE: 307

Gly Ala Pro Gly Gly Gly Gly Ser Gly Gly Gly Ser Gly Gly Gly
1               5                   10                  15
```

Gly Ser Gly Gly Gly Gly Ser Gly Gly Gly Ser Gly Gly Gly
            20                  25                  30

Ser Pro Ala Pro Ala Pro Thr Xaa Xaa Xaa Xaa Xaa Gly Ala Pro
        35                  40                  45

<210> SEQ ID NO 308
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(45)
<223> OTHER INFORMATION: Xaa can be any naturally occurring amino acid

<400> SEQUENCE: 308

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Pro Ala Pro Ala Pro Thr Xaa Xaa Xaa Xaa Xaa Xaa Gly Ala Pro
        35                  40                  45

<210> SEQ ID NO 309
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(46)
<223> OTHER INFORMATION: Xaa can be any naturally occurring amino acid

<400> SEQUENCE: 309

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Pro Ala Pro Ala Pro Thr Xaa Xaa Xaa Xaa Xaa Xaa Xaa Gly Ala
        35                  40                  45

Pro

<210> SEQ ID NO 310
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(45)
<223> OTHER INFORMATION: Xaa can be any naturally occurring amino acid

<400> SEQUENCE: 310

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Pro Ala Pro Ala Pro Thr Xaa Gly Ala Pro
        35                  40                  45

<210> SEQ ID NO 311

<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(46)
<223> OTHER INFORMATION: Xaa can be any naturally occurring amino acid

<400> SEQUENCE: 311

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Thr Xaa Xaa Gly Ala
        35                  40                  45

Pro

<210> SEQ ID NO 312
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(47)
<223> OTHER INFORMATION: Xaa can be any naturally occurring amino acid

<400> SEQUENCE: 312

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Thr Xaa Xaa Xaa Gly
        35                  40                  45

Ala Pro
    50

<210> SEQ ID NO 313
<211> LENGTH: 51
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(48)
<223> OTHER INFORMATION: Xaa can be any naturally occurring amino acid

<400> SEQUENCE: 313

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
                20                  25                  30

Ser Gly Gly Gly Gly Ser Pro Ala Pro Ala Pro Thr Xaa Xaa Xaa Xaa
        35                  40                  45

Gly Ala Pro
    50

<210> SEQ ID NO 314
<211> LENGTH: 52
<212> TYPE: PRT

<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(49)
<223> OTHER INFORMATION: Xaa can be any naturally occurring amino acid

<400> SEQUENCE: 314

Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly
                20                  25                  30

Ser Gly Gly Gly Gly Ser Pro Ala Pro Ala Pro Thr Xaa Xaa Xaa Xaa
        35                  40                  45

Xaa Gly Ala Pro
    50

<210> SEQ ID NO 315
<211> LENGTH: 53
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(50)
<223> OTHER INFORMATION: Xaa can be any naturally occurring amino acid

<400> SEQUENCE: 315

Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly
                20                  25                  30

Ser Gly Gly Gly Gly Ser Pro Ala Pro Ala Pro Thr Xaa Xaa Xaa Xaa
        35                  40                  45

Xaa Xaa Gly Ala Pro
    50

<210> SEQ ID NO 316
<211> LENGTH: 54
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(51)
<223> OTHER INFORMATION: Xaa can be any naturally occurring amino acid

<400> SEQUENCE: 316

Gly Ala Pro Gly Gly Gly Gly Ser Gly Gly Gly Ser Gly Gly
1               5                   10                  15

Gly Ser Gly Gly Gly Gly Ser Gly Gly Gly Ser Gly Gly Gly
                20                  25                  30

Ser Gly Gly Gly Gly Ser Pro Ala Pro Ala Pro Thr Xaa Xaa Xaa Xaa
        35                  40                  45

Xaa Xaa Xaa Gly Ala Pro
    50

<210> SEQ ID NO 317
<211> LENGTH: 10
<212> TYPE: PRT
<213> ORGANISM: Artificial Sequence

```
<220> FEATURE:
<223> OTHER INFORMATION: Synthetic peptide

<400> SEQUENCE: 317

Gly Gly Gly Gly Ala Gly Gly Gly Ala
1               5                   10

<210> SEQ ID NO 318
<211> LENGTH: 25
<212> TYPE: PRT
<213> ORGANISM: Artificial Sequence
<220> FEATURE:
<223> OTHER INFORMATION: Synthetic peptide

<400> SEQUENCE: 318

Gly Gly Gly Gly Ala Gly Gly Gly Gly Ala Gly Gly Gly Gly Ala Gly
1               5                   10                  15

Gly Gly Gly Ala Gly Gly Gly Gly Ala
            20                  25

<210> SEQ ID NO 319
<211> LENGTH: 30
<212> TYPE: PRT
<213> ORGANISM: Artificial Sequence
<220> FEATURE:
<223> OTHER INFORMATION: Synthetic peptide

<400> SEQUENCE: 319

Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Gly Ala
            20                  25                  30

<210> SEQ ID NO 320
<211> LENGTH: 35
<212> TYPE: PRT
<213> ORGANISM: Artificial Sequence
<220> FEATURE:
<223> OTHER INFORMATION: Synthetic peptide

<400> SEQUENCE: 320

Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Gly Ala Gly Gly
            20                  25                  30

Gly Gly Ala
        35

<210> SEQ ID NO 321
<211> LENGTH: 10
<212> TYPE: PRT
<213> ORGANISM: Artificial Sequence
<220> FEATURE:
<223> OTHER INFORMATION: Synthetic peptide

<400> SEQUENCE: 321

Gly Gly Gly Gly Ala Gly Gly Gly Pro Ser
1               5                   10

<210> SEQ ID NO 322
<211> LENGTH: 15
<212> TYPE: PRT
<213> ORGANISM: Artificial Sequence
<220> FEATURE:
<223> OTHER INFORMATION: Synthetic peptide
```

<400> SEQUENCE: 322

Gly Gly Gly Gly Ala Gly Gly Gly Gly Ala Gly Gly Gly Pro Ser
1               5                   10                  15

<210> SEQ ID NO 323
<211> LENGTH: 20
<212> TYPE: PRT
<213> ORGANISM: Artificial Sequence
<220> FEATURE:
<223> OTHER INFORMATION: Synthetic peptide

<400> SEQUENCE: 323

Gly Gly Gly Gly Ala Gly Gly Gly Gly Ala Gly Gly Gly Gly Ala Gly
1               5                   10                  15

Gly Gly Pro Ser
            20

<210> SEQ ID NO 324
<211> LENGTH: 30
<212> TYPE: PRT
<213> ORGANISM: Artificial Sequence
<220> FEATURE:
<223> OTHER INFORMATION: Synthetic peptide

<400> SEQUENCE: 324

Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Pro Ser
            20                  25                  30

<210> SEQ ID NO 325
<211> LENGTH: 35
<212> TYPE: PRT
<213> ORGANISM: Artificial Sequence
<220> FEATURE:
<223> OTHER INFORMATION: Synthetic peptide

<400> SEQUENCE: 325

Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Ala Gly Gly
            20                  25                  30

Gly Pro Ser
        35

<210> SEQ ID NO 326
<211> LENGTH: 40
<212> TYPE: PRT
<213> ORGANISM: Artificial Sequence
<220> FEATURE:
<223> OTHER INFORMATION: Synthetic peptide

<400> SEQUENCE: 326

Gly Gly Gly Gly Ala Gly Gly Gly Gly Ala Gly Gly Gly Gly Ala Gly
1               5                   10                  15

Gly Gly Gly Ala Gly Gly Gly Gly Ala Gly Gly Gly Ala Gly Gly Gly
            20                  25                  30

Gly Gly Ala Gly Gly Gly Pro Ser
        35                  40

<210> SEQ ID NO 327
<211> LENGTH: 13

<212> TYPE: PRT
<213> ORGANISM: Artificial Sequence
<220> FEATURE:
<223> OTHER INFORMATION: Synthetic peptide

<400> SEQUENCE: 327

Gly Ala Pro Gly Gly Gly Gly Ala Gly Gly Pro Ser
1               5                   10

<210> SEQ ID NO 328
<211> LENGTH: 18
<212> TYPE: PRT
<213> ORGANISM: Artificial Sequence
<220> FEATURE:
<223> OTHER INFORMATION: Synthetic peptide

<400> SEQUENCE: 328

Gly Ala Pro Gly Gly Gly Gly Ala Gly Gly Gly Ala Gly Gly Gly
1               5                   10                  15

Pro Ser

<210> SEQ ID NO 329
<211> LENGTH: 23
<212> TYPE: PRT
<213> ORGANISM: Artificial Sequence
<220> FEATURE:
<223> OTHER INFORMATION: Synthetic peptide

<400> SEQUENCE: 329

Gly Ala Pro Gly Gly Gly Gly Ala Gly Gly Gly Ala Gly Gly Gly
1               5                   10                  15

Gly Ala Gly Gly Gly Pro Ser
            20

<210> SEQ ID NO 330
<211> LENGTH: 28
<212> TYPE: PRT
<213> ORGANISM: Artificial Sequence
<220> FEATURE:
<223> OTHER INFORMATION: Synthetic peptide

<400> SEQUENCE: 330

Gly Ala Pro Gly Gly Gly Gly Ala Gly Gly Gly Ala Gly Gly Gly
1               5                   10                  15

Gly Ala Gly Gly Gly Gly Ala Gly Gly Pro Ser
            20                  25

<210> SEQ ID NO 331
<211> LENGTH: 33
<212> TYPE: PRT
<213> ORGANISM: Artificial Sequence
<220> FEATURE:
<223> OTHER INFORMATION: Synthetic peptide

<400> SEQUENCE: 331

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Pro
            20                  25                  30

Ser

<210> SEQ ID NO 332
<211> LENGTH: 38
<212> TYPE: PRT

-continued

<213> ORGANISM: Artificial Sequence
<220> FEATURE:
<223> OTHER INFORMATION: Synthetic peptide

<400> SEQUENCE: 332

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Pro Ser
        35

<210> SEQ ID NO 333
<211> LENGTH: 43
<212> TYPE: PRT
<213> ORGANISM: Artificial Sequence
<220> FEATURE:
<223> OTHER INFORMATION: Synthetic peptide

<400> SEQUENCE: 333

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Gly Pro Ser
        35                  40

<210> SEQ ID NO 334
<211> LENGTH: 16
<212> TYPE: PRT
<213> ORGANISM: Artificial Sequence
<220> FEATURE:
<223> OTHER INFORMATION: Synthetic peptide

<400> SEQUENCE: 334

Gly Ala Pro Gly Gly Gly Gly Ala Gly Gly Pro Ser Gly Ala Pro
1               5                   10                  15

<210> SEQ ID NO 335
<211> LENGTH: 21
<212> TYPE: PRT
<213> ORGANISM: Artificial Sequence
<220> FEATURE:
<223> OTHER INFORMATION: Synthetic peptide

<400> SEQUENCE: 335

Gly Ala Pro Gly Gly Gly Gly Ala Gly Gly Gly Ala Gly Gly
1               5                   10                  15

Pro Ser Gly Ala Pro
        20

<210> SEQ ID NO 336
<211> LENGTH: 26
<212> TYPE: PRT
<213> ORGANISM: Artificial Sequence
<220> FEATURE:
<223> OTHER INFORMATION: Synthetic peptide

<400> SEQUENCE: 336

Gly Ala Pro Gly Gly Gly Gly Ala Gly Gly Gly Ala Gly Gly
1               5                   10                  15

Gly Ala Gly Gly Gly Pro Ser Gly Ala Pro
            20                  25

```
<210> SEQ ID NO 337
<211> LENGTH: 31
<212> TYPE: PRT
<213> ORGANISM: Artificial Sequence
<220> FEATURE:
<223> OTHER INFORMATION: Synthetic peptide

<400> SEQUENCE: 337

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Ala Pro
            20                  25                  30

<210> SEQ ID NO 338
<211> LENGTH: 36
<212> TYPE: PRT
<213> ORGANISM: Artificial Sequence
<220> FEATURE:
<223> OTHER INFORMATION: Synthetic peptide

<400> SEQUENCE: 338

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Pro
            20                  25                  30

Ser Gly Ala Pro
        35

<210> SEQ ID NO 339
<211> LENGTH: 41
<212> TYPE: PRT
<213> ORGANISM: Artificial Sequence
<220> FEATURE:
<223> OTHER INFORMATION: Synthetic peptide

<400> SEQUENCE: 339

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Ala Pro
        35                  40

<210> SEQ ID NO 340
<211> LENGTH: 46
<212> TYPE: PRT
<213> ORGANISM: Artificial Sequence
<220> FEATURE:
<223> OTHER INFORMATION: Synthetic peptide

<400> SEQUENCE: 340

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Pro Ser Gly Ala Pro
        35                  40                  45

<210> SEQ ID NO 341
<211> LENGTH: 21
<212> TYPE: PRT
<213> ORGANISM: Artificial Sequence
<220> FEATURE:
```

<223> OTHER INFORMATION: Synthetic peptide

<400> SEQUENCE: 341

Gly Ala Pro Gly Gly Gly Gly Ala Gly Gly Pro Ser Gly Gly Gly
1               5                   10                  15

Gly Ala Gly Ala Pro
            20

<210> SEQ ID NO 342
<211> LENGTH: 26
<212> TYPE: PRT
<213> ORGANISM: Artificial Sequence
<220> FEATURE:
<223> OTHER INFORMATION: Synthetic peptide

<400> SEQUENCE: 342

Gly Ala Pro Gly Gly Gly Gly Ala Gly Gly Pro Ser Gly Gly Gly
1               5                   10                  15

Gly Ala Gly Gly Gly Gly Ala Gly Ala Pro
            20                  25

<210> SEQ ID NO 343
<211> LENGTH: 31
<212> TYPE: PRT
<213> ORGANISM: Artificial Sequence
<220> FEATURE:
<223> OTHER INFORMATION: Synthetic peptide

<400> SEQUENCE: 343

Gly Ala Pro Gly Gly Gly Gly Ala Gly Gly Pro Ser Gly Gly Gly
1               5                   10                  15

Gly Ala Gly Gly Gly Gly Ala Gly Gly Gly Ala Gly Ala Pro
            20                  25                  30

<210> SEQ ID NO 344
<211> LENGTH: 36
<212> TYPE: PRT
<213> ORGANISM: Artificial Sequence
<220> FEATURE:
<223> OTHER INFORMATION: Synthetic peptide

<400> SEQUENCE: 344

Gly Ala Pro Gly Gly Gly Gly Ala Gly Gly Pro Ser Gly Gly Gly
1               5                   10                  15

Gly Ala Gly Gly Gly Gly Ala Gly Gly Gly Ala Gly Gly Gly Gly
            20                  25                  30

Ala Gly Ala Pro
        35

<210> SEQ ID NO 345
<211> LENGTH: 41
<212> TYPE: PRT
<213> ORGANISM: Artificial Sequence
<220> FEATURE:
<223> OTHER INFORMATION: Synthetic peptide

<400> SEQUENCE: 345

Gly Ala Pro Gly Gly Gly Gly Ala Gly Gly Pro Ser Gly Gly Gly
1               5                   10                  15

Gly Ala Gly Gly Gly Gly Ala Gly Gly Gly Ala Gly Gly Gly Gly
            20                  25                  30

Ala Gly Gly Gly Gly Ala Gly Ala Pro
        35                  40

<210> SEQ ID NO 346
<211> LENGTH: 46
<212> TYPE: PRT
<213> ORGANISM: Artificial Sequence
<220> FEATURE:
<223> OTHER INFORMATION: Synthetic peptide

<400> SEQUENCE: 346

Gly Ala Pro Gly Gly Gly Gly Ala Gly Gly Pro Ser Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Gly Ala Gly Ala Pro
        35                  40                  45

<210> SEQ ID NO 347
<211> LENGTH: 51
<212> TYPE: PRT
<213> ORGANISM: Artificial Sequence
<220> FEATURE:
<223> OTHER INFORMATION: Synthetic peptide

<400> SEQUENCE: 347

Gly Ala Pro Gly Gly Gly Gly Ala Gly Gly Pro Ser Gly Gly Gly
1               5                   10                  15

Gly Ala Gly Gly Gly Ala Gly Gly Gly Ala Gly Gly Gly Gly
            20                  25                  30

Ala Gly Gly Gly Gly Ala Gly Gly Gly Ala Gly Gly Gly Ala
        35                  40                  45

Gly Ala Pro
    50

<210> SEQ ID NO 348
<211> LENGTH: 26
<212> TYPE: PRT
<213> ORGANISM: Artificial Sequence
<220> FEATURE:
<223> OTHER INFORMATION: Synthetic peptide

<400> SEQUENCE: 348

Gly Ala Pro Gly Gly Gly Gly Ala Gly Gly Gly Ala Gly Gly Gly
1               5                   10                  15

Pro Ser Gly Gly Gly Gly Ala Gly Ala Pro
            20                  25

<210> SEQ ID NO 349
<211> LENGTH: 31
<212> TYPE: PRT
<213> ORGANISM: Artificial Sequence
<220> FEATURE:
<223> OTHER INFORMATION: Synthetic peptide

<400> SEQUENCE: 349

Gly Ala Pro Gly Gly Gly Gly Ala Gly Gly Gly Ala Gly Gly Gly
1               5                   10                  15

Pro Ser Gly Gly Gly Gly Ala Gly Gly Gly Gly Ala Gly Ala Pro
            20                  25                  30

<210> SEQ ID NO 350
<211> LENGTH: 36
<212> TYPE: PRT
<213> ORGANISM: Artificial Sequence

```
<220> FEATURE:
<223> OTHER INFORMATION: Synthetic peptide

<400> SEQUENCE: 350

Gly Ala Pro Gly Gly Gly Ala Gly Gly Gly Ala Gly Gly
1               5                   10                  15

Pro Ser Gly Gly Gly Ala Gly Gly Gly Ala Gly Gly Gly
                20                  25                  30

Ala Gly Ala Pro
        35

<210> SEQ ID NO 351
<211> LENGTH: 41
<212> TYPE: PRT
<213> ORGANISM: Artificial Sequence
<220> FEATURE:
<223> OTHER INFORMATION: Synthetic peptide

<400> SEQUENCE: 351

Gly Ala Pro Gly Gly Gly Ala Gly Gly Gly Ala Gly Gly
1               5                   10                  15

Pro Ser Gly Gly Gly Gly Ala Gly Gly Gly Ala Gly Gly Gly
                20                  25                  30

Ala Gly Gly Gly Gly Ala Gly Ala Pro
        35                  40

<210> SEQ ID NO 352
<211> LENGTH: 46
<212> TYPE: PRT
<213> ORGANISM: Artificial Sequence
<220> FEATURE:
<223> OTHER INFORMATION: Synthetic peptide

<400> SEQUENCE: 352

Gly Ala Pro Gly Gly Gly Ala Gly Gly Gly Ala Gly Gly
1               5                   10                  15

Pro Ser Gly Gly Gly Gly Ala Gly Gly Gly Ala Gly Gly Gly
                20                  25                  30

Ala Gly Gly Gly Gly Ala Gly Gly Gly Ala Gly Ala Pro
        35                  40                  45

<210> SEQ ID NO 353
<211> LENGTH: 51
<212> TYPE: PRT
<213> ORGANISM: Artificial Sequence
<220> FEATURE:
<223> OTHER INFORMATION: Synthetic peptide

<400> SEQUENCE: 353

Gly Ala Pro Gly Gly Gly Ala Gly Gly Gly Ala Gly Gly
1               5                   10                  15

Pro Ser Gly Gly Gly Gly Ala Gly Gly Gly Ala Gly Gly Gly
                20                  25                  30

Ala Gly Gly Gly Gly Ala Gly Gly Gly Ala Gly Gly Gly Ala
        35                  40                  45

Gly Ala Pro
    50

<210> SEQ ID NO 354
<211> LENGTH: 56
<212> TYPE: PRT
<213> ORGANISM: Artificial Sequence
```

```
<220> FEATURE:
<223> OTHER INFORMATION: Synthetic peptide

<400> SEQUENCE: 354

Gly Ala Pro Gly Gly Gly Ala Gly Gly Gly Ala Gly Gly
1               5                   10                  15

Pro Ser Gly Gly Gly Ala Gly Gly Gly Ala Gly Gly Gly
            20                  25                  30

Ala Gly Gly Gly Ala Gly Gly Gly Ala Gly Gly Gly Ala
        35                  40                  45

Gly Gly Gly Ala Gly Ala Pro
    50                  55

<210> SEQ ID NO 355
<211> LENGTH: 31
<212> TYPE: PRT
<213> ORGANISM: Artificial Sequence
<220> FEATURE:
<223> OTHER INFORMATION: Synthetic peptide

<400> SEQUENCE: 355

Gly Ala Pro Gly Gly Gly Gly Ala Gly Gly Gly Ala Gly Gly
1               5                   10                  15

Gly Ala Gly Gly Gly Pro Ser Gly Gly Gly Ala Gly Ala Pro
            20                  25                  30

<210> SEQ ID NO 356
<211> LENGTH: 36
<212> TYPE: PRT
<213> ORGANISM: Artificial Sequence
<220> FEATURE:
<223> OTHER INFORMATION: Synthetic peptide

<400> SEQUENCE: 356

Gly Ala Pro Gly Gly Gly Gly Ala Gly Gly Gly Ala Gly Gly
1               5                   10                  15

Gly Ala Gly Gly Gly Pro Ser Gly Gly Gly Ala Gly Gly Gly
            20                  25                  30

Ala Gly Ala Pro
        35

<210> SEQ ID NO 357
<211> LENGTH: 41
<212> TYPE: PRT
<213> ORGANISM: Artificial Sequence
<220> FEATURE:
<223> OTHER INFORMATION: Synthetic peptide

<400> SEQUENCE: 357

Gly Ala Pro Gly Gly Gly Ala Gly Gly Gly Ala Gly Gly
1               5                   10                  15

Gly Ala Gly Gly Gly Pro Ser Gly Gly Gly Ala Gly Gly Gly
            20                  25                  30

Ala Gly Gly Gly Gly Ala Gly Ala Pro
        35                  40

<210> SEQ ID NO 358
<211> LENGTH: 46
<212> TYPE: PRT
<213> ORGANISM: Artificial Sequence
<220> FEATURE:
<223> OTHER INFORMATION: Synthetic peptide
```

```
<400> SEQUENCE: 358

Gly Ala Pro Gly Gly Gly Gly Ala Gly Gly Gly Ala Gly Gly Gly
1               5                   10                  15

Gly Ala Gly Gly Gly Pro Ser Gly Gly Gly Ala Gly Gly Gly
            20                  25                  30

Ala Gly Gly Gly Ala Gly Gly Gly Ala Gly Ala Pro
        35                  40                  45

<210> SEQ ID NO 359
<211> LENGTH: 51
<212> TYPE: PRT
<213> ORGANISM: Artificial Sequence
<220> FEATURE:
<223> OTHER INFORMATION: Synthetic peptide

<400> SEQUENCE: 359

Gly Ala Pro Gly Gly Gly Ala Gly Gly Gly Ala Gly Gly Gly
1               5                   10                  15

Gly Ala Gly Gly Gly Pro Ser Gly Gly Gly Ala Gly Gly Gly
            20                  25                  30

Ala Gly Gly Gly Ala Gly Gly Gly Ala Gly Gly Gly Ala
        35                  40                  45

Gly Ala Pro
    50

<210> SEQ ID NO 360
<211> LENGTH: 56
<212> TYPE: PRT
<213> ORGANISM: Artificial Sequence
<220> FEATURE:
<223> OTHER INFORMATION: Synthetic peptide

<400> SEQUENCE: 360

Gly Ala Pro Gly Gly Gly Gly Ala Gly Gly Gly Ala Gly Gly Gly
1               5                   10                  15

Gly Ala Gly Gly Gly Pro Ser Gly Gly Gly Ala Gly Gly Gly
            20                  25                  30

Ala Gly Gly Gly Ala Gly Gly Gly Ala Gly Gly Gly Ala
        35                  40                  45

Gly Gly Gly Gly Ala Gly Ala Pro
    50                  55

<210> SEQ ID NO 361
<211> LENGTH: 61
<212> TYPE: PRT
<213> ORGANISM: Artificial Sequence
<220> FEATURE:
<223> OTHER INFORMATION: Synthetic peptide

<400> SEQUENCE: 361

Gly Ala Pro Gly Gly Gly Gly Ala Gly Gly Gly Ala Gly Gly Gly
1               5                   10                  15

Gly Ala Gly Gly Gly Pro Ser Gly Gly Gly Ala Gly Gly Gly
            20                  25                  30

Ala Gly Gly Gly Ala Gly Gly Gly Ala Gly Gly Gly Ala
        35                  40                  45

Gly Gly Gly Gly Ala Gly Gly Gly Ala Gly Ala Pro
    50                  55                  60

<210> SEQ ID NO 362
```

<211> LENGTH: 36
<212> TYPE: PRT
<213> ORGANISM: Artificial Sequence
<220> FEATURE:
<223> OTHER INFORMATION: Synthetic peptide

<400> SEQUENCE: 362

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Ala Pro
        35

<210> SEQ ID NO 363
<211> LENGTH: 41
<212> TYPE: PRT
<213> ORGANISM: Artificial Sequence
<220> FEATURE:
<223> OTHER INFORMATION: Synthetic peptide

<400> SEQUENCE: 363

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Gly Gly Gly Ala Gly Ala Pro
        35                  40

<210> SEQ ID NO 364
<211> LENGTH: 46
<212> TYPE: PRT
<213> ORGANISM: Artificial Sequence
<220> FEATURE:
<223> OTHER INFORMATION: Synthetic peptide

<400> SEQUENCE: 364

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Gly Gly Gly Ala Gly Gly Gly Gly Ala Gly Ala Pro
        35                  40                  45

<210> SEQ ID NO 365
<211> LENGTH: 51
<212> TYPE: PRT
<213> ORGANISM: Artificial Sequence
<220> FEATURE:
<223> OTHER INFORMATION: Synthetic peptide

<400> SEQUENCE: 365

Gly Ala Pro Gly Gly Gly Gly Ala Gly Gly Gly Ala Gly Gly
1               5                   10                  15

Gly Ala Gly Gly Gly Gly Ala Gly Gly Pro Ser Gly Gly Gly Gly
            20                  25                  30

Ala Gly Gly Gly Gly Ala Gly Gly Gly Ala Gly Gly Gly Ala
        35                  40                  45

Gly Ala Pro
    50

<210> SEQ ID NO 366

<211> LENGTH: 56
<212> TYPE: PRT
<213> ORGANISM: Artificial Sequence
<220> FEATURE:
<223> OTHER INFORMATION: Synthetic peptide

<400> SEQUENCE: 366

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Gly Gly Gly Ala Gly Gly Gly Ala Gly Gly Gly Ala
        35                  40                  45

Gly Gly Gly Gly Ala Gly Ala Pro
    50                  55

<210> SEQ ID NO 367
<211> LENGTH: 61
<212> TYPE: PRT
<213> ORGANISM: Artificial Sequence
<220> FEATURE:
<223> OTHER INFORMATION: Synthetic peptide

<400> SEQUENCE: 367

Gly Ala Pro Gly Gly Gly Ala Gly Gly Gly Ala Gly Gly
1               5                   10                  15

Gly Ala Gly Gly Gly Ala Gly Gly Gly Pro Ser Gly Gly Gly Gly
            20                  25                  30

Ala Gly Gly Gly Gly Ala Gly Gly Gly Ala Gly Gly Gly Ala
        35                  40                  45

Gly Gly Gly Gly Ala Gly Gly Gly Ala Gly Ala Pro
    50                  55                  60

<210> SEQ ID NO 368
<211> LENGTH: 66
<212> TYPE: PRT
<213> ORGANISM: Artificial Sequence
<220> FEATURE:
<223> OTHER INFORMATION: Synthetic peptide

<400> SEQUENCE: 368

Gly Ala Pro Gly Gly Gly Gly Ala Gly Gly Gly Ala Gly Gly
1               5                   10                  15

Gly Ala Gly Gly Gly Gly Ala Gly Gly Gly Pro Ser Gly Gly Gly Gly
            20                  25                  30

Ala Gly Gly Gly Gly Ala Gly Gly Gly Ala Gly Gly Gly Ala
        35                  40                  45

Gly Gly Gly Gly Ala Gly Gly Gly Ala Gly Gly Gly Ala Gly
    50                  55                  60

Ala Pro
65

<210> SEQ ID NO 369
<211> LENGTH: 41
<212> TYPE: PRT
<213> ORGANISM: Artificial Sequence
<220> FEATURE:
<223> OTHER INFORMATION: Synthetic peptide

<400> SEQUENCE: 369

Gly Ala Pro Gly Gly Gly Ala Gly Gly Gly Ala Gly Gly
1               5                   10                  15

Gly Ala Gly Gly Gly Ala Gly Gly Gly Ala Gly Gly Pro
            20                  25                  30

Ser Gly Gly Gly Gly Ala Gly Ala Pro
        35                  40

<210> SEQ ID NO 370
<211> LENGTH: 46
<212> TYPE: PRT
<213> ORGANISM: Artificial Sequence
<220> FEATURE:
<223> OTHER INFORMATION: Synthetic peptide

<400> SEQUENCE: 370

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Pro
            20                  25                  30

Ser Gly Gly Gly Gly Ala Gly Gly Gly Ala Gly Ala Pro
        35                  40                  45

<210> SEQ ID NO 371
<211> LENGTH: 51
<212> TYPE: PRT
<213> ORGANISM: Artificial Sequence
<220> FEATURE:
<223> OTHER INFORMATION: Synthetic peptide

<400> SEQUENCE: 371

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Pro
            20                  25                  30

Ser Gly Gly Gly Gly Ala Gly Gly Gly Ala Gly Gly Gly Ala
        35                  40                  45

Gly Ala Pro
    50

<210> SEQ ID NO 372
<211> LENGTH: 56
<212> TYPE: PRT
<213> ORGANISM: Artificial Sequence
<220> FEATURE:
<223> OTHER INFORMATION: Synthetic peptide

<400> SEQUENCE: 372

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Pro
            20                  25                  30

Ser Gly Gly Gly Gly Ala Gly Gly Gly Ala Gly Gly Gly Ala
        35                  40                  45

Gly Gly Gly Gly Ala Gly Ala Pro
    50                  55

<210> SEQ ID NO 373
<211> LENGTH: 61
<212> TYPE: PRT
<213> ORGANISM: Artificial Sequence
<220> FEATURE:
<223> OTHER INFORMATION: Synthetic peptide

<400> SEQUENCE: 373

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Pro
                20                  25                  30

Ser Gly Gly Gly Ala Gly Gly Gly Ala Gly Gly Gly Ala
        35                  40                  45

Gly Gly Gly Gly Ala Gly Gly Gly Ala Gly Ala Pro
    50                  55              60

<210> SEQ ID NO 374
<211> LENGTH: 66
<212> TYPE: PRT
<213> ORGANISM: Artificial Sequence
<220> FEATURE:
<223> OTHER INFORMATION: Synthetic peptide

<400> SEQUENCE: 374

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Pro
                20                  25                  30

Ser Gly Gly Gly Ala Gly Gly Gly Ala Gly Gly Gly Ala
        35                  40                  45

Gly Gly Gly Gly Ala Gly Gly Gly Ala Gly Gly Gly Ala Gly
    50                  55                  60

Ala Pro
65

<210> SEQ ID NO 375
<211> LENGTH: 71
<212> TYPE: PRT
<213> ORGANISM: Artificial Sequence
<220> FEATURE:
<223> OTHER INFORMATION: Synthetic peptide

<400> SEQUENCE: 375

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Pro
                20                  25                  30

Ser Gly Gly Gly Ala Gly Gly Gly Ala Gly Gly Gly Ala
        35                  40                  45

Gly Gly Gly Gly Ala Gly Gly Gly Ala Gly Gly Gly Ala Gly
    50                  55                  60

Gly Gly Gly Ala Gly Ala Pro
65                  70

<210> SEQ ID NO 376
<211> LENGTH: 46
<212> TYPE: PRT
<213> ORGANISM: Artificial Sequence
<220> FEATURE:
<223> OTHER INFORMATION: Synthetic peptide

<400> SEQUENCE: 376

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Pro Ser Gly Gly Gly Ala Gly Ala Pro
            35                  40                  45

<210> SEQ ID NO 377
<211> LENGTH: 51
<212> TYPE: PRT
<213> ORGANISM: Artificial Sequence
<220> FEATURE:
<223> OTHER INFORMATION: Synthetic peptide

<400> SEQUENCE: 377

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
            35                  40                  45

Gly Ala Pro
    50

<210> SEQ ID NO 378
<211> LENGTH: 56
<212> TYPE: PRT
<213> ORGANISM: Artificial Sequence
<220> FEATURE:
<223> OTHER INFORMATION: Synthetic peptide

<400> SEQUENCE: 378

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
            35                  40                  45

Gly Gly Gly Gly Ala Gly Ala Pro
    50                  55

<210> SEQ ID NO 379
<211> LENGTH: 61
<212> TYPE: PRT
<213> ORGANISM: Artificial Sequence
<220> FEATURE:
<223> OTHER INFORMATION: Synthetic peptide

<400> SEQUENCE: 379

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
            35                  40                  45

Gly Gly Gly Gly Ala Gly Gly Gly Ala Gly Ala Pro
    50                  55                  60

<210> SEQ ID NO 380
<211> LENGTH: 66
<212> TYPE: PRT
<213> ORGANISM: Artificial Sequence
<220> FEATURE:
<223> OTHER INFORMATION: Synthetic peptide

<400> SEQUENCE: 380

```
Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
        35                  40                  45

Gly Gly Gly Gly Ala Gly Gly Gly Ala Gly Gly Gly Ala Gly
        50                  55                  60

Ala Pro
65

<210> SEQ ID NO 381
<211> LENGTH: 71
<212> TYPE: PRT
<213> ORGANISM: Artificial Sequence
<220> FEATURE:
<223> OTHER INFORMATION: Synthetic peptide

<400> SEQUENCE: 381

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
        35                  40                  45

Gly Gly Gly Gly Ala Gly Gly Gly Ala Gly Gly Gly Ala Gly
        50                  55                  60

Gly Gly Gly Ala Gly Ala Pro
65                  70

<210> SEQ ID NO 382
<211> LENGTH: 76
<212> TYPE: PRT
<213> ORGANISM: Artificial Sequence
<220> FEATURE:
<223> OTHER INFORMATION: Synthetic peptide

<400> SEQUENCE: 382

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Pro Ser Gly Gly Gly Ala Gly Gly Gly Ala
        35                  40                  45

Gly Gly Gly Gly Ala Gly Gly Gly Ala Gly Gly Gly Ala Gly
        50                  55                  60

Gly Gly Gly Ala Gly Gly Gly Ala Gly Ala Pro
65                  70                  75

<210> SEQ ID NO 383
<211> LENGTH: 51
<212> TYPE: PRT
<213> ORGANISM: Artificial Sequence
<220> FEATURE:
<223> OTHER INFORMATION: Synthetic peptide

<400> SEQUENCE: 383

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
```

```
            20                  25                  30

Ala Gly Gly Gly Gly Ala Gly Gly Pro Ser Gly Gly Gly Ala
        35                  40                  45

Gly Ala Pro
    50

<210> SEQ ID NO 384
<211> LENGTH: 56
<212> TYPE: PRT
<213> ORGANISM: Artificial Sequence
<220> FEATURE:
<223> OTHER INFORMATION: Synthetic peptide

<400> SEQUENCE: 384

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Pro Ser Gly Gly Gly Ala
        35                  40                  45

Gly Gly Gly Gly Ala Gly Ala Pro
    50                  55

<210> SEQ ID NO 385
<211> LENGTH: 61
<212> TYPE: PRT
<213> ORGANISM: Artificial Sequence
<220> FEATURE:
<223> OTHER INFORMATION: Synthetic peptide

<400> SEQUENCE: 385

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Pro Ser Gly Gly Gly Ala
        35                  40                  45

Gly Gly Gly Gly Ala Gly Gly Gly Ala Gly Ala Pro
    50                  55                  60

<210> SEQ ID NO 386
<211> LENGTH: 66
<212> TYPE: PRT
<213> ORGANISM: Artificial Sequence
<220> FEATURE:
<223> OTHER INFORMATION: Synthetic peptide

<400> SEQUENCE: 386

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Pro Ser Gly Gly Gly Ala
        35                  40                  45

Gly Gly Gly Gly Ala Gly Gly Gly Ala Gly Gly Gly Ala Gly
    50                  55                  60

Ala Pro
65

<210> SEQ ID NO 387
```

<211> LENGTH: 71
<212> TYPE: PRT
<213> ORGANISM: Artificial Sequence
<220> FEATURE:
<223> OTHER INFORMATION: Synthetic peptide

<400> SEQUENCE: 387

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Gly Gly Pro Ser Gly Gly Gly Ala
        35                  40                  45

Gly Gly Gly Gly Ala Gly Gly Gly Ala Gly Gly Gly Ala Gly
    50                  55                  60

Gly Gly Gly Ala Gly Ala Pro
65                  70

<210> SEQ ID NO 388
<211> LENGTH: 76
<212> TYPE: PRT
<213> ORGANISM: Artificial Sequence
<220> FEATURE:
<223> OTHER INFORMATION: Synthetic peptide

<400> SEQUENCE: 388

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Gly Gly Pro Ser Gly Gly Gly Ala
        35                  40                  45

Gly Gly Gly Gly Ala Gly Gly Gly Ala Gly Gly Gly Ala Gly
    50                  55                  60

Gly Gly Gly Ala Gly Gly Gly Gly Ala Gly Ala Pro
65                  70                  75

<210> SEQ ID NO 389
<211> LENGTH: 81
<212> TYPE: PRT
<213> ORGANISM: Artificial Sequence
<220> FEATURE:
<223> OTHER INFORMATION: Synthetic peptide

<400> SEQUENCE: 389

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Gly Gly Pro Ser Gly Gly Gly Ala
        35                  40                  45

Gly Gly Gly Gly Ala Gly Gly Gly Ala Gly Gly Gly Ala Gly
    50                  55                  60

Gly Gly Gly Ala Gly Gly Gly Gly Ala Gly Gly Gly Ala Gly Ala
65                  70                  75                  80

Pro

<210> SEQ ID NO 390
<211> LENGTH: 16
<212> TYPE: PRT

-continued

<213> ORGANISM: Artificial Sequence
<220> FEATURE:
<223> OTHER INFORMATION: Synthetic peptide

<400> SEQUENCE: 390

Gly Ala Pro Gly Gly Gly Pro Ser Gly Gly Gly Ala Gly Ala Pro
1               5                   10                  15

<210> SEQ ID NO 391
<211> LENGTH: 21
<212> TYPE: PRT
<213> ORGANISM: Artificial Sequence
<220> FEATURE:
<223> OTHER INFORMATION: Synthetic peptide

<400> SEQUENCE: 391

Gly Ala Pro Gly Gly Gly Pro Ser Gly Gly Gly Ala Gly Gly Gly
1               5                   10                  15

Gly Ala Gly Ala Pro
            20

<210> SEQ ID NO 392
<211> LENGTH: 26
<212> TYPE: PRT
<213> ORGANISM: Artificial Sequence
<220> FEATURE:
<223> OTHER INFORMATION: Synthetic peptide

<400> SEQUENCE: 392

Gly Ala Pro Gly Gly Gly Pro Ser Gly Gly Gly Ala Gly Gly Gly
1               5                   10                  15

Gly Ala Gly Gly Gly Gly Ala Gly Ala Pro
            20                  25

<210> SEQ ID NO 393
<211> LENGTH: 31
<212> TYPE: PRT
<213> ORGANISM: Artificial Sequence
<220> FEATURE:
<223> OTHER INFORMATION: Synthetic peptide

<400> SEQUENCE: 393

Gly Ala Pro Gly Gly Gly Pro Ser Gly Gly Gly Ala Gly Gly Gly
1               5                   10                  15

Gly Ala Gly Gly Gly Gly Ala Gly Gly Gly Gly Ala Gly Ala Pro
            20                  25                  30

<210> SEQ ID NO 394
<211> LENGTH: 36
<212> TYPE: PRT
<213> ORGANISM: Artificial Sequence
<220> FEATURE:
<223> OTHER INFORMATION: Synthetic peptide

<400> SEQUENCE: 394

Gly Ala Pro Gly Gly Gly Pro Ser Gly Gly Gly Ala Gly Gly Gly
1               5                   10                  15

Gly Ala Gly Gly Gly Gly Ala Gly Gly Gly Gly Ala Gly Gly Gly
            20                  25                  30

Ala Gly Ala Pro
        35

<210> SEQ ID NO 395
<211> LENGTH: 41

```
<212> TYPE: PRT
<213> ORGANISM: Artificial Sequence
<220> FEATURE:
<223> OTHER INFORMATION: Synthetic peptide

<400> SEQUENCE: 395

Gly Ala Pro Gly Gly Gly Pro Ser Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Ala Pro
        35                  40

<210> SEQ ID NO 396
<211> LENGTH: 46
<212> TYPE: PRT
<213> ORGANISM: Artificial Sequence
<220> FEATURE:
<223> OTHER INFORMATION: Synthetic peptide

<400> SEQUENCE: 396

Gly Ala Pro Gly Gly Gly Pro Ser Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Gly Gly Gly Ala Gly Ala Pro
        35                  40                  45

<210> SEQ ID NO 397
<211> LENGTH: 30
<212> TYPE: PRT
<213> ORGANISM: Artificial Sequence
<220> FEATURE:
<223> OTHER INFORMATION: Synthetic peptide

<400> SEQUENCE: 397

Gly Ala Pro Gly Gly Gly Gly Ala Ala Ala Ala Ser Gly Gly Gly
1               5                   10                  15

Pro Ser Gly Gly Gly Gly Ala Ala Ala Ala Gly Ala Pro
            20                  25                  30

<210> SEQ ID NO 398
<211> LENGTH: 35
<212> TYPE: PRT
<213> ORGANISM: Artificial Sequence
<220> FEATURE:
<223> OTHER INFORMATION: Synthetic peptide

<400> SEQUENCE: 398

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Ala Ala Ala Ala
            20                  25                  30

Gly Ala Pro
        35

<210> SEQ ID NO 399
<211> LENGTH: 40
<212> TYPE: PRT
<213> ORGANISM: Artificial Sequence
<220> FEATURE:
<223> OTHER INFORMATION: Synthetic peptide

<400> SEQUENCE: 399
```

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Gly Gly Gly
            20                  25                  30

Ala Ala Ala Ala Ala Gly Ala Pro
        35                  40

<210> SEQ ID NO 400
<211> LENGTH: 45
<212> TYPE: PRT
<213> ORGANISM: Artificial Sequence
<220> FEATURE:
<223> OTHER INFORMATION: Synthetic peptide

<400> SEQUENCE: 400

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Gly Gly Gly
            20                  25                  30

Ala Gly Gly Gly Gly Ala Ala Ala Ala Ala Gly Ala Pro
        35                  40                  45

<210> SEQ ID NO 401
<211> LENGTH: 50
<212> TYPE: PRT
<213> ORGANISM: Artificial Sequence
<220> FEATURE:
<223> OTHER INFORMATION: Synthetic peptide

<400> SEQUENCE: 401

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Gly Gly Gly
            20                  25                  30

Ala Gly Gly Gly Gly Ala Gly Gly Gly Ala Ala Ala Ala Ala Gly
        35                  40                  45

Ala Pro
    50

<210> SEQ ID NO 402
<211> LENGTH: 55
<212> TYPE: PRT
<213> ORGANISM: Artificial Sequence
<220> FEATURE:
<223> OTHER INFORMATION: Synthetic peptide

<400> SEQUENCE: 402

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Gly Gly Gly
            20                  25                  30

Ala Gly Gly Gly Gly Ala Gly Gly Gly Ala Gly Gly Gly Ala
        35                  40                  45

Ala Ala Ala Ala Gly Ala Pro
    50                  55

<210> SEQ ID NO 403
<211> LENGTH: 60
<212> TYPE: PRT
<213> ORGANISM: Artificial Sequence
<220> FEATURE:

<223> OTHER INFORMATION: Synthetic peptide

<400> SEQUENCE: 403

Gly Ala Pro Gly Gly Gly Gly Ala Ala Ala Ala Ser Gly Gly Gly
1               5                   10                  15

Pro Ser Gly Gly Gly Gly Ala Gly Gly Gly Ala Gly Gly Gly
            20                  25                  30

Ala Gly Gly Gly Ala Gly Gly Gly Ala Gly Gly Gly Ala
        35                  40                  45

Gly Gly Gly Gly Ala Ala Ala Ala Ala Gly Ala Pro
        50                  55                  60

<210> SEQ ID NO 404
<211> LENGTH: 35
<212> TYPE: PRT
<213> ORGANISM: Artificial Sequence
<220> FEATURE:
<223> OTHER INFORMATION: Synthetic peptide

<400> SEQUENCE: 404

Gly Ala Pro Gly Gly Gly Gly Ala Gly Gly Gly Gly Ala Ala Ala Ala
1               5                   10                  15

Ala Ser Gly Gly Gly Pro Ser Gly Gly Gly Ala Ala Ala Ala Ala
            20                  25                  30

Gly Ala Pro
        35

<210> SEQ ID NO 405
<211> LENGTH: 40
<212> TYPE: PRT
<213> ORGANISM: Artificial Sequence
<220> FEATURE:
<223> OTHER INFORMATION: Synthetic peptide

<400> SEQUENCE: 405

Gly Ala Pro Gly Gly Gly Gly Ala Gly Gly Gly Gly Ala Ala Ala Ala
1               5                   10                  15

Ala Ser Gly Gly Gly Pro Ser Gly Gly Gly Ala Gly Gly Gly Gly
            20                  25                  30

Ala Ala Ala Ala Ala Gly Ala Pro
        35                  40

<210> SEQ ID NO 406
<211> LENGTH: 45
<212> TYPE: PRT
<213> ORGANISM: Artificial Sequence
<220> FEATURE:
<223> OTHER INFORMATION: Synthetic peptide

<400> SEQUENCE: 406

Gly Ala Pro Gly Gly Gly Gly Ala Gly Gly Gly Gly Ala Ala Ala Ala
1               5                   10                  15

Ala Ser Gly Gly Gly Pro Ser Gly Gly Gly Ala Gly Gly Gly Gly
            20                  25                  30

Ala Gly Gly Gly Gly Ala Ala Ala Ala Ala Gly Ala Pro
        35                  40                  45

<210> SEQ ID NO 407
<211> LENGTH: 50
<212> TYPE: PRT
<213> ORGANISM: Artificial Sequence
<220> FEATURE:

<223> OTHER INFORMATION: Synthetic peptide

<400> SEQUENCE: 407

Gly Ala Pro Gly Gly Gly Gly Ala Gly Gly Gly Ala Ala Ala Ala
1               5                   10                  15

Ala Ser Gly Gly Gly Pro Ser Gly Gly Gly Ala Gly Gly Gly
            20                  25                  30

Ala Gly Gly Gly Gly Ala Gly Gly Gly Ala Ala Ala Ala Gly
        35                  40                  45

Ala Pro
    50

<210> SEQ ID NO 408
<211> LENGTH: 55
<212> TYPE: PRT
<213> ORGANISM: Artificial Sequence
<220> FEATURE:
<223> OTHER INFORMATION: Synthetic peptide

<400> SEQUENCE: 408

Gly Ala Pro Gly Gly Gly Gly Ala Gly Gly Gly Ala Ala Ala Ala
1               5                   10                  15

Ala Ser Gly Gly Gly Pro Ser Gly Gly Gly Ala Gly Gly Gly
            20                  25                  30

Ala Gly Gly Gly Gly Ala Gly Gly Gly Ala Gly Gly Gly Ala
        35                  40                  45

Ala Ala Ala Ala Gly Ala Pro
    50                  55

<210> SEQ ID NO 409
<211> LENGTH: 60
<212> TYPE: PRT
<213> ORGANISM: Artificial Sequence
<220> FEATURE:
<223> OTHER INFORMATION: Synthetic peptide

<400> SEQUENCE: 409

Gly Ala Pro Gly Gly Gly Gly Ala Gly Gly Gly Ala Ala Ala Ala
1               5                   10                  15

Ala Ser Gly Gly Gly Pro Ser Gly Gly Gly Ala Gly Gly Gly
            20                  25                  30

Ala Gly Gly Gly Ala Gly Gly Gly Ala Gly Gly Gly Gly Ala
        35                  40                  45

Gly Gly Gly Gly Ala Ala Ala Ala Ala Gly Ala Pro
    50                  55                  60

<210> SEQ ID NO 410
<211> LENGTH: 65
<212> TYPE: PRT
<213> ORGANISM: Artificial Sequence
<220> FEATURE:
<223> OTHER INFORMATION: Synthetic peptide

<400> SEQUENCE: 410

Gly Ala Pro Gly Gly Gly Gly Ala Gly Gly Gly Ala Ala Ala Ala
1               5                   10                  15

Ala Ser Gly Gly Gly Pro Ser Gly Gly Gly Ala Gly Gly Gly
            20                  25                  30

Ala Gly Gly Gly Gly Ala Gly Gly Gly Ala Gly Gly Gly Ala
        35                  40                  45

-continued

```
Gly Gly Gly Gly Ala Gly Gly Ala Ala Ala Ala Gly Ala
    50                  55                  60

Pro
65

<210> SEQ ID NO 411
<211> LENGTH: 40
<212> TYPE: PRT
<213> ORGANISM: Artificial Sequence
<220> FEATURE:
<223> OTHER INFORMATION: Synthetic peptide

<400> SEQUENCE: 411

Gly Ala Pro Gly Gly Gly Ala Gly Gly Gly Ala Gly Gly Gly
1               5                   10                  15

Gly Ala Ala Ala Ala Ala Ser Gly Gly Gly Pro Ser Gly Gly Gly Gly
            20                  25                  30

Ala Ala Ala Ala Ala Gly Ala Pro
        35                  40

<210> SEQ ID NO 412
<211> LENGTH: 45
<212> TYPE: PRT
<213> ORGANISM: Artificial Sequence
<220> FEATURE:
<223> OTHER INFORMATION: Synthetic peptide

<400> SEQUENCE: 412

Gly Ala Pro Gly Gly Gly Gly Ala Gly Gly Gly Ala Gly Gly Gly
1               5                   10                  15

Gly Ala Ala Ala Ala Ala Ser Gly Gly Gly Pro Ser Gly Gly Gly Gly
            20                  25                  30

Ala Gly Gly Gly Gly Ala Ala Ala Ala Ala Gly Ala Pro
        35                  40                  45

<210> SEQ ID NO 413
<211> LENGTH: 50
<212> TYPE: PRT
<213> ORGANISM: Artificial Sequence
<220> FEATURE:
<223> OTHER INFORMATION: Synthetic peptide

<400> SEQUENCE: 413

Gly Ala Pro Gly Gly Gly Gly Ala Gly Gly Gly Ala Gly Gly Gly
1               5                   10                  15

Gly Ala Ala Ala Ala Ala Ser Gly Gly Gly Pro Ser Gly Gly Gly Gly
            20                  25                  30

Ala Gly Gly Gly Gly Ala Gly Gly Gly Ala Ala Ala Ala Ala Gly
        35                  40                  45

Ala Pro
    50

<210> SEQ ID NO 414
<211> LENGTH: 55
<212> TYPE: PRT
<213> ORGANISM: Artificial Sequence
<220> FEATURE:
<223> OTHER INFORMATION: Synthetic peptide

<400> SEQUENCE: 414

Gly Ala Pro Gly Gly Gly Gly Ala Gly Gly Gly Ala Gly Gly Gly
1               5                   10                  15
```

Gly Ala Ala Ala Ala Ala Ser Gly Gly Gly Pro Ser Gly Gly Gly
            20                  25                  30

Ala Gly Gly Gly Gly Ala Gly Gly Gly Ala Gly Gly Gly Ala
        35                  40                  45

Ala Ala Ala Ala Gly Ala Pro
    50                  55

<210> SEQ ID NO 415
<211> LENGTH: 60
<212> TYPE: PRT
<213> ORGANISM: Artificial Sequence
<220> FEATURE:
<223> OTHER INFORMATION: Synthetic peptide

<400> SEQUENCE: 415

Gly Ala Pro Gly Gly Gly Gly Ala Gly Gly Gly Ala Gly Gly Gly
1               5                   10                  15

Gly Ala Ala Ala Ala Ala Ser Gly Gly Gly Pro Ser Gly Gly Gly
            20                  25                  30

Ala Gly Gly Gly Gly Ala Gly Gly Gly Ala Gly Gly Gly Ala
        35                  40                  45

Gly Gly Gly Gly Ala Ala Ala Ala Ala Gly Ala Pro
    50                  55                  60

<210> SEQ ID NO 416
<211> LENGTH: 65
<212> TYPE: PRT
<213> ORGANISM: Artificial Sequence
<220> FEATURE:
<223> OTHER INFORMATION: Synthetic peptide

<400> SEQUENCE: 416

Gly Ala Pro Gly Gly Gly Gly Ala Gly Gly Gly Ala Gly Gly Gly
1               5                   10                  15

Gly Ala Ala Ala Ala Ala Ser Gly Gly Gly Pro Ser Gly Gly Gly
            20                  25                  30

Ala Gly Gly Gly Gly Ala Gly Gly Gly Ala Gly Gly Gly Ala
        35                  40                  45

Gly Gly Gly Gly Ala Gly Gly Gly Ala Ala Ala Ala Gly Ala
    50                  55                  60

Pro
65

<210> SEQ ID NO 417
<211> LENGTH: 70
<212> TYPE: PRT
<213> ORGANISM: Artificial Sequence
<220> FEATURE:
<223> OTHER INFORMATION: Synthetic peptide

<400> SEQUENCE: 417

Gly Ala Pro Gly Gly Gly Gly Ala Gly Gly Gly Ala Gly Gly Gly
1               5                   10                  15

Gly Ala Ala Ala Ala Ala Ser Gly Gly Gly Pro Ser Gly Gly Gly
            20                  25                  30

Ala Gly Gly Gly Gly Ala Gly Gly Gly Ala Gly Gly Gly Ala
        35                  40                  45

Gly Gly Gly Gly Ala Gly Gly Gly Ala Gly Gly Gly Ala Ala
    50                  55                  60

Ala Ala Ala Gly Ala Pro

```
            65                  70

<210> SEQ ID NO 418
<211> LENGTH: 45
<212> TYPE: PRT
<213> ORGANISM: Artificial Sequence
<220> FEATURE:
<223> OTHER INFORMATION: Synthetic peptide

<400> SEQUENCE: 418

Gly Ala Pro Gly Gly Gly Gly Ala Gly Gly Gly Ala Gly Gly Gly
1               5                   10                  15

Gly Ala Gly Gly Gly Gly Ala Ala Ala Ala Ser Gly Gly Gly Pro
                20                  25                  30

Ser Gly Gly Gly Gly Ala Ala Ala Ala Ala Gly Ala Pro
        35                  40                  45

<210> SEQ ID NO 419
<211> LENGTH: 50
<212> TYPE: PRT
<213> ORGANISM: Artificial Sequence
<220> FEATURE:
<223> OTHER INFORMATION: Synthetic peptide

<400> SEQUENCE: 419

Gly Ala Pro Gly Gly Gly Gly Ala Gly Gly Gly Ala Gly Gly Gly
1               5                   10                  15

Gly Ala Gly Gly Gly Gly Ala Ala Ala Ala Ser Gly Gly Gly Pro
                20                  25                  30

Ser Gly Gly Gly Gly Ala Gly Gly Gly Ala Ala Ala Ala Ala Gly
        35                  40                  45

Ala Pro
    50

<210> SEQ ID NO 420
<211> LENGTH: 55
<212> TYPE: PRT
<213> ORGANISM: Artificial Sequence
<220> FEATURE:
<223> OTHER INFORMATION: Synthetic peptide

<400> SEQUENCE: 420

Gly Ala Pro Gly Gly Gly Gly Ala Gly Gly Gly Ala Gly Gly Gly
1               5                   10                  15

Gly Ala Gly Gly Gly Gly Ala Ala Ala Ala Ser Gly Gly Gly Pro
                20                  25                  30

Ser Gly Gly Gly Gly Ala Gly Gly Gly Ala Gly Gly Gly Gly Ala
        35                  40                  45

Ala Ala Ala Ala Gly Ala Pro
    50                  55

<210> SEQ ID NO 421
<211> LENGTH: 60
<212> TYPE: PRT
<213> ORGANISM: Artificial Sequence
<220> FEATURE:
<223> OTHER INFORMATION: Synthetic peptide

<400> SEQUENCE: 421

Gly Ala Pro Gly Gly Gly Gly Ala Gly Gly Gly Ala Gly Gly Gly
1               5                   10                  15

Gly Ala Gly Gly Gly Gly Ala Ala Ala Ala Ser Gly Gly Gly Pro
```

```
            20                  25                  30

Ser Gly Gly Gly Gly Ala Gly Gly Gly Ala Gly Gly Gly Ala
        35                  40                  45

Gly Gly Gly Gly Ala Ala Ala Ala Gly Ala Pro
    50                  55                  60

<210> SEQ ID NO 422
<211> LENGTH: 65
<212> TYPE: PRT
<213> ORGANISM: Artificial Sequence
<220> FEATURE:
<223> OTHER INFORMATION: Synthetic peptide

<400> SEQUENCE: 422

Gly Ala Pro Gly Gly Gly Gly Ala Gly Gly Gly Ala Gly Gly Gly
1               5                   10                  15

Gly Ala Gly Gly Gly Gly Ala Ala Ala Ala Ala Ser Gly Gly Pro
                20                  25                  30

Ser Gly Gly Gly Gly Ala Gly Gly Gly Ala Gly Gly Gly Ala
        35                  40                  45

Gly Gly Gly Gly Ala Gly Gly Gly Ala Ala Ala Ala Gly Ala
    50                  55                  60

Pro
65

<210> SEQ ID NO 423
<211> LENGTH: 70
<212> TYPE: PRT
<213> ORGANISM: Artificial Sequence
<220> FEATURE:
<223> OTHER INFORMATION: Synthetic peptide

<400> SEQUENCE: 423

Gly Ala Pro Gly Gly Gly Gly Ala Gly Gly Gly Ala Gly Gly Gly
1               5                   10                  15

Gly Ala Gly Gly Gly Gly Ala Ala Ala Ala Ala Ser Gly Gly Pro
                20                  25                  30

Ser Gly Gly Gly Gly Ala Gly Gly Gly Ala Gly Gly Gly Ala
        35                  40                  45

Gly Gly Gly Gly Ala Gly Gly Gly Ala Gly Gly Gly Ala Ala
    50                  55                  60

Ala Ala Ala Gly Ala Pro
65                  70

<210> SEQ ID NO 424
<211> LENGTH: 75
<212> TYPE: PRT
<213> ORGANISM: Artificial Sequence
<220> FEATURE:
<223> OTHER INFORMATION: Synthetic peptide

<400> SEQUENCE: 424

Gly Ala Pro Gly Gly Gly Gly Ala Gly Gly Gly Ala Gly Gly Gly
1               5                   10                  15

Gly Ala Gly Gly Gly Gly Ala Ala Ala Ala Ala Ser Gly Gly Pro
                20                  25                  30

Ser Gly Gly Gly Gly Ala Gly Gly Gly Ala Gly Gly Gly Ala
        35                  40                  45

Gly Gly Gly Gly Ala Gly Gly Gly Ala Gly Gly Gly Ala Gly
    50                  55                  60
```

Gly Gly Gly Ala Ala Ala Ala Gly Ala Pro
        65                  70                  75

<210> SEQ ID NO 425
<211> LENGTH: 50
<212> TYPE: PRT
<213> ORGANISM: Artificial Sequence
<220> FEATURE:
<223> OTHER INFORMATION: Synthetic peptide

<400> SEQUENCE: 425

Gly Ala Pro Gly Gly Gly Ala Gly Gly Gly Ala Gly Gly Gly
1               5                   10                  15

Gly Ala Gly Gly Gly Gly Ala Gly Gly Gly Ala Ala Ala Ala
                20                  25                  30

Ser Gly Gly Gly Pro Ser Gly Gly Gly Ala Ala Ala Ala Gly
        35                  40                  45

Ala Pro
    50

<210> SEQ ID NO 426
<211> LENGTH: 55
<212> TYPE: PRT
<213> ORGANISM: Artificial Sequence
<220> FEATURE:
<223> OTHER INFORMATION: Synthetic peptide

<400> SEQUENCE: 426

Gly Ala Pro Gly Gly Gly Ala Gly Gly Gly Ala Gly Gly Gly
1               5                   10                  15

Gly Ala Gly Gly Gly Gly Ala Gly Gly Gly Ala Ala Ala Ala
                20                  25                  30

Ser Gly Gly Gly Pro Ser Gly Gly Gly Ala Gly Gly Gly Ala
        35                  40                  45

Ala Ala Ala Ala Gly Ala Pro
    50                  55

<210> SEQ ID NO 427
<211> LENGTH: 60
<212> TYPE: PRT
<213> ORGANISM: Artificial Sequence
<220> FEATURE:
<223> OTHER INFORMATION: Synthetic peptide

<400> SEQUENCE: 427

Gly Ala Pro Gly Gly Gly Ala Gly Gly Gly Ala Gly Gly Gly
1               5                   10                  15

Gly Ala Gly Gly Gly Gly Ala Gly Gly Gly Ala Ala Ala Ala
                20                  25                  30

Ser Gly Gly Gly Pro Ser Gly Gly Gly Ala Gly Gly Gly Ala
        35                  40                  45

Gly Gly Gly Gly Ala Ala Ala Ala Gly Ala Pro
    50                  55                  60

<210> SEQ ID NO 428
<211> LENGTH: 65
<212> TYPE: PRT
<213> ORGANISM: Artificial Sequence
<220> FEATURE:
<223> OTHER INFORMATION: Synthetic peptide

<400> SEQUENCE: 428

Gly Ala Pro Gly Gly Gly Ala Gly Gly Gly Ala Gly Gly
1               5                   10                  15

Gly Ala Gly Gly Gly Ala Gly Gly Gly Ala Ala Ala Ala
            20                  25                  30

Ser Gly Gly Gly Pro Ser Gly Gly Gly Ala Gly Gly Gly Ala
        35                  40                  45

Gly Gly Gly Ala Gly Gly Gly Ala Ala Ala Ala Gly Ala
    50                  55                  60

Pro
65

<210> SEQ ID NO 429
<211> LENGTH: 70
<212> TYPE: PRT
<213> ORGANISM: Artificial Sequence
<220> FEATURE:
<223> OTHER INFORMATION: Synthetic peptide

<400> SEQUENCE: 429

Gly Ala Pro Gly Gly Gly Ala Gly Gly Gly Ala Gly Gly
1               5                   10                  15

Gly Ala Gly Gly Gly Ala Gly Gly Gly Ala Ala Ala Ala
            20                  25                  30

Ser Gly Gly Gly Pro Ser Gly Gly Gly Ala Gly Gly Gly Ala
        35                  40                  45

Gly Gly Gly Ala Gly Gly Gly Ala Gly Gly Gly Ala Ala
    50                  55                  60

Ala Ala Ala Gly Ala Pro
65                  70

<210> SEQ ID NO 430
<211> LENGTH: 75
<212> TYPE: PRT
<213> ORGANISM: Artificial Sequence
<220> FEATURE:
<223> OTHER INFORMATION: Synthetic peptide

<400> SEQUENCE: 430

Gly Ala Pro Gly Gly Gly Ala Gly Gly Gly Ala Gly Gly
1               5                   10                  15

Gly Ala Gly Gly Gly Ala Gly Gly Gly Ala Ala Ala Ala
            20                  25                  30

Ser Gly Gly Gly Pro Ser Gly Gly Gly Ala Gly Gly Gly Ala
        35                  40                  45

Gly Gly Gly Ala Gly Gly Gly Ala Gly Gly Gly Ala Gly
    50                  55                  60

Gly Gly Ala Ala Ala Ala Ala Gly Ala Pro
65                  70                  75

<210> SEQ ID NO 431
<211> LENGTH: 80
<212> TYPE: PRT
<213> ORGANISM: Artificial Sequence
<220> FEATURE:
<223> OTHER INFORMATION: Synthetic peptide

<400> SEQUENCE: 431

Gly Ala Pro Gly Gly Gly Ala Gly Gly Gly Ala Gly Gly
1               5                   10                  15

Gly Ala Gly Gly Gly Ala Gly Gly Gly Ala Ala Ala Ala
        20                  25                  30

Ser Gly Gly Gly Pro Ser Gly Gly Gly Ala Gly Gly Gly Ala
            35                  40                  45

Gly Gly Gly Gly Ala Gly Gly Gly Ala Gly Gly Gly Ala Gly
        50                  55                  60

Gly Gly Gly Ala Gly Gly Gly Ala Ala Ala Ala Gly Ala Pro
65                  70                  75                  80

<210> SEQ ID NO 432
<211> LENGTH: 55
<212> TYPE: PRT
<213> ORGANISM: Artificial Sequence
<220> FEATURE:
<223> OTHER INFORMATION: Synthetic peptide

<400> SEQUENCE: 432

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
        20                  25                  30

Ala Ala Ala Ala Ala Ser Gly Gly Gly Pro Ser Gly Gly Gly Ala
            35                  40                  45

Ala Ala Ala Ala Gly Ala Pro
    50                  55

<210> SEQ ID NO 433
<211> LENGTH: 60
<212> TYPE: PRT
<213> ORGANISM: Artificial Sequence
<220> FEATURE:
<223> OTHER INFORMATION: Synthetic peptide

<400> SEQUENCE: 433

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
        20                  25                  30

Ala Ala Ala Ala Ala Ser Gly Gly Gly Pro Ser Gly Gly Gly Ala
            35                  40                  45

Gly Gly Gly Gly Ala Ala Ala Ala Ala Gly Ala Pro
    50                  55                  60

<210> SEQ ID NO 434
<211> LENGTH: 65
<212> TYPE: PRT
<213> ORGANISM: Artificial Sequence
<220> FEATURE:
<223> OTHER INFORMATION: Synthetic peptide

<400> SEQUENCE: 434

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
        20                  25                  30

Ala Ala Ala Ala Ala Ser Gly Gly Gly Pro Ser Gly Gly Gly Ala
            35                  40                  45

Gly Gly Gly Gly Ala Gly Gly Gly Ala Ala Ala Ala Ala Gly Ala
    50                  55                  60

Pro

65

<210> SEQ ID NO 435
<211> LENGTH: 70
<212> TYPE: PRT
<213> ORGANISM: Artificial Sequence
<220> FEATURE:
<223> OTHER INFORMATION: Synthetic peptide

<400> SEQUENCE: 435

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Ala Ala Ala Ala Ser Gly Gly Gly Pro Ser Gly Gly Gly Ala
        35                  40                  45

Gly Gly Gly Gly Ala Gly Gly Gly Ala Gly Gly Gly Ala Ala
    50                  55                  60

Ala Ala Ala Gly Ala Pro
65                  70

<210> SEQ ID NO 436
<211> LENGTH: 75
<212> TYPE: PRT
<213> ORGANISM: Artificial Sequence
<220> FEATURE:
<223> OTHER INFORMATION: Synthetic peptide

<400> SEQUENCE: 436

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Ala Ala Ala Ala Ser Gly Gly Gly Pro Ser Gly Gly Gly Ala
        35                  40                  45

Gly Gly Gly Gly Ala Gly Gly Gly Ala Gly Gly Gly Ala Gly
    50                  55                  60

Gly Gly Gly Ala Ala Ala Ala Ala Gly Ala Pro
65                  70                  75

<210> SEQ ID NO 437
<211> LENGTH: 80
<212> TYPE: PRT
<213> ORGANISM: Artificial Sequence
<220> FEATURE:
<223> OTHER INFORMATION: Synthetic peptide

<400> SEQUENCE: 437

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Ala Ala Ala Ala Ser Gly Gly Gly Pro Ser Gly Gly Gly Ala
        35                  40                  45

Gly Gly Gly Gly Ala Gly Gly Gly Ala Gly Gly Gly Ala Gly
    50                  55                  60

Gly Gly Gly Ala Gly Gly Gly Ala Ala Ala Ala Ala Gly Ala Pro
65                  70                  75                  80

<210> SEQ ID NO 438

<211> LENGTH: 85
<212> TYPE: PRT
<213> ORGANISM: Artificial Sequence
<220> FEATURE:
<223> OTHER INFORMATION: Synthetic peptide

<400> SEQUENCE: 438

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Ala Ala Ala Ala Ser Gly Gly Gly Pro Ser Gly Gly Gly Ala
            35                  40                  45

Gly Gly Gly Ala Gly Gly Gly Gly Ala Gly Gly Gly Gly Ala Gly
        50                  55                  60

Gly Gly Gly Ala Gly Gly Gly Ala Gly Gly Gly Ala Ala Ala
65                  70                  75                  80

Ala Ala Gly Ala Pro
                85

<210> SEQ ID NO 439
<211> LENGTH: 60
<212> TYPE: PRT
<213> ORGANISM: Artificial Sequence
<220> FEATURE:
<223> OTHER INFORMATION: Synthetic peptide

<400> SEQUENCE: 439

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Ala Ala Ala Ala Ala Ser Gly Gly Gly Pro Ser
            35                  40                  45

Gly Gly Gly Gly Ala Ala Ala Ala Ala Gly Ala Pro
        50                  55                  60

<210> SEQ ID NO 440
<211> LENGTH: 65
<212> TYPE: PRT
<213> ORGANISM: Artificial Sequence
<220> FEATURE:
<223> OTHER INFORMATION: Synthetic peptide

<400> SEQUENCE: 440

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Ala Ala Ala Ala Ala Ser Gly Gly Gly Pro Ser
            35                  40                  45

Gly Gly Gly Gly Ala Gly Gly Gly Ala Ala Ala Ala Ala Gly Ala
        50                  55                  60

Pro
65

<210> SEQ ID NO 441
<211> LENGTH: 70
<212> TYPE: PRT
<213> ORGANISM: Artificial Sequence
<220> FEATURE:

<223> OTHER INFORMATION: Synthetic peptide

<400> SEQUENCE: 441

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
                20                  25                  30

Ala Gly Gly Gly Ala Ala Ala Ala Ala Ser Gly Gly Pro Ser
        35                  40                  45

Gly Gly Gly Gly Ala Gly Gly Gly Ala Gly Gly Gly Ala Ala
    50                  55                  60

Ala Ala Ala Gly Ala Pro
65                  70

<210> SEQ ID NO 442
<211> LENGTH: 75
<212> TYPE: PRT
<213> ORGANISM: Artificial Sequence
<220> FEATURE:
<223> OTHER INFORMATION: Synthetic peptide

<400> SEQUENCE: 442

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
                20                  25                  30

Ala Gly Gly Gly Ala Ala Ala Ala Ala Ser Gly Gly Pro Ser
        35                  40                  45

Gly Gly Gly Gly Ala Gly Gly Gly Ala Gly Gly Gly Ala Gly
    50                  55                  60

Gly Gly Gly Ala Ala Ala Ala Gly Ala Pro
65                  70                  75

<210> SEQ ID NO 443
<211> LENGTH: 80
<212> TYPE: PRT
<213> ORGANISM: Artificial Sequence
<220> FEATURE:
<223> OTHER INFORMATION: Synthetic peptide

<400> SEQUENCE: 443

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
                20                  25                  30

Ala Gly Gly Gly Ala Ala Ala Ala Ala Ser Gly Gly Pro Ser
        35                  40                  45

Gly Gly Gly Gly Ala Gly Gly Gly Ala Gly Gly Gly Ala Gly
    50                  55                  60

Gly Gly Gly Ala Gly Gly Gly Ala Ala Ala Ala Gly Ala Pro
65                  70                  75                  80

<210> SEQ ID NO 444
<211> LENGTH: 85
<212> TYPE: PRT
<213> ORGANISM: Artificial Sequence
<220> FEATURE:
<223> OTHER INFORMATION: Synthetic peptide

<400> SEQUENCE: 444

```
Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Ala Ala Ala Ala Ser Gly Gly Pro Ser
        35                  40                  45

Gly Gly Gly Gly Ala Gly Gly Gly Ala Gly Gly Gly Ala Gly
    50                  55                  60

Gly Gly Gly Ala Gly Gly Gly Ala Gly Gly Gly Ala Ala Ala
65                  70                  75                  80

Ala Ala Gly Ala Pro
            85
```

<210> SEQ ID NO 445
<211> LENGTH: 90
<212> TYPE: PRT
<213> ORGANISM: Artificial Sequence
<220> FEATURE:
<223> OTHER INFORMATION: Synthetic peptide

<400> SEQUENCE: 445

```
Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Ala Ala Ala Ala Ser Gly Gly Pro Ser
        35                  40                  45

Gly Gly Gly Gly Ala Gly Gly Gly Ala Gly Gly Gly Ala Gly
    50                  55                  60

Gly Gly Gly Ala Gly Gly Gly Ala Gly Gly Gly Ala Gly Gly
65                  70                  75                  80

Gly Gly Ala Ala Ala Ala Ala Gly Ala Pro
            85                  90
```

<210> SEQ ID NO 446
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(14)
<223> OTHER INFORMATION: Xaa can be any naturally occurring amino acid

<400> SEQUENCE: 446

```
Gly Ala Pro Gly Gly Gly Gly Ala Pro Ala Pro Ala Pro Xaa Gly Ala
1               5                   10                  15

Pro
```

<210> SEQ ID NO 447
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(15)
<223> OTHER INFORMATION: Xaa can be any naturally occurring amino acid

<400> SEQUENCE: 447

```
Gly Ala Pro Gly Gly Gly Gly Ala Pro Ala Pro Ala Pro Xaa Xaa Gly
1               5                   10                  15

Ala Pro

<210> SEQ ID NO 448
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(16)
<223> OTHER INFORMATION: Xaa can be any naturally occurring amino acid

<400> SEQUENCE: 448

Gly Ala Pro Gly Gly Gly Gly Ala Pro Ala Pro Ala Pro Xaa Xaa Xaa
1               5                   10                  15

Gly Ala Pro

<210> SEQ ID NO 449
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(17)
<223> OTHER INFORMATION: Xaa can be any naturally occurring amino acid

<400> SEQUENCE: 449

Gly Ala Pro Gly Gly Gly Gly Ala Pro Ala Pro Ala Pro Xaa Xaa Xaa
1               5                   10                  15

Xaa Gly Ala Pro
        20

<210> SEQ ID NO 450
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(18)
<223> OTHER INFORMATION: Xaa can be any naturally occurring amino acid

<400> SEQUENCE: 450

Gly Ala Pro Gly Gly Gly Gly Ala Pro Ala Pro Ala Pro Xaa Xaa Xaa
1               5                   10                  15

Xaa Xaa Gly Ala Pro
        20

<210> SEQ ID NO 451
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(19)
<223> OTHER INFORMATION: Xaa can be any naturally occurring amino acid

<400> SEQUENCE: 451

Gly Ala Pro Gly Gly Gly Gly Ala Pro Ala Pro Ala Pro Xaa Xaa Xaa
```

```
                1               5                   10                  15

Xaa Xaa Xaa Gly Ala Pro
            20

<210> SEQ ID NO 452
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(20)
<223> OTHER INFORMATION: Xaa can be any naturally occurring amino acid

<400> SEQUENCE: 452

Gly Ala Pro Gly Gly Gly Gly Ala Pro Ala Pro Ala Pro Xaa Xaa Xaa
1               5                   10                  15

Xaa Xaa Xaa Xaa Gly Ala Pro
            20

<210> SEQ ID NO 453
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(19)
<223> OTHER INFORMATION: Xaa can be any naturally occurring amino acid

<400> SEQUENCE: 453

Gly Ala Pro Gly Gly Gly Gly Ala Gly Gly Gly Ala Pro Ala Pro
1               5                   10                  15

Ala Pro Xaa Gly Ala Pro
            20

<210> SEQ ID NO 454
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(20)
<223> OTHER INFORMATION: Xaa can be any naturally occurring amino acid

<400> SEQUENCE: 454

Gly Ala Pro Gly Gly Gly Gly Ala Gly Gly Gly Ala Pro Ala Pro
1               5                   10                  15

Ala Pro Xaa Xaa Gly Ala Pro
            20

<210> SEQ ID NO 455
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid

<400> SEQUENCE: 455
```

Gly Ala Pro Gly Gly Gly Gly Ala Gly Gly Gly Ala Pro Ala Pro
1               5                   10                  15

Ala Pro Xaa Xaa Xaa Gly Ala Pro
            20

<210> SEQ ID NO 456
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(22)
<223> OTHER INFORMATION: Xaa can be any naturally occurring amino acid

<400> SEQUENCE: 456

Gly Ala Pro Gly Gly Gly Gly Ala Gly Gly Gly Ala Pro Ala Pro
1               5                   10                  15

Ala Pro Xaa Xaa Xaa Xaa Gly Ala Pro
            20                  25

<210> SEQ ID NO 457
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(23)
<223> OTHER INFORMATION: Xaa can be any naturally occurring amino acid

<400> SEQUENCE: 457

Gly Ala Pro Gly Gly Gly Gly Ala Gly Gly Gly Ala Pro Ala Pro
1               5                   10                  15

Ala Pro Xaa Xaa Xaa Xaa Xaa Gly Ala Pro
            20                  25

<210> SEQ ID NO 458
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(24)
<223> OTHER INFORMATION: Xaa can be any naturally occurring amino acid

<400> SEQUENCE: 458

Gly Ala Pro Gly Gly Gly Gly Ala Gly Gly Gly Ala Pro Ala Pro
1               5                   10                  15

Ala Pro Xaa Xaa Xaa Xaa Xaa Xaa Gly Ala Pro
            20                  25

<210> SEQ ID NO 459
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(25)
<223> OTHER INFORMATION: Xaa can be any naturally occurring amino acid

<400> SEQUENCE: 459

Gly Ala Pro Gly Gly Gly Gly Ala Gly Gly Gly Ala Pro Ala Pro
1               5                   10                  15

Ala Pro Xaa Xaa Xaa Xaa Xaa Xaa Gly Ala Pro
            20                  25

<210> SEQ ID NO 460
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 460

Gly Ala Pro Gly Gly Gly Gly Ala Gly Gly Gly Ala Gly Gly Gly
1               5                   10                  15

Gly Ala Pro Ala Pro Ala Pro Xaa Gly Ala Pro
            20                  25

<210> SEQ ID NO 461
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(25)
<223> OTHER INFORMATION: Xaa can be any naturally occurring amino acid

<400> SEQUENCE: 461

Gly Ala Pro Gly Gly Gly Gly Ala Gly Gly Gly Ala Gly Gly Gly
1               5                   10                  15

Gly Ala Pro Ala Pro Ala Pro Xaa Xaa Gly Ala Pro
            20                  25

<210> SEQ ID NO 462
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(26)
<223> OTHER INFORMATION: Xaa can be any naturally occurring amino acid

<400> SEQUENCE: 462

Gly Ala Pro Gly Gly Gly Gly Ala Gly Gly Gly Ala Gly Gly Gly
1               5                   10                  15

Gly Ala Pro Ala Pro Ala Pro Xaa Xaa Xaa Gly Ala Pro
            20                  25

<210> SEQ ID NO 463
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(27)
<223> OTHER INFORMATION: Xaa can be any naturally occurring amino acid

```
<400> SEQUENCE: 463

Gly Ala Pro Gly Gly Gly Gly Ala Gly Gly Gly Ala Gly Gly Gly
1               5                   10                  15

Gly Ala Pro Ala Pro Ala Pro Xaa Xaa Xaa Xaa Gly Ala Pro
            20                  25                  30

<210> SEQ ID NO 464
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(28)
<223> OTHER INFORMATION: Xaa can be any naturally occurring amino acid

<400> SEQUENCE: 464

Gly Ala Pro Gly Gly Gly Gly Ala Gly Gly Gly Ala Gly Gly Gly
1               5                   10                  15

Gly Ala Pro Ala Pro Ala Pro Xaa Xaa Xaa Xaa Xaa Gly Ala Pro
            20                  25                  30

<210> SEQ ID NO 465
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(29)
<223> OTHER INFORMATION: Xaa can be any naturally occurring amino acid

<400> SEQUENCE: 465

Gly Ala Pro Gly Gly Gly Gly Ala Gly Gly Gly Ala Gly Gly Gly
1               5                   10                  15

Gly Ala Pro Ala Pro Ala Pro Xaa Xaa Xaa Xaa Xaa Xaa Gly Ala Pro
            20                  25                  30

<210> SEQ ID NO 466
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(30)
<223> OTHER INFORMATION: Xaa can be any naturally occurring amino acid

<400> SEQUENCE: 466

Gly Ala Pro Gly Gly Gly Gly Ala Gly Gly Gly Ala Gly Gly Gly
1               5                   10                  15

Gly Ala Pro Ala Pro Ala Pro Xaa Xaa Xaa Xaa Xaa Xaa Xaa Gly Ala
            20                  25                  30

Pro

<210> SEQ ID NO 467
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (29)..(29)
<223> OTHER INFORMATION: Xaa can be any naturally occurring amino acid

<400> SEQUENCE: 467

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Xaa Gly Ala Pro
            20                  25                  30

<210> SEQ ID NO 468
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(30)
<223> OTHER INFORMATION: Xaa can be any naturally occurring amino acid

<400> SEQUENCE: 468

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Xaa Xaa Gly Ala
            20                  25                  30

Pro

<210> SEQ ID NO 469
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(31)
<223> OTHER INFORMATION: Xaa can be any naturally occurring amino acid

<400> SEQUENCE: 469

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Xaa Xaa Xaa Gly
            20                  25                  30

Ala Pro

<210> SEQ ID NO 470
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(32)
<223> OTHER INFORMATION: Xaa can be any naturally occurring amino acid

<400> SEQUENCE: 470

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Xaa Xaa Xaa Xaa
            20                  25                  30

Gly Ala Pro
        35
```

```
<210> SEQ ID NO 471
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(33)
<223> OTHER INFORMATION: Xaa can be any naturally occurring amino acid

<400> SEQUENCE: 471

Gly Ala Pro Gly Gly Gly Gly Ala Gly Gly Gly Ala Gly Gly
1               5                   10                  15

Gly Ala Gly Gly Gly Gly Ala Pro Ala Pro Ala Pro Xaa Xaa Xaa Xaa
            20                  25                  30

Xaa Gly Ala Pro
        35

<210> SEQ ID NO 472
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(34)
<223> OTHER INFORMATION: Xaa can be any naturally occurring amino acid

<400> SEQUENCE: 472

Gly Ala Pro Gly Gly Gly Gly Ala Gly Gly Gly Ala Gly Gly
1               5                   10                  15

Gly Ala Gly Gly Gly Gly Ala Pro Ala Pro Ala Pro Xaa Xaa Xaa Xaa
            20                  25                  30

Xaa Xaa Gly Ala Pro
        35

<210> SEQ ID NO 473
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(35)
<223> OTHER INFORMATION: Xaa can be any naturally occurring amino acid

<400> SEQUENCE: 473

Gly Ala Pro Gly Gly Gly Gly Ala Gly Gly Gly Ala Gly Gly
1               5                   10                  15

Gly Ala Gly Gly Gly Gly Ala Pro Ala Pro Ala Pro Xaa Xaa Xaa Xaa
            20                  25                  30

Xaa Xaa Xaa Gly Ala Pro
        35

<210> SEQ ID NO 474
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(34)
<223> OTHER INFORMATION: Xaa can be any naturally occurring amino acid
```

```
<400> SEQUENCE: 474

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Gly Ala Pro
        35

<210> SEQ ID NO 475
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(35)
<223> OTHER INFORMATION: Xaa can be any naturally occurring amino acid

<400> SEQUENCE: 475

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Gly Ala Pro
        35

<210> SEQ ID NO 476
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(36)
<223> OTHER INFORMATION: Xaa can be any naturally occurring amino acid

<400> SEQUENCE: 476

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Xaa Gly Ala Pro
        35

<210> SEQ ID NO 477
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(37)
<223> OTHER INFORMATION: Xaa can be any naturally occurring amino acid

<400> SEQUENCE: 477

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Xaa Xaa Gly Ala Pro
```

35                  40

<210> SEQ ID NO 478
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(38)
<223> OTHER INFORMATION: Xaa can be any naturally occurring amino acid

<400> SEQUENCE: 478

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Xaa Xaa Xaa Gly Ala Pro
        35                  40

<210> SEQ ID NO 479
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(39)
<223> OTHER INFORMATION: Xaa can be any naturally occurring amino acid

<400> SEQUENCE: 479

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Xaa Xaa Xaa Xaa Gly Ala Pro
        35                  40

<210> SEQ ID NO 480
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(40)
<223> OTHER INFORMATION: Xaa can be any naturally occurring amino acid

<400> SEQUENCE: 480

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Xaa Xaa Xaa Xaa Xaa Xaa Xaa Gly Ala Pro
        35                  40

<210> SEQ ID NO 481
<211> LENGTH: 42
<212> TYPE: PRT
<213> ORGANISM: Artificial Sequence
<220> FEATURE:
<223> OTHER INFORMATION: Synthetic peptide
<220> FEATURE:

```
<221> NAME/KEY: misc_feature
<222> LOCATION: (39)..(39)
<223> OTHER INFORMATION: Xaa can be any naturally occurring amino acid

<400> SEQUENCE: 481

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Gly Ala Pro
            35                  40

<210> SEQ ID NO 482
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(40)
<223> OTHER INFORMATION: Xaa can be any naturally occurring amino acid

<400> SEQUENCE: 482

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Xaa Gly Ala Pro
            35                  40

<210> SEQ ID NO 483
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(41)
<223> OTHER INFORMATION: Xaa can be any naturally occurring amino acid

<400> SEQUENCE: 483

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Xaa Xaa Gly Ala Pro
            35                  40

<210> SEQ ID NO 484
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(42)
<223> OTHER INFORMATION: Xaa can be any naturally occurring amino acid

<400> SEQUENCE: 484

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
```

```
                20                  25                  30

Ala Pro Ala Pro Ala Pro Xaa Xaa Xaa Xaa Gly Ala Pro
        35                  40                  45

<210> SEQ ID NO 485
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(43)
<223> OTHER INFORMATION: Xaa can be any naturally occurring amino acid

<400> SEQUENCE: 485

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Xaa Xaa Xaa Xaa Gly Ala Pro
        35                  40                  45

<210> SEQ ID NO 486
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(44)
<223> OTHER INFORMATION: Xaa can be any naturally occurring amino acid

<400> SEQUENCE: 486

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Xaa Xaa Xaa Xaa Xaa Gly Ala Pro
        35                  40                  45

<210> SEQ ID NO 487
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(45)
<223> OTHER INFORMATION: Xaa can be any naturally occurring amino acid

<400> SEQUENCE: 487

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Pro Ala Pro Ala Pro Xaa Xaa Xaa Xaa Xaa Xaa Xaa Gly Ala Pro
        35                  40                  45

<210> SEQ ID NO 488
<211> LENGTH: 47
<212> TYPE: PRT
<213> ORGANISM: Artificial Sequence
```

<220> FEATURE:
<223> OTHER INFORMATION: Synthetic peptide
<220> FEATURE:
<221> NAME/KEY: misc_feature
<222> LOCATION: (44)..(44)
<223> OTHER INFORMATION: Xaa can be any naturally occurring amino acid

<400> SEQUENCE: 488

```
Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Xaa Gly Ala Pro
        35                  40                  45
```

<210> SEQ ID NO 489
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(45)
<223> OTHER INFORMATION: Xaa can be any naturally occurring amino acid

<400> SEQUENCE: 489

```
Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Xaa Xaa Gly Ala Pro
        35                  40                  45
```

<210> SEQ ID NO 490
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(46)
<223> OTHER INFORMATION: Xaa can be any naturally occurring amino acid

<400> SEQUENCE: 490

```
Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Xaa Xaa Xaa Gly Ala
        35                  40                  45

Pro
```

<210> SEQ ID NO 491
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(47)
<223> OTHER INFORMATION: Xaa can be any naturally occurring amino acid

<400> SEQUENCE: 491

```
Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Pro Ala Pro Ala Pro Xaa Xaa Xaa Xaa Gly
        35                  40                  45

Ala Pro
    50

<210> SEQ ID NO 492
<211> LENGTH: 51
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(48)
<223> OTHER INFORMATION: Xaa can be any naturally occurring amino acid

<400> SEQUENCE: 492

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Pro Ala Pro Ala Pro Xaa Xaa Xaa Xaa Xaa
        35                  40                  45

Gly Ala Pro
    50

<210> SEQ ID NO 493
<211> LENGTH: 52
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(49)
<223> OTHER INFORMATION: Xaa can be any naturally occurring amino acid

<400> SEQUENCE: 493

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
                20                  25                  30

Ala Gly Gly Gly Gly Ala Pro Ala Pro Ala Pro Xaa Xaa Xaa Xaa Xaa
        35                  40                  45

Xaa Gly Ala Pro
    50

<210> SEQ ID NO 494
<211> LENGTH: 53
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(50)
<223> OTHER INFORMATION: Xaa can be any naturally occurring amino acid

<400> SEQUENCE: 494
```

```
Gly Ala Pro Gly Gly Gly Ala Gly Gly Gly Ala Gly Gly Gly
1               5                   10                  15
Gly Ala Gly Gly Gly Ala Gly Gly Gly Ala Gly Gly Gly
            20                  25                  30
Ala Gly Gly Gly Ala Pro Ala Pro Ala Pro Xaa Xaa Xaa Xaa Xaa
        35                  40                  45
Xaa Xaa Gly Ala Pro
        50
```

<210> SEQ ID NO 495
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(15)
<223> OTHER INFORMATION: Xaa can be any naturally occurring amino acid

<400> SEQUENCE: 495

```
Gly Ala Pro Gly Gly Gly Gly Ala Pro Ala Pro Ala Pro Thr Xaa Gly
1               5                   10                  15
Ala Pro
```

<210> SEQ ID NO 496
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(16)
<223> OTHER INFORMATION: Xaa can be any naturally occurring amino acid

<400> SEQUENCE: 496

```
Gly Ala Pro Gly Gly Gly Gly Ala Pro Ala Pro Ala Pro Thr Xaa Xaa
1               5                   10                  15
Gly Ala Pro
```

<210> SEQ ID NO 497
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(17)
<223> OTHER INFORMATION: Xaa can be any naturally occurring amino acid

<400> SEQUENCE: 497

```
Gly Ala Pro Gly Gly Gly Gly Ala Pro Ala Pro Ala Pro Thr Xaa Xaa
1               5                   10                  15
Xaa Gly Ala Pro
        20
```

<210> SEQ ID NO 498
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature

```
<222> LOCATION: (15)..(18)
<223> OTHER INFORMATION: Xaa can be any naturally occurring amino acid

<400> SEQUENCE: 498

Gly Ala Pro Gly Gly Gly Ala Pro Ala Pro Ala Pro Thr Xaa Xaa
1               5                   10                  15

Xaa Xaa Gly Ala Pro
            20

<210> SEQ ID NO 499
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(19)
<223> OTHER INFORMATION: Xaa can be any naturally occurring amino acid

<400> SEQUENCE: 499

Gly Ala Pro Gly Gly Gly Gly Ala Pro Ala Pro Ala Pro Thr Xaa Xaa
1               5                   10                  15

Xaa Xaa Xaa Gly Ala Pro
            20

<210> SEQ ID NO 500
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(20)
<223> OTHER INFORMATION: Xaa can be any naturally occurring amino acid

<400> SEQUENCE: 500

Gly Ala Pro Gly Gly Gly Gly Ala Pro Ala Pro Ala Pro Thr Xaa Xaa
1               5                   10                  15

Xaa Xaa Xaa Xaa Gly Ala Pro
            20

<210> SEQ ID NO 501
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(21)
<223> OTHER INFORMATION: Xaa can be any naturally occurring amino acid

<400> SEQUENCE: 501

Gly Ala Pro Gly Gly Gly Gly Ala Pro Ala Pro Ala Pro Thr Xaa Xaa
1               5                   10                  15

Xaa Xaa Xaa Xaa Xaa Gly Ala Pro
            20

<210> SEQ ID NO 502
<211> LENGTH: 23
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (20)..(20)
<223> OTHER INFORMATION: Xaa can be any naturally occurring amino acid

<400> SEQUENCE: 502

Gly Ala Pro Gly Gly Gly Gly Ala Gly Gly Gly Ala Pro Ala Pro
1               5                   10                  15

Ala Pro Thr Xaa Gly Ala Pro
            20

<210> SEQ ID NO 503
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(21)
<223> OTHER INFORMATION: Xaa can be any naturally occurring amino acid

<400> SEQUENCE: 503

Gly Ala Pro Gly Gly Gly Gly Ala Gly Gly Gly Ala Pro Ala Pro
1               5                   10                  15

Ala Pro Thr Xaa Xaa Gly Ala Pro
            20

<210> SEQ ID NO 504
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(22)
<223> OTHER INFORMATION: Xaa can be any naturally occurring amino acid

<400> SEQUENCE: 504

Gly Ala Pro Gly Gly Gly Gly Ala Gly Gly Gly Ala Pro Ala Pro
1               5                   10                  15

Ala Pro Thr Xaa Xaa Xaa Gly Ala Pro
            20                  25

<210> SEQ ID NO 505
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(23)
<223> OTHER INFORMATION: Xaa can be any naturally occurring amino acid

<400> SEQUENCE: 505

Gly Ala Pro Gly Gly Gly Gly Ala Gly Gly Gly Ala Pro Ala Pro
1               5                   10                  15

Ala Pro Thr Xaa Xaa Xaa Xaa Gly Ala Pro
            20                  25

<210> SEQ ID NO 506
<211> LENGTH: 27
<212> TYPE: PRT
<213> ORGANISM: Artificial Sequence
<220> FEATURE:
<223> OTHER INFORMATION: Synthetic peptide
```

-continued

<220> FEATURE:
<221> NAME/KEY: misc_feature
<222> LOCATION: (20)..(24)
<223> OTHER INFORMATION: Xaa can be any naturally occurring amino acid

<400> SEQUENCE: 506

Gly Ala Pro Gly Gly Gly Gly Ala Gly Gly Gly Ala Pro Ala Pro
1               5                   10                  15

Ala Pro Thr Xaa Xaa Xaa Xaa Xaa Gly Ala Pro
            20                  25

<210> SEQ ID NO 507
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(25)
<223> OTHER INFORMATION: Xaa can be any naturally occurring amino acid

<400> SEQUENCE: 507

Gly Ala Pro Gly Gly Gly Gly Ala Gly Gly Gly Ala Pro Ala Pro
1               5                   10                  15

Ala Pro Thr Xaa Xaa Xaa Xaa Xaa Xaa Gly Ala Pro
            20                  25

<210> SEQ ID NO 508
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(26)
<223> OTHER INFORMATION: Xaa can be any naturally occurring amino acid

<400> SEQUENCE: 508

Gly Ala Pro Gly Gly Gly Gly Ala Gly Gly Gly Ala Pro Ala Pro
1               5                   10                  15

Ala Pro Thr Xaa Xaa Xaa Xaa Xaa Xaa Xaa Gly Ala Pro
            20                  25

<210> SEQ ID NO 509
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 509

Gly Ala Pro Gly Gly Gly Gly Ala Gly Gly Gly Ala Gly Gly Gly
1               5                   10                  15

Gly Ala Pro Ala Pro Ala Pro Thr Xaa Gly Ala Pro
            20                  25

<210> SEQ ID NO 510
<211> LENGTH: 29
<212> TYPE: PRT
<213> ORGANISM: Artificial Sequence
<220> FEATURE:

```
<223> OTHER INFORMATION: Synthetic peptide
<220> FEATURE:
<221> NAME/KEY: misc_feature
<222> LOCATION: (25)..(26)
<223> OTHER INFORMATION: Xaa can be any naturally occurring amino acid

<400> SEQUENCE: 510

Gly Ala Pro Gly Gly Gly Gly Ala Gly Gly Gly Gly Ala Gly Gly Gly
1               5                   10                  15

Gly Ala Pro Ala Pro Ala Pro Thr Xaa Xaa Gly Ala Pro
            20                  25

<210> SEQ ID NO 511
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(27)
<223> OTHER INFORMATION: Xaa can be any naturally occurring amino acid

<400> SEQUENCE: 511

Gly Ala Pro Gly Gly Gly Gly Ala Gly Gly Gly Gly Ala Gly Gly Gly
1               5                   10                  15

Gly Ala Pro Ala Pro Ala Pro Thr Xaa Xaa Xaa Gly Ala Pro
            20                  25                  30

<210> SEQ ID NO 512
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(28)
<223> OTHER INFORMATION: Xaa can be any naturally occurring amino acid

<400> SEQUENCE: 512

Gly Ala Pro Gly Gly Gly Gly Ala Gly Gly Gly Gly Ala Gly Gly Gly
1               5                   10                  15

Gly Ala Pro Ala Pro Ala Pro Thr Xaa Xaa Xaa Xaa Gly Ala Pro
            20                  25                  30

<210> SEQ ID NO 513
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(29)
<223> OTHER INFORMATION: Xaa can be any naturally occurring amino acid

<400> SEQUENCE: 513

Gly Ala Pro Gly Gly Gly Gly Ala Gly Gly Gly Gly Ala Gly Gly Gly
1               5                   10                  15

Gly Ala Pro Ala Pro Ala Pro Thr Xaa Xaa Xaa Xaa Xaa Gly Ala Pro
            20                  25                  30

<210> SEQ ID NO 514
<211> LENGTH: 33
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (25)..(30)
<223> OTHER INFORMATION: Xaa can be any naturally occurring amino acid

<400> SEQUENCE: 514

Gly Ala Pro Gly Gly Gly Gly Ala Gly Gly Gly Ala Gly Gly Gly
1               5                   10                  15

Gly Ala Pro Ala Pro Ala Pro Thr Xaa Xaa Xaa Xaa Xaa Xaa Gly Ala
            20                  25                  30

Pro

<210> SEQ ID NO 515
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(31)
<223> OTHER INFORMATION: Xaa can be any naturally occurring amino acid

<400> SEQUENCE: 515

Gly Ala Pro Gly Gly Gly Gly Ala Gly Gly Gly Ala Gly Gly Gly
1               5                   10                  15

Gly Ala Pro Ala Pro Ala Pro Thr Xaa Xaa Xaa Xaa Xaa Xaa Xaa Gly
            20                  25                  30

Ala Pro

<210> SEQ ID NO 516
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(30)
<223> OTHER INFORMATION: Xaa can be any naturally occurring amino acid

<400> SEQUENCE: 516

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Gly Ala
            20                  25                  30

Pro

<210> SEQ ID NO 517
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(31)
<223> OTHER INFORMATION: Xaa can be any naturally occurring amino acid

<400> SEQUENCE: 517

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Gly
```

20                  25                  30

Ala Pro

<210> SEQ ID NO 518
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(32)
<223> OTHER INFORMATION: Xaa can be any naturally occurring amino acid

<400> SEQUENCE: 518

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Xaa
            20                  25                  30

Gly Ala Pro
        35

<210> SEQ ID NO 519
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(33)
<223> OTHER INFORMATION: Xaa can be any naturally occurring amino acid

<400> SEQUENCE: 519

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Xaa
            20                  25                  30

Xaa Gly Ala Pro
        35

<210> SEQ ID NO 520
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(34)
<223> OTHER INFORMATION: Xaa can be any naturally occurring amino acid

<400> SEQUENCE: 520

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Xaa
            20                  25                  30

Xaa Xaa Gly Ala Pro
        35

<210> SEQ ID NO 521
<211> LENGTH: 38
<212> TYPE: PRT
<213> ORGANISM: Artificial Sequence
<220> FEATURE:

```
<223> OTHER INFORMATION: Synthetic peptide
<220> FEATURE:
<221> NAME/KEY: misc_feature
<222> LOCATION: (30)..(35)
<223> OTHER INFORMATION: Xaa can be any naturally occurring amino acid

<400> SEQUENCE: 521

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Xaa
            20                  25                  30

Xaa Xaa Xaa Gly Ala Pro
        35

<210> SEQ ID NO 522
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(36)
<223> OTHER INFORMATION: Xaa can be any naturally occurring amino acid

<400> SEQUENCE: 522

Gly Ala Pro Gly Gly Gly Gly Ala Gly Gly Gly Ala Gly Gly Gly
1               5                   10                  15

Gly Ala Gly Gly Gly Gly Ala Pro Ala Pro Ala Pro Thr Xaa Xaa Xaa
            20                  25                  30

Xaa Xaa Xaa Xaa Gly Ala Pro
        35

<210> SEQ ID NO 523
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(35)
<223> OTHER INFORMATION: Xaa can be any naturally occurring amino acid

<400> SEQUENCE: 523

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Pro Ala Pro Ala
            20                  25                  30

Pro Thr Xaa Gly Ala Pro
        35

<210> SEQ ID NO 524
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(36)
<223> OTHER INFORMATION: Xaa can be any naturally occurring amino acid

<400> SEQUENCE: 524

Gly Ala Pro Gly Gly Gly Gly Ala Gly Gly Gly Ala Gly Gly Gly
1               5                   10                  15
```

Gly Ala Gly Gly Gly Gly Ala Gly Gly Gly Ala Pro Ala Pro Ala
            20                  25                  30

Pro Thr Xaa Xaa Gly Ala Pro
        35

<210> SEQ ID NO 525
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(37)
<223> OTHER INFORMATION: Xaa can be any naturally occurring amino acid

<400> SEQUENCE: 525

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Pro Ala Pro Ala
            20                  25                  30

Pro Thr Xaa Xaa Xaa Gly Ala Pro
        35                  40

<210> SEQ ID NO 526
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(38)
<223> OTHER INFORMATION: Xaa can be any naturally occurring amino acid

<400> SEQUENCE: 526

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Pro Ala Pro Ala
            20                  25                  30

Pro Thr Xaa Xaa Xaa Xaa Gly Ala Pro
        35                  40

<210> SEQ ID NO 527
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(39)
<223> OTHER INFORMATION: Xaa can be any naturally occurring amino acid

<400> SEQUENCE: 527

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Pro Ala Pro Ala
            20                  25                  30

Pro Thr Xaa Xaa Xaa Xaa Xaa Gly Ala Pro
        35                  40

<210> SEQ ID NO 528
<211> LENGTH: 43

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(40)
<223> OTHER INFORMATION: Xaa can be any naturally occurring amino acid

<400> SEQUENCE: 528

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Thr Xaa Xaa Xaa Xaa Xaa Xaa Gly Ala Pro
        35                  40

<210> SEQ ID NO 529
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (35)..(41)
<223> OTHER INFORMATION: Xaa can be any naturally occurring amino acid

<400> SEQUENCE: 529

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Pro Ala Pro Ala
            20                  25                  30

Pro Thr Xaa Xaa Xaa Xaa Xaa Xaa Xaa Gly Ala Pro
        35                  40

<210> SEQ ID NO 530
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(40)
<223> OTHER INFORMATION: Xaa can be any naturally occurring amino acid

<400> SEQUENCE: 530

Gly Ala Pro Gly Gly Gly Gly Ala Gly Gly Gly Ala Gly Gly Gly
1               5                   10                  15

Gly Ala Gly Gly Gly Gly Ala Gly Gly Gly Gly Ala Gly Gly Gly Gly
            20                  25                  30

Ala Pro Ala Pro Ala Pro Thr Xaa Gly Ala Pro
        35                  40

<210> SEQ ID NO 531
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(41)
<223> OTHER INFORMATION: Xaa can be any naturally occurring amino acid

<400> SEQUENCE: 531
```

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
            20                  25                  30

Ala Pro Ala Pro Ala Pro Thr Xaa Xaa Gly Ala Pro
        35                  40

<210> SEQ ID NO 532
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(42)
<223> OTHER INFORMATION: Xaa can be any naturally occurring amino acid

<400> SEQUENCE: 532

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
            20                  25                  30

Ala Pro Ala Pro Ala Pro Thr Xaa Xaa Xaa Gly Ala Pro
        35                  40                  45

<210> SEQ ID NO 533
<211> LENGTH: 46
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(43)
<223> OTHER INFORMATION: Xaa can be any naturally occurring amino acid

<400> SEQUENCE: 533

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
            20                  25                  30

Ala Pro Ala Pro Ala Pro Thr Xaa Xaa Xaa Xaa Gly Ala Pro
        35                  40                  45

<210> SEQ ID NO 534
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(44)
<223> OTHER INFORMATION: Xaa can be any naturally occurring amino acid

<400> SEQUENCE: 534

Gly Ala Pro Gly Gly Gly Gly Ala Gly Gly Gly Ala Gly Gly Gly
1               5                   10                  15

Gly Ala Gly Gly Gly Gly Ala Gly Gly Gly Ala Gly Gly Gly Gly
            20                  25                  30

Ala Pro Ala Pro Ala Pro Thr Xaa Xaa Xaa Xaa Xaa Gly Ala Pro
        35                  40                  45

<210> SEQ ID NO 535
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(45)
<223> OTHER INFORMATION: Xaa can be any naturally occurring amino acid

<400> SEQUENCE: 535

Gly Ala Pro Gly Gly Gly Gly Ala Gly Gly Gly Gly Ala Gly Gly Gly
1               5                   10                  15

Gly Ala Gly Gly Gly Gly Ala Gly Gly Gly Gly Ala Gly Gly Gly Gly
                20                  25                  30

Ala Pro Ala Pro Ala Pro Thr Xaa Xaa Xaa Xaa Xaa Xaa Gly Ala Pro
            35                  40                  45

<210> SEQ ID NO 536
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (40)..(46)
<223> OTHER INFORMATION: Xaa can be any naturally occurring amino acid

<400> SEQUENCE: 536

Gly Ala Pro Gly Gly Gly Gly Ala Gly Gly Gly Gly Ala Gly Gly Gly
1               5                   10                  15

Gly Ala Gly Gly Gly Gly Ala Gly Gly Gly Gly Ala Gly Gly Gly Gly
                20                  25                  30

Ala Pro Ala Pro Ala Pro Thr Xaa Xaa Xaa Xaa Xaa Xaa Xaa Gly Ala
            35                  40                  45

Pro

<210> SEQ ID NO 537
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(45)
<223> OTHER INFORMATION: Xaa can be any naturally occurring amino acid

<400> SEQUENCE: 537

Gly Ala Pro Gly Gly Gly Gly Ala Gly Gly Gly Gly Ala Gly Gly Gly
1               5                   10                  15

Gly Ala Gly Gly Gly Gly Ala Gly Gly Gly Gly Ala Gly Gly Gly Gly
                20                  25                  30

Ala Gly Gly Gly Gly Ala Pro Ala Pro Ala Pro Thr Xaa Gly Ala Pro
            35                  40                  45

<210> SEQ ID NO 538
<211> LENGTH: 49
<212> TYPE: PRT
<213> ORGANISM: Artificial Sequence
<220> FEATURE:
<223> OTHER INFORMATION: Synthetic peptide
<220> FEATURE:

<221> NAME/KEY: misc_feature
<222> LOCATION: (45)..(46)
<223> OTHER INFORMATION: Xaa can be any naturally occurring amino acid

<400> SEQUENCE: 538

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Thr Xaa Xaa Gly Ala
        35                  40                  45

Pro

<210> SEQ ID NO 539
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(47)
<223> OTHER INFORMATION: Xaa can be any naturally occurring amino acid

<400> SEQUENCE: 539

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Thr Xaa Xaa Xaa Gly
        35                  40                  45

Ala Pro
    50

<210> SEQ ID NO 540
<211> LENGTH: 51
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(48)
<223> OTHER INFORMATION: Xaa can be any naturally occurring amino acid

<400> SEQUENCE: 540

Gly Ala Pro Gly Gly Gly Gly Ala Gly Gly Gly Ala Gly Gly
1               5                   10                  15

Gly Ala Gly Gly Gly Gly Ala Gly Gly Gly Ala Gly Gly Gly
            20                  25                  30

Ala Gly Gly Gly Gly Ala Pro Ala Pro Ala Pro Thr Xaa Xaa Xaa Xaa
        35                  40                  45

Gly Ala Pro
    50

<210> SEQ ID NO 541
<211> LENGTH: 52
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(49)

<223> OTHER INFORMATION: Xaa can be any naturally occurring amino acid

<400> SEQUENCE: 541

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Gly
            20                  25                  30

Ala Gly Gly Gly Gly Ala Pro Ala Pro Ala Pro Thr Xaa Xaa Xaa Xaa
        35                  40                  45

Xaa Gly Ala Pro
    50

<210> SEQ ID NO 542
<211> LENGTH: 53
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(50)
<223> OTHER INFORMATION: Xaa can be any naturally occurring amino acid

<400> SEQUENCE: 542

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Gly
            20                  25                  30

Ala Gly Gly Gly Gly Ala Pro Ala Pro Ala Pro Thr Xaa Xaa Xaa Xaa
        35                  40                  45

Xaa Xaa Gly Ala Pro
    50

<210> SEQ ID NO 543
<211> LENGTH: 54
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (45)..(51)
<223> OTHER INFORMATION: Xaa can be any naturally occurring amino acid

<400> SEQUENCE: 543

Gly Ala Pro Gly Gly Gly Ala Gly Gly Gly Ala Gly Gly Gly
1               5                   10                  15

Gly Ala Gly Gly Gly Ala Gly Gly Gly Ala Gly Gly Gly
            20                  25                  30

Ala Gly Gly Gly Gly Ala Pro Ala Pro Ala Pro Thr Xaa Xaa Xaa Xaa
        35                  40                  45

Xaa Xaa Xaa Gly Ala Pro
    50

<210> SEQ ID NO 544
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 544

Gly Ala Pro Gly Gly Gly Gly Ser Xaa Pro Ala Pro Ala Pro Xaa Ala
1               5                   10                  15

Ala Ala Lys Glu Xaa Gly Gly Gly Gly Ser Gly Ala Pro
            20                  25

<210> SEQ ID NO 545
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid

<400> SEQUENCE: 545

Gly Ala Pro Gly Gly Gly Gly Ser Gly Gly Gly Gly Ser Xaa Xaa Pro
1               5                   10                  15

Ala Pro Ala Pro Xaa Xaa Ala Ala Ala Lys Glu Ala Ala Ala Lys Glu
            20                  25                  30

Xaa Xaa Gly Gly Gly Gly Ser Gly Gly Gly Gly Ser Gly Ala Pro
        35                  40                  45

<210> SEQ ID NO 546
<211> LENGTH: 65
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid

<400> SEQUENCE: 546

Gly Ala Pro Gly Gly Gly Gly Ser Gly Gly Gly Gly Ser Gly Gly Gly
1               5                   10                  15

Gly Ser Xaa Xaa Xaa Pro Ala Pro Ala Pro Xaa Xaa Xaa Ala Ala Ala
            20                  25                  30

Lys Glu Ala Ala Ala Lys Glu Ala Ala Ala Lys Glu Xaa Xaa Xaa Gly
        35                  40                  45

-continued

Gly Gly Gly Ser Gly Gly Gly Ser Gly Gly Gly Ser Gly Ala
    50                  55                  60

Pro
65

<210> SEQ ID NO 547
<211> LENGTH: 83
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (33)..(36)
<223> OTHER INFORMATION: Xaa can be any naturally occurring amino acid
<220> FEATURE:
<221> NAME/KEY: misc_feature
<222> LOCATION: (57)..(60)
<223> OTHER INFORMATION: Xaa can be any naturally occurring amino acid

<400> SEQUENCE: 547

Gly Ala Pro Gly Gly Gly Gly Ser Gly Gly Gly Ser Gly Gly Gly
1               5                   10                  15

Gly Ser Gly Gly Gly Gly Ser Xaa Xaa Xaa Xaa Pro Ala Pro Ala Pro
                20                  25                  30

Xaa Xaa Xaa Xaa Ala Ala Ala Lys Glu Ala Ala Ala Lys Glu Ala Ala
        35                  40                  45

Ala Lys Glu Ala Ala Ala Lys Glu Xaa Xaa Xaa Xaa Gly Gly Gly Gly
    50                  55                  60

Ser Gly Gly Gly Gly Ser Gly Gly Gly Ser Gly Gly Gly Gly Ser
65                  70                  75                  80

Gly Ala Pro

<210> SEQ ID NO 548
<211> LENGTH: 101
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (69)..(73)
<223> OTHER INFORMATION: Xaa can be any naturally occurring amino acid

<400> SEQUENCE: 548

Gly Ala Pro Gly Gly Gly Gly Ser Gly Gly Gly Ser Gly Gly Gly
1               5                   10                  15

Gly Ser Gly Gly Gly Gly Ser Gly Gly Gly Ser Xaa Xaa Xaa Xaa
                20                  25                  30

Xaa Pro Ala Pro Ala Pro Xaa Xaa Xaa Xaa Xaa Ala Ala Ala Lys Glu
        35                  40                  45

Ala Ala Ala Lys Glu Ala Ala Ala Lys Glu Ala Ala Ala Lys Glu Ala
    50                  55                  60

```
Ala Ala Lys Glu Xaa Xaa Xaa Xaa Gly Gly Gly Gly Ser Gly Gly
 65                  70                  75                  80

Gly Gly Ser Gly Gly Gly Ser Gly Gly Gly Ser Gly Gly Gly
             85                  90                  95

Gly Ser Gly Ala Pro
        100

<210> SEQ ID NO 549
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(39)
<223> OTHER INFORMATION: Xaa can be any naturally occurring amino acid
<220> FEATURE:
<221> NAME/KEY: misc_feature
<222> LOCATION: (45)..(50)
<223> OTHER INFORMATION: Xaa can be any naturally occurring amino acid
<220> FEATURE:
<221> NAME/KEY: misc_feature
<222> LOCATION: (81)..(86)
<223> OTHER INFORMATION: Xaa can be any naturally occurring amino acid

<400> SEQUENCE: 549

Gly Ala Pro Gly Gly Gly Gly Ser Gly Gly Gly Gly Ser Gly Gly Gly
 1               5                  10                  15

Gly Ser Gly Gly Gly Gly Ser Gly Gly Gly Ser Gly Gly Gly Gly
             20                  25                  30

Ser Xaa Xaa Xaa Xaa Xaa Xaa Pro Ala Pro Ala Pro Xaa Xaa Xaa Xaa
             35                  40                  45

Xaa Xaa Ala Ala Ala Lys Glu Ala Ala Ala Lys Glu Ala Ala Ala Lys
     50                  55                  60

Glu Ala Ala Ala Lys Glu Ala Ala Ala Lys Glu Ala Ala Ala Lys Glu
 65                  70                  75                  80

Xaa Xaa Xaa Xaa Xaa Xaa Gly Gly Gly Ser Gly Gly Gly Gly Ser
             85                  90                  95

Gly Gly Gly Gly Ser Gly Gly Gly Ser Gly Gly Gly Ser Gly
            100                 105                 110

Gly Gly Gly Ser Gly Ala Pro
            115

<210> SEQ ID NO 550
<211> LENGTH: 137
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(45)
<223> OTHER INFORMATION: Xaa can be any naturally occurring amino acid
<220> FEATURE:
<221> NAME/KEY: misc_feature
<222> LOCATION: (51)..(57)
<223> OTHER INFORMATION: Xaa can be any naturally occurring amino acid
<220> FEATURE:
<221> NAME/KEY: misc_feature
<222> LOCATION: (93)..(99)
<223> OTHER INFORMATION: Xaa can be any naturally occurring amino acid

<400> SEQUENCE: 550

Gly Ala Pro Gly Gly Gly Gly Ser Gly Gly Gly Gly Ser Gly Gly Gly
 1               5                  10                  15
```

```
Gly Ser Gly Gly Gly Gly Ser Gly Gly Gly Ser Gly Gly Gly
        20                  25                  30

Ser Gly Gly Gly Ser Xaa Xaa Xaa Xaa Xaa Xaa Pro Ala Pro
        35                  40                  45

Ala Pro Xaa Xaa Xaa Xaa Xaa Xaa Xaa Ala Ala Lys Glu Ala Ala
 50                  55                  60

Ala Lys Glu Ala Ala Ala Lys Glu Ala Ala Ala Lys Glu Ala Ala Ala
 65                  70                  75                  80

Lys Glu Ala Ala Ala Lys Glu Ala Ala Ala Lys Glu Xaa Xaa Xaa Xaa
                 85                  90                  95

Xaa Xaa Xaa Gly Gly Gly Gly Ser Gly Gly Gly Ser Gly Gly Gly
            100                 105                 110

Gly Ser Gly Gly Gly Gly Ser Gly Gly Gly Ser Gly Gly Gly
        115                 120                 125

Ser Gly Gly Gly Gly Ser Gly Ala Pro
    130                 135
```

<210> SEQ ID NO 551
<211> LENGTH: 137
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(12)
<223> OTHER INFORMATION: Xaa is Gly or is absent
<220> FEATURE:
<221> NAME/KEY: MISC_FEATURE
<222> LOCATION: (13)..(13)
<223> OTHER INFORMATION: Xaa is Ser or is absent
<220> FEATURE:
<221> NAME/KEY: MISC_FEATURE
<222> LOCATION: (14)..(17)
<223> OTHER INFORMATION: Xaa is Gly or is absent
<220> FEATURE:
<221> NAME/KEY: MISC_FEATURE
<222> LOCATION: (18)..(18)
<223> OTHER INFORMATION: Xaa is Ser or is absent
<220> FEATURE:
<221> NAME/KEY: MISC_FEATURE
<222> LOCATION: (19)..(22)
<223> OTHER INFORMATION: Xaa is Gly or is absent
<220> FEATURE:
<221> NAME/KEY: MISC_FEATURE
<222> LOCATION: (23)..(23)
<223> OTHER INFORMATION: Xaa is Ser or is absent
<220> FEATURE:
<221> NAME/KEY: MISC_FEATURE
<222> LOCATION: (24)..(27)
<223> OTHER INFORMATION: Xaa is Gly or is absent
<220> FEATURE:
<221> NAME/KEY: MISC_FEATURE
<222> LOCATION: (28)..(28)
<223> OTHER INFORMATION: Xaa is Ser or is absent
<220> FEATURE:
<221> NAME/KEY: MISC_FEATURE
<222> LOCATION: (29)..(32)
<223> OTHER INFORMATION: Xaa is Gly or is absent
<220> FEATURE:
<221> NAME/KEY: MISC_FEATURE
<222> LOCATION: (33)..(33)
<223> OTHER INFORMATION: Xaa is Ser or is absent
<220> FEATURE:
<221> NAME/KEY: MISC_FEATURE
<222> LOCATION: (34)..(37)
<223> OTHER INFORMATION: Xaa is Gly or is absent
<220> FEATURE:
<221> NAME/KEY: MISC_FEATURE
<222> LOCATION: (38)..(38)

```
<223> OTHER INFORMATION: Xaa is Ser or is absent
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(45)
<223> OTHER INFORMATION: Xaa is any amino acid or is absent
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (52)..(57)
<223> OTHER INFORMATION: Xaa is any amino acid or is absent
<220> FEATURE:
<221> NAME/KEY: MISC_FEATURE
<222> LOCATION: (63)..(65)
<223> OTHER INFORMATION: Xaa is Ala or is absent
<220> FEATURE:
<221> NAME/KEY: MISC_FEATURE
<222> LOCATION: (66)..(66)
<223> OTHER INFORMATION: Xaa is Lys or is absent
<220> FEATURE:
<221> NAME/KEY: MISC_FEATURE
<222> LOCATION: (67)..(67)
<223> OTHER INFORMATION: Xaa is Glu or is absent
<220> FEATURE:
<221> NAME/KEY: MISC_FEATURE
<222> LOCATION: (68)..(70)
<223> OTHER INFORMATION: Xaa is Ala or is absent
<220> FEATURE:
<221> NAME/KEY: MISC_FEATURE
<222> LOCATION: (71)..(71)
<223> OTHER INFORMATION: Xaa is Lys or is absent
<220> FEATURE:
<221> NAME/KEY: MISC_FEATURE
<222> LOCATION: (72)..(72)
<223> OTHER INFORMATION: Xaa is Glu or is absent
<220> FEATURE:
<221> NAME/KEY: MISC_FEATURE
<222> LOCATION: (73)..(75)
<223> OTHER INFORMATION: Xaa is Ala or is absent
<220> FEATURE:
<221> NAME/KEY: MISC_FEATURE
<222> LOCATION: (76)..(76)
<223> OTHER INFORMATION: Xaa is Lys or is absent
<220> FEATURE:
<221> NAME/KEY: MISC_FEATURE
<222> LOCATION: (77)..(77)
<223> OTHER INFORMATION: Xaa is Glu or is absent
<220> FEATURE:
<221> NAME/KEY: MISC_FEATURE
<222> LOCATION: (78)..(80)
<223> OTHER INFORMATION: Xaa is Ala or is absent
<220> FEATURE:
<221> NAME/KEY: MISC_FEATURE
<222> LOCATION: (81)..(81)
<223> OTHER INFORMATION: Xaa is Lys or is absent
<220> FEATURE:
<221> NAME/KEY: MISC_FEATURE
<222> LOCATION: (82)..(82)
<223> OTHER INFORMATION: Xaa is Glu or is absent
<220> FEATURE:
<221> NAME/KEY: MISC_FEATURE
<222> LOCATION: (83)..(85)
<223> OTHER INFORMATION: Xaa is Ala or is absent
<220> FEATURE:
<221> NAME/KEY: MISC_FEATURE
<222> LOCATION: (86)..(86)
<223> OTHER INFORMATION: Xaa is Lys or is absent
<220> FEATURE:
<221> NAME/KEY: MISC_FEATURE
<222> LOCATION: (87)..(87)
<223> OTHER INFORMATION: Xaa is Glu or is absent
<220> FEATURE:
<221> NAME/KEY: MISC_FEATURE
```

```
<222> LOCATION: (88)..(90)
<223> OTHER INFORMATION: Xaa is Ala or is absent
<220> FEATURE:
<221> NAME/KEY: MISC_FEATURE
<222> LOCATION: (91)..(91)
<223> OTHER INFORMATION: Xaa is Lys or is absent
<220> FEATURE:
<221> NAME/KEY: MISC_FEATURE
<222> LOCATION: (92)..(92)
<223> OTHER INFORMATION: Xaa is Glu or is absent
<220> FEATURE:
<221> NAME/KEY: MISC_FEATURE
<222> LOCATION: (93)..(93)
<223> OTHER INFORMATION: Xaa is any amino acid
<220> FEATURE:
<221> NAME/KEY: MISC_FEATURE
<222> LOCATION: (94)..(99)
<223> OTHER INFORMATION: Xaa is any amino acid or is absent
<220> FEATURE:
<221> NAME/KEY: MISC_FEATURE
<222> LOCATION: (105)..(108)
<223> OTHER INFORMATION: Xaa is Gly or is absent
<220> FEATURE:
<221> NAME/KEY: MISC_FEATURE
<222> LOCATION: (109)..(109)
<223> OTHER INFORMATION: Xaa is Ser or is absent
<220> FEATURE:
<221> NAME/KEY: MISC_FEATURE
<222> LOCATION: (110)..(113)
<223> OTHER INFORMATION: Xaa is Gly or is absent
<220> FEATURE:
<221> NAME/KEY: MISC_FEATURE
<222> LOCATION: (114)..(114)
<223> OTHER INFORMATION: Xaa is Ser or is absent
<220> FEATURE:
<221> NAME/KEY: MISC_FEATURE
<222> LOCATION: (115)..(118)
<223> OTHER INFORMATION: Xaa is Gly or is absent
<220> FEATURE:
<221> NAME/KEY: MISC_FEATURE
<222> LOCATION: (119)..(119)
<223> OTHER INFORMATION: Xaa is Ser or is absent
<220> FEATURE:
<221> NAME/KEY: MISC_FEATURE
<222> LOCATION: (120)..(123)
<223> OTHER INFORMATION: Xaa is Gly or is absent
<220> FEATURE:
<221> NAME/KEY: MISC_FEATURE
<222> LOCATION: (124)..(124)
<223> OTHER INFORMATION: Xaa is Ser or is absent
<220> FEATURE:
<221> NAME/KEY: MISC_FEATURE
<222> LOCATION: (125)..(128)
<223> OTHER INFORMATION: Xaa is Gly or is absent
<220> FEATURE:
<221> NAME/KEY: MISC_FEATURE
<222> LOCATION: (129)..(129)
<223> OTHER INFORMATION: Xaa is Ser or is absent
<220> FEATURE:
<221> NAME/KEY: MISC_FEATURE
<222> LOCATION: (130)..(133)
<223> OTHER INFORMATION: Xaa is Gly or is absent
<220> FEATURE:
<221> NAME/KEY: MISC_FEATURE
<222> LOCATION: (134)..(134)
<223> OTHER INFORMATION: Xaa is Ser or is absent

<400> SEQUENCE: 551

Gly Ala Pro Gly Gly Gly Ser Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Pro Ala Pro
        35                  40                  45

Ala Pro Xaa Xaa Xaa Xaa Xaa Xaa Xaa Ala Ala Ala Lys Glu Xaa Xaa
```

```
                50                  55                  60
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Gly Gly Gly Gly Ser Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Gly Ala Pro
    130                 135

<210> SEQ ID NO 552
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 552

Gly Ala Pro Gly Gly Gly Gly Ala Xaa Pro Ala Pro Ala Pro Xaa Ala
 1               5                  10                  15

Ala Ala Lys Glu Xaa Gly Gly Gly Gly Ala Gly Ala Pro
             20                  25

<210> SEQ ID NO 553
<211> LENGTH: 47
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid

<400> SEQUENCE: 553

Gly Ala Pro Gly Gly Gly Gly Ala Gly Gly Gly Gly Ala Xaa Xaa Pro
 1               5                  10                  15

Ala Pro Ala Pro Xaa Xaa Ala Ala Ala Lys Glu Ala Ala Ala Lys Glu
             20                  25                  30

Xaa Xaa Gly Gly Gly Gly Ala Gly Gly Gly Gly Ala Gly Ala Pro
         35                  40                  45

<210> SEQ ID NO 554
<211> LENGTH: 65
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid

<400> SEQUENCE: 554

Gly Ala Pro Gly Gly Gly Gly Ala Gly Gly Gly Ala Gly Gly
1               5                   10                  15

Gly Ala Xaa Xaa Xaa Pro Ala Pro Ala Pro Xaa Xaa Xaa Ala Ala Ala
                20                  25                  30

Lys Glu Ala Ala Ala Lys Glu Ala Ala Ala Lys Glu Xaa Xaa Xaa Gly
        35                  40                  45

Gly Gly Gly Ala Gly Gly Gly Gly Ala Gly Gly Gly Ala Gly Ala
    50                  55                  60

Pro
65

<210> SEQ ID NO 555
<211> LENGTH: 83
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (33)..(36)
<223> OTHER INFORMATION: Xaa can be any naturally occurring amino acid
<220> FEATURE:
<221> NAME/KEY: misc_feature
<222> LOCATION: (57)..(60)
<223> OTHER INFORMATION: Xaa can be any naturally occurring amino acid

<400> SEQUENCE: 555

Gly Ala Pro Gly Gly Gly Gly Ala Gly Gly Gly Ala Gly Gly
1               5                   10                  15

Gly Ala Gly Gly Gly Gly Ala Xaa Xaa Xaa Xaa Pro Ala Pro Ala Pro
                20                  25                  30

Xaa Xaa Xaa Xaa Ala Ala Ala Lys Glu Ala Ala Ala Lys Glu Ala Ala
        35                  40                  45

Ala Lys Glu Ala Ala Ala Lys Glu Xaa Xaa Xaa Xaa Gly Gly Gly Gly
    50                  55                  60

Ala Gly Gly Gly Gly Ala Gly Gly Gly Ala Gly Gly Gly Ala
65                  70                  75                  80

Gly Ala Pro

<210> SEQ ID NO 556
<211> LENGTH: 101
<212> TYPE: PRT
<213> ORGANISM: Artificial Sequence
<220> FEATURE:
```

<223> OTHER INFORMATION: Synthetic peptide
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (69)..(73)
<223> OTHER INFORMATION: Xaa can be any naturally occurring amino acid

<400> SEQUENCE: 556

Gly Ala Pro Gly Gly Gly Ala Gly Gly Gly Ala Gly Gly Gly
1               5                   10                  15

Gly Ala Gly Gly Gly Gly Ala Gly Gly Gly Ala Xaa Xaa Xaa Xaa
            20                  25                  30

Xaa Pro Ala Pro Ala Pro Xaa Xaa Xaa Xaa Ala Ala Ala Lys Glu
        35                  40                  45

Ala Ala Ala Lys Glu Ala Ala Ala Lys Glu Ala Ala Ala Lys Glu Ala
    50                  55                  60

Ala Ala Lys Glu Xaa Xaa Xaa Xaa Xaa Gly Gly Gly Gly Ala Gly Gly
65                  70                  75                  80

Gly Gly Ala Gly Gly Gly Ala Gly Gly Gly Ala Gly Gly Gly
            85                  90                  95

Gly Ala Gly Ala Pro
            100

<210> SEQ ID NO 557
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(39)
<223> OTHER INFORMATION: Xaa can be any naturally occurring amino acid
<220> FEATURE:
<221> NAME/KEY: misc_feature
<222> LOCATION: (45)..(50)
<223> OTHER INFORMATION: Xaa can be any naturally occurring amino acid
<220> FEATURE:
<221> NAME/KEY: misc_feature
<222> LOCATION: (81)..(86)
<223> OTHER INFORMATION: Xaa can be any naturally occurring amino acid

<400> SEQUENCE: 557

Gly Ala Pro Gly Gly Gly Ala Gly Gly Gly Ala Gly Gly Gly
1               5                   10                  15

Gly Ala Gly Gly Gly Gly Ala Gly Gly Gly Ala Gly Gly Gly
            20                  25                  30

Ala Xaa Xaa Xaa Xaa Xaa Xaa Pro Ala Pro Ala Pro Xaa Xaa Xaa Xaa
        35                  40                  45

Xaa Xaa Ala Ala Ala Lys Glu Ala Ala Ala Lys Glu Ala Ala Ala Lys
    50                  55                  60

Glu Ala Ala Ala Lys Glu Ala Ala Ala Lys Glu Ala Ala Ala Lys Glu
65                  70                  75                  80

Xaa Xaa Xaa Xaa Xaa Xaa Gly Gly Gly Gly Ala Gly Gly Gly Ala
            85                  90                  95

Gly Gly Gly Gly Ala Gly Gly Gly Gly Ala Gly Gly Gly Ala Gly
            100                 105                 110

Gly Gly Gly Ala Gly Ala Pro
        115

<210> SEQ ID NO 558
<211> LENGTH: 137
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(45)
<223> OTHER INFORMATION: Xaa can be any naturally occurring amino acid
<220> FEATURE:
<221> NAME/KEY: misc_feature
<222> LOCATION: (51)..(57)
<223> OTHER INFORMATION: Xaa can be any naturally occurring amino acid
<220> FEATURE:
<221> NAME/KEY: misc_feature
<222> LOCATION: (93)..(99)
<223> OTHER INFORMATION: Xaa can be any naturally occurring amino acid

<400> SEQUENCE: 558

Gly Ala Pro Gly Gly Gly Ala Gly Gly Gly Ala Gly Gly Gly
1               5                  10                  15

Gly Ala Gly Gly Gly Gly Ala Gly Gly Gly Ala Gly Gly Gly
                20                  25                  30

Ala Gly Gly Gly Gly Ala Xaa Xaa Xaa Xaa Xaa Xaa Xaa Pro Ala Pro
            35                  40                  45

Ala Pro Xaa Xaa Xaa Xaa Xaa Xaa Xaa Ala Ala Ala Lys Glu Ala Ala
        50                  55                  60

Ala Lys Glu Ala Ala Ala Lys Glu Ala Ala Ala Lys Glu Ala Ala Ala
65                  70                  75                  80

Lys Glu Ala Ala Ala Lys Glu Ala Ala Ala Lys Glu Xaa Xaa Xaa Xaa
                85                  90                  95

Xaa Xaa Xaa Gly Gly Gly Gly Ala Gly Gly Gly Ala Gly Gly Gly
            100                 105                 110

Gly Ala Gly Gly Gly Gly Ala Gly Gly Gly Ala Gly Gly Gly
        115                 120                 125

Ala Gly Gly Gly Gly Ala Gly Ala Pro
    130                 135

<210> SEQ ID NO 559
<211> LENGTH: 137
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(12)
<223> OTHER INFORMATION: Xaa is Gly or is absent
<220> FEATURE:
<221> NAME/KEY: MISC_FEATURE
<222> LOCATION: (13)..(13)
<223> OTHER INFORMATION: Xaa is Ala or is absent
<220> FEATURE:
<221> NAME/KEY: MISC_FEATURE
<222> LOCATION: (14)..(17)
<223> OTHER INFORMATION: Xaa is Gly or is absent
<220> FEATURE:
<221> NAME/KEY: MISC_FEATURE
<222> LOCATION: (18)..(18)
<223> OTHER INFORMATION: Xaa is Ala or is absent
<220> FEATURE:
<221> NAME/KEY: MISC_FEATURE
<222> LOCATION: (19)..(22)

```
<223> OTHER INFORMATION: Xaa is Gly or is absent
<220> FEATURE:
<221> NAME/KEY: MISC_FEATURE
<222> LOCATION: (23)..(23)
<223> OTHER INFORMATION: Xaa is Ala or is absent
<220> FEATURE:
<221> NAME/KEY: MISC_FEATURE
<222> LOCATION: (24)..(27)
<223> OTHER INFORMATION: Xaa is Gly or is absent
<220> FEATURE:
<221> NAME/KEY: MISC_FEATURE
<222> LOCATION: (28)..(28)
<223> OTHER INFORMATION: Xaa is Ala or is absent
<220> FEATURE:
<221> NAME/KEY: MISC_FEATURE
<222> LOCATION: (29)..(32)
<223> OTHER INFORMATION: Xaa is Gly or is absent
<220> FEATURE:
<221> NAME/KEY: MISC_FEATURE
<222> LOCATION: (33)..(33)
<223> OTHER INFORMATION: Xaa is Ala or is absent
<220> FEATURE:
<221> NAME/KEY: MISC_FEATURE
<222> LOCATION: (34)..(37)
<223> OTHER INFORMATION: Xaa is Gly or is absent
<220> FEATURE:
<221> NAME/KEY: MISC_FEATURE
<222> LOCATION: (38)..(38)
<223> OTHER INFORMATION: Xaa is Ala or is absent
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(45)
<223> OTHER INFORMATION: Xaa is any amino acid or is absent
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (52)..(57)
<223> OTHER INFORMATION: Xaa is any amino acid or is absent
<220> FEATURE:
<221> NAME/KEY: MISC_FEATURE
<222> LOCATION: (63)..(65)
<223> OTHER INFORMATION: Xaa is Ala or is absent
<220> FEATURE:
<221> NAME/KEY: MISC_FEATURE
<222> LOCATION: (66)..(66)
<223> OTHER INFORMATION: Xaa is Lys or is absent
<220> FEATURE:
<221> NAME/KEY: MISC_FEATURE
<222> LOCATION: (67)..(67)
<223> OTHER INFORMATION: Xaa is Glu or is absent
<220> FEATURE:
<221> NAME/KEY: MISC_FEATURE
<222> LOCATION: (68)..(70)
<223> OTHER INFORMATION: Xaa is Ala or is absent
<220> FEATURE:
<221> NAME/KEY: MISC_FEATURE
<222> LOCATION: (71)..(71)
<223> OTHER INFORMATION: Xaa is Lys or is absent
<220> FEATURE:
<221> NAME/KEY: MISC_FEATURE
<222> LOCATION: (72)..(72)
<223> OTHER INFORMATION: Xaa is Glu or is absent
<220> FEATURE:
<221> NAME/KEY: MISC_FEATURE
<222> LOCATION: (73)..(75)
<223> OTHER INFORMATION: Xaa is Ala or is absent
<220> FEATURE:
<221> NAME/KEY: MISC_FEATURE
<222> LOCATION: (76)..(76)
<223> OTHER INFORMATION: Xaa is Lys or is absent
<220> FEATURE:
<221> NAME/KEY: MISC_FEATURE
```

```
<222> LOCATION: (77)..(77)
<223> OTHER INFORMATION: Xaa is Glu or is absent
<220> FEATURE:
<221> NAME/KEY: MISC_FEATURE
<222> LOCATION: (78)..(80)
<223> OTHER INFORMATION: Xaa is Ala or is absent
<220> FEATURE:
<221> NAME/KEY: MISC_FEATURE
<222> LOCATION: (81)..(81)
<223> OTHER INFORMATION: Xaa is Lys or is absent
<220> FEATURE:
<221> NAME/KEY: MISC_FEATURE
<222> LOCATION: (82)..(82)
<223> OTHER INFORMATION: Xaa is Glu or is absent
<220> FEATURE:
<221> NAME/KEY: MISC_FEATURE
<222> LOCATION: (83)..(85)
<223> OTHER INFORMATION: Xaa is Ala or is absent
<220> FEATURE:
<221> NAME/KEY: MISC_FEATURE
<222> LOCATION: (86)..(86)
<223> OTHER INFORMATION: Xaa is Lys or is absent
<220> FEATURE:
<221> NAME/KEY: MISC_FEATURE
<222> LOCATION: (87)..(87)
<223> OTHER INFORMATION: Xaa is Glu or is absent
<220> FEATURE:
<221> NAME/KEY: MISC_FEATURE
<222> LOCATION: (88)..(90)
<223> OTHER INFORMATION: Xaa is Ala or is absent
<220> FEATURE:
<221> NAME/KEY: MISC_FEATURE
<222> LOCATION: (91)..(91)
<223> OTHER INFORMATION: Xaa is Lys or is absent
<220> FEATURE:
<221> NAME/KEY: MISC_FEATURE
<222> LOCATION: (92)..(92)
<223> OTHER INFORMATION: Xaa is Glu or is absent
<220> FEATURE:
<221> NAME/KEY: MISC_FEATURE
<222> LOCATION: (93)..(93)
<223> OTHER INFORMATION: Xaa is any amino acid
<220> FEATURE:
<221> NAME/KEY: MISC_FEATURE
<222> LOCATION: (94)..(99)
<223> OTHER INFORMATION: Xaa is any amino acid or is absent
<220> FEATURE:
<221> NAME/KEY: MISC_FEATURE
<222> LOCATION: (105)..(108)
<223> OTHER INFORMATION: Xaa is Gly or is absent
<220> FEATURE:
<221> NAME/KEY: MISC_FEATURE
<222> LOCATION: (109)..(109)
<223> OTHER INFORMATION: Xaa is Ala or is absent
<220> FEATURE:
<221> NAME/KEY: MISC_FEATURE
<222> LOCATION: (110)..(113)
<223> OTHER INFORMATION: Xaa is Gly or is absent
<220> FEATURE:
<221> NAME/KEY: MISC_FEATURE
<222> LOCATION: (114)..(114)
<223> OTHER INFORMATION: Xaa is Ala or is absent
<220> FEATURE:
<221> NAME/KEY: MISC_FEATURE
<222> LOCATION: (115)..(118)
<223> OTHER INFORMATION: Xaa is Gly or is absent
<220> FEATURE:
<221> NAME/KEY: MISC_FEATURE
<222> LOCATION: (119)..(119)
<223> OTHER INFORMATION: Xaa is Ala or is absent
<220> FEATURE:
<221> NAME/KEY: MISC_FEATURE
<222> LOCATION: (120)..(123)
<223> OTHER INFORMATION: Xaa is Gly or is absent
<220> FEATURE:
<221> NAME/KEY: MISC_FEATURE
<222> LOCATION: (124)..(124)
<223> OTHER INFORMATION: Xaa is Ala or is absent
<220> FEATURE:
```

<221> NAME/KEY: MISC_FEATURE
<222> LOCATION: (125)..(128)
<223> OTHER INFORMATION: Xaa is Gly or is absent
<220> FEATURE:
<221> NAME/KEY: MISC_FEATURE
<222> LOCATION: (129)..(129)
<223> OTHER INFORMATION: Xaa is Ala or is absent
<220> FEATURE:
<221> NAME/KEY: MISC_FEATURE
<222> LOCATION: (130)..(133)
<223> OTHER INFORMATION: Xaa is Gly or is absent
<220> FEATURE:
<221> NAME/KEY: MISC_FEATURE
<222> LOCATION: (134)..(134)
<223> OTHER INFORMATION: Xaa is Ala or is absent

<400> SEQUENCE: 559

```
Gly Ala Pro Gly Gly Gly Ala Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Pro Ala Pro
            35                  40                  45

Ala Pro Xaa Xaa Xaa Xaa Xaa Xaa Ala Ala Ala Lys Glu Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Gly Gly Gly Gly Ala Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Gly Ala Pro
        130                 135
```

<210> SEQ ID NO 560
<211> LENGTH: 812
<212> TYPE: PRT
<213> ORGANISM: Artificial Sequence
<220> FEATURE:
<223> OTHER INFORMATION: Synthetic peptide

<400> SEQUENCE: 560

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125
```

```
Tyr Arg Tyr Tyr Gln Asn Val Cys Thr Gln Ser Tyr Ser Phe Val Trp
        130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
```

```
                545                 550                 555                 560
Leu Asp Leu Thr Arg Gln Ala Val Gln Glu Leu Val Ser Leu Tyr Tyr
                    565                 570                 575

Glu Glu Ala Arg Ser Ala Tyr Leu Ser Lys Glu Leu Ala Ser Leu Leu
                580                 585                 590

Arg Ala Gly Gly Val Leu Ala Tyr Glu Leu Pro Ala Leu Asp Glu
            595                 600                 605

Val Leu Ala Ser Asp Ser Arg Phe Leu Leu Gly Ser Trp Leu Glu Gln
        610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
                660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
        690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Glu Phe Gly Gly Gly Ser Thr Arg
                740                 745                 750

Leu Cys Gly Gly Glu Leu Val Asp Thr Leu Gln Phe Val Cys Gly Asp
                755                 760                 765

Arg Gly Phe Tyr Phe Ser Arg Pro Ala Ser Arg Val Ser Ala Arg Ser
                770                 775                 780

Arg Gly Ile Val Glu Glu Cys Cys Phe Arg Ser Cys Asp Leu Ala Leu
785                 790                 795                 800

Leu Glu Thr Tyr Cys Ala Thr Pro Ala Lys Ser Glu
                805                 810

<210> SEQ ID NO 561
<211> LENGTH: 806
<212> TYPE: PRT
<213> ORGANISM: Artificial Sequence
<220> FEATURE:
<223> OTHER INFORMATION: Synthetic peptide

<400> SEQUENCE: 561

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
```

```
              100                 105                 110
Pro Leu Pro Ala Val Pro Gly Glu Leu Thr Glu Ala Thr Pro Asn Arg
            115                 120                 125
Tyr Arg Tyr Tyr Gln Asn Val Cys Thr Gln Ser Tyr Ser Phe Val Trp
130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
                180                 185                 190
Phe Thr Gly Pro Ala Phe Leu Ala Trp Gly Arg Met Gly Asn Leu His
            195                 200                 205
Thr Trp Asp Gly Pro Leu Pro Ser Trp His Ile Lys Gln Leu Tyr
210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
            275                 280                 285
Pro Ile Ile Gly Ser Leu Phe Leu Arg Glu Leu Ile Lys Glu Phe Gly
            290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
            355                 360                 365
Val Leu Gly Ala Val Pro Arg Gly Arg Leu Leu Val Leu Asp Leu Phe
            370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
                420                 425                 430
Phe Pro Asn Ser Thr Met Val Gly Thr Gly Met Ala Pro Glu Gly Ile
            435                 440                 445
Ser Gln Asn Glu Val Val Tyr Ser Leu Met Ala Glu Leu Gly Trp Arg
            450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
            515                 520                 525
```

Ile Trp Tyr Asn Arg Ser Asp Val Phe Glu Ala Trp Arg Leu Leu Leu
530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Leu Cys Gly Gly Glu Leu
            740                 745                 750

Val Asp Thr Leu Gln Phe Val Cys Gly Asp Arg Gly Phe Tyr Phe Ser
        755                 760                 765

Arg Pro Ala Ser Arg Val Ser Ala Arg Ser Arg Gly Ile Val Glu Glu
770                 775                 780

Cys Cys Phe Arg Ser Cys Asp Leu Ala Leu Leu Glu Thr Tyr Cys Ala
785                 790                 795                 800

Thr Pro Ala Lys Ser Glu
                805

<210> SEQ ID NO 562
<211> LENGTH: 808
<212> TYPE: PRT
<213> ORGANISM: Artificial Sequence
<220> FEATURE:
<223> OTHER INFORMATION: Synthetic peptide

<400> SEQUENCE: 562

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

-continued

```
Thr Gly Val Ala Ala Ala Gly Leu His Arg Tyr Leu Arg Asp Phe
                85                  90                  95
Cys Gly Cys His Val Ala Trp Ser Gly Ser Gln Leu Arg Leu Pro Arg
                100                 105                 110
Pro Leu Pro Ala Val Pro Gly Glu Leu Thr Glu Ala Thr Pro Asn Arg
                115                 120                 125
Tyr Arg Tyr Tyr Gln Asn Val Cys Thr Gln Ser Tyr Ser Phe Val Trp
            130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
                180                 185                 190
Phe Thr Gly Pro Ala Phe Leu Ala Trp Gly Arg Met Gly Asn Leu His
                195                 200                 205
Thr Trp Asp Gly Pro Leu Pro Pro Ser Trp His Ile Lys Gln Leu Tyr
        210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
                260                 265                 270
Cys Ser Tyr Ser Cys Ser Phe Leu Leu Ala Pro Glu Asp Pro Ile Phe
            275                 280                 285
Pro Ile Ile Gly Ser Leu Phe Leu Arg Glu Leu Ile Lys Glu Phe Gly
        290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
        355                 360                 365
Val Leu Gly Ala Val Pro Arg Gly Arg Leu Leu Val Leu Asp Leu Phe
    370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
        435                 440                 445
Ser Gln Asn Glu Val Val Tyr Ser Leu Met Ala Glu Leu Gly Trp Arg
    450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
```

-continued

```
Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Gly Gly Ser Leu Cys Gly Gly
            740                 745                 750

Glu Leu Val Asp Thr Leu Gln Phe Val Cys Gly Asp Arg Gly Phe Tyr
        755                 760                 765

Phe Ser Arg Pro Ala Ser Arg Val Ser Ala Arg Ser Arg Gly Ile Val
    770                 775                 780

Glu Glu Cys Cys Phe Arg Ser Cys Asp Leu Ala Leu Leu Glu Thr Tyr
785                 790                 795                 800

Cys Ala Thr Pro Ala Lys Ser Glu
                805
```

<210> SEQ ID NO 563
<211> LENGTH: 810
<212> TYPE: PRT
<213> ORGANISM: Artificial Sequence
<220> FEATURE:
<223> OTHER INFORMATION: Synthetic peptide

<400> SEQUENCE: 563

```
Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45
```

-continued

Ser Val Ser Val Glu Arg Ala Leu Ala Ala Lys Pro Gly Leu Asp Thr
 50                  55                  60

Tyr Ser Leu Gly Gly Gly Ala Ala Arg Val Arg Val Arg Gly Ser
 65                  70                  75                  80

Thr Gly Val Ala Ala Ala Gly Leu His Arg Tyr Leu Arg Asp Phe
                 85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
 130                 135                 140

Trp Asp Trp Ala Arg Trp Glu Arg Glu Ile Asp Trp Met Ala Leu Asn
 145                 150                 155                 160

Gly Ile Asn Leu Ala Leu Ala Trp Ser Gly Gln Glu Ala Ile Trp Gln
                 165                 170                 175

Arg Val Tyr Leu Ala Leu Gly Leu Thr Gln Ala Glu Ile Asn Glu Phe
                 180                 185                 190

Phe Thr Gly Pro Ala Phe Leu Ala Trp Gly Arg Met Gly Asn Leu His
                 195                 200                 205

Thr Trp Asp Gly Pro Leu Pro Pro Ser Trp His Ile Lys Gln Leu Tyr
 210                 215                 220

Leu Gln His Arg Val Leu Asp Gln Met Arg Ser Phe Gly Met Thr Pro
 225                 230                 235                 240

Val Leu Pro Ala Phe Ala Gly His Val Pro Glu Ala Val Thr Arg Val
                 245                 250                 255

Phe Pro Gln Val Asn Val Thr Lys Met Gly Ser Trp Gly His Phe Asn
                 260                 265                 270

Cys Ser Tyr Ser Cys Ser Phe Leu Leu Ala Pro Glu Asp Pro Ile Phe
                 275                 280                 285

Pro Ile Ile Gly Ser Leu Phe Leu Arg Glu Leu Ile Lys Glu Phe Gly
                 290                 295                 300

Thr Asp His Ile Tyr Gly Ala Asp Thr Phe Asn Glu Met Gln Pro Pro
 305                 310                 315                 320

Ser Ser Glu Pro Ser Tyr Leu Ala Ala Thr Thr Ala Val Tyr Glu
                 325                 330                 335

Ala Met Thr Ala Val Asp Thr Glu Ala Val Trp Leu Leu Gln Gly Trp
                 340                 345                 350

Leu Phe Gln His Gln Pro Gln Phe Trp Gly Pro Ala Gln Ile Arg Ala
                 355                 360                 365

Val Leu Gly Ala Val Pro Arg Gly Arg Leu Leu Val Leu Asp Leu Phe
 370                 375                 380

Ala Glu Ser Gln Pro Val Tyr Thr Arg Thr Ala Ser Phe Gln Gly Gln
 385                 390                 395                 400

Pro Phe Ile Trp Cys Met Leu His Asn Phe Gly Gly Asn His Gly Leu
                 405                 410                 415

Phe Gly Ala Leu Glu Ala Val Asn Gly Gly Pro Glu Ala Ala Arg Leu
                 420                 425                 430

Phe Pro Asn Ser Thr Met Val Gly Thr Gly Met Ala Pro Glu Gly Ile
                 435                 440                 445

Ser Gln Asn Glu Val Val Tyr Ser Leu Met Ala Glu Leu Gly Trp Arg
 450                 455                 460

Lys Asp Pro Val Pro Asp Leu Ala Ala Trp Val Thr Ser Phe Ala Ala

```
            465                 470                 475                 480
    Arg Arg Tyr Gly Val Ser His Pro Asp Ala Gly Ala Ala Trp Arg Leu
                    485                 490                 495

Leu Leu Arg Ser Val Tyr Asn Cys Ser Gly Glu Ala Cys Arg Gly His
                    500                 505                 510

Asn Arg Ser Pro Leu Val Arg Pro Ser Leu Gln Met Asn Thr Ser
                515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
    545                 550                 555                 560

Leu Asp Leu Thr Arg Gln Ala Val Gln Glu Leu Val Ser Leu Tyr Tyr
                    565                 570                 575

Glu Glu Ala Arg Ser Ala Tyr Leu Ser Lys Glu Leu Ala Ser Leu Leu
                    580                 585                 590

Arg Ala Gly Gly Val Leu Ala Tyr Glu Leu Pro Ala Leu Asp Glu
                595                 600                 605

Val Leu Ala Ser Asp Ser Arg Phe Leu Leu Gly Ser Trp Leu Glu Gln
            610                 615                 620

Ala Arg Ala Ala Ala Val Ser Glu Ala Glu Ala Asp Phe Tyr Glu Gln
    625                 630                 635                 640

Asn Ser Arg Tyr Gln Leu Thr Leu Trp Gly Pro Glu Gly Asn Ile Leu
                    645                 650                 655

Asp Tyr Ala Asn Lys Gln Leu Ala Gly Leu Val Ala Asn Tyr Tyr Thr
                    660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
            690                 695                 700

Glu Gln Ala Phe Val Leu Ser Lys Gln Arg Tyr Pro Ser Gln Pro Arg
    705                 710                 715                 720

Gly Asp Thr Val Asp Leu Ala Lys Lys Ile Phe Leu Lys Tyr Tyr Pro
                    725                 730                 735

Arg Trp Val Ala Gly Ser Trp Gly Pro Ser Gly Ser Pro Gly Leu Cys
                    740                 745                 750

Gly Gly Glu Leu Val Asp Thr Leu Gln Phe Val Cys Gly Asp Arg Gly
                755                 760                 765

Phe Tyr Phe Ser Arg Pro Ala Ser Arg Val Ser Ala Arg Ser Arg Gly
            770                 775                 780

Ile Val Glu Glu Cys Cys Phe Arg Ser Cys Asp Leu Ala Leu Leu Glu
    785                 790                 795                 800

Thr Tyr Cys Ala Thr Pro Ala Lys Ser Glu
                    805                 810

<210> SEQ ID NO 564
<211> LENGTH: 828
<212> TYPE: PRT
<213> ORGANISM: Artificial Sequence
<220> FEATURE:
<223> OTHER INFORMATION: Synthetic peptide

<400> SEQUENCE: 564

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
```

-continued

```
                20                  25                  30
Arg Ala Leu Val Ala Arg Leu Leu Gly Pro Gly Pro Ala Ala Asp Phe
                35                  40                  45
Ser Val Ser Val Glu Arg Ala Leu Ala Lys Pro Gly Leu Asp Thr
    50                  55                  60
Tyr Ser Leu Gly Gly Gly Ala Ala Arg Val Arg Val Arg Gly Ser
65                  70                  75                  80
Thr Gly Val Ala Ala Ala Gly Leu His Arg Tyr Leu Arg Asp Phe
                85                  90                  95
Cys Gly Cys His Val Ala Trp Ser Gly Ser Gln Leu Arg Leu Pro Arg
                100                 105                 110
Pro Leu Pro Ala Val Pro Gly Glu Leu Thr Glu Ala Thr Pro Asn Arg
            115                 120                 125
Tyr Arg Tyr Tyr Gln Asn Val Cys Thr Gln Ser Tyr Ser Phe Val Trp
            130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
                180                 185                 190
Phe Thr Gly Pro Ala Phe Leu Ala Trp Gly Arg Met Gly Asn Leu His
                195                 200                 205
Thr Trp Asp Gly Pro Leu Pro Pro Ser Trp His Ile Lys Gln Leu Tyr
            210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
            275                 280                 285
Pro Ile Ile Gly Ser Leu Phe Leu Arg Glu Leu Ile Lys Glu Phe Gly
            290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
                325                 330                 335
Ala Met Thr Ala Val Asp Thr Glu Ala Val Trp Leu Leu Gln Gly Trp
                340                 345                 350
Leu Phe Gln His Gln Pro Gln Phe Trp Gly Pro Ala Gln Ile Arg Ala
                355                 360                 365
Val Leu Gly Ala Val Pro Arg Gly Arg Leu Leu Val Leu Asp Leu Phe
            370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
            405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
            435                 440                 445
```

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Gly Gly Ser Gly Gly Gly Gly
            740                 745                 750

Ser Gly Gly Gly Ser Gly Gly Gly Ser Gly Gly Gly Pro Ser
        755                 760                 765

Leu Cys Gly Gly Glu Leu Val Asp Thr Leu Gln Phe Val Cys Gly Asp
    770                 775                 780

Arg Gly Phe Tyr Phe Ser Arg Pro Ala Ser Arg Val Ser Ala Arg Ser
785                 790                 795                 800

Arg Gly Ile Val Glu Glu Cys Cys Phe Arg Ser Cys Asp Leu Ala Leu
                805                 810                 815

Leu Glu Thr Tyr Cys Ala Thr Pro Ala Lys Ser Glu
            820                 825

<210> SEQ ID NO 565
<211> LENGTH: 859
<212> TYPE: PRT
<213> ORGANISM: Artificial Sequence
<220> FEATURE:

<223> OTHER INFORMATION: Synthetic peptide

<400> SEQUENCE: 565

```
Met Glu Ala Val Ala Val Ala Ala Val Gly Val Leu Leu Leu Ala
1               5                   10                  15

Gly Ala Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
                115                 120                 125

Tyr Arg Tyr Tyr Gln Asn Val Cys Thr Gln Ser Tyr Ser Phe Val Trp
                130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190

Phe Thr Gly Pro Ala Phe Leu Ala Trp Gly Arg Met Gly Asn Leu His
                195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
                275                 280                 285

Pro Ile Ile Gly Ser Leu Phe Leu Arg Glu Leu Ile Lys Glu Phe Gly
                290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
                355                 360                 365

Val Leu Gly Ala Val Pro Arg Gly Arg Leu Leu Val Leu Asp Leu Phe
                370                 375                 380

Ala Glu Ser Gln Pro Val Tyr Thr Arg Thr Ala Ser Phe Gln Gly Gln
385                 390                 395                 400
```

```
Pro Phe Ile Trp Cys Met Leu His Asn Phe Gly Gly Asn His Gly Leu
            405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
            450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
            485                 490                 495

Leu Leu Arg Ser Val Tyr Asn Cys Ser Gly Glu Ala Cys Arg Gly His
            500                 505                 510

Asn Arg Ser Pro Leu Val Arg Pro Ser Leu Gln Met Asn Thr Ser
            515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
            565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
            610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
            645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
            690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
            725                 730                 735

Arg Trp Val Ala Gly Ser Trp Gly Ala Pro Gly Gly Ser Pro Ala Gly
            740                 745                 750

Ser Pro Thr Ser Thr Glu Glu Gly Thr Glu Ser Ala Thr Pro Glu
            755                 760                 765

Ser Gly Pro Gly Thr Ser Thr Glu Pro Ser Glu Gly Ser Ala Pro Gly
            770                 775                 780

Ser Pro Ala Gly Ser Pro Thr Ser Thr Gly Pro Ser Gly Ala Pro Leu
785                 790                 795                 800

Cys Gly Gly Glu Leu Val Asp Thr Leu Gln Phe Val Cys Gly Asp Arg
            805                 810                 815

Gly Phe Tyr Phe Ser Arg Pro Ala Ser Arg Val Ser Ala Arg Ser Arg
```

```
            820                 825                 830
Gly Ile Val Glu Glu Cys Cys Phe Arg Ser Cys Asp Leu Ala Leu Leu
                835                 840                 845
Glu Thr Tyr Cys Ala Thr Pro Ala Lys Ser Glu
    850                 855
```

<210> SEQ ID NO 566
<211> LENGTH: 834
<212> TYPE: PRT
<213> ORGANISM: Artificial Sequence
<220> FEATURE:
<223> OTHER INFORMATION: Synthetic peptide

<400> SEQUENCE: 566

```
Met Glu Ala Val Ala Val Ala Ala Ala Val Gly Val Leu Leu Leu Ala
1               5                   10                  15
Gly Ala Gly Gly Ala Ala Gly Asp Glu Ala Arg Glu Ala Ala Ala Val
                20                  25                  30
Arg Ala Leu Val Ala Arg Leu Leu Gly Pro Gly Pro Ala Ala Asp Phe
            35                  40                  45
Ser Val Ser Val Glu Arg Ala Leu Ala Ala Lys Pro Gly Leu Asp Thr
    50                  55                  60
Tyr Ser Leu Gly Gly Gly Ala Ala Arg Val Arg Val Arg Gly Ser
65                  70                  75                  80
Thr Gly Val Ala Ala Ala Gly Leu His Arg Tyr Leu Arg Asp Phe
                85                  90                  95
Cys Gly Cys His Val Ala Trp Ser Gly Ser Gln Leu Arg Leu Pro Arg
            100                 105                 110
Pro Leu Pro Ala Val Pro Gly Glu Leu Thr Glu Ala Thr Pro Asn Arg
    115                 120                 125
Tyr Arg Tyr Tyr Gln Asn Val Cys Thr Gln Ser Tyr Ser Phe Val Trp
130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
            180                 185                 190
Phe Thr Gly Pro Ala Phe Leu Ala Trp Gly Arg Met Gly Asn Leu His
    195                 200                 205
Thr Trp Asp Gly Pro Leu Pro Pro Ser Trp His Ile Lys Gln Leu Tyr
210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
    275                 280                 285
Pro Ile Ile Gly Ser Leu Phe Leu Arg Glu Leu Ile Lys Glu Phe Gly
290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
```

-continued

```
                325                 330                 335
Ala Met Thr Ala Val Asp Thr Glu Ala Val Trp Leu Leu Gln Gly Trp
                340                 345                 350
Leu Phe Gln His Gln Pro Gln Phe Trp Gly Pro Ala Gln Ile Arg Ala
                355                 360                 365
Val Leu Gly Ala Val Pro Arg Gly Arg Leu Leu Val Leu Asp Leu Phe
            370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
            435                 440                 445
Ser Gln Asn Glu Val Val Tyr Ser Leu Met Ala Glu Leu Gly Trp Arg
        450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
        515                 520                 525
Ile Trp Tyr Asn Arg Ser Asp Val Phe Glu Ala Trp Arg Leu Leu Leu
    530                 535                 540
Thr Ser Ala Pro Ser Leu Ala Thr Ser Pro Ala Phe Arg Tyr Asp Leu
545                 550                 555                 560
Leu Asp Leu Thr Arg Gln Ala Val Gln Glu Leu Val Ser Leu Tyr Tyr
                565                 570                 575
Glu Glu Ala Arg Ser Ala Tyr Leu Ser Lys Glu Leu Ala Ser Leu Leu
            580                 585                 590
Arg Ala Gly Gly Val Leu Ala Tyr Glu Leu Leu Pro Ala Leu Asp Glu
        595                 600                 605
Val Leu Ala Ser Asp Ser Arg Phe Leu Leu Gly Ser Trp Leu Glu Gln
    610                 615                 620
Ala Arg Ala Ala Val Ser Glu Ala Glu Ala Asp Phe Tyr Glu Gln
625                 630                 635                 640
Asn Ser Arg Tyr Gln Leu Thr Leu Trp Gly Pro Glu Gly Asn Ile Leu
                645                 650                 655
Asp Tyr Ala Asn Lys Gln Leu Ala Gly Leu Val Ala Asn Tyr Tyr Thr
            660                 665                 670
Pro Arg Trp Arg Leu Phe Leu Glu Ala Leu Val Asp Ser Val Ala Gln
        675                 680                 685
Gly Ile Pro Phe Gln Gln His Gln Phe Asp Lys Asn Val Phe Gln Leu
    690                 695                 700
Glu Gln Ala Phe Val Leu Ser Lys Gln Arg Tyr Pro Ser Gln Pro Arg
705                 710                 715                 720
Gly Asp Thr Val Asp Leu Ala Lys Lys Ile Phe Leu Lys Tyr Tyr Pro
                725                 730                 735
Arg Trp Val Ala Gly Ser Trp Gly Ala Pro Gly Gly Ser Pro Ala
            740                 745                 750
```

```
Pro Ala Pro Thr Pro Ala Pro Ala Pro Thr Pro Ala Pro Ala Gly Gly
            755                 760                 765

Gly Pro Ser Gly Ala Pro Leu Cys Gly Gly Glu Leu Val Asp Thr Leu
        770                 775                 780

Gln Phe Val Cys Gly Asp Arg Gly Phe Tyr Phe Ser Arg Pro Ala Ser
785                 790                 795                 800

Arg Val Ser Ala Arg Ser Arg Gly Ile Val Glu Glu Cys Cys Phe Arg
                805                 810                 815

Ser Cys Asp Leu Ala Leu Leu Glu Thr Tyr Cys Ala Thr Pro Ala Lys
            820                 825                 830

Ser Glu

<210> SEQ ID NO 567
<211> LENGTH: 846
<212> TYPE: PRT
<213> ORGANISM: Artificial Sequence
<220> FEATURE:
<223> OTHER INFORMATION: Synthetic peptide

<400> SEQUENCE: 567

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270
```

```
Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
    435                 440                 445

Ser Gln Asn Glu Val Val Tyr Ser Leu Met Ala Glu Leu Gly Trp Arg
            450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
```

```
                    690                 695                 700
Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                    725                 730                 735

Arg Trp Val Ala Gly Ser Trp Gly Ala Pro Gly Gly Ser Pro Ala
                740                 745                 750

Glu Ala Ala Lys Glu Ala Ala Lys Glu Ala Ala Lys Glu
                755                 760                 765

Ala Ala Ala Lys Glu Ala Ala Lys Ala Pro Ser Gly Gly Gly
            770                 775                 780

Ala Pro Leu Cys Gly Gly Glu Leu Val Asp Thr Leu Gln Phe Val Cys
785                 790                 795                 800

Gly Asp Arg Gly Phe Tyr Phe Ser Arg Pro Ala Ser Arg Val Ser Ala
                805                 810                 815

Arg Ser Arg Gly Ile Val Glu Glu Cys Cys Phe Arg Ser Cys Asp Leu
                820                 825                 830

Ala Leu Leu Glu Thr Tyr Cys Ala Thr Pro Ala Lys Ser Glu
                835                 840                 845

<210> SEQ ID NO 568
<211> LENGTH: 828
<212> TYPE: PRT
<213> ORGANISM: Artificial Sequence
<220> FEATURE:
<223> OTHER INFORMATION: Synthetic peptide

<400> SEQUENCE: 568

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
```

```
            210                 215                 220
Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
            245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
        290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
            325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
        370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
            405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
        450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
            485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
        530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
            565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
        610                 615                 620

Ala Arg Ala Ala Ala Val Ser Glu Ala Glu Ala Asp Phe Tyr Glu Gln
625                 630                 635                 640
```

```
Asn Ser Arg Tyr Gln Leu Thr Leu Trp Gly Pro Gly Asn Ile Leu
            645                 650                 655

Asp Tyr Ala Asn Lys Gln Leu Ala Gly Leu Val Ala Asn Tyr Tyr Thr
        660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
        690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
            725                 730                 735

Arg Trp Val Ala Gly Ser Trp Gly Gly Gly Ser Gly Gly Gly Gly
            740                 745                 750

Ser Gly Gly Gly Gly Ser Gly Gly Gly Gly Ser Gly Gly Gly Pro Ser
            755                 760                 765

Leu Cys Gly Gly Glu Leu Val Asp Thr Leu Gln Phe Val Cys Gly Asp
        770                 775                 780

Arg Gly Phe Tyr Phe Ser Arg Pro Ala Ser Arg Val Ser Ala Arg Ser
785                 790                 795                 800

Arg Gly Ile Val Glu Glu Cys Cys Phe Arg Ser Cys Asp Leu Ala Leu
            805                 810                 815

Leu Glu Thr Tyr Cys Ala Thr Pro Ala Lys Ser Glu
            820                 825

<210> SEQ ID NO 569
<211> LENGTH: 828
<212> TYPE: PRT
<213> ORGANISM: Artificial Sequence
<220> FEATURE:
<223> OTHER INFORMATION: Synthetic peptide

<400> SEQUENCE: 569

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
            85                  90                  95

Cys Gly Cys His Val Ala Trp Ser Gly Ser Gln Leu Arg Leu Pro Arg
        100                 105                 110

Pro Leu Pro Ala Val Pro Gly Glu Leu Thr Glu Ala Thr Pro Asn Arg
    115                 120                 125

Tyr Arg Tyr Tyr Gln Asn Val Cys Thr Gln Ser Tyr Ser Phe Val Trp
130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
            165                 170                 175
```

```
Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
            195                 200                 205

Thr Trp Asp Gly Pro Leu Pro Pro Ser Trp His Ile Lys Gln Leu Tyr
            210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
            485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590
```

```
Arg Ala Gly Gly Val Leu Ala Tyr Glu Leu Pro Ala Leu Asp Glu
            595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Gly Gly Ala Gly Gly Gly Gly
            740                 745                 750

Ala Gly Gly Gly Ala Gly Gly Gly Ala Gly Gly Pro Ser
        755                 760                 765

Leu Cys Gly Gly Glu Leu Val Asp Thr Leu Gln Phe Val Cys Gly Asp
    770                 775                 780

Arg Gly Phe Tyr Phe Ser Arg Pro Ala Ser Arg Val Ser Ala Arg Ser
785                 790                 795                 800

Arg Gly Ile Val Glu Glu Cys Cys Phe Arg Ser Cys Asp Leu Ala Leu
                805                 810                 815

Leu Glu Thr Tyr Cys Ala Thr Pro Ala Lys Ser Glu
            820                 825

<210> SEQ ID NO 570
<211> LENGTH: 8
<212> TYPE: DNA
<213> ORGANISM: Artificial Sequence
<220> FEATURE:
<223> OTHER INFORMATION: AscI restriction site

<400> SEQUENCE: 570 ggcgcgcc                                                              8

<210> SEQ ID NO 571
<211> LENGTH: 60
<212> TYPE: PRT
<213> ORGANISM: Homo sapiens

<400> SEQUENCE: 571

Leu Cys Gly Gly Glu Leu Val Asp Thr Leu Gln Phe Val Cys Gly Asp
1               5                   10                  15

Arg Gly Phe Tyr Phe Ser Arg Pro Ala Ser Arg Val Ser Arg Arg Ser
                20                  25                  30

Arg Gly Ile Val Glu Glu Cys Cys Phe Arg Ser Cys Asp Leu Ala Leu
            35                  40                  45

Leu Glu Thr Tyr Cys Ala Thr Pro Ala Lys Ser Glu
        50                  55                  60
```

TARGETED THERAPEUTIC LYSOSOMAL ENZYME FUSION PROTEINS AND USES THEREOF

This application claims the priority benefit of U.S. Provisional Application No. 61/730,378, filed Nov. 27, 2012, and U.S. Provisional Application No. 61/788,968, filed Mar. 15, 2013, herein incorporated by reference in their entireties.

FIELD OF THE INVENTION

The present invention relates in general to therapeutic fusion proteins useful to treat lyssomal storage diseases and methods for treating such diseases. Exemplary therapeutic fusion proteins comprise a lysosomal enzyme, a lysosomal targeting moiety, e.g., an IGF-II peptide, and a spacer peptide. It is contemplated that the lysosomal enzyme is alpha-N-acetylglucosaminidase (Naglu) and the disease is Mucopolysaccharidosis Type IIIB (Sanfilippo B Syndrome).

BACKGROUND

Normally, mammalian lysosomal enzymes are synthesized in the cytosol and traverse the ER where they are glycosylated with N-linked, high mannose type carbohydrate. In the golgi, the high mannose carbohydrate is modified on lysosomal enzymes by the addition of mannose-6-phosphate (M6P) which targets these proteins to the lysosome. The M6P-modified proteins are delivered to the lysosome via interaction with either of two M6P receptors. The most favorable form of modification is when two M6Ps are added to a high mannose carbohydrate.

More than forty lysosomal storage diseases (LSDs) are caused, directly or indirectly, by the absence of one or more lysosomal enzymes in the lysosome. Enzyme replacement therapy for LSDs is being actively pursued. Therapy generally requires that LSD proteins be taken up and delivered to the lysosomes of a variety of cell types in an M6P-dependent fashion. One possible approach involves purifying an LSD protein and modifying it to incorporate a carbohydrate moiety with M6P. This modified material may be taken up by the cells more efficiently than unmodified LSD proteins due to interaction with M6P receptors on the cell surface.

The inventors of the present application have previously developed a peptide based targeting technology that allows more efficient delivery of therapeutic enzymes to the lysosomes. This proprietary technology is termed Glycosylation Independent Lysosomal Targeting (GILT) because a peptide tag replaces M6P as the moiety targeting the lysosomes. Details of the GILT technology are described in U.S. Application Publication Nos. 2003-0082176, 2004-0006008, 2003-0072761, 2005-0281805, 2005-0244400, and international publications WO 03/032913, WO 03/032727, WO 02/087510, WO 03/102583, WO 2005/078077, the disclosures of all of which are hereby incorporated by reference.

SUMMARY OF THE INVENTION

The present invention provides further improved compositions and methods for efficient lysosomal targeting based on the GILT technology. Among other things, the present invention provides methods and compositions for targeting lysosomal enzymes to lysosomes using lysosomal targeting peptides. The present invention also provides methods and compositions for targeting lysosomal enzymes to lysosomes using a lysosomal targeting peptide that has reduced or diminished binding affinity for the IGF-I receptor and/or reduced or diminished binding affinity for the insulin receptor, and/or is resistant to furin cleavage. The present invention also provides lysosomal enzyme fusion proteins comprising a lysosomal enzyme and IGF-II and spacer peptides that provide for improved production and uptake into lysosomes of the lysosomal enzyme fusion protein. In certain embodiments, the lysosomal enzyme is alpha-N-acetylglucosaminidase (Naglu).

In one aspect, the invention provides a targeted therapeutic fusion protein comprising a lysosomal enzyme, a peptide tag having an amino acid sequence at least 70% identical to amino acids 8-67 of mature human IGF-II and a spacer peptide between the lysosomal enzyme and the IGF-II peptide tag. In various embodiments, the spacer peptide comprises one or more GGGPS (SEQ ID NO: 14) or GGGSP (SEQ ID NO: 15) amino acid sequences, and optionally further comprises one or more of (i) GAP (SEQ ID NO: 9), (ii) GGGGS (SEQ ID NO: 12), (iii) GGGS (SEQ ID NO: 16), (iv) AAAAS (SEQ ID NO: 17), (v) AAAS (SEQ ID NO: 18), (vi) PAPA (SEQ ID NO: 19), (vii) TPAPA (SEQ ID NO: 20), (viii) AAAKE (SEQ ID NO: 21) or (ix) GGGGA (SEQ ID NO: 60).

Exemplary lysosomal enzymes contemplated herein include those set out in Table 1.

In various embodiments, the targeted therapeutic fusion protein comprises an amino acid sequence at least 85% identical to a human α-N-acetylglucosaminidase (Naglu) protein (FIG. 1, SEQ ID NO: 1), a peptide tag having an amino acid sequence at least 70% identical to amino acids 8-67 of mature human IGF-II and a spacer peptide located between the Naglu amino acid sequence and the IGF-II peptide tag. In various embodiments, the spacer comprises the amino acid sequence GAP (SEQ ID NO: 9), GPS (SEQ ID NO: 10), or GGS (SEQ ID NO: 11). In various embodiments, the spacer sequence comprises amino acids Gly-Pro-Ser (GPS) (SEQ ID NO: 10) between the amino acids of mature human IGF-II and the amino acids of human Naglu.

In various embodiments, the spacer peptide comprises one or more GGGGS (SEQ ID NO: 12) or GGGS (SEQ ID NO: 16) amino acid sequences. In various embodiments, the spacer peptide comprises one or more GGGPS (SEQ ID NO: 14) or GGGSP (SEQ ID NO: 15) amino acid sequences. In various embodiments, the spacer peptide comprises one or more AAAAS (SEQ ID NO: 17) or AAAS (SEQ ID NO: 18) amino acid sequences. In various embodiments, the spacer peptide comprises one or more PAPA (SEQ ID NO: 19) or TPAPA (SEQ ID NO: 20) amino acid sequences. In various embodiments, the spacer peptide comprises one or more AAAKE (SEQ ID NO: 21) amino acid sequences. In various embodiments, the spacer peptide comprises one or more GGGGA (SEQ ID NO: 60) amino acid sequences.

In various embodiments, the spacer peptide comprises an amino acid sequence selected from the group consisting of: (GGGGS)$_n$ (SEQ ID NOs: 12, 56, 58, 91-94), (GGGGS)$_n$-GGGPS (SEQ ID NOs: 36, 95-100), GAP-(GGGGS)$_n$-GGGPS (SEQ ID NOs: 101-107), GAP-(GGGGS)$_n$-GGGPS-GAP (SEQ ID NOs: 37, 108-113), GAP-(GGGS)$_n$- GGGPS-(GGGGS)$_n$-GAP (SEQ ID NOs: 114-162), GAP-GGGPS-(GGGGS)$_n$-GAP (SEQ ID NOs: 163-169), GAP-(GGGGS)$_n$-AAAAS-GGGPS-(GGGGS)$_n$-AAAA-GAP (SEQ ID NOs: 170-218), GAP-(GGGGS)$_n$-PAPAP-(Xaa)$_n$-GAP (SEQ ID NOs: 219-267), GAP-(GGGGS)$_n$-PAPAPT-(Xaa)$_n$-GAP (SEQ ID NOs: 268-316), GAP-(GGGGS)$_n$-(Xaa)n-PAPAP-(Xaa)n-(AAAKE)n-(Xaa)n-(GGGGS)$_n$-GAP (SEQ ID NOs: 544-551), (GGGGA)$_n$ (SEQ ID NOs: 60, 79, 81, 317-320), (GGGGA)$_n$-GGGPS (SEQ ID NOs: 321-326), GAP-(GGGGA)$_n$-GGGPS (SEQ ID NOs: 327-333), GAP-(GGGGA)$_n$-GGGPS-GAP (SEQ ID NOs: 334-340), GAP-(GGGGA)$_n$-GGGPS-(GGGGA)$_n$-GAP (SEQ ID NOs: 341-389), GAP-GGGPS-(GGGGA)$_n$-GAP (SEQ ID NOs: 390-396), GAP-(GGGGA)$_n$-AAAAS-GGGPS-(GGGGA)$_n$-AAAA-GAP (SEQ ID NOs: 397-445), GAP-(GGGGA)$_n$-PAPAP-(Xaa)$_n$-GAP (SEQ ID NOs: 446-494), GAP-(GGGGA)$_n$-PAPAPT-(Xaa)$_n$-GAP (SEQ ID NOs: 495-543), GAP-(GGGGA)$_n$-(Xaa)n-PAPAP-(Xaa)$_n$-(AAAKE)$_n$-(Xaa)$_n$-(GGGGA)$_n$-GAP (SEQ ID NOs: 552-559); wherein n is 1 to 7. In various embodiments, n is 1 to 4.

In various embodiments, the present invention provides an IGF-II peptide for use as a peptide tag for targeting the peptide or fusion protein comprising the peptide to a mammalian lysosome. In various embodiments, the present invention provides an IGF-II mutein. In various embodiments, the invention provides a furin-resistant IGF-II mutein having an amino acid sequence at least 70% identical to mature human IGF-II (AYRPSETLCGGELVDTLQFVCGDRGFYF-SRPASRVSRRSRGIVEECCFRSCDLALLET YCATPAKSE) (SEQ ID NO: 5) and a mutation that abolishes at least one furin protease cleavage site.

In some embodiments, the present invention provides an IGF-II mutein comprising an amino acid sequence at least 70% identical to mature human IGF-II. In various embodiments, the IGF-II mutein peptide tag comprises amino acids 8-67 of mature human IGF-II. In various embodiments, the IGF-II mutein comprises a mutation that reduces or diminishes the binding affinity for the insulin receptor as compared to the wild-type human IGF-II.

In some embodiments, the IGF-II mutein has diminished binding affinity for the IGF-I receptor relative to the affinity of naturally-occurring human IGF-II for the IGF-I receptor.

In various embodiments, the present invention provides a targeted therapeutic fusion protein containing a lysosomal enzyme; and an IGF-II mutein having an amino acid sequence at least 70% identical to mature human IGF-II, wherein the IGF-II mutein is resistant to furin cleavage and binds to the human cation-independent mannose-6-phosphate receptor in a mannose-6-phosphate-independent manner.

In some embodiments, the present invention provides a targeted therapeutic fusion protein containing a lysosomal enzyme; and an IGF-II mutein having an amino acid sequence at least 70% identical to mature human IGF-II, and having diminished binding affinity for the insulin receptor relative to the affinity of naturally-occurring human IGF-II for the insulin receptor. In a related embodiment, the IGF-II mutein is resistant to furin cleavage and binds to the human cation-independent mannose-6-phosphate receptor in a mannose-6-phosphate-independent manner.

In various embodiments, an IGF-II mutein suitable for the invention includes a mutation within a region corresponding to amino acids 30-40 of mature human IGF-II. In some embodiments, an IGF-II mutein suitable for the invention includes a mutation within a region corresponding to amino acids 34-40 of mature human IGF-II such that the mutation abolishes at least one furin protease cleavage site. In some embodiments, a suitable mutation is an amino acid substitution, deletion and/or insertion. In some embodiments, the mutation is an amino acid substitution at a position corresponding to Arg37 or Arg40 of mature human IGF-II. In some embodiments, the amino acid substitution is a Lys or Ala substitution.

In some embodiments, a suitable mutation is a deletion or replacement of amino acid residues corresponding to positions selected from the group consisting of 30-40, 31-40, 32-40, 33-40, 34-40, 30-39, 31-39, 32-39, 34-37, 33-39, 34-39, 35-39, 36-39, 37-40 of mature human IGF-II, and combinations thereof.

In various embodiments, an IGF-II mutein according to the invention further contains a deletion or a replacement of amino acids corresponding to positions 2-7 of mature human IGF-II. In various embodiments, an IGF-II mutein according to the invention further includes a deletion or a replacement of amino acids corresponding to positions 1-7 of mature human IGF-II. In various embodiments, an IGF-II mutein according to the invention further contains a deletion or a replacement of amino acids corresponding to positions 62-67 of mature human IGF-II. In various embodiments, an IGF-II mutein according to the invention further contains an amino acid substitution at a position corresponding to Tyr27, Leu43, or Ser26 of mature human IGF-II. In various embodiments, an IGF-II mutein according to the invention contains at least an amino acid substitution selected from the group consisting of Tyr27Leu, Leu43Val, Ser26Phe and combinations thereof. In various embodiments, an IGF-II mutein according to the invention contains amino acids corresponding to positions 48-55 of mature human IGF-II. In various embodiments, an IGF-II mutein according to the invention contains at least three amino acids selected from the group consisting of amino acids corresponding to positions 8, 48, 49, 50, 54, and 55 of mature human IGF-II. In various embodiments, an IGF-II mutein of the invention contains, at positions corresponding to positions 54 and 55 of mature human IGF-II, amino acids each of which is uncharged or negatively charged at pH 7.4. In various embodiments, the IGF-II mutein has diminished binding affinity for the IGF-I receptor relative to the affinity of naturally-occurring human IGF-II for the IGF-I receptor. In various embodiments, the IGF-II mutein is IGF2 Δ8-67 R37A (i.e., amino acids 8-67 of mature human IGF-II with the Arg at position 37 of mature human IGF-II substituted by Ala).

In various embodiments, the peptide tag is attached to the N-terminus or C-terminus of the lysosomal enzyme, therefore is an N-terminal tag or a C-terminal tag, respectively. In various embodiments, the peptide tag is a C-terminal tag.

In some embodiments, a lysosomal enzyme suitable for the invention is human alpha-N-acetylglucosaminidase (Naglu) (FIG. 1), or a functional fragment or variant thereof. In some embodiments, a lysosomal enzyme suitable for the invention includes amino acids 1-743 of human alpha-N-acetylglucosaminidase or amino acids 24-743 of human alpha-N-acetylglucosaminidase, which lacks a signal sequence.

In various embodiments, a targeted therapeutic fusion protein of the invention further includes a spacer between the lysosomal enzyme and the IGF-II mutein.

In various embodiments, the spacer comprises an alpha-helical structure or a rigid structure.

In various embodiments, the spacer comprises one or more Gly-Ala-Pro (GAP) (SEQ ID NO: 9), Gly-Pro-Ser (GPS) (SEQ ID NO: 10), or Gly-Gly-Ser (GGS) (SEQ ID NO: 11) amino acid sequences.

In some embodiments, the spacer is selected from the group consisting of EFGGGGSTR (SEQ ID NO: 22), GAP (SEQ ID NO: 9), GGGGS (SEQ ID NO: 12), GPSGSPG (SEQ ID NO: 23), GPSGSPGT (SEQ ID NO: 24), GPSGSPGH (SEQ ID NO: 25), GGGGSGGGGSGGGGSGGGGSGGGPST (SEQ ID NO: 26), GGGGSGGGGSGGGGSGGGGSGGGPSH (SEQ ID NO: 27), GGGGSGGGGSGGGGSGGGGSGGGPSGGGGSGGGPS (SEQ ID NO: 28), GAPGGGGSGGGGSGGGGSGGGGSGGGPSGGG GSGGGPSGAP (SEQ ID NO: 29), GGGGSGGGGSGGGGSGGGGSGGGPSGGGGSGG GGSGGGGSGGGGSGGGPS (SEQ ID NO: 30), GAPGGGGSGGGGSGGGGSGGGGSGGGPSGGG
GSGGGGSGGGGSGGGGSGGGPSGA P (SEQ ID NO: 31),
GGGGSGGGGSGGGGSGGGPSGGGGSGGGGSGGGPS (SEQ ID NO: 32),
GAPGGGSGGGGSGGGGSGGGPSGGGGSGGGGSGGGPSGAP (SEQ ID NO: 33),
GGGGSGGGGSGGGGSGGGPSGGGGSGGGGSGGGPSGGGGSGGGGSGGGPS (SEQ ID NO: 34),
GAPGGGGSGGGGSGGGGSGGGPSGGGGSGGGGSGGGPSGGGGSGGGGSGGGPSGA P (SEQ ID NO: 35),
GGGGSGGGGSGGGGSGGGGSGGGPS (SEQ ID NO: 36), GAPGGGSGGGGSGGGGSGGGGSGGGPSGAP (SEQ ID NO: 37),
GGGGSGGGGSAAAASGGGGSGGGPS (SEQ ID NO: 38), GAPGGGSGGGGSAAAASGGGGSGGGPSGAP (SEQ ID NO: 39),
GGGGSGGGGSAAAASGGGGSGGGGSAAAASGGGGSGGGGSAAAASGGGPS (SEQ ID NO: 40),
GAPGGGGSGGGGSAAAASGGGGSGGGGSAAAASGGGGSGGGGSAAAASGGGPSG AP (SEQ ID NO: 41),
GGGGSGGGGSAAAASGGGPSGGGGSAAAASGGGPSGGGGSAAAASGGGPS (SEQ ID NO: 42),
GAPGGGGSGGGGSAAAASGGGPSGGGGSAAAASGGGPSGGGGSAAAASGGGPSGA P (SEQ ID NO: 43),
GGSPAGSPTSTEEGTSESATPESGPGT-STEPSEGSAPGSPAGSPGPS (SEQ ID NO: 44),
GAPGGSPAGSPTSTEEGTSESATPESG-PGTSTEPSEGSAPGSPAGSPGPSGAP (SEQ ID NO: 45),
GGSPAGSPTSTEEGTSESATPESGPGT-STEPSEGSAPGSPAGSPTSTGPS (SEQ ID NO: 46),
GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAKEAAAKEAAAKAGGPSGAP (SEQ ID NO: 53), GGGSPAE-AAAKEAAAKEAAAKEAAAKAPSGGG (SEQ ID NO: 54), GAPGGGSPAE-AAAKEAAAKEAAAKEAAAKAPSGGGGAP (SEQ ID NO: 55), GGGGSGGGGSGGGGS (SEQ ID NO: 56), GAPGGGGSGGGGSGGGGSGAP (SEQ ID NO: 57), GGGGSGGGGSGGGGSGGGGS (SEQ ID NO: 58), GAPGGGGSGGGGSGGGGSGGGGSGAP (SEQ ID NO: 59), GGGGA (SEQ ID NO: 60), GGGGAGGGGAGGG-GAGGGGAGGGPST (SEQ ID NO: 61), GGGGAGGG-GAGGGGAGGGGAGGGPSH (SEQ ID NO: 62), GGG-GAGGGGAGGGGAGGGGAGGGPSGGGAGGGPS (SEQ ID NO: 63), GAPGGGGAGGGGAGGGGAGGG-GAGGGPSGGGGAGGGPSGAP (SEQ ID NO: 64), GGG-GAGGGGAGGGGAGGGGAGGGPSGGG-GAGGGGAGGGGAGGGGAGGGPS (SEQ ID NO: 65), GAPGGGGAGGGGAGGGGAGGG-GAGGGPSGGGGAGGGGAGGGGAGGGGAGGGPS GAP (SEQ ID NO:66), GGGGAGGGGAGGG-GAGGGPSGGGGAGGGGAGGGPS (SEQ ID NO: 67), GAPGGGGAGGGGAGGGGAGGGPSGGG-GAGGGGAGGGPSGAP (SEQ ID NO: 68), GGGGAGGG-GAGGGGAGGGPSGGGGAGGG-GAGGGPSGGGGAGGGGAGGGPS (SEQ ID NO: 69), GAPGGGGAGGGGAGGGGAGGGPSGGG-GAGGGGAGGGPSGGGGAGGGGAGGGPS GAP (SEQ ID NO: 70), GGGGAGGGGAGGGGAGGGGAGGGPS (SEQ ID NO: 71), GAPGGGGAGGGGAGGGGAGGG-GAGGGPSGAP (SEQ ID NO: 72), GGGGAGGG-GAAAAASGGGGAGGGPS (SEQ ID NO: 73), GAPGGG-GAGGGGAAAAASGGGGAGGGPSGAP (SEQ ID NO: 74), GGGGAGGGGAAAASGGGGAGGG-GAAAAASGGGGAGGGGAAAAASGGGPS (SEQ ID NO: 75), GAPGGGGAGGGGAAAAASGGGGAGGG-GAAAAASGGGGAGGGGAAAAASGGGPS GAP (SEQ ID NO: 76), GGGGAGGGGAAAAASGGGPSGGG-GAAAAASGGGPSGGGGAAAAASGGGPS (SEQ ID NO: 77), GAPGGGGAGGGGAAAAASGGGPSGGG-GAAAAASGGGPSGGGGAAAAASGGGPSG AP (SEQ ID NO: 78), GGGGAGGGGAGGGGA (SEQ ID NO: 79), GAPGGGGAGGGGAGGGGAGAP (SEQ ID NO: 80), GGGGAGGGGAGGGGAGGGGA (SEQ ID NO: 81), GAPGGGGAGGGGAGGGGAGGGGAGAP (SEQ ID NO: 82), GGGGAGGGGAGGGGAGGGGAGGG-GAGGGGAGGGGAGGGPS [or (GGGGA)$_8$GGGPS] (SEQ ID NO: 83), GGGGAGGGGAGGGGAGGGGAGGG-GAGGGGAGGGGAGGGPSH [or (GGGGA)$_8$ GGGPSH] (SEQ ID NO: 84), GGGGAGGGGAGGG-GAGGGGAGGGGAGGGGAGGG-GAGGGGAGGGPS [or (GGGGA)$_9$GGGPS] (SEQ ID NO: 85), GGGGAGGGGAGGGGAGGGGAGGG-GAGGGGAGGGGAGGGGAGGGPSH [or (GGGGA)$_9$ GGGPSH] (SEQ ID NO: 86), GGGGPAPGPGPAPGPAPG-PAGGGPS (SEQ ID NO: 87), GAPGGGGPAPGPGPAPG-PAPGPAGGGPGGAP (SEQ ID NO: 88), GGGGPAPAPG-PAPAPGPAPAGGGPS (SEQ ID NO: 89), and GAPGGGGPAPAPGPAPAPGPAPAGGGPGGAP (SEQ ID NO: 90).

In some embodiments, the spacer is selected from the group consisting of GGGGSGGGGSGGGGSGGGGSGGGPS (SEQ ID NO: 36), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAKEAAAKEAAAKAGGPSGAP (SEQ ID NO: 53), GGGSPAE-AAAKEAAAKEAAAKEAAAKAPSGGG (SEQ ID NO: 54), GAPGGGSPAE-AAAKEAAAKEAAAKEAAAKAPSGGGGAP (SEQ ID NO: 55), and GGGGAGGGGAGGGGAGGG-GAGGGPS (SEQ ID NO: 71).

In some embodiments, the spacer is selected from the group consisting of GGGGSGGGGSGGGGSGGGGSGGGPS (SEQ ID NO: 36), GAPGGSPAGSPTSTEEGTSESATPESG-PGTSTEPSEGSAPGSPAGSPTSTGPSGAP (SEQ ID NO: 47), GAPGGGSPAPAPTPAPAPTPAPAGGGPSGAP (SEQ ID NO: 51), GAPGGGSPAE-AAAKEAAAKEAAAKEAAAKAPSGGGGAP (SEQ ID NO: 55), and GGGGAGGGGAGGGGAGGG-GAGGGPS (SEQ ID NO: 71).

In various embodiments, the fusion protein further comprises a pharmaceutically acceptable carrier, diluents or excipient.

The present invention also provides nucleic acids encoding the IGF-II mutein or the targeted therapeutic fusion protein as described in various embodiments above. The present invention further provides various cells containing the nucleic acid of the invention.

The present invention provides pharmaceutical compositions suitable for treating lysosomal storage disease containing a therapeutically effective amount of a targeted therapeutic fusion protein of the invention. The invention further provides methods of treating lysosomal storage diseases comprising administering to a subject in need of treatment a targeted therapeutic fusion protein according to the invention. In some embodiments, the lysosomal storage disease is Mucopolysaccharidosis Type IIIB (Sanfilippo B Syndrome).

In another aspect, the present invention provides a method of producing a targeted therapeutic fusion protein including a step of culturing mammalian cells in a cell culture medium, wherein the mammalian cells carry the nucleic acid of the invention, in particular, as described in various embodiments herein; and the culturing is performed under conditions that permit expression of the targeted therapeutic fusion protein.

In yet another aspect, the present invention provides a method of producing a targeted therapeutic fusion protein including a step of culturing furin-deficient cells (e.g., furin-deficient mammalian cells) in a cell culture medium, wherein the furin-deficient cells carry a nucleic acid encoding a fusion protein comprising a lysosomal enzyme and an IGF-II mutein having an amino acid sequence at least 70% identical to mature human IGF-II, wherein the IGF-II mutein binds to the human cation-independent mannose-6-phosphate receptor in a mannose-6-phosphate-independent manner; and wherein the culturing is performed under conditions that permit expression of the targeted therapeutic fusion protein.

In various embodiments, it is contemplated that certain of the targeted therapeutic proteins comprising a spacer as described herein exhibit increased expression of active protein when expressed recombinantly compared to targeted therapeutic proteins comprising a different spacer peptide. In various embodiments, it is also contemplated that targeted therapeutic proteins described herein may have increased activity compared to other targeted therapeutic proteins herein. It is contemplated that those targeted therapeutic proteins exhibiting increased expression of active protein and/or having increased activity compared to other targeted therapeutic proteins comprising a different spacer peptide are used for further experimentation.

In another aspect, the invention provides a method for treating a lysosomal storage disease in a subject comprising administering to the subject a therapeutically effective amount of a pharmaceutical composition comprising a fusion protein comprising a lysosomal enzyme, a peptide tag having an amino acid sequence at least 70% identical to amino acids 8-67 of mature human IGF-II and a spacer peptide located between the lysosomal enzyme amino acid sequence and the IGF-II peptide tag. In various embodiments, the spacer peptide comprises one or more GGGPS (SEQ ID NO: 14) or GGGSP (SEQ ID NO: 15) amino acid sequences, and optionally further comprises one or more of (i) GAP (SEQ ID NO: 9), (ii) GGGGS (SEQ ID NO: 12), (iii) GGGS (SEQ ID NO: 16), (iv) AAAAS (SEQ ID NO: 17), (v) AAAS (SEQ ID NO: 18), (vi) PAPA (SEQ ID NO: 19), (vii) TPAPA (SEQ ID NO: 20), (viii) AAAKE (SEQ ID NO: 21) or (ix) GGGGA (SEQ ID NO: 60).

In various embodiments, the spacer peptide comprises an amino acid sequence selected from the group consisting of: (GGGGS)$_n$ (SEQ ID NOs: 12, 56, 58, 91-94), (GGGGS)$_n$-GGGPS (SEQ ID NOs: 36, 95-100), GAP-(GGGGS)$_n$-GGGPS (SEQ ID NOs: 101-107), GAP-(GGGGS)$_n$-GGGPS-GAP (SEQ ID NOs: 37, 108-113), GAP-(GGGGS)$_n$-GGGPS-(GGGGS)$_n$-GAP (SEQ ID NOs: 114-162), GAP-GGGPS-(GGGGS)$_n$-GAP (SEQ ID NOs: 163-169), GAP-(GGGGS)$_n$-AAAAS-GGGPS-(GGGGS)$_n$-AAAA-GAP (SEQ ID NOs: 170-218), GAP-(GGGGS)$_n$-PAPAP-(Xaa)$_n$-GAP (SEQ ID NOs: 219-267), GAP-(GGGGS)$_n$-PAPAPT-(Xaa)$_n$-GAP (SEQ ID NOs: 268-316), GAP-(GGGGS)$_n$-(Xaa)n-PAPAP-(Xaa)n-(AAAKE)n-(Xaa)n-(GGGGS)$_n$-GAP (SEQ ID NOs: 544-551), (GGGGA)$_n$ (SEQ ID NOs: 60, 79, 81, 317-320), (GGGGA)$_n$-GGGPS (SEQ ID NOs: 321-326), GAP-(GGGGA)$_n$-GGGPS (SEQ ID NOs: 327-333), GAP-(GGGGA)$_n$-GGGPS-GAP (SEQ ID NOs: 334-340), GAP-(GGGGA)$_n$-GGGPS-(GGGGA)$_n$-GAP (SEQ ID NOs: 341-389), GAP-GGGPS-(GGGGA)$_n$-GAP (SEQ ID NOs: 390-396), GAP-(GGGGA)$_n$-AAAAS-GGGPS-(GGGGA)$_n$-AAAA-GAP (SEQ ID NOs: 397-445), GAP-(GGGGA)$_n$-PAPAP-(Xaa)$_n$-GAP (SEQ ID NOs: 446-494), GAP-(GGGGA)$_n$-PAPAPT-(Xaa)$_n$-GAP (SEQ ID NOs: 495-543), GAP-(GGGGA)$_n$-(Xaa)$_n$-PAPAP-(Xaa)$_n$-(AAAKE)$_n$-(Xaa)$_n$-(GGGGA)$_n$-GAP (SEQ ID NOs: 552-559); wherein n is 1 to 7, optionally n is 1 to 4.

In various embodiments, the spacer peptide has an amino acid sequence selected from the group consisting of EFGGGGSTR (SEQ ID NO: 22), GAP (SEQ ID NO: 9), GGGGS (SEQ ID NO: 12), GPSGSPG (SEQ ID NO: 23), GPSGSPGT (SEQ ID NO: 24), GPSGSPGH (SEQ ID NO: 25), GGGGSGGGGSGGGGSGGGGSGGGPST (SEQ ID NO: 26), GGGGSGGGGSGGGGSGGGGSGGGPSH (SEQ ID NO: 27), GGGGSGGGGSGGGGSGGGGSGGGPSGGGGSGGGPS (SEQ ID NO: 28), GAPGGGGSGGGGSGGGGSGGGGSGGGPSGGGGSGGGPSGAP (SEQ ID NO: 29), GGGGSGGGGSGGGGSGGGGSGGGPSGGGGSGGGGSGGGGSGGGPS (SEQ ID NO: 30), GAPGGGGSGGGGSGGGGSGGGGSGGGPSGGGGSGGGGSGGGGSGGGPSGAP (SEQ ID NO: 31), GGGGSGGGGSGGGGSGGGPSGGGGSGGGGSGGGPS (SEQ ID NO: 32), GAPGGGGSGGGGSGGGGSGGGPSGGGGSGGGGSGGGPSGAP (SEQ ID NO: 33), GGGGSGGGGSGGGGSGGGPSGGGGSGGGGSGGGPSGGGGSGGGGSGGGPS (SEQ ID NO: 34), GAPGGGGSGGGGSGGGGSGGGPSGGGGSGGGGSGGGPSGGGGSGGGGSGGGPSGAP (SEQ ID NO: 35), GGGGSGGGGSGGGGSGGGGSGGGPS (SEQ ID NO: 36), GAPGGGGSGGGGSGGGGSGGGGSGGGPSGAP (SEQ ID NO: 37), GGGGSGGGGSAAAASGGGGSGGGPS (SEQ ID NO: 38), GAPGGGGSGGGGSAAAASGGGGSGGGPSGAP (SEQ ID NO: 39), GGGGSGGGGSAAAASGGGGSGGGGSAAAASGGGGSGGGGSAAAASGGGPS (SEQ ID NO: 40), GAPGGGGSGGGGSAAAASGGGGSGGGGSAAAASGGGGSGGGGSAAAASGGGPSGAP (SEQ ID NO: 41), GGGGSGGGGSAAAASGGGPSGGGGSAAAASGGGPSGGGGSAAAASGGGPS (SEQ ID NO: 42), GAPGGGGSGGGGSAAAASGGGPSGGGGSAAAASGGGPSGGGGSAAAASGGGPSGAP (SEQ ID NO: 43), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAGGPS (SEQ ID NO: 52), GAPGGGSAEAAAKEAAAKEAAAKAGGPSGAP (SEQ ID NO: 53), GGGSPAEAAAKEAAAKEAAAKEAAAKEAAAKAPSGGG (SEQ ID NO: 54), GAPGGGSPAEAAAKEAAAKEAAAKEAAAKEAAAKAPSGGGGAP (SEQ ID NO: 55), GGGGSGGGGSGGGGS (SEQ ID NO: 56), GAPGGGGSGGGGSGGGGSGAP (SEQ ID NO: 57), GGGGSGGGGSGGGGSGGGGS (SEQ ID NO: 58), GAPGGGGSGGGGSGGGGSGGGGSGAP (SEQ ID NO: 59), GGGGA (SEQ ID NO: 60), GGGGAGGGGAGGGGAGGGGAGGGPST (SEQ ID NO: 61), GGGGAGGGGAGGGGAGGGGAGGGPSH (SEQ ID NO: 62), GGGGAGGGGAGGGGAGGGGAGGGPSGGGGAGGGPS (SEQ ID NO: 63), GAPGGGGAGGGGAGGGGAGGGGAGGGPSGGGGAGGGPSGAP (SEQ ID NO: 64), GGGGAGGGGAGGGGAGGGGAGGGPSGGGGAGGGGAGGGGAGGGGAGGGPS (SEQ ID NO: 65), GAPGGGGAGGGGAGGGGAGGGGAGGGPSGGGGAGGGGAGGGGAGGGGAGGGPS GAP (SEQ ID NO:66), GGGGAGGGGAGGGGAGGGPSGGGGAGGGGAGGGPS (SEQ ID NO: 67), GAPGGGGAGGGGAGGGGAGGGPSGGGGAGGGGAGGGPSGAP (SEQ ID NO: 68), GGGGAGGGGAGGGGAGGGPSGGGGAGGGGAGGGPSGGGGAGGGGAGGGPS (SEQ ID NO: 69), GAPGGGGAGGGGAGGGGAGGGPSGGGGAGGGGAGGGPSGGGGAGGGGAGGGPS GAP (SEQ ID NO: 70), GGGGAGGGGAGGGGAGGGGAGGGPS (SEQ ID NO: 71), GAPGGGGAGGGGAGGGGAGGGGAGGGPSGAP (SEQ ID NO: 72), GGGGAGGGGAAAAASGGGGAGGGPS (SEQ ID NO: 73), GAPGGGGAGGGGAAAAASGGGGAGGGPSGAP (SEQ ID NO: 74), GGGGAGGGGAAAAASGGGGAGGGGAAAAASGGGGAGGGGAAAAASGGGPS (SEQ ID NO: 75), GAPGGGGAGGGGAAAAASGGGGAGGGGAAAAASGGGGAAAAASGGGPS GAP (SEQ ID NO: 76), GGGGAGGGGAAAAASGGGPSGGGGAAAAASGGGPSGGGGAAAAASGGGPS (SEQ ID NO: 77), GAPGGGGAGGGGAAAAASGGGPSGGGGAAAAASGGGPSGGGGAAAAASGGGPSG AP (SEQ ID NO: 78), GGGGAGGGGAGGGGA (SEQ ID NO: 79), GAPGGGGAGGGGAGGGGAGAP (SEQ ID NO: 80), GGGGAGGGGAGGGGAGGGGA (SEQ ID NO: 81), GAPGGGGAGGGGAGGGGAGGGGAGAP (SEQ ID NO: 82), GGGGAGGGGAGGGGAGGGGAGGGGAGGGGAGGGGAGGGPS [or (GGGGA)$_8$GGGPS] (SEQ ID NO: 83), GGGGAGGGGAGGGGAGGGGAGGGGAGGGGAGGGGAGGGPSH [or (GGGGA)$_8$GGGPSH] (SEQ ID NO: 84), GGGGAGGGGAGGGGAGGGGAGGGGAGGGGAGGGGAGGGGAGGGPS [or (GGGGA)$_9$GGGPS] (SEQ ID NO: 85), GGGGAGGGGAGGGGAGGGGAGGGGAGGGGAGGGGAGGGGAGGGPSH [or (GGGGA)$_9$GGGPSH] (SEQ ID NO: 86), GGGGPAPGPGPAPGPAPGPAGGGPS (SEQ ID NO: 87), GAPGGGGPAPGPGPAPGPAPGPAGGGPGGAP (SEQ ID NO: 88), GGGGPAPAPGPAPAPGPAPAGGGPS (SEQ ID NO: 89), and GAPGGGGPAPAPGPAPAPGPAPAGGGPGGAP (SEQ ID NO: 90).

In various embodiments, the spacer peptide has an amino acid sequence selected from the group consisting of GGGGSGGGGSGGGGSGGGGSGGGPS (SEQ ID NO: 36), GGSPAGSPTSTEEGTSESATPESGPGTSTEPSEGSAPGSPAGSPGPGS (SEQ ID NO: 44), GAPGGSPAGSPTSTEEGTSESATPESGPGTSTEPSEGSAPGSPAGSPGPSGAP (SEQ ID NO: 45), GGSPAGSPTSTEEGTSESATPESGPGTSTEPSEGSAPGSPAGSPTSTGPS (SEQ ID NO: 46), GAPGGSPAGSPTSTEEGTSESATPESGPGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAGGPS (SEQ ID NO: 52), GAPGGGSAEAAAKEAAAKEAAAKAGGPSGAP (SEQ ID NO: 53), GGGSPAEAAAKEAAAKEAAAKEAAAKEAAAKAPSGGG (SEQ ID NO: 54), GAPGGGSPAEAAAKEAAAKEAAAKEAAAKEAAAKAPSGGGGAP (SEQ ID NO: 55), and GGGGAGGGGAGGGGAGGGGAGGGPS (SEQ ID NO: 71).

In various embodiments, the spacer peptide has an amino acid sequence selected from the group consisting of GGGGSGGGGSGGGGSGGGGSGGGPS (SEQ ID NO: 36), GAPGGSPAGSPTSTEEGTSESATPESGPGTSTEPSEGSAPGSPAGSPTSTGPSGAP (SEQ ID NO: 47), GAPGGGSPAPAPTPAPAPTPAPAGGGPSGAP (SEQ ID NO: 51), GAPGGGSPAEAAAKEAAAKEAAAKEAAAKEAAAKAPSGGGGAP (SEQ ID NO: 55), and GGGGAGGGGAGGGGAGGGGAGGGPS (SEQ ID NO: 71).

Exemplary lysosomal storage diseases contemplated by the methods herein include those set out in Table 1. It is contemplated that the lysosomal storage disease is treated using a targeted therapeutic fusion protein comprising the enzyme deficient in the lysosomal storage disease, also disclosed in Table 1.

In various embodiments, the invention provides a method for treating Mucopolysaccharidosis Type IIIB (Sanfilippo B Syndrome) in a subject comprising administering to the subject a therapeutically effective amount of a pharmaceutical composition comprising a fusion protein comprising an amino acid sequence at least 85% identical to a human α-N-acetylglucosaminidase (Naglu) protein (SEQ ID NO: 1), a peptide tag having an amino acid sequence at least 70% identical to amino acids 8-67 of mature human IGF-II and a spacer peptide located between the Naglu amino acid sequence and the IGF-II peptide tag. In various embodiments, the spacer comprises the amino acid sequence GAP (SEQ ID NO: 9), GPS (SEQ ID NO: 10), or GGS (SEQ ID NO: 11).

In various embodiments, the spacer sequence comprises amino acids Gly-Pro-Ser (GPS) (SEQ ID NO: 10) between the amino acids of mature human IGF-II and the amino acids of human Naglu.

In various embodiments, the spacer peptide comprises one or more GGGGS (SEQ ID NO: 12) or GGGS (SEQ ID NO: 16) amino acid sequences. In various embodiments, the spacer peptide comprises one or more GGGPS (SEQ ID NO: 14) or GGGSP (SEQ ID NO: 15) amino acid sequences. In various embodiments, the spacer peptide comprises one or more AAAAS (SEQ ID NO: 17) or AAAS (SEQ ID NO: 18) amino acid sequences. In various embodiments, the spacer peptide comprises one or more PAPA (SEQ ID NO: 19) or TPAPA (SEQ ID NO: 20) amino acid sequences. In various embodiments, the spacer peptide comprises one or more AAAKE (SEQ ID NO: 21) amino acid sequences. In various embodiments, the spacer peptide comprises one or more GGGGA (SEQ ID NO: 60) amino acid sequences.

In various embodiments, the spacer peptide comprises an amino acid sequence selected from the group consisting of: (GGGGS)$_n$ (SEQ ID NOs: 12, 56, 58, 91-94), (GGGGS)$_n$-GGGPS (SEQ ID NOs: 36, 95-100), GAP-(GGGGS)$_n$-GGGPS (SEQ ID NOs: 101-107), GAP-(GGGGS)$_n$-GGGPS-GAP (SEQ ID NOs: 37, 108-113), GAP-(GGGGS)$_n$-GGGPS-(GGGGS)$_n$-GAP (SEQ ID NOs: 114-162), GAP-GGGPS-(GGGGS)$_n$-GAP (SEQ ID NOs: 163-169), GAP-(GGGGS)$_n$-AAAAS-GGGPS-(GGGGS)$_n$-AAAA-GAP (SEQ ID NOs: 170-218), GAP-(GGGGS)$_n$-PAPAP-(Xaa)$_n$-GAP (SEQ ID NOs: 219-267), GAP-(GGGGS)$_n$-PAPAPT-(Xaa)$_n$-GAP (SEQ ID NOs: 268-316), GAP-(GGGGS)$_n$-(Xaa)n-PAPAP-(Xaa)n-(AAAKE)n-(Xaa)n-(GGGGS)$_n$-GAP (SEQ ID NOs: 544-551), (GGGGA)$_n$ (SEQ ID NOs: 60, 79, 81, 317-320), (GGGGA)$_n$-GGGPS (SEQ ID NOs: 321-326), GAP-(GGGGA)$_n$-GGGPS (SEQ ID NOs: 327-333), GAP-(GGGGA)$_n$-GGGPS-GAP (SEQ ID NOs: 334-340), GAP-(GGGGA)$_n$-GGGPS-(GGGGA)$_n$-GAP (SEQ ID NOs: 341-389), GAP-GGGPS-(GGGGA)$_n$-GAP (SEQ ID NOs: 390-396), GAP-(GGGGA)$_n$-AAAAS-GGGPS-(GGGGA)$_n$-AAAA-GAP (SEQ ID NOs: 397-445), GAP-(GGGGA)$_n$-PAPAP-(Xaa)$_n$-GAP (SEQ ID NOs: 446-494), GAP-(GGGGA)$_n$-PAPAPT-(Xaa)$_n$-GAP (SEQ ID NOs: 495-543), GAP-(GGGGA)$_n$-(Xaa)n-PAPAP-(Xaa)$_n$-(AAAKE)n-(Xaa)$_n$-(GGGGA)$_n$-GAP (SEQ ID NOs: 552-559); wherein n is 1 to 7, optionally wherein n is 1 to 4.

In various embodiments, the invention provides a method for reducing glycosaminoglycan (GAG) levels in vivo comprising administering to a subject suffering from Mucopolysaccharidosis Type IIIB (Sanfilippo B Syndrome) an effective amount of a fusion protein comprising i) an amino acid sequence at least 85% identical to a human α-N-acetylglucosaminidase (Naglu) protein (SEQ ID NO: 1), ii) a peptide tag having an amino acid sequence at least 70% identical to amino acids 8-67 of mature human IGF-II, and iii) a spacer peptide located between the Naglu amino acid sequence and the IGF-II peptide tag.

In various embodiments, the spacer sequence comprises one or more copies of amino acids Gly-Ala-Pro (GAP) (SEQ ID NO: 9) between the amino acids of mature human IGF-II and the amino acids of human Naglu.

In various embodiments, the spacer peptide is selected from the group consisting of EFGGGGSTR (SEQ ID NO: 22), GAP (SEQ ID NO: 9), GGGGS (SEQ ID NO: 12), GPSGSPG (SEQ ID NO: 23), GPSGSPGT (SEQ ID NO: 24), GPSGSPGH (SEQ ID NO: 25), GGGGSGGGGSGGGGSGGGGSGGGPST (SEQ ID NO: 26), GGGGSGGGGSGGGGSGGGGSGGGPSH (SEQ ID NO: 27), GGGGSGGGGSGGGGSGGGGSGGGPSGGGGSGGGPS (SEQ ID NO: 28), GAPGGGSGGGGSGGGGSGGGGSGGGPSGGGGSGGGPSGAP (SEQ ID NO: 29), GGGGSGGGGSGGGGSGGGGSGGGPSGGGGSGGGGSGGGGSGGGPS (SEQ ID NO: 30), GAPGGGSGGGGSGGGGSGGGGSGGGPSGGGGSGGGGSGGGGSGGGPSGAP (SEQ ID NO: 31), GGGGSGGGGSGGGGSGGGPSGGGGSGGGGSGGGPS (SEQ ID NO: 32), GAPGGGSGGGGSGGGGSGGGPSGGGGSGGGGSGGGPSGAP (SEQ ID NO: 33), GGGGSGGGGSGGGGSGGGPSGGGGSGGGGSGGGGSGGGPS (SEQ ID NO: 34), GAPGGGSGGGGSGGGGSGGGPSGGGGSGGGGSGGGGSGGGPSGAP (SEQ ID NO: 35), GGGGSGGGGSGGGGSGGGGSGGGPS (SEQ ID NO: 36), GAPGGGGSGGGGSGGGGSGGGGSGGGGPSGAP (SEQ ID NO: 37), GGGGSGGGGSAAAASGGGGSGGGPS (SEQ ID NO: 38), GAPGGGGSGGGGSAAAASGGGGSGGGPSGAP (SEQ ID NO: 39), GGGGSGGGGSAAAASGGGGSGGGGSAAAASGGGGSGGGGSAAAASGGGPS (SEQ ID NO: 40), GAPGGGGSGGGGSAAAASGGGGSGGGGSAAAASGGGGSGGGGSAAAASGGGPSGAP (SEQ ID NO: 41), GGGGSGGGGSAAAASGGGPSGGGGSAAAASGGGPSGGGGSAAAASGGGPS (SEQ ID NO: 42), GAPGGGGSGGGGSAAAASGGGPSGGGGSAAAASGGGPSGGGGSAAAASGGGPSGAP (SEQ ID NO: 43), GGSPAGSPTSTEEGTSESATPESGPGTSTEPSEGSAPGSPAGSPGPS (SEQ ID NO: 44), GAPGGSPAGSPTSTEEGTSESATPESGPGTSTEPSEGSAPGSPAGSPGPSGAP (SEQ ID NO: 45), GGSPAGSPTSTEEGTSESATPESGPGTSTEPSEGSAPGSPAGSPTSTGPS (SEQ ID NO: 46), GAPGGSPAGSPTSTEEGTSESATPESGPGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAGGPS (SEQ ID NO: 52), GAPGGGSAEAAAKEAAAKEAAAKAGGPSGAP (SEQ ID NO: 53), GGGSPAEAAAKEAAAKEAAAKEAAAKEAAAKAPSGGG (SEQ ID NO: 54), GAPGGGSPAEAAAKEAAAKEAAAKEAAAKEAAAKAPSGGGGAP (SEQ ID NO: 55), GGGGSGGGGSGGGGS (SEQ ID NO: 56), GAPGGGGSGGGGSGGGGSGAP (SEQ ID NO: 57), GGGGSGGGGSGGGGSGGGGS (SEQ ID NO: 58), GAPGGGGSGGGGSGGGGSGGGGSGAP (SEQ ID NO: 59), GGGGA (SEQ ID NO: 60), GGGGAGGGGAGGGGAGGGGAGGGPST (SEQ ID NO: 61), GGGGAGGGGAGGGGAGGGGAGGGPSH (SEQ ID NO: 62), GGGGAGGGGAGGGGAGGGGAGGGPSGGGGAGGGPS (SEQ ID NO: 63), GAPGGGGAGGGGAGGGGAGGGGAGGGPSGGGGAGGGPSGAP (SEQ ID NO: 64), GGGGAGGGGAGGGGAGGGGAGGGPSGGGGAGGGGAGGGGAGGGPS (SEQ ID NO: 65), GAPGGGGAGGGGAGGGGAGGGGAGGGPSGGGGAGGGGAGGGGAGGGPS GAP (SEQ ID NO:66), GGGGAGGGGAGGGGAGGGPSGGGGAGGGGAGGGPS (SEQ ID NO: 67), GAPGGGGAGGGGAGGGGAGGGPSGGGGAGGGGAGGGPSGAP (SEQ ID NO: 68), GGGGAGGGGAGGGGAGGGPSGGGGAGGGGAGGGPS (SEQ ID NO: 69), GAPGGGGAGGGGAGGGGAGGGPSGGGGAGGGGAGGGPSGGGGAGGGPSGAP (SEQ ID NO: 70), GGGGAGGGGAGGGGAGGGGAGGGPS (SEQ ID NO: 71), GAPGGGGAGGGGAGGGGAGGGGAGGGPSGAP (SEQ ID NO: 72), GGGGAGGGGAAAAASGGGGAGGGPS (SEQ ID NO: 73), GAPGGGGAGGGGAAAAASGGGGAGGGPSGAP (SEQ ID NO: 74), GGGGAGGGGAAAAASGGGGAGGGGAAAAASGGGGAGGGGAAAAASGGGPS (SEQ ID NO: 75), GAPGGGGAGGGGAAAAASGGGGAGGGGAAAAASGGGGAGGGGAAAAASGGGPSGAP (SEQ ID NO: 76), GGGGAGGGGAAAAASGGGPSGGGGAAAAASGGGPSGGGGAAAAASGGGPS (SEQ ID NO: 77), GAPGGGGAGGGGAAAAASGGGPSGGGGAAAAASGGGPSGGGGAAAAASGGGPSGAP (SEQ ID NO: 78), GGGGAGGGGAGGGGA (SEQ ID NO: 79), GAPGGGGAGGGGAGGGGAGAP (SEQ ID NO: 80), GGGGAGGGGAGGGGAGGGGA (SEQ ID NO: 81), GAPGGGGAGGGGAGGGGAGGGGAGAP (SEQ ID NO: 82), GGGGAGGGGAGGGGAGGGGAGGGGAGGG-GAGGGGAGGGGAGGGPS [or (GGGGA)₈GGGPS] (SEQ ID NO: 83), GGGGAGGGGAGGGGAGGGGAGGG-GAGGGGAGGGGAGGGGAGGGPSH [or (GGGGA)₈ GGGPSH] (SEQ ID NO: 84), GGGGAGGGGAGGG-GAGGGGAGGGGAGGGGAGGGGAGGG-GAGGGGAGGGPS [or (GGGGA)₉GGGPS] (SEQ ID NO: 85), GGGGAGGGGAGGGGAGGGGAGGGGAGGG-GAGGGGAGGGGAGGGGAGGGPSH [or (GGGGA)₉ GGGPSH] (SEQ ID NO: 86), GGGGPAPGPGPAPGPAPG-PAGGGPS (SEQ ID NO: 87), GAPGGGGPAPGPGPAPG-PAPGPAGGGPGGAP (SEQ ID NO: 88), GGGGPAPAPG-PAPAPGPAPAGGGPS (SEQ ID NO: 89), and GAPGGGGPAPAPGPAPAPGPAPAGGGPGGAP (SEQ ID NO: 90).

In various embodiments, the spacer peptide is selected from the group consisting of GGGGSGGGGSGGGGSGGGGSGGGPS (SEQ ID NO: 36), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAKEAAAKEAAAKAGGPSGAP (SEQ ID NO: 53), GGGSPAE-AAAKEAAAKEAAAKEAAAKEAAAKAPSGGG (SEQ ID NO: 54), GAPGGGSPAE-AAAKEAAAKEAAAKEAAAKEAAAKAPSGGGGAP (SEQ ID NO: 55), and GGGGAGGGGAGGGGAGGG-GAGGGPS (SEQ ID NO: 71).

In various embodiments, the spacer peptide is selected from the group consisting of GGGGSGGGGSGGGGSGGGGSGGGPS (SEQ ID NO: 36), GAPGGSPAGSPTSTEEGTSESATPESG-PGTSTEPSEGSAPGSPAGSPTSTGPSGAP (SEQ ID NO: 47), GAPGGGSPAPAPTPAPAPTPAPAGGGPSGAP (SEQ ID NO: 51), GAPGGGSPAE-AAAKEAAAKEAAAKEAAAKEAAAKAPSGGGGAP (SEQ ID NO: 55), and GGGGAGGGGAGGGGAGGG-GAGGGPS (SEQ ID NO: 71).

In various embodiments, the lysosomal targeting domain or IGF-II peptide tag comprises amino acids 8-67 of mature human IGF-II (SEQ ID NO: 2, 4). In various embodiments, the IGF-II peptide tag comprises a mutation at residue Arg37. In various embodiments, the mutation is a substitution of alanine for arginine. In various embodiments, the lysosomal targeting domain or IGF-II peptide tag comprises IGF2 Δ8-67 R37A.

In various embodiments, the fusion protein comprises amino acids 1-743 of human Naglu (SEQ ID NO: 1, 3). In various embodiments, the fusion protein comprises amino acids 24-743 of human Naglu.

In various embodiments, the effective amount of fusion protein is in the range of about 0.1-1 mg/kg, about 1-5 mg/kg, about 2.5-20 mg/kg, about 5-20 mg/kg, about 10-50 mg/kg, or 20-100 mg/kg of body weight of the subject. In various embodiments, the effective amount of fusion protein is about 2.5-20 mg per kilogram of body weight of the subject.

In various embodiments, the fusion protein is administered intrathecally, intravenously, intramuscularly, parenterally, transdermally, or transmucosally. In various embodiments, the fusion protein is administered intrathecally. In various embodiments, the intrathecal administration optionally further comprises administering the fusion protein intravenously.

In various embodiments, intrathecal administration comprises introducing the fusion protein into a cerebral ventricle, lumbar area, or cisterna magna.

In various embodiments, the fusion protein is administered bimonthly, monthly, triweekly, biweekly, weekly, daily, or at variable intervals.

In various embodiments, the treatment results in reducing glycosaminoglycan (GAG) levels in a brain tissue. It is further contemplated that the treatment results in reducing lysosomal storage granules in a brain tissue.

Also contemplated are compositions comprising the targeted therapeutic fusion proteins as described herein for use in treating lysosomal storage diseases. Exemplary lysosomal storage diseases include those set out in Table 1.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 1 depicts the amino acid sequences of a portion of an exemplary therapeutic fusion protein comprising (A) Naglu and (B) an IGF-II peptide comprising residues 8-67 of IGF-II and having an amino acid substitution at residue 37, R37A (Arg37Ala).

FIG. 2 depicts the nucleotide sequences of a portion of an exemplary therapeutic fusion protein comprising (A) Naglu and (B) an IGF-II peptide comprising residues 8-67 of IGF-II and having an amino acid substitution at residue 37, R37A (Arg37Ala).

FIG. 3 discloses exemplary spacer sequences contemplated for use in the therapeutic fusion protein.

DEFINITIONS

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes reduction of accumulated materials inside lysosomes of relevant diseases tissues.

Furin-resistant IGF-II mutein: As used herein, the term "furin-resistant IGF-II mutein" refers to an IGF-II-based peptide containing an altered amino acid sequence that abolishes at least one native furin protease cleavage site or changes a sequence close or adjacent to a native furin protease cleavage site such that the furin cleavage is prevented, inhibited, reduced, or slowed down as compared to a wild-type human IGF-II peptide. As used herein, a furin-resistant IGF-II mutein is also referred to as an IGF-II mutein that is resistant to furin.

Furin protease cleavage site: As used herein, the term "furin protease cleavage site" (also referred to as "furin cleavage site" or "furin cleavage sequence") refers to the amino acid sequence of a peptide or protein that serves as a recognition sequence for enzymatic protease cleavage by furin or furin-like proteases. Typically, a furin protease cleavage site has a consensus sequence Arg-X-X-Arg (SEQ ID NO: 6), X is any amino acid. The cleavage site is positioned after the carboxy-terminal arginine (Arg) residue in the sequence. In some embodiments, a furin cleavage site may have a consensus sequence Lys/Arg-X-X-X-Lys/Arg-Arg (SEQ ID NO: 7), X is any amino acid. The cleavage site is positioned after the carboxy-terminal arginine (Arg) residue in the sequence.

Furin: As used herein, the term "furin" refers to any protease that can recognize and cleave the furin protease cleavage site as defined herein, including furin or furin-like protease. Furin is also known as paired basic amino acid cleaving enzyme (PACE). Furin belongs to the subtilisin-like proprotein convertase family. The gene encoding furin was known as FUR (FES Upstream Region).

Furin-deficient cells: As used herein, the term "furin-deficient cells" refers to any cells whose furin protease activity is inhibited, reduced or eliminated. Furin-deficient cells include both mammalian and non-mammalian cells that do not produce furin or produce reduced amount of furin or defective furin protease.

Glycosylation Independent Lysosomal Targeting: As used herein, the term "glycosylation independent lysosomal targeting" (also referred to as "GILT") refer to lysosomal targeting that is mannose-6-phosphate-independent.

Human Alpha-N-acetylglucosaminidase: As used herein, the term "human alpha-N-acetylglucosaminidase" (also referred to as "Naglu") refers to precursor (i.e., containing the native Naglu signal peptide sequence) or processed (i.e., lacking the native Naglu signal peptide sequence) wild-type form of human alpha-N-acetylglucosaminidase, or a functional fragment or variant thereof, that is capable of reducing glycosaminoglycan (GAG) levels in mammalian lysosomes or that can rescue or ameliorate one or more MPS IIIB (Sanfilippo B Syndrome) symptoms. As used herein, the term "functional" as it relates to Naglu refers to a Naglu enzyme that is capable of being taken up by mammalian lysosomes and having sufficient enzymatic activity to reduce storage material, i.e., glycosaminoglycan (GAG), in the mammalian lysosome.

IGF-II mutein: As used herein, the term "IGF-II mutein" refers to an IGF-II-based peptide containing an altered amino acid sequence. As used herein, the term "furin-resistant IGF-II mutein" refers to an IGF-II-based peptide containing an altered amino acid sequence that abolishes at least one native furin protease cleavage site or changes a sequence close or adjacent to a native furin protease cleavage site such that the furin cleavage is prevented, inhibited, reduced, or slowed down as compared to a wild-type human IGF-II peptide. As used herein, a furin-resistant IGF-II mutein is also referred to as an IGF-II mutein that is resistant to furin.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., MPS IIIB (Sanfilippo B Syndrome)) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a lysosomal storage disease, for example, MPS IIIB (Sanfilippo B Syndrome) (i.e., either infantile-, juvenile-, or adult-onset or severe/classical type or attenuated type MPS IIIB (Sanfilippo B Syndrome)) or having the potential to develop a lysosomal storage disease (e.g., MPS IIIB (Sanfilippo B Syndrome)).

Lysosomal storage diseases: As used herein, "lysosomal storage diseases" refer to a group of genetic disorders that result from deficiency in at least one of the enzymes (e.g., acid hydrolases) that are required to break macromolecules down to peptides, amino acids, monosaccharides, nucleic acids and fatty acids in lysosomes. As a result, individuals suffering from lysosomal storage diseases have accumulated materials in lysosomes. Exemplary lysosomal storage diseases are listed in Table 1.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Spacer: As used herein, the term "spacer" (also referred to as "linker") refers to a peptide sequence between two protein moieties in a fusion protein. A spacer is generally designed to be flexible or to interpose a structure, such as an alpha-helix, between the two protein moieties. A spacer can be relatively short, such for example, the sequence Gly-Ala-Pro (GAP) (SEQ ID NO: 9), Gly-Gly-Gly-Gly-Ser (GGGGS) (SEQ ID NO: 12), Gly-Gly-Gly-Gly-Ala (GGGGA) (SEQ ID NO: 60) or Gly-Gly-Gly-Gly-Gly-Pro (GGGGGP) (SEQ ID NO: 13), or can be longer, such as, for example, 10-25 amino acids in length, 25-50 amino acids in length or 35-55 amino acids in length. Exemplary spacer seqeunces are disclosed in greater detail in the Detailed Description.

Therapeutically effective amount: As used herein, the term "therapeutically effective amount" or "effective amount" refers to an amount of a targeted therapeutic fusion protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic fusion protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic fusion protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a therapeutic fusion protein or pharmaceutical composition comprising said therapeutic fusion protein that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. For example, treatment can refer to improvement of cardiac status (e.g., increase of end-diastolic and/or end-systolic volumes, or reduction, amelioration or prevention of the progressive cardiomyopathy that is typically found in, e.g., Pompe disease) or of pulmonary function (e.g., increase in crying vital capacity over baseline capacity, and/or normalization of oxygen desaturation during crying); improvement in neurodevelopment and/or motor skills (e.g., increase in AIMS score); reduction of storage (e.g., glycosaminoglycan (GAG), levels in tissue of the individual affected by the disease; or any combination of these effects. In some embodiments, treatment includes improvement of glycosaminoglycan (GAG) clearance, particularly in reduction or prevention of MPS IIIB (Sanfilippo B Syndrome)-associated neuronal symptoms.

As used in this application, the terms "about" and "approximately" are used as equivalents. Any numerals used in this application with or without about/approximately are meant to cover any normal fluctuations appreciated by one of ordinary skill in the relevant art.

DETAILED DESCRIPTION OF THE INVENTION

The present invention provides improved methods and compositions for targeting lysosomal enzymes based on the glycosylation-independent lysosomal targeting (GILT) technology. Among other things, the present invention provides IGF-II muteins that are resistant to furin and/or has reduced or diminished binding affinity for the insulin receptor, and/or has reduced or diminished binding affinity for the IGF-I receptor and targeted therapeutic fusion proteins containing an IGF-II mutein of the invention. The present invention also provides methods of making and using the same.

Various aspects of the invention are described in detail in the following sections. The use of sections is not meant to limit the invention. Each section can apply to any aspect of the invention. In this application, the use of "or" means "and/or" unless stated otherwise.

Lysosomal Enzymes

A lysosomal enzyme suitable for the invention includes any enzyme that is capable of reducing accumulated materials in mammalian lysosomes or that can rescue or ameliorate one or more lysosomal storage disease symptoms. Suitable lysosomal enzymes include both wild-type or modified lysosomal enzymes and can be produced using recombinant or synthetic methods or purified from natural sources. Exemplary lysosomal enzymes are listed in Table 1.

TABLE 1

Lysosomal Storage Diseases and associated enzyme defects

| Disease Name | Enzyme Defect | Substance Stored |
|---|---|---|
| A. Glycogenosis Disorders | | |
| Pompe Disease | Acid-α1, 4-Glucosidase | Glycogen α1-4 linked Oligosaccharides |
| B. Glycolipidosis Disorders | | |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |

TABLE 1-continued

Lysosomal Storage Diseases and associated enzyme defects

| Disease Name | Enzyme Defect | Substance Stored |
|---|---|---|
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders | | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other | | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Late Infantile Neuronal Ceroid Lipofuscinosis | Tripeptidyl Peptidase I | Lipofuscins |
| Mucolipidosis IV | Unknown | Gangliosides & Hyaluronic Acid |
| Prosaposin | Saposins A, B, C or D | |

In some embodiments, a lysosomal enzyme contemplated herein includes a polypeptide sequence having 50-100%, including 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%, sequence identity to the naturally-occurring polynucleotide sequence of a human enzyme shown in Table 1, while still encoding a protein that is functional, i.e., capable of reducing accumulated materials, e.g., glycosaminoglycan (GAG), in mammalian lysosomes or that can rescue or ameliorate one or more lysosomal storage disease symptoms.

"Percent (%) amino acid sequence identity" with respect to the lysosomal enzyme sequences is defined as the percentage of amino acid residues in a candidate sequence that are identical with the amino acid residues in the naturally-occurring human enzyme sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

Alpha-N-acetylglucosaminidase

Alpha-N-acetylglucosaminidase, Naglu, is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids (SEQ ID NO: 1). The N-terminal 23 amino acids are cleaved as the precursor protein enters the endoplasmic reticulum, resulting in a processed or mature form. Thus, it is contemplated that the N-terminal 23 amino acids are generally not required for the Naglu protein activity. The amino acid sequences of the mature form and full-length precursor form of a typical wild-type or naturally-occurring human Naglu protein are shown in FIG. 1 and set out in SEQ ID NO: 1. The nucleotide sequence of the coding region of human Naglu is set out in SEQ ID NO: 3. The mRNA sequence of human Naglu is described in Genbank Accession number NM_000263. In various embodiments, the Naglu is human Naglu, with (amino acids 1-743) or without (amino acids 24-743) signal sequence.

U.S. Pat. No. 6,255,096 describes that the molecular weight of purified human alpha-N-acetylglucosaminidase (i.e. 82 kDa and 77 kDa) and recombinant mammalian alpha-N-acetylglucosaminidase produced in CHO cells (i.e. 89 kDa and 79 kDa) are greater than the deduced molecular weight of the Naglu polypeptide (i.e. 70 kDa), suggesting that the purified and recombinant polypeptide are post-translationally modified. See also Weber et al., Hum Mol Genet 5:771-777, 1996.

Mucopolysaccharidosis III B (Sanfilippo B Syndrome)

One exemplary lysosomal storage disease is Mucopolysaccharidosis III B (MPS IIIB) disease, also known as Sanfilippo Type B Syndrome. MPS IIIB, Sanfilippo B Syndrome, is a rare autosomal recessive genetic disorder that is characterized by a deficiency of the enzyme alpha-N-acetyl-glucosaminidase (Naglu). In the absence of this enzyme, glycosaminoglycans (GAG), for example the GAG heparan sulfate, and partially degraded GAG molecules cannot be cleared from the body and accumulate in lysosomes of various tissues, resulting in progressive widespread somatic dysfunction (Kakkis et al., N Engl J. Med. 344(3):182-8, 2001). It has been shown that GAGs accumulate in lysosomes of neurons and glial cells, with lesser accumulation outside the brain.

Four distinct forms of MPS III, designated MPS IIIA, B, C, and D, have been identified. Each represents a deficiency in one of four enzymes involved in the degradation of the GAG heparan sulfate (Table 1). All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley et al., Ann N Y Acad. Sci. 845:188-99, 1998).

A characteristic clinical feature of Sanfilippo B Syndrome is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

MPS III diseases all have similar symptoms that typically manifest in young children. Affected infants are apparently normal, although some mild facial dysmorphism may be noticeable. The stiff joints, hirsuteness and coarse hair typical of other mucopolysaccharidoses are usually not present until late in the disease. After an initial symptom-free interval, patients usually present with a slowing of development and/or behavioral problems, followed by progressive intellectual decline resulting in severe dementia and progressive motor disease. Acquisition of speech is often slow and incomplete. The disease progresses to increasing behavioral disturbance including temper tantrums, hyperactivity, destructiveness, aggressive behavior, pica and sleep disturbance. As affected children have normal muscle strength and mobility, the behavioral disturbances are very difficult to manage. In the final phase of the illness, children become increasingly immobile and unresponsive, often require wheelchairs, and develop swallowing difficulties and seizures. The life-span of an affected child does not usually extend beyond late teens to early twenties.

An alpha-N-acetylglucosaminidase enzyme suitable for treating MPS IIIB (Sanfilippo B Syndrome) includes a wild-type human alpha-N-acetylglucosaminidase (SEQ ID NO: 1 or 3), or a functional fragment or sequence variant thereof which retains the ability to be taken up into mammalian lysosomes and to hydrolyze alpha, 1,4 linkages at the terminal N-acetyl-D-glucosamine residue in linear oligosaccharides.

Efficacy of treatment of MPS IIIB (Sanfilippo B Syndrome) using recombinant targeted therapeutic fusion proteins as described herein can be measured using techniques known in the art, as well as by analysis of lysosomal and neuronal biomarkers. Initial experiments are conducted on Naglu knock-out animals (see Li et al., Proc Natl Acad Sci USA 96:14505-510, 1999). Naglu knockouts present with large amounts of heparan sulfate in the liver and kidney and elevation of gangliosides in brain.

Assays include analysis of the activity of and biodistribution of the exogenous enzyme, reduction of GAG storage in the lysosomes, particularly in brain cells, and activation of astrocytes and microglia. Levels of various lysosomal or neuronal biomarkers include, but are not limited to, Lysosomal-associated membrane protein 1 (LAMP1), glypican, gangliosides, cholesterol, Subunit c of Mitochondrial ATP Synthase (SCMAS), ubiquitin, P-GSK3b, beta amyloid and P-tau. Survival and behavioral analysis is also performed using techniques known in the field.

Experiments have shown that Subunit c of Mitochondrial ATP Synthase (SCMAS) protein accumulates in the lysosomes of MPS IIIB animals (Ryazantsev et al., Mol Genet Metab. 90(4): 393-401, 2007). LAMP-1 and GM130 have also been shown to be elevated in MPS IIIB animals (Vitry et al., Am J. Pathol. 177(6):2984-99, 2010).

In various embodiments, treatment of a lysosomal storage disease refers to decreased lysosomal storage (e.g., of GAG) in various tissues. In various embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In various embodiments, lysosomal storage is decreased by at least 1-fold, 2-fold, 3-fold, 4-fold, 5-fold, 6-fold, 7-fold, 8-fold, 9-fold, 10-fold or more as compared to a control.

In various embodiments, treatment refers to increased enzyme activity in various tissues. In various embodiments, treatment refers to increased enzyme activity in brain target tissues, spinal cord neurons and/or peripheral target tissues. In various embodiments, enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In various embodiments, enzyme activity is increased by at least 1-fold, 2-fold, 3-fold, 4-fold, 5-fold, 6-fold, 7-fold, 8-fold, 9-fold, 10-fold or more as compared to a control. In various embodiments, increased enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In various embodiments, the lysosomal enzyme is Naglu.

Enzyme Replacement Therapy

Enzyme replacement therapy (ERT) is a therapeutic strategy to correct an enzyme deficiency by infusing the missing enzyme into the bloodstream. As the blood perfuses patient tissues, enzyme is taken up by cells and transported to the lysosome, where the enzyme acts to eliminate material that has accumulated in the lysosomes due to the enzyme deficiency. For lysosomal enzyme replacement therapy to be effective, the therapeutic enzyme must be delivered to lysosomes in the appropriate cells in tissues where the storage defect is manifest. Conventional lysosomal enzyme replacement therapeutics are delivered using carbohydrates naturally attached to the protein to engage specific receptors on the surface of the target cells. One receptor, the cation-independent M6P receptor (CI-MPR), is particularly useful for targeting replacement lysosomal enzymes because the CI-MPR is present on the surface of most cell types.

The terms "cation-independent mannose-6-phosphate receptor (CI-MPR)," "M6P/IGF-II receptor," "CI-MPR/IGF-II receptor," "IGF-II receptor" or "IGF2 Receptor," or abbreviations thereof, are used interchangeably herein, referring to the cellular receptor which binds both M6P and IGF-II.

Combination Therapy to Tolerize Subject to Enzyme Replacement Therapy

It has been found that during administration of agents such as recombinant proteins and other therapeutic agents, a subject can mount an immune response against these agents, leading to the production of antibodies that bind and interfere with the therapeutic activity as well as cause acute or chronic immunologic reactions. This problem is most significant for protein therapeutics because proteins are complex antigens and in many cases, the subject is immunologically naive to the antigens. Thus, in certain aspects of the present invention, it may be useful to render the subject receiving the therapeutic enzyme tolerant to the enzyme replacement therapy. In this context, the enzyme replacement therapy may be given to the subject as a combination therapy with a tolerizing regimen.

U.S. Pat. No. 7,485,314 (incorporated herein by reference) discloses treatment of lysosomal storage disorders using immune tolerance induction. Briefly, use of such a tolerization regimen may be useful to prevent the subject mounting an immune response to the enzyme replacement therapy and thereby decreasing or otherwise rendering ineffective the potential beneficial effects of the enzyme replacement therapy.

In one method, the invention contemplates reducing or preventing a clinically significant antigen-specific immune response to recombinant therapeutic fusion protein, for example, comprising Naglu, used to treat a lysosomal storage disorder, for example mucopolysaccharidosis IIIB (MPS IIIB or Sanfilippo B Syndrome), where the fusion protein is administered intrathecally. The method employs an initial 30-60 day regimen of a T-cell immunosuppressive agent such as cyclosporin A (CsA) and an antiproliferative agent, such as, azathioprine (Aza), combined with weekly intrathecal infusions of low doses of the enzyme, e.g., Naglu. The typical strong IgG response to weekly infusions of enzyme becomes greatly reduced or prevented using a 60 day regimen of immunosuppressive drugs, cyclosporin A (CsA) and azathioprine (Aza), combined with weekly intrathecal or intravenous infusions of low doses of fusion protein comprising enzyme. Using such tolerization regimens, it will be possible to render the subject tolerant to higher therapeutic doses of therapeutic fusion protein for up to 6 months without an increase in antibody titer against Naglu, or indeed any other enzyme that could be used for enzyme replacement of a lysosomal storage disease. Such tolerization regimens have been described in U.S. Pat. No. 7,485,314.

Glycasylation Independent Lysosomal Targeting

A Glycosylation Independent Lysosomal Targeting (GILT) technology was developed to target therapeutic enzymes to lysosomes. Specifically, the GILT technology uses a peptide tag instead of M6P to engage the CI-MPR for lysosomal targeting. Typically, a GILT tag is a protein, peptide, or other moiety that binds the CI-MPR in a mannose-6-phosphate-independent manner. Advantageously, this technology mimics the normal biological mechanism for uptake of lysosomal enzymes, yet does so in a manner independent of mannose-6-phosphate.

A preferred GILT tag is derived from human insulin-like growth factor II (IGF-II). Human IGF-II is a high affinity ligand for the CI-MPR, which is also referred to as IGF-II receptor. Binding of GILT-tagged therapeutic enzymes to the M6P/IGF-II receptor targets the protein to the lysosome via the endocytic pathway. This method has numerous advantages over methods involving glycosylation including simplicity and cost effectiveness, because once the protein is isolated, no further modifications need be made.

Detailed description of the GILT technology and GILT tag can be found in U.S. Publication Nos. 20030082176, 20040006008, 20040005309, and 20050281805, the teachings of all of which are hereby incorporated by references in their entireties.

Furin-resistant GILT Tag

During the course of development of GILT-tagged lysosomal enzymes for treating lysosomal storage disease, it has become apparent that the IGF-II derived GILT tag may be subjected to proteolytic cleavage by furin during production in mammalian cells (see the examples section). Furin protease typically recognizes and cleaves a cleavage site having a consensus sequence Arg-X-X-Arg (SEQ ID NO: 6), X is any amino acid. The cleavage site is positioned after the carboxy-terminal arginine (Arg) residue in the sequence. In some embodiments, a furin cleavage site has a consensus sequence Lys/Arg-X-X-X-Lys/Arg-Arg (SEQ ID NO: 7), X is any amino acid. The cleavage site is positioned after the carboxy-terminal arginine (Arg) residue in the sequence. As used herein, the term “furin” refers to any protease that can recognize and cleave the furin protease cleavage site as defined herein, including furin or furin-like protease. Furin is also known as paired basic amino acid cleaving enzyme (PACE). Furin belongs to the subtilisin-like proprotein convertase family that includes PC3, a protease responsible for maturation of proinsulin in pancreatic islet cells. The gene encoding furin was known as FUR (FES Upstream Region).

The mature human IGF-II peptide sequence is shown below.

AYRPSETLCGGELVDTLQFVCGDRGFYFSRPAS RVSR↑RSR↑GIVEECCFRS CDLALLETYC ATPAKSE (SEQ ID NO: 5)

As can be seen, the mature human IGF-II contains two potential overlapping furin cleavage sites between residues 34-40 (bolded and underlined). Arrows are inserted at two potential furin cleavage positions.

Modified GILT tags that are resistant to cleavage by furin and still retain ability to bind to the CI-MPR in a mannose-6-phosphate-independent manner are disclosed in US 20110223147. Specifically, furin-resistant GILT tags can be designed by mutating the amino acid sequence at one or more furin cleavage sites such that the mutation abolishes at least one furin cleavage site. Thus, in some embodiments, a furin-resistant GILT tag is a furin-resistant IGF-II mutein containing a mutation that abolishes at least one furin protease cleavage site or changes a sequence adjacent to the furin protease cleavage site such that the furin cleavage is prevented, inhibited, reduced or slowed down as compared to a wild-type IGF-II peptide (e.g., wild-type human mature IGF-II). Typically, a suitable mutation does not impact the ability of the furin-resistant GILT tag to bind to the human cation-independent mannose-6-phosphate receptor. In particular, a furin-resistant IGF-II mutein suitable for the invention binds to the human cation-independent mannose-6-phosphate receptor in a mannose-6-phosphate-independent manner with a dissociation constant of $10^{-7}$ M or less (e.g., $10^{-8}$, $10^{-9}$, $10^{-10}$, $10^{-11}$, or less) at pH 7.4. In some embodiments, a furin-resistant IGF-II mutein contains a mutation within a region corresponding to amino acids 30-40 (e.g., 30-40, 31-40, 32-40, 33-40, 34-40, 30-39, 31-39, 32-39, 34-37, 33-39, 34-39, 35-39, 36-39, 37-40) of mature human IGF-II. In some embodiments, a suitable mutation abolishes at least one furin protease cleavage site. A mutation can be amino acid substitutions, deletions, insertions. For example, any one amino acid within the region corresponding to residues 30-40 (e.g., 30-40, 31-40, 32-40, 33-40, 34-40, 30-39, 31-39, 32-39, 34-37, 33-39, 34-39, 35-39, 36-39, 37-40) of SEQ ID NO:5 can be substituted with any other amino acid or deleted. For example, substitutions at position 34 may affect furin recognition of the first cleavage site. Insertion of one or more additional amino acids within each recognition site may abolish one or both furin cleavage sites. Deletion of one or more of the residues in the degenerate positions may also abolish both furin cleavage sites.

In various embodiments, a furin-resistant IGF-II mutein contains amino acid substitutions at positions corresponding to Arg37 or Arg40 of mature human IGF-II. In some embodiments, a furin-resistant IGF-II mutein contains a Lys or Ala substitution at positions Arg37 or Arg40. Other substitutions are possible, including combinations of Lys and/or Ala mutations at both positions 37 and 40, or substitutions of amino acids other than Lys or Ala.

In various embodiments, an IGF-II mutein suitable for use herein may contain additional mutations. For example, up to 30% or more of the residues of SEQ ID NO:1 may be changed (e.g., up to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% or more residues may be changed). Thus, an IGF-II mutein suitable for use herein may have an amino acid sequence at least 70%, including at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to mature human IGF-II.

In various embodiments, an IGF-II mutein suitable for use herein is targeted specifically to the CI-MPR. Particularly useful are mutations in the IGF-II polypeptide that result in a protein that binds the CI-MPR with high affinity (e.g., with a dissociation constant of $10^{-7}$M or less at pH 7.4) while binding other receptors known to be bound by IGF-II with reduced affinity relative to native IGF-II. For example, a furin-resistant IGF-II mutein suitable for the invention can be modified to have diminished binding affinity for the IGF-I receptor relative to the affinity of naturally-occurring human IGF-II for the IGF-I receptor. For example, substitution of IGF-II residues Tyr 27 with Leu, Leu 43 with Val or Ser 26 with Phe diminishes the affinity of IGF-II for the IGF-I receptor by 94-, 56-, and 4-fold respectively (Tones et al. (1995) J. Mol. Biol. 248(2):385-401). Deletion of residues 1-7 of human IGF-II resulted in a 30-fold decrease in affinity for the human IGF-I receptor and a concomitant 12 fold increase in affinity for the rat IGF-II receptor (Hashimoto et al. (1995) J. Biol. Chem. 270(30):18013-8). The NMR structure of IGF-II shows that Thr-7 is located near residues Phe-48 Phe and Ser-50 as well as near the Cys-9-Cys-47 disulfide bridge. It is thought that interaction of Thr-7 with these residues can stabilize the flexible N-terminal hexapeptide required for IGF-I receptor binding (Terasawa et al. (1994) EMBO J. 13(23)5590-7). At the same time this interaction can modulate binding to the IGF-II receptor. Truncation of the C-terminus of IGF-II (residues 62-67) also appear to lower the affinity of IGF-II for the IGF-I receptor by 5 fold (Roth et al. (1991) Biochem. Biophys. Res. Commun. 181(2):907-14).

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids (e.g., 1-7 or 2-7) and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) Trends Biochem. Sci. 279-281). Thus, for example, amino acids 8-28, or a conservative substitution variant thereof, could be fused to a lysosomal enzyme; the resulting fusion protein could be admixed with amino acids 41-61, or a conservative substitution variant thereof, and administered to a patient.

IGF-II can also be modified to minimize binding to serum IGF-binding proteins (Baxter (2000) Am. J. Physiol Endocrinol Metab. 278(6):967-76) to avoid sequestration of IGF-II/GILT constructs. A number of studies have localized residues in IGF-II necessary for binding to IGF-binding proteins. Constructs with mutations at these residues can be screened for retention of high affinity binding to the M6P/IGF-II receptor and for reduced affinity for IGF-binding proteins. For example, replacing Phe-26 of IGF-II with Ser is reported to reduce affinity of IGF-II for IGFBP-1 and -6 with no effect on binding to the M6P/IGF-II receptor (Bach et al. (1993) J. Biol. Chem. 268(13):9246-54). Other substitutions, such as Lys for Glu-9, can also be advantageous. The analogous mutations, separately or in combination, in a region of IGF-I that is highly conserved with IGF-II result in large decreases in IGF-BP binding (Magee et al. (1999) Biochemistry 38(48): 15863-70).

An alternate approach is to identify minimal regions of IGF-II that can bind with high affinity to the M6P/IGF-II receptor. The residues that have been implicated in IGF-II binding to the M6P/IGF-II receptor mostly cluster on one face of IGF-II (Terasawa et al. (1994) EMBO J. 13(23):5590-7). Although IGF-II tertiary structure is normally maintained by three intramolecular disulfide bonds, a peptide incorporating the amino acid sequence on the M6P/IGF-II receptor binding surface of IGF-II can be designed to fold properly and have binding activity. Such a minimal binding peptide is a highly preferred lysosomal targeting domain. For example, a preferred lysosomal targeting domain is amino acids 8-67 of human IGF-II. Designed peptides, based on the region around amino acids 48-55, which bind to the M6P/IGF-II receptor, are also desirable lysosomal targeting domains. Alternatively, a random library of peptides can be screened for the ability to bind the M6P/IGF-II receptor either via a yeast two hybrid assay, or via a phage display type assay.

Binding Affinity for the Insulin Receptor

Many IGF-II muteins, including furin-resistant IGF-II muteins, described herein have reduced or diminished binding affinity for the insulin receptor. Thus, in some embodiments, a peptide tag suitable for the invention has reduced or diminished binding affinity for the insulin receptor relative to the affinity of naturally-occurring human IGF-II for the insulin receptor. In some embodiments, peptide tags with reduced or diminished binding affinity for the insulin receptor suitable for the invention include peptide tags having a binding affinity for the insulin receptor that is more than 1.5-fold, 2-fold, 3-fold, 4-fold, 5-fold, 6-fold, 7-fold, 8-fold, 9-fold, 10-fold, 12-fold, 14-fold, 16-fold, 18-fold, 20-fold, 30-fold, 40-fold, 50-fold, 60-fold, 70-fold, 80-fold, 90-fold, or 100-fold less than that of the wild-type mature human IGF-II. The binding affinity for the insulin receptor can be measured using various in vitro and in vivo assays known in the art. Exemplary binding assays are described in the Examples section.

Mutagenesis

IGF-II muteins can be prepared by introducing appropriate nucleotide changes into the IGF-II DNA, or by synthesis of the desired IGF-II polypeptide. Variations in the IGF-II sequence can be made, for example, using any of the techniques and guidelines for conservative and non-conservative mutations set forth, for instance, in U.S. Pat. No. 5,364,934. Variations may be a substitution, deletion or insertion of one or more codons encoding IGF-II that results in a change in the amino acid sequence of IGF-II as compared with a naturally-occurring sequence of mature human IGF-II. Amino acid substitutions can be the result of replacing one amino acid with another amino acid having similar structural and/or chemical properties, such as the replacement of a leucine with a serine, i.e., conservative amino acid replacements. Amino acid substitutions can also be the result of replacing one amino acid with another amino acid having dis-similar structural and/or chemical properties, i.e., non-conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vivo or in vitro assays known in the art (such as binding assays to the CI-MPR or furin cleavage assays).

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce IGF-II muteins.

Spacer

A GILT tag can be fused to the N-terminus or C-terminus of a lysosomal enzyme. The GILT tag can be fused directly to the lysosomal enzyme or can be separated from the lysosomal enzyme by a linker or a spacer. An amino acid linker or spacer is generally designed to be rigid, flexible or to interpose a structure, such as an alpha-helix, between the two protein moieties. A linker or spacer can be relatively short, such as, for example, the sequence Gly-Ala-Pro (GAP) (SEQ ID NO: 9), Gly-Gly-Gly-Gly-Ala (GGGGA) (SEQ ID NO: 60) or Gly-Gly-Gly-Gly-Ser (GGGGS) (SEQ ID NO: 12), or can be longer, such as, for example, 10-25 amino acids in length, 25-50 amino acids in length or 35-55 amino acids in length. The site of a fusion junction should be selected with care to promote proper folding and activity of both fusion partners and to prevent premature separation of a peptide tag from the lysosomal enzyme, e.g., alpha-N-acetylglucosaminidase.

In various embodiments, the spacer peptide comprises one or more GGGPS (SEQ ID NO: 14) or GGGSP (SEQ ID NO: 15) amino acid sequences, and optionally further comprises one or more of (i) GAP (SEQ ID NO: 9), (ii) GGGGS (SEQ ID NO: 12), (iii) GGGS (SEQ ID NO: 16), (iv) AAAAS (SEQ ID NO: 17), (v) AAAS (SEQ ID NO: 18), (vi) PAPA (SEQ ID NO: 19), (vii) TPAPA (SEQ ID NO: 20), (viii) AAAKE (SEQ ID NO: 21) or (ix) GGGGA (SEQ ID NO: 60). In various embodiments, the spacer comprises the amino acid sequence GAP (SEQ ID NO: 9), GPS (SEQ ID NO: 10), or GGS (SEQ ID NO: 11).

In various embodiments, the spacer peptide comprises one or more GGGGS (SEQ ID NO: 12) or GGGS (SEQ ID NO: 16) amino acid sequences. In various embodiments, the spacer peptide comprises one or more GGGPS (SEQ ID NO: 14) or GGGSP (SEQ ID NO: 15) amino acid sequences. In various embodiments, the spacer peptide comprises one or more AAAAS (SEQ ID NO: 17) or AAAS (SEQ ID NO: 18) amino acid sequences. In various embodiments, the spacer peptide comprises one or more PAPA (SEQ ID NO: 19) or TPAPA (SEQ ID NO: 20) amino acid sequences. In various embodiments, the spacer peptide comprises one or more AAAKE (SEQ ID NO: 21) amino acid sequences. In various embodiments, the spacer peptide comprises one or more GGGGA (SEQ ID NO: 60) amino acid sequences.

In various embodiments, the spacer peptide comprises an amino acid sequence selected from the group consisting of: (GGGGS)$_n$ (SEQ ID NOs: 12, 56, 58, 91-94), (GGGGS)$_n$-GGGPS (SEQ ID NOs: 36, 95-100), GAP-(GGGGS)$_n$-GGGPS (SEQ ID NOs: 101-107), GAP-(GGGGS)$_n$-GGGPS-GAP (SEQ ID NOs: 37, 108-113), GAP-(GGGGS)$_n$-GGGPS-(GGGGS)$_n$-GAP (SEQ ID NOs: 114-162), GAP-GGGPS-(GGGGS)$_n$-GAP (SEQ ID NOs: 163-169), GAP-(GGGGS)$_n$-AAAAS-GGGPS-(GGGGS)$_n$-AAAA-GAP (SEQ ID NOs: 170-218), GAP-(GGGGS)$_n$-PAPAP-(Xaa)$_n$-GAP (SEQ ID NOs: 219-267), GAP-(GGGGS)$_n$-PAPAPT-(Xaa)$_n$-GAP (SEQ ID NOs: 268-316), GAP-(GGGGS)$_n$-(Xaa)n-PAPAP-(Xaa)n-(AAAKE)n-(Xaa)n-(GGGGS)$_n$-GAP (SEQ ID NOs: 544-551), (GGGGA)$_n$ (SEQ ID NOs: 60, 79, 81, 317-320), (GGGGA)$_n$-GGGPS (SEQ ID NOs: 321-326), GAP-(GGGGA)$_n$-GGGPS (SEQ ID NOs: 327-333), GAP-(GGGGA)$_n$-GGGPS-GAP (SEQ ID NOs: 334-340), GAP-(GGGGA)$_n$-GGGPS-(GGGGA)$_n$-GAP (SEQ ID NOs: 341-389), GAP-GGGPS-(GGGGA)$_n$-GAP (SEQ ID NOs: 390-396), GAP-(GGGGA)$_n$-AAAAS-GGGPS-(GGGGA)$_n$-AAAA-GAP (SEQ ID NOs: 397-445), GAP-(GGGGA)$_n$-PAPAP-(Xaa)$_n$-GAP (SEQ ID NOs: 446-494), GAP-(GGGGA)$_n$-PAPAPT-(Xaa)$_n$-GAP (SEQ ID NOs: 495-543), GAP-(GGGGA)$_n$-(Xaa)n-PAPAP-(Xaa)$_n$-(AAAKE)n-(Xaa)$_n$-(GGGGA)$_n$-GAP (SEQ ID NOs: 552-559); wherein n is 1 to 7. In various embodiments, n is 1 to 4.

In various embodiments, the spacer is selected from the group consisting of EFGGGGSTR (SEQ ID NO: 22), GAP (SEQ ID NO: 9), GGGGS (SEQ ID NO: 12), GPSGSPG (SEQ ID NO: 23), GPSGSPGT (SEQ ID NO: 24), GPSGSPGH (SEQ ID NO: 25), GGGGSGGGGSGGGGSGGGGSGGGPST (SEQ ID NO: 26), GGGGSGGGGSGGGGSGGGGSGGGPSH (SEQ ID NO: 27), GGGGSGGGGSGGGGSGGGGSGGGPSGGGGSGGGPS (SEQ ID NO: 28), GAPGGGGSGGGGSGGGGSGGGGSGGGPSGGGGSGGGPSGAP (SEQ ID NO: 29), GGGGSGGGGSGGGGSGGGGSGGGPSGGGGSGGGGSGGGGSGGGPS (SEQ ID NO: 30), GAPGGGGSGGGGSGGGGSGGGGSGGGPSGGGGSGGGGSGGGGSGGGPSGA P (SEQ ID NO: 31), GGGGSGGGGSGGGGSGGGPSGGGGSGGGGSGGGPS (SEQ ID NO: 32), GAPGGGGSGGGGSGGGGSGGGPSGGGGSGGGGSGGGPSGAP (SEQ ID NO: 33), GGGGSGGGGSGGGGSGGGPSGGGGSGGGGSGGGPSGGGGSGGGGSGGGPS (SEQ ID NO: 34), GAPGGGGSGGGGSGGGGSGGGPSGGGGSGGGGSGGGPSGGGGSGGGGSGGGPSGA P (SEQ ID NO: 35), GGGGSGGGGSGGGGSGGGGSGGGPS (SEQ ID NO: 36), GAPGGGGSGGGGSGGGGSGGGGSGGGPS-GAP (SEQ ID NO: 37), GGGGSGGGGSAAAASGGGGSGGGPS (SEQ ID NO: 38), GAPGGGGSGGGGSAAAASGGGGSGGGPSGAP (SEQ ID NO: 39), GGGGSGGGGSAAAASGGGGSGGGGSAAAASGGGSGGGGSAAAASGGGPS (SEQ ID NO: 40), GAPGGGGSGGGGSAAAASGGGGSGGGGSAAAASGGGSGGGGSAAAASGGGPSG AP (SEQ ID NO: 41), GGGGSGGGGSAAAASGGGPSGGGGSAAAASGGGPSGGGGSAAAASGGGPS (SEQ ID NO: 42), GAPGGGGSGGGGSAAAASGGGPSGGGGSAAAASGGGPSGGGGSAAAASGGGPSGA P (SEQ ID NO:

43), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAKEAAAKEAAAKAGGPSGAP (SEQ ID NO: 53), GGGSPAE-AAAKEAAAKEAAAKEAAAKAPSGGG (SEQ ID NO: 54), GAPGGGSPAE-AAAKEAAAKEAAAKEAAAKAPSGGGAP (SEQ ID NO: 55), GGGGSGGGGSGGGGS (SEQ ID NO: 56), GAPGGGGSGGGGSGGGGSGAP (SEQ ID NO: 57), GGGGSGGGGSGGGGSGGGGS (SEQ ID NO: 58), GAPGGGGSGGGGSGGGGSGGGGSGAP (SEQ ID NO: 59), GGGGA (SEQ ID NO: 60), GGGGAGGGGAGGG-GAGGGGAGGGPST (SEQ ID NO: 61), GGGGAGGG-GAGGGGAGGGGAGGGPSH (SEQ ID NO: 62), GGG-GAGGGGAGGGGAGGGGAGGGPSGGGGAGGGPS (SEQ ID NO: 63), GAPGGGGAGGGGAGGGGAGGG-GAGGGPSGGGGAGGGPSGAP (SEQ ID NO: 64), GGG-GAGGGGAGGGGAGGGGAGGGPSGGG-GAGGGGAGGGGAGGGGAGGGPS (SEQ ID NO: 65), GAPGGGGAGGGGAGGGGAGGG-GAGGGPSGGGGAGGGGAGGGGAGGGGAGGGPS GAP (SEQ ID NO:66), GGGGAGGGGAGGG-GAGGGPSGGGGAGGGGAGGGPS (SEQ ID NO: 67), GAPGGGGAGGGGAGGGGAGGGPSGGG-GAGGGGAGGGPSGAP (SEQ ID NO: 68), GGGGAGGG-GAGGGGAGGGPSGGGGAGGG-GAGGGPSGGGGAGGGGAGGGPS (SEQ ID NO: 69), GAPGGGGAGGGGAGGGGAGGGPSGGG-GAGGGGAGGGPSGGGGAGGGGAGGGPS GAP (SEQ ID NO: 70), GGGGAGGGGAGGGGAGGGGAGGGPS (SEQ ID NO: 71), GAPGGGGAGGGGAGGGGAGGG-GAGGGPSGAP (SEQ ID NO: 72), GGGGAGGG-GAAAAASGGGGAGGGPS (SEQ ID NO: 73), GAPGGG-GAGGGGAAAAASGGGGAGGGPSGAP (SEQ ID NO: 74), GGGGAGGGGAAAAASGGGGAGGG-GAAAAASGGGGAGGGGAAAAASGGGPS (SEQ ID NO: 75), GAPGGGGAGGGGAAAAASGGGGAGGG-GAAAAASGGGGAGGGGAAAAASGGGPS GAP (SEQ ID NO: 76), GGGGAGGGGAAAAASGGGPSGGG-GAAAAASGGGPSGGGGAAAAASGGGPS (SEQ ID NO: 77), GAPGGGGAGGGGAAAAASGGGPSGGG-GAAAAASGGGPSGGGGAAAAASGGGPSG AP (SEQ ID NO: 78), GGGGAGGGGAGGGGA (SEQ ID NO: 79), GAPGGGGAGGGGAGGGGAGAP (SEQ ID NO: 80), GGGGAGGGGAGGGGAGGGGA (SEQ ID NO: 81), GAPGGGGAGGGGAGGGGAGGGGAGAP (SEQ ID NO: 82), GGGGAGGGGAGGGGAGGGGAGGGGAGGG-GAGGGGAGGGGAGGGPS [or (GGGGA)₈GGGPS] (SEQ ID NO: 83), GGGGAGGGGAGGGGAGGGGAGGG-GAGGGGAGGGGAGGGGAGGGPSH [or (GGGGA)[GGGPSH] (SEQ ID NO: 84), GGGGAGGGGAGGG-GAGGGGAGGGGAGGGGAGGGGAGGG-GAGGGGAGGGPS [or (GGGGA)]GGGPS] (SEQ ID NO: 85), GGGGAGGGGAGGGGAGGGGAGGGGAGGG-GAGGGGAGGGGAGGGGAGGGPSH [or (GGGGA)] GGGPSH] (SEQ ID NO: 86), GGGGPAPGPGPAPGPAPG-PAGGGPS (SEQ ID NO: 87), GAPGGGGPAPGPGPAPGPAPGPAGGGPGGAP (SEQ ID NO: 88), GGGGPAPAPGPAPAPGPAPAGGGPS (SEQ ID NO: 89), and GAPGGGGPAPAPGPAPAPGPAPAGGGPG-GAP (SEQ ID NO: 90).

In various embodiments, the spacer is selected from the group consisting of GGGGSGGGGSGGGGSGGGGSGGGPS (SEQ ID NO: 36), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAKEAAAKEAAAKAGGPSGAP (SEQ ID NO: 53), GGGSPAE-AAAKEAAAKEAAAKEAAAKAPSGGG (SEQ ID NO: 54), GAPGGGSPAE-AAAKEAAAKEAAAKEAAAKAPSGGGAP (SEQ ID NO: 55), and GGGGAGGGGAGGGGAGGG-GAGGGPS (SEQ ID NO: 71).

In various embodiments, the spacer is selected from the group consisting of GGGGSGGGGSGGGGSGGGGSGGGPS (SEQ ID NO: 36), GAPGGSPAGSPTSTEEGTSESATPESG-PGTSTEPSEGSAPGSPAGSPTSTGPSGAP (SEQ ID NO: 47), GAPGGGSPAPAPTPAPAPTPAPAGGGPSGAP (SEQ ID NO: 51), GAPGGGSPAE-AAAKEAAAKEAAAKEAAAKAPSGGGAP (SEQ ID NO: 55), and GGGGAGGGGAGGGGAGGG-GAGGGPS (SEQ ID NO: 71).

Additional constructs of GILT-tagged alpha-N-acetylglucosaminidase proteins that can be used in the methods and compositions of the present invention were described in detail in U.S. Publication Nos. 20050244400 and 20050281805, the entire disclosures of which is incorporated herein by reference.

Cells

Any mammalian cell or cell type susceptible to cell culture, and to expression of polypeptides, may be utilized in accordance with the present invention, such as, for example, human embryonic kidney (HEK) 293, Chinese hamster ovary (CHO), monkey kidney (COS), HT1080, C10, HeLa, baby hamster kidney (BHK), 3T3, C127, CV-1, HaK, NS/0, and L-929 cells. Non-limiting examples of mammalian cells that may be used in accordance with the present invention include, but are not limited to, BALB/c mouse myeloma line (NS0/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587);

human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In some embodiments, the fusion protein of the present invention is produced from CHO cell lines.

The fusion protein of the invention can also be expressed in a variety of non-mammalian host cells such as, for example, insect (e.g., Sf-9, Sf-21, Hi5), plant (e.g., *Leguminosa*, cereal, or tobacco), yeast (e.g., *S. cerivisae, P. pastoris*), prokaryote (e.g., *E. Coli, B. subtilis* and other *Bacillus* spp., *Pseudomonas* spp., *Streptomyces* spp), or fungus.

In some embodiments, a fusion protein with or without a furin-resistant GILT tag can be produced in furin-deficient cells. As used herein, the term "furin-deficient cells" refers to any cells whose furin protease activity is inhibited, reduced or eliminated. Furin-deficient cells include both mammalian and non-mammalian cells that do not produce furin or produce reduced amount or defective furin protease. Exemplary furin deficient cells that are known and available to the skilled artisan, including but not limited to FD11 cells (Gordon et al (1997) Infection and Immunity 65(8):3370 3375), and those mutant cells described in Moebring and Moehring (1983) Infection and Immunity 41(3):998 1009. Alternatively, a furin deficient cell may be obtained by exposing the above-described mammalian and non-mammalian cells to mutagenesis treatment, e.g., irradiation, ethidium bromide, bromidated uridine (BrdU) and others, preferably chemical mutagenesis, and more preferred ethyl methane sulfonate mutagenesis, recovering the cells which survive the treatment and selecting for those cells which are found to be resistant to the toxicity of *Pseudomonas* exotoxin A (see Moehring and Moehrin (1983) Infection and Immunity 41(3):998 1009).

In various embodiments, it is contemplated that certain of the targeted therapeutic proteins comprising a spacer as described herein may exhibit increased expression of active protein when expressed recombinantly compared to targeted therapeutic proteins comprising a different spacer peptide. In various embodiments, it is also contemplated that targeted therapeutic proteins described herein may have increased activity compared to other targeted therapeutic proteins herein. It is contemplated that those targeted therapeutic proteins exhibiting increased expression of active protein and/or having increased activity compared to other targeted therapeutic proteins comprising a different spacer peptide are used for further experimentation.

Administration of Therapeutic Proteins

In accordance of the invention, a therapeutic protein of the invention is typically administered to the individual alone, or in compositions or medicaments comprising the therapeutic protein (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The therapeutic protein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A therapeutic protein (or a composition or medicament containing a therapeutic protein) is administered by any appropriate route. In various embodiments, a therapeutic protein is administered intravenously. In other embodiments, a therapeutic protein is administered by direct administration to a target tissue, such as heart or muscle (e.g., intramuscular), or nervous system (e.g., direct injection into the brain; intraventricularly; intrathecally). In various embodiments, a therapeutic protein is administered intrathecally. Alternatively, a therapeutic protein (or a composition or medicament containing a therapeutic protein) can be administered parenterally, transdermally, or transmucosally (e.g., orally or nasally). More than one route can be used concurrently, if desired, e.g., a therapeutic protein is administered intravenously and intrathecally. Concurrent intravenous and intrathecal administration need not be simultaneous, but can be sequential.

A therapeutic protein (or a composition or medicament containing a therapeutic protein) can be administered alone, or in conjunction with other agents, such as antihistamines (e.g., diphenhydramine) or immunosuppressants or other immunotherapeutic agents which counteract anti-GILT-tagged lysosomal enzyme antibodies. The term, "in conjunction with," indicates that the agent is administered prior to, at about the same time as, or following the therapeutic protein (or a composition or medicament containing the therapeutic protein). For example, the agent can be mixed into a composition containing the therapeutic protein, and thereby administered contemporaneously with the therapeutic protein; alternatively, the agent can be administered contemporaneously, without mixing (e.g., by "piggybacking" delivery of the agent on the intravenous line by which the therapeutic protein is also administered, or vice versa). In another example, the agent can be administered separately (e.g., not admixed), but within a short time frame (e.g., within 24 hours) of administration of the therapeutic protein.

The therapeutic protein (or composition or medicament containing the therapeutic protein) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The dose which will be therapeutically effective for the treatment of the disease will depend on the nature and extent of the disease's effects, and can be determined by standard clinical techniques. In addition, in vitro or in vivo assays may optionally be employed to help identify optimal dosage ranges using methods known in the art. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. The therapeutically effective dosage amount can be, for example, about 0.1-1 mg/kg, about 1-5 mg/kg, about 2.5-20 mg/kg, about 5-20 mg/kg, about 20-50 mg/kg, or about 20-100 mg/kg or about 50-200 mg/kg, or about 2.5 to 20 mg/kg of body weight. The effective dose for a particular individual can be varied (e.g., increased or decreased) over time, depending on the needs of the individual. For example, in times of physical illness or stress, or if disease symptoms worsen, the dosage amount can be increased.

The therapeutically effective amount of the therapeutic protein (or composition or medicament containing the therapeutic protein) is administered at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, the therapeutic protein is administered bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress, or if disease symptoms worsen, the interval between doses can be decreased.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The disclosure additionally pertains to a pharmaceutical composition comprising a therapeutic protein, as described herein, in a container (e.g., a vial, bottle, bag for intravenous administration, syringe, etc.) with a label containing instructions for administration of the composition for treatment of Mucopolysaccharidosis Type IIIB (Sanfilippo B Syndrome), such as by the methods described herein.

Intrathecal Administration of the Pharmaceutically Acceptable Formulations

In various embodiments, the enzyme fusion protein is administered by introduction into the central nervous system of the subject, e.g., into the cerebrospinal fluid of the subject. In certain aspects of the invention, the enzyme is introduced intrathecally, e.g., into the lumbar area, or the cisterna magna or intraventricularly (or intracerebroventricularly) into a cerebral ventricle space. Methods of administering a lysosomal enzyme intrathecally are described in U.S. Pat. No. 7,442,372, incorporated herein by reference in its entirety.

Those of skill in the art are aware of devices that may be used to effect intrathecal administration of a therapeutic composition. For example, the therapy may be given using an Ommaya reservoir which is in common use for intrathecally administering drugs for meningeal carcinomatosis (Ommaya A K, Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions to an individual are described in U.S. Pat. No. 6,217,552, incorporated herein by reference. Alternatively, the composition may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection (i.e., intracerebroventricularly) through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae and, more inclusively, the L2-S1 region of the spine. The term "cisterna magna" is intended to include access to the space around and below the cerebellum via the opening between the skull and the top of the spine. The term "cerebral ventricle" is intended to include the cavities in the brain that are continuous with the central canal of the spinal cord. Administration of a pharmaceutical composition in accordance with the present invention to any of the above mentioned sites can be achieved by direct injection of the composition or by the use of infusion pumps. For injection, the composition of the invention can be formulated in liquid solutions, preferably in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In various embodiments of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger, even though injection into the third and fourth smaller ventricles can also be made.

In various embodiments, the pharmaceutical compositions used in the present invention are administered by injection into the cisterna magna, or lumbar area of a subject. In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

In various embodiments, a therapeutic fusion protein is delivered to one or more surface or shallow tissues of the brain or spinal cord. For example, in various embodiments, a therapeutic fusion protein is delivered to one or more surface or shallow tissues of the cerebrum or spinal cord. In some embodiments, the targeted surface or shallow tissues of the cerebrum or spinal cord are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, a therapeutic fusion protein is delivered to one or more deep tissues of the cerebrum or spinal cord. In some embodiments, the targeted surface or shallow tissues of the cerebrum or spinal cord are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In various embodiments, a targeted surface or shallow tissue of the spinal cord contains pia matter and/or the tracts of white matter. In various embodiments, a targeted deep tissue of the spinal cord contains spinal cord grey matter and/or ependymal cells. In some embodiments, a therapeutic fusion protein is delivered to neurons of the spinal cord.

In various embodiments, a therapeutic fusion protein is delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In various embodiments, a therapeutic fusion protein is delivered to one or more tissues of the brainstem. In some embodiments, the targeted one or more tissues of the brainstem include brain stem white matter tissue and/or brain stem nuclei tissue.

In various embodiments, a therapeutic fusion protein is delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In various embodiments, a therapeutic fusion protein is delivered to various cells in the brain including, but not limited to, neurons, glial cells, perivascular cells and/or meningeal cells. In some embodiments, a therapeutic protein is delivered to oligodendrocytes of deep white matter.

Kits for Use in the Methods of the Invention

The agents utilized in the methods of the invention may be provided in a kit, which kit may further include instructions for use. Such a kit will comprise a fusion protein as described herein ccomprising an enzyme for use in the treatment of a lysosomal storage disease and a lysosomal targeting moiety, usually in a dose and form suitable for administration to the host. In various embodiments, the kit will usually comprise a device for delivering the enzyme intrathecally.

A kit may also be provided for the conjugation of an antigen, particularly a polypeptide antigen, to a high uptake moiety, in order to generate a therapeutic composition. For example, a moiety such as an IGF-II mutein, either conjugated to a linker suitable for linking polypeptides, as described above, may be provided. The high uptake moiety may also be provided in an unconjugated form, in combination with a suitable linker, and instructions for use.

Another kit may comprise instructions for the intrathecal administration of the therapeutic compositions of the present invention, in addition to the therapeutic compositions. In certain embodiments, the kits of the invention may comprise catheters or other devices for the intrathecal administration of the enzyme replacement therapy that are preloaded with the therapeutic compositions of the present invention. For example, catheters preloaded with 0.001-0.01 mg, 0.01-0.1 mg, 0.1-1.0 mg, 1.0-10 mg, 10-100 mg, or more of a therapeutic fusion protein comprising a lysosomal enzyme and lysosomal targeting moiety, such as Naglu and IGF-II mutein, in a pharmaceutically acceptable formulation are specifically contemplated. Exemplary catheters may single use catheters that can be discarded after use. Alternatively, the preloaded catheters may be refillable and presented in kits that have appropriate amounts of the enzyme for refilling such catheters.

The invention will be further and more specifically described by the following examples. Examples, however, are included for illustration purposes, not for limitation.

EXAMPLE 1

Generation of Spacer Sequences

Lysosomal enzymes comprising GILT tags and spacers have been disclosed in US Patent Publication Nos. 20030082176, 20040006008, 20040005309, and 20050281805. Alpha-N-acetylglucosaminidase (Naglu) fusion proteins comprising spacer peptides are disclosed in US Patent Publication No. 201120232021. Additional spacer peptides for use in targeted therapeutic fusion proteins comprising a lysosomal enzyme and a GILT tag were developed as described below.

Spacers can be developed to link both IGF-II muteins and furin-resistant IGF-II muteins. Exemplary spacers include the following amino acid sequences: EFGGGGSTR (SEQ ID NO: 22) GAP (SEQ ID NO: 9), GGGGS (SEQ ID NO: 12), GGGGA (SEQ ID NO: 60), GPSGSPG (SEQ ID NO: 23), GPSGSPGT (SEQ ID NO: 24), GPSGSPH (SEQ ID NO: 25), GGGGSGGGGSGGGGSGGGGSGGGPS (SEQ ID NO: 36), GGGGAGGGGAGGGGAGGGGAGGGPS (SEQ ID NO: 71), GGGGSGGGGSGGGGSGGGGSGGGPST (SEQ ID NO: 26), GGGGSGGGGSGGGGSGGGGSGGGPSH (SEQ ID NO: 27), and GGGGAGGGGAGGGGAGGG-GAGGGPSH (SEQ ID NO: 62).

Constructs comprising a spacer, full-length Naglu (including the signal sequence) and an IGF-II peptide were generated in which the spacer sequence (EFGGGGSTR spacer (SEQ ID NO: 22), GAP spacer (SEQ ID NO: 9), GGGGS spacer (SEQ ID NO: 12), GPSGSPG spacer (SEQ ID NO: 23), or GGGGSGGGGSGGGGSGGGGSGGGPS spacer (SEQ ID NO: 36)) was inserted between full-length Naglu and IGF2 8-67 R37A (SEQ ID NOs: 560-564).

Additional linkers were made based on the XTEN method as described in Schellenberger et al. (Nat Biotech 27:1186-1190, 2009). XTEN-like linkers may provide a longer half-life for the generated fusion protein as compared to other linkers. Exemplary spacers have the amino acid sequences GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), and GAPGGSPAGSPTSTEEGTSESATPESG-PGTSTEPSEGSAPGSPAGSPTSTGPSGAP (SEQ ID NO: 47). The spacer can be inserted between Naglu and IGF-2 mutein, optionally via the AscI sites on the constructs.

Protein expression has been associated with the DNA codon used to encode a particular amino acid, e.g., changing the codon for an amino acid can increase expression of the protein without changing the amino acid sequence of the protein (Trinh et al, Mol. Immunol 40:717-722, 2004). Altering the codon encoding the peptide resulted in increased levels of recombinant fusion protein production. Using this technique additional spacer sequences were developed for use in the therapeutic fusion protein with lysosomal enzyme, such as GGGGSGGGGSGGGGS (SEQ ID NO: 56), GAPGGGSGGGGSGGGGSGAP (SEQ ID NO: 57), GGGGSGGGGSGGGGSGGGGS (SEQ ID NO: 58) and GAPGGGSGGGGSGGGGSGGGGSGAP (SEQ ID NO: 59). Additional spacer sequences are GGGGAGGG-GAGGGGA (SEQ ID NO: 79), GAPGGGGAGGGGAGGG-GAGAP (SEQ ID NO: 80), GGGGAGGGGAGGG-GAGGGGA (SEQ ID NO: 81) and GAPGGGGAGGGGAGGGGAGGGGAGAP (SEQ ID NO: 82). Any one of these spacers is inserted between Naglu and IGF-II mutein, optionally via the AscI sites on the constructs.

An exemplary rigid linker which comprises multiple prolines to contribute to rigidity, has the following sequence GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), or GAPGGGSPAPAPTPAPAPTPAPAGGGPSGAP (SEQ ID NO: 51), whereas an exemplary helical linker has the following sequence GGGSAEAAAKEAAAKEAAAK-AGGPS (SEQ ID NO: 52), GAPGGGSAE-AAAKEAAAKEAAAKAGGPSGAP (SEQ ID NO: 53), GGGSPAE-AAAKEAAAKEAAAKEAAAKAPSGGG (SEQ ID NO: 54), or GAPGGGSPAE-AAAKEAAAKEAAAKEAAAKAPSGGGGAP (SEQ ID NO: 55). Any one of these spacers is inserted between Naglu and IGF-II mutein, optionally via the AscI sites on the constructs.

Additional spacers can be generated using codon optimization using technology developed by DNA 2.0 (Menlo Park, Calif.). The spacers contemplated include GGGGSGGGGSGGGGSGGGPSGGGGSGGGGSGGGPS (SEQ ID NO: 32), GAPGGGSGGGGSGGGGSGGGPSGGGGSGGGG SGGGPSGAP (SEQ ID NO: 33), GGGGSGGGGSGGGGSGGGGSGGGPSGGGGSGGGPS (SEQ ID NO:28), GAPGGGSGGGGSGGGGSGGGGSGGGPSGGG GSGGGPSGAP (SEQ ID NO: 29), GGGGSGGGGSGGGGSGGGGSGGGPSGGGGSG GGGSGGGGSGGGGSGGGPS (SEQ ID NO: 30), GAPGGGSGGGGSGGGGSGGGGSGGGPSGGG GSGGGGSGGGGSGGGGSGGGPSGA P (SEQ ID NO: 31), GGGGSGGGGSGGGGSGGGPSGGGGSGGGGS GGGPSGGGGSGGGGSGGGPS (SEQ ID NO: 34), GAPGGGSGGGGSGGGGSGGGPSGGGGSGGG GSGGGPSGGGGSGGGGSGGGPSGA P (SEQ ID NO: 35), GGGGSGGGGSGGGGSGGGGSGGGPS (SEQ ID NO: 36), GAPGGGSGGGGSGGGGSGGGGSGGGPS-GAP (SEQ ID NO: 37), GGGGSGGGGSAAAASGGGGSGGGPS (SEQ ID NO: 38), GAPGGGGSGGGGSAAAASGGGGSGGGPSGAP (SEQ ID NO: 39), GGGGSGGGGSAAAASGGGGSGGGGSAAAASG GGGSGGGGSAAAASGGGPS (SEQ ID NO: 40), GAPGGGSGGGGSAAAASGGGGSGGGGSAA AASGGGGSGGGGSAAAASGGGPSAP (SEQ ID NO: 41), GGGGSGGGGSAAAASGGGPSGGGGSAAAASG GGPSGGGGSAAAASGGGPS (SEQ ID NO: 42), GAPGGGGSGGGGSAAAASGGGPSGGGGSAAAA SGGGPSGGGGSAAAASGGGPSGA P (SEQ ID NO: 43), GGGGAGGGGAGGGGAGGGPSGGGGAGGG-GAGGGPS (SEQ ID NO: 67), GAPGGGGAGGGGAGGG-GAGGGPSGGGGAGGGGAGGGPSGAP (SEQ ID NO: 68), GGGGAGGGGAGGGGAGGGGAGGGPSGGG-GAGGGPS (SEQ ID NO: 63), GAPGGGGAGGGGAGGG-GAGGGGAGGGPSGGGGAGGGPSGAP (SEQ ID NO:64), GGGGAGGGGAGGGGAGGGGAGGGPSGGG-GAGGGGAGGGGAGGGGAGGGPS (SEQ ID NO: 65), GAPGGGGAGGGGAGGGGAGGG-GAGGGPSGGGGAGGGGAGGGGAGGGGAGGGPS GAP (SEQ ID NO:66), GGGGAGGGGAGGG-GAGGGPSGGGGAGGGGAGGGPSGGG-GAGGGGAGGGPS (SEQ ID NO: 69), GAPGGGGAGGG-GAGGGGAGGGPSGGGGAGGGGAGGGPSGGG GAGGGGAGGGPS GAP (SEQ ID NO: 70), GGGGAGGG-GAGGGGAGGGGAGGGPS (SEQ ID NO: 71), GAPGGG-GAGGGGAGGGGAGGGGAGGGPSGAP (SEQ ID NO: 72), GGGGAGGGGAAAASGGGGAGGGPS (SEQ ID NO: 73), GAPGGGGAGGGGAAAASGGGGAGGGPS-GAP (SEQ ID NO: 74), GGGGAGGGGAAAASGGG-GAGGGGAAAASGGGGAGGGGAAAASGGGPS (SEQ ID NO: 75), GAPGGGGAGGGGAAAASGGG-GAGGGGAAAASGGGGAGGGGAAAASGGGPS GAP (SEQ ID NO: 76), GGGGAGGG-GAAAASGGGPSGGG-GAAAAASGGGPSGGGGAAAAASGGGPS (SEQ ID NO: 77), GAPGGGGAGGGGAAAAASGGGPSGGG-GAAAAASGGGPSGGGGAAAAASGGGPSG AP (SEQ ID NO: 78), GGGGPAPGPGPAPGPAPGPAGGGPS (SEQ ID NO: 87), GAPGGGGPAPGPGPAPGPAPGPAGGGPG-GAP (SEQ ID NO: 88), GGGGPAPAPGPAPAPG- PAPAGGGPS (SEQ ID NO: 89), and GAPGGGGPAPAPG-PAPAPGPAPAGGGPGGAP (SEQ ID NO: 90). Any one of these spacers is inserted between Naglu and IGF-II mutein, optionally via the AscI sites on the constructs.

In certain embodiments if the BM-40 extracellular matrix protein signal peptide sequence (Nischt et al., Eur J. Biochem 200:529-536, 1991) is used, the Naglu in the construct does not comprise its own signal peptide sequence. The spacer is inserted between the Naglu sequence and the IGF-II mutein sequence (e.g., IGF2 8-67 R37A). An exemplary BM-40 signal peptide sequence is MRAWIFFLLCLAGRALA (SEQ ID NO: 8). A GAP peptide may be added to the spacer to facilitate cloning and addition of an AscI cloning site. In certain embodiments, if the native Naglu signal peptide sequence (Weber et al., Hum Mol Genet. 5:771-777, 1996) is used, the Naglu is full-length Naglu and the spacer is inserted between the full-length Naglu and the IGF-II mutein sequence (e.g., IGF2 8-67 R37A). A GAP peptide may be added to the spacer to facilitate cloning and addition of an AscI cloning site.

In exemplary constructs, the human Naglu has been "codon optimized" using DNA 2.0 technology. It is contemplated that the Naglu comprises amino acids 1-743 or amino acids 24-743 of human Naglu. In an exemplary construct, the spacer optionally comprises a GAP spacer (AscI restriction enzyme site used for cloning) or any of the following sequences: EFGGGGSTR (SEQ ID NO: 22), GAP (SEQ ID NO: 9), GGGGS (SEQ ID NO: 12), GPSGSPG (SEQ ID NO: 23), GPSGSPGT (SEQ ID NO: 24), GPSGSPGH (SEQ ID NO: 25), GGGGSGGGGSGGGGSGGGGSGGGPST (SEQ ID NO: 26), GGGGSGGGGSGGGGSGGGGSGGGPSH (SEQ ID NO: 27), GGGGSGGGGSGGGGSGGGGSGGGPSGGGGSGGGPS (SEQ ID NO: 28), GAPGGGGSGGGGSGGGGSGGGGSGGGPSGGG GSGGGPSGAP (SEQ ID NO: 29), GGGGSGGGGSGGGGSGGGGSGGGPSGGGGS GGGGSGGGGSGGGGSGGGPS (SEQ ID NO: 30), GAPGGGGSGGGGSGGGGSGGGGSGGGPSGGGGS GGGGSGGGGSGGGGSGGGPSGA P (SEQ ID NO: 31), GGGGSGGGGSGGGGSGGGPSGGGGSGGGGSGGGPS (SEQ ID NO: 32), GAPGGGGSGGGGSGGGGSGGGPSGGGGSGG GGSGGGPSGAP (SEQ ID NO: 33), GGGGSGGGGSGGGGSGGGPSGGGGSGGGG SGGGPSGGGGSGGGGSGGGPS (SEQ ID NO: 34), GAPGGGGSGGGGSGGGGSGGGPSGGGGSGGG GSGGGPSGGGGSGGGGSGGGPSGA P (SEQ ID NO: 35), GGGGSGGGGSGGGGSGGGGSGGGPS (SEQ ID NO: 36), GAPGGGGSGGGGSGGGGSGGGGSGGGPS-GAP (SEQ ID NO: 37), GGGGSGGGGSAAAASGGGGSGGGPS (SEQ ID NO: 38), GAPGGGGSGGGGSAAAASGGGGSGGGPSGAP (SEQ ID NO: 39), GGGGSGGGGSAAAASGGGGSGGGGSAAAAS GGGGSGGGGSAAAASGGGPS (SEQ ID NO: 40), GAPGGGGSGGGGSAAAASGGGGSGGGGSAAAA SGGGGSGGGGSAAAASGGGPSG AP (SEQ ID NO: 41), GGGGSGGGGSAAAASGGGPSGGGGSAAAASG GGPSGGGGSAAAASGGGPS (SEQ ID NO: 42), GAPGGGGSGGGGSAAAASGGGPSGGGGSAAAAS GGGPSGGGGSAAAASGGGPSGA P (SEQ ID NO: 43), GGSPAGSPTSTEEGTSESATPESGPGT-STEPSEGSAPGSPAGSPGPS (SEQ ID NO: 44), GAPGGSPAGSPTSTEEGTSESATPESG-PGTSTEPSEGSAPGSPAGSPGPSGAP (SEQ ID NO: 45), GGSPAGSPTSTEEGTSESATPESGPGT-STEPSEGSAPGSPAGSPTSTGPS (SEQ ID NO: 46), GAPGGSPAGSPTSTEEGTSESATPESG-PGTSTEPSEGSAPGSPAGSPTSTGPSGAP (SEQ ID NO: 47), GGGSPAPTPTPAPTPAPTPAGGGPS (SEQ ID NO: 48), GAPGGGSPAPTPTPAPTPAPTPAGGGPSGAP (SEQ ID NO: 49), GGGSPAPAPTPAPAPTPAPAGGGPS (SEQ ID NO: 50), GAPGGGSPAPAPTPAPAPTPAPAGGGPSGAP (SEQ ID NO: 51), GGGSAEAAAKEAAAKEAAAKAG-GPS (SEQ ID NO: 52), GAPGGGSAE-AAAAKEAAAKEAAAKAGGPSGAP (SEQ ID NO: 53), GGGSPAE-AAAKEAAAKEAAAKEAAAKEAAAKAPSGGG (SEQ ID NO: 54), GAPGGGSPAE-AAAKEAAAKEAAAKEAAAKEAAAKAPSGGGGAP (SEQ ID NO: 55), GGGGSGGGGSGGGGS (SEQ ID NO: 56), GAPGGGGSGGGGSGGGGSGAP (SEQ ID NO: 57), GGGGSGGGGSGGGGSGGGGS (SEQ ID NO: 58), GAPGGGGSGGGGSGGGGSGGGGSGAP (SEQ ID NO: 59), GGGGA (SEQ ID NO: 60), GGGGAGGGGAGGG-GAGGGGAGGGGPST (SEQ ID NO: 61), GGGGAGGG-GAGGGGAGGGGAGGGPSH (SEQ ID NO: 62), GGG-GAGGGGAGGGGAGGGGAGGGPSGGGGAGGGPS (SEQ ID NO: 63), GAPGGGGAGGGGAGGGGAGGG-GAGGGPSGGGGAGGGPSGAP (SEQ ID NO: 64), GGG-GAGGGGAGGGGAGGGGAGGGPSGGG-GAGGGGAGGGGAGGGGAGGGPS (SEQ ID NO: 65), GAPGGGGAGGGGAGGGGAGGG-GAGGGPSGGGGAGGGGAGGGGAGGGGAGGGPS GAP (SEQ ID NO:66), GGGGAGGGGAGGG-GAGGGPSGGGGAGGGGAGGGPS (SEQ ID NO: 67), GAPGGGGAGGGGAGGGGAGGGPSGGG-GAGGGGAGGGPSGAP (SEQ ID NO: 68), GGGGAGGG-GAGGGGAGGGPSGGGGAGGG-GAGGGPSGGGGAGGGGAGGGPS (SEQ ID NO: 69), GAPGGGGAGGGGAGGGGAGGGPSGGG-GAGGGGAGGGPSGGGGAGGGGAGGGPS GAP (SEQ ID NO: 70), GGGGAGGGGAGGGGAGGGGAGGGPS (SEQ ID NO: 71), GAPGGGGAGGGGAGGGGAGGG-GAGGGPSGAP (SEQ ID NO: 72), GGGGAGGG-GAAAAASGGGGAGGGPS (SEQ ID NO: 73), GAPGGG-GAGGGGAAAAASGGGGAGGGPSGAP (SEQ ID NO: 74), GGGGAGGGGAAAAASGGGGAGGG-GAAAAASGGGGAGGGGAAAAASGGGPS (SEQ ID NO: 75), GAPGGGGAGGGGAAAAASGGGGAGGG-GAAAAASGGGGAGGGGAAAAASGGGPS GAP (SEQ ID NO: 76), GGGGAGGGGAAAAASGGGPSGGG-GAAAAASGGGPSGGGGAAAAASGGGPS (SEQ ID NO: 77), GAPGGGGAGGGGAAAAASGGGPSGGG-GAAAAASGGGPSGGGGAAAAASGGGPSG AP (SEQ ID NO: 78), GGGGAGGGGAGGGA (SEQ ID NO: 79), GAPGGGGAGGGGAGGGGAGAP (SEQ ID NO: 80), GGGGAGGGGAGGGGAGGGGA (SEQ ID NO: 81), GAPGGGGAGGGGAGGGGAGGGGAGAP (SEQ ID NO: 82), GGGGAGGGGAGGGGAGGGGAGGGGAGGG-GAGGGGAGGGGAGGGPS [or (GGGGA)$_8$GGGPS] (SEQ ID NO: 83), GGGGAGGGGAGGGGAGGGGAGGG-GAGGGGAGGGGAGGGPSH [or (GGGGA)$_8$ GGGPSH] (SEQ ID NO: 84), GGGGAGGGGAGGG-GAGGGGAGGGGAGGGGAGGGGAGGG-GAGGGGAGGGPS [or (GGGGA)$_9$GGGPS] (SEQ ID NO: 85), GGGGAGGGGAGGGGAGGGGAGGGGAGGG-GAGGGGAGGGGAGGGGAGGGPSH [or (GGGGA)$_9$ GGGPSH] (SEQ ID NO: 86), GGGGPAPGPGAPGPAPG-PAGGGPS (SEQ ID NO: 87), GAPGGGGPAPGPGAPG-PAPGPAGGGPGGAP (SEQ ID NO: 88), GGGGPAPAPG-PAPAPGPAPAGGGPS (SEQ ID NO: 89), and GAPGGGGPAPAPGPAPAPGPAPAGGGPGGAP (SEQ ID NO: 90). The above spacers are optionally "codon optimized" using DNA 2.0 technology.

Any of the IGF-II muteins described herein, which are optionally "codon optimized" using DNA 2.0 technology, are useful in the present constructs. In exemplary constructs, the IGF-II mutein is a furin-resistant IGF-II mutein, IGF2 Δ8-67 R37A.

EXAMPLE 2

Expression and Purification of Constructs

Constructs comprising the above spacers, the Naglu enzyme and the IGF-II targeting peptide are made and recombinantly expressed. In certain embodiments, the constructs comprise a signal peptide. Exemplary signal peptides include, for example and not for limitation, the Naglu signal peptide comprising amino acids 1-23 of full-length Naglu (Weber et al., Hum Mol Genet 5:771-777, 1996) or a signal peptide derived from the BM-40 extracellular matrix protein (Nischt et al., Eur J Biochem 200:529-536, 1991).

DNA encoding the Naglu sequence, the IGF-II mutein and the spacer peptide are inserted into an appropriate expression vector, such as the pEE and pXC GS expression vectors (Lonza Biologics, Berkshire, UK) and the pC3B (BioMarin, in-house) expression vector. An AscI restriction site (ggcgcgcc (SEQ ID NO: 570)) can be inserted into the vector to aid in cloning the therapeutic fusion proteins described herein.

An exemplary construct comprises the full-length Naglu sequence (FIG. 1 and FIG. 2), including signal peptide, a spacer peptide (FIG. 3) and an IGF-II peptide comprising residues 8-67 and having an Ala amino acid substitution at residue Arg-37, R37A (FIGS. 1 and 2), that confers furin resistance to the IGF-II peptide.

Various linker or spacer sequences described in Example 1, connecting the Naglu and IGF-II peptide, are initially evaluated using a transient expression system. GILT-tagged Naglu plasmids (pXC17.4, Lonza) are transfected into suspsension CHOK1SV GS KO cells (Lonza). 15 μg of plasmid DNA is transfected into $10^6$ cells using electroporation. Media is completely exchanged at 24 hours post-transfection. The transfected cells are seeded in shaker flasks at $1.5 \times 10^6$ cells/ml without selection. Cell growth, viability, titer and specific productivity are determined as the cells are grown at 30° C. for up to 14 days.

GILT-tagged Naglu plasmids are transfected into suspension CHOK1SV cells (Lonza). The cells are grown in CDCHO media (Invitrogen) with 6 mM glutamine in shake flasks at 37° C. and 8% $CO_2$. 30 μg of linearized plasmid DNA in $1 \times 10^7$ cells is transfected into the cells using electroporation. The cells are plated at 5000 cells/well in CDCHO media +40 μM MSX 48 hours after transfection. The plates are incubated at 37° C. and 8% $CO_2$ for approximately 4-6 weeks to identify clonal growth. The colonies are then screened by the 4MU activity assay for Naglu (see Example 3) and the highest expressing colonies are transferred to 24 well plates in CDCHO media +40 μM MSX, and then continued to passage the highest expressing clones to 6 well plates, then to shake flasks to identify the highest expressing clones to produce the GILT-tagged Naglu fusion proteins.

Purification is carried out using standard protein purification techniques. For example, in an exemplary purification method, starting material of mammalian cell culture supernatant, as described above, is thawed from storage at −80° C. The material is adjusted with NaCl to reach a final concentration of 1M, followed by 0.2 μm sterile filtration.

The filtered material is loaded onto a butyl hydrophobic interaction column, pre-equilibrated with butyl load buffer (20 mM Tris, 1 M NaCl, pH 7.5). The bound materials are eluted with a linear gradient over 10 column volumes, using butyl elution buffer (20 mM Tris, pH 7.5). Samples from the elution peaks are pooled, buffer exchanged into 20 mM Tris, pH 7.5, and loaded onto a Q anion exchange column. Bound proteins are then eluted with a linear gradient (10 column volumes) using Q elution buffer (20 mM Tris, 1 M NaCl, pH 7.5). Purified samples are then buffer exchanged using centrifugal spin concentrators and sterile-filtered for storage.

Construction, Expression, Production, Purification and Formulation of an Exemplary Naglu Fusion Protein: Naglu-(GGGGS)$_4$GGGPS-IGF-II (SEQ ID NO: 568). A DNA construct encoding Naglu-(GGGGS)$_4$GGGPS-IGF-II (SEQ ID NO: 568) was generated by standard recombinant DNA methods. Naglu corresponds to amino acids 1-743 of full-length human Naglu and IGF-II corresponds to the IGF-II mutein comprising amino acids 8-67 of mature human IGF-II with the R37A amino acid substitution that confers furin-resistance. CHOK1SV cells were transfected with the DNA construct, and a stable GILT-tagged Naglu-IGF-II fusion protein expressing clone was isolated as described above.

Cells expressing Naglu-(GGGGS)$_4$GGGPS-IGF-II (SEQ ID NO: 568) were grown in a bioreactor, and the Naglu fusion protein was purified from the culture medium as follows. The harvest was salt-adjusted to 1 M NaCl, then loaded onto a Butyl Sepharose 4 FF column. The Naglu fusion protein was salt-eluted from the Butyl Sepharose 4 FF column, collected and dialyzed, and then loaded onto a Heparin Sepharose 6 FF column. The Naglu fusion protein was collected in the flow-through fraction, and loaded onto a Q Sepharose HP column. The Naglu fusion protein was salt-eluted from the Q Sepharose HP column, concentrated, and then polished by preparative Sephacryl 5300 size exclusion chromatography.

Using this purification procedure, a highly purified, enzymatically active Naglu fusion protein, Naglu-(GGGGS)$_4$GGGPS-IGF-II (SEQ ID NO: 568), was produced. The purified Naglu fusion protein was formulated at 20 mg/mL in artificial CSF (1 mM sodium phosphate, 148 mM sodium chloride, 3 mM potassium chloride, 0.8 mM magnesium chloride, 1.4 mM calcium chloride, pH 7.2).

Construction, Expression, Production, Purification and Formulation of Exemplary Naglu Fusion Proteins. DNA constructs encoding Naglu-(GGGGA)$_4$GGGPS-IGF-II (SEQ ID NO: 569), Naglu-Rigid-IGF-II (SEQ ID NO: 566), Naglu-Helical-IGF-II (SEQ ID NO: 567), and Naglu-XTEN-IGF-II (SEQ ID NO: 565) were generated by standard recombinant DNA methods. Naglu corresponds to amino acids 1-743 of full-length human Naglu and IGF-II corresponds to the IGF-II mutein comprising amino acids 8-67 of mature human IGF-II with the R37A amino acid substitution that confers furin-resistance. Exemplary Rigid, Helical and XTEN linkers are described in Example 1. CHOK1SV cells were transfected with the DNA constructs, and stable GILT-tagged Naglu-IGF-II fusion protein expressing clones were isolated as described above.

Cells expressing the Naglu-IGF-II fusion proteins were grown in a bioreactor. In typical fed-batch production runs (10~16 days), Naglu-IGF-II constructs with the various linkers all reached titers above 30 mg/L with high cell viability above 80%.

The Naglu fusion proteins were purified from the culture medium as described above. Using this purification procedure, enzymatically active untagged Naglu and Naglu-IGF-II fusion proteins, such as Naglu-Rigid-IGF-II (SEQ ID NO: 566), Naglu-Helical-IGF-II (SEQ ID NO: 567), Naglu-XTEN-IGF-II (SEQ ID NO: 565) and Naglu-(GGGGA)$_4$GGGPS-IGF-II (SEQ ID NO: 569), were purified to ~99% purity, as determined by reverse-phase HPLC. The purified untagged Naglu and Naglu fusion proteins were formulated at 20 mg/mL in artificial CSF (1 mM sodium phosphate, 148 mM sodium chloride, 3 mM potassium chloride, 0.8 mM magnesium chloride, 1.4 mM calcium chloride, pH 7.2).

It is contemplated that fusion proteins as described herein that demonstrate higher levels of recombinant expression of active protein and/or increased enzymatic activity compared to fusion proteins comprising a different spacer peptide may be used in further experimentation, such as activity assays, binding assays, uptake assays and in vivo activity assays as described further below.

EXAMPLE 3

Activity Assays

To determine the enzymatic activity of the Naglu fusion proteins, an in vitro Naglu activity assay is carried out using a fluorescent labeled synthetic substrate.

Materials used in the assay include: 4-Methylumbelliferyl-N-acetyl-α-D-glucosaminide (4MU-NaGlu Substrate) (Calbiochem, Cat#474500) prepared to final 20 mM concentration in 10% DMSO in the assay buffer (0.2 M Sodium Acetate, with or without 1 mg/ml BSA, and 0.005% Tween 20, pH 4.3-4.8) and stored at −80° C. Stock solution of 4-Methylumbelliferone (4-MU Standard) (Sigma, Cat# M1381) is prepared at 10 mM in DMSO and stored at −20° C. in small aliquots. A rhNaglu-His6 control (0.5 mg/ml, R&D Systems, Cat #7096-GH) is diluted to 10 μg/ml in 25 mM Tris, 125 mM NaCl, 0.001% Tween 20, pH7.5 and stored at −80° C. in small aliquots.

On a clear 96 well dilution plate (Granger), 2× serial dilutions of standards in Dilution Buffer (1×PBS, with or without 1 mg/ml BSA, 0.005% Tween 20, pH 7.4 are used, from 200 μM to 1.563 μM plus one blank. On a clear dilution plate, samples are prepared in several dilutions (in Dilution Buffer) to ensure that they are within the standard curve.

10 μl of standards (200 μM to 1.563 μM), control and working samples are transferred to a black non-treated polystyrene 96 well plate (Costar, Cat#3915). 75 μl of substrate (2 mM) is added to each well, followed by incubation for 30 minutes at 37° C. The reaction is then quenched by addition of 200 μl of stop buffer (0.5 M Glycine/NaOH, pH 10.7). The plates are read on an Ex355 Em460 with 455 cut off on a 96-well fluorescent plate reader.

Using this assay, exemplary Naglu fusion proteins, including Naglu-(GGGGS)$_4$GGGPS-IGF-II (SEQ ID NO: 568), Naglu-(GGGGA)$_4$GGGPS-IGF-II (SEQ ID NO: 569), Naglu-Rigid-IGF-II (SEQ ID NO: 566), Naglu-Helical-IGF-II (SEQ ID NO: 567), and Naglu-XTEN-IGF-II (SEQ ID NO: 565), were shown to have enzymatic activity in vitro, with specific activities toward the synthetic 4MU-Naglu substrate ranging from ~175,000 to ~220,000 nmol/hr/mg. The enzymatic activity of the Naglu fusion proteins was comparable to that of the untagged Naglu protein (~190,000 nmol/hr/mg). Enzymatic activity data for exemplary Naglu fusion proteins is provided in Table 1.

TABLE 2

Activity of Naglu Fusion Proteins

| Naglu[1] | Linker[2] | Sp. Act.[3] | IC$_{50}$[4] | K$_{uptake}$[5] | t$_{1/2}$[5] |
|---|---|---|---|---|---|
| Untagged Naglu | — | 190,000 | — | — | 9.7 |
| Naglu-(GGGGS)$_4$GGGPS-IGF-II | 36 | 190,000 | 0.27, 0.23 | 5.4 | ND |
| Naglu-(GGGGA)$_4$GGGPS-IGF-II | 71 | 220,000 | 0.36 | 6.3 | ND |
| Naglu-Rigid-IGF-II | 51 | 190,000 | 0.23 | 2.4 | 9.5 |
| Naglu-Helical-IGF-II | 55 | 175,000 | 0.25 | 2.3 | 9.4 |
| Naglu-XTEN-IGF-II | 47 | 170,000 | 0.24 | 3.7 | ND |

[1]Untagged Naglu and Naglu fusion proteins were constructed, expressed and purified as described in Example 2; exemplary Rigid, Helical and XTEN linkers are described in Example 1
[2]SEQ ID NO: of linkers in the Naglu fusion proteins tested in Examples 3 to 5
[3]Specific activity (nmol/hr/mg) for Naglu proteins was measured as described in Example 3
[4]IC$_{50}$ for Naglu proteins for IGF2R competitive binding was measured as described in Example 4
[5]K$_{uptake}$ and half life (t$_{1/2}$) for Naglu proteins in MPS-IIIB fibroblasts were measured as described in Example 5

EXAMPLE 4

Binding Assays

Binding assays to determine binding of the Naglu fusion proteins to IGF-I, IGF-II and insulin receptors are carried out generally as described in US 20120213762. Briefly, fusion protein constructs are tested for binding affinity for the insulin receptor in an assay measuring the competition of biotinylated insulin binding to plate-bound insulin. An insulin receptor binding assay is conducted by competing insulin, IGF-II, and fusion protein with biotinylated-insulin binding to the insulin receptor (Insulin-R).

Specifically, white Reacti-Bind plates are coated with Insulin-R at a concentration of 1 μg/well/100 μl (38.4 nM). The coated plates are incubated over night at room temperature, then washed 3× with washing buffer (300 μl/well). The plates are then blocked with blocking buffer (300 μl/well) for 1 hour. The washing steps are repeated and any trace of solution in the plates taken out. Biotinylated-insulin is mixed at 20 nM with different concentrations of insulin, IGF-II, or fusion protein, by serial dilutions. 100 μl of diluted Insulin, IGF-II, or Naglu fusion protein in 20 nM Insulin-biotin are added into the coated plates and the plates are incubated at room temperature for 2 hours. The plates are then washed 3 times with washing buffer. 100 μl of strepavidin-HRP working solution (50 μl strepavidin-HRP in 10 ml blocking buffer) is added into the plates and the plates are incubated at room temperature for 30 minutes. 100 μl of Elisa-Pico working solution containing Elisa-Pico chemiluminescent substrate is added and the chemiluminescence is measured at 425 nm.

IGF2R Competitive Binding Assay

To measure the ability of the Naglu fusion protein constructs to bind to the IGF-II receptor a competitive binding assay is carried out. A fragment of the IGFIIR involved with IGF-II binding (domains 10-13, named protein 1288) is coated onto 96-well plates. Biotinylated IGF-II is incubated with the receptor in the presence of increasing amounts of competitors: either control IGF-II (non-biotinylated), or fusion protein sample (containing an IGF-II-derived GILT epitope tag). Receptor-bound biotinylated IGF-II is detected with streptavidin conjugated to horseradish peroxidase (HRP) and a chemiluminescent HRP substrate. The ability of the fusion protein to inhibit binding of biotinylated IGF-II to the IGFIIR is calculated from inhibition curves and reported as an $IC_{50}$ value (concentration required to achieve 50% binding inhibition).

For the assay, IGFIIR is coated in a white Reacti-bind plate (Pierce, Cat#437111) at 0.5 µg/well in a volume of 100 µl (69.6 nM/per well) in coating buffer. The plate is sealed and incubated overnight at room temperature. The plate is then washed 3× with wash buffer, blocked with blocking buffer and then washed again 3× with wash buffer (300 µl/well).

Next, 8 nM IGF-II-biotin is mixed with different concentrations of competitors (IGF-II (non-biotinylated), Reference Protein, or Naglu fusion protein samples, and added into an IGFIIR-coated plate in 2× serial dilutions.

The plate is incubated at room temperature for 2 hours, followed by washing the plate 3× with wash buffer. Streptavidin-HRP is prepared in blocking buffer (1:200 dilution), and 100 µl/well added to the plate. IGF-II-Biotin binding activity is detected via streptavidin-HRP using Pico-Elisa reagents. Briefly, the prepared Pico-Elisa working solution is added per well (100 µl/well), and incubated at room temperature for 5 minutes with gentle rocking, then the chemiluminescence at 425 nm is measured.

The $IC_{50}$ of the samples are calculated using the percent IGF-II-Biotin Bound for each concentration of inhibitor.

Using this competitive IGFIIR binding assay, an exemplary Naglu fusion proteins, including Naglu-(GGGGS)$_4$GGGPS-IGF-II (SEQ ID NO: 568), Naglu-(GGGGA)$_4$GGGPS-IGF-II (SEQ ID NO: 569), Naglu-Rigid-IGF-II (SEQ ID NO: 566), Naglu-Helical-IGF-II (SEQ ID NO: 567), and Naglu-XTEN-IGF-II (SEQ ID NO: 565), were shown to have an $IC_{50}$ value of 0.23-0.36 nM. Untagged Naglu protein had no detectable binding in this assay. IGF2R competitive binding data for exemplary Naglu fusion proteins is provided in Table 1.

EXAMPLE 5

Uptake Assays

To measure the ability of a Lysosomal Storage Disease enzyme to enter cells via receptor-mediated endocytosis an uptake assay is carried out which measures enzyme uptake using the CI-MPR receptor in rat myoblast L6 cells or in human MPS IIIB fibrobalsts. Mannose-6-phosphate (M6P) and IGF-II are used as inhibitors to determine the site of binding to the CI-MPR receptor. Data is collected to generate a saturation curve for enzynme uptake and determine the kinetic parameter, $K_{uptake}$, of the process.

Prior to the uptake assay (24 hours), L6 cells (L6 Rat Myoblasts, ATCC# CRL-1458) or human MPS IIIB fibroblasts are plated at a density of $1 \times 10^5$ cells per well in 24-well plates (VWR #62406-183) and seeded 0.5 ml per well. On the morning of assay, enzyme is mixed with uptake media (1 L DMEM, 1.5 g Sodium Bicarbonate. 0.5 g Bovine Serum Albumin, 20 ml of L-glutamine (200 mM (Gibco #25030-081)), 20 ml of 1M of HEPES (Gibco #1563080)) (20 mM final), pH 7.2) in a tissue culture hood. Enzyme amounts may range from 2-500 nM. The final volume of uptake media+ enzyme is 0.5 ml per well. M6P (5 mM final concentration) and/or IGF-II (2.4 µM or 18 µg/ml final concentration) are added to appropriate samples. For uptake inhibition, 18 µl IGF-II stock (1 mg/ml, 133.9 µM) is added per mL of uptake media.

Growth media is aspirated from cells and 0.450 ml of enzyme in uptake buffer added to each well. Note time and return cells to incubator for 18 hours. Plate is removed from incubator and uptake buffer aspirated off cells. Plates are washed 4× by addition of 0.5 ml Dulbecco's PBS and aspirating off. 200 µl of CelLytic M lysis buffer (Sigma) is added to the plates and shaken at room temperature for 20-30 minutes. Lysate is removed from cells and stored in a tape-covered clear 96-well plate (VWR) at −80° C. until ready to assay.

For the enzyme assay, 5 µA of each lysate is added in duplicate by adding to 15 µA of enzyme reaction mix (e.g., Naglu+4MU assays) in black 96-well plate (VWR) (see above) and enzyme/units/ml/hr determined in each lysate.

For the lysate protein assay, 10 µl of each lysate in duplicate are assayed using a Pierce BCA protein Assay kit according to manufacturer's instructions. To measure absorbance, absorbance is read at 562 nm with a plate reader (BMG FluoStar Optima Plate reader) and ug/ml concentration determined.

For each enzyme load, uptake is units of enzyme activity/mg lysate. To determine uptake, the enzyme units/ml are divided by protein ug/ml and multiplied by 1000 (uptake from blank wells subtracted). Results of the assays with or without inhibitors are compared to determine receptor uptake specificity.

For saturation curves, 10 enzyme load concentrations ranging from 0.2-100 nM are used to generate a saturation curve using the assays described above.

Using this assay, an exemplary Naglu fusion protein, Naglu-(GGGGS)$_4$GGGPS-IGF-II (SEQ ID NO: 568), was shown to have a $K_{uptake}$ of 7-9 nM in MPS-IIIB fibroblasts.

Alternatively, prior to the uptake assay (24 hours), L6 cells or human MPS IIIB fibroblasts are plated at a density of $1 \times 10^5$ cells per 0.5 ml per well in the 24-well plates. Enzyme samples at 1.6~50 nM are prepared in uptake media: 1 L DMEM, 1.5 g Sodium Bicarbonate. 0.5 g Bovine Serum Albumin, 20 ml of 200 mM L-glutamine and 20 ml of 1M HEPES, pH7.2. For uptake inhibition, M6P (up to 5.0 mM final) and/or IGF-II (up to 1.0 µM final) are added to appropriate samples.

Growth media is aspirated from cells and replaced by 0.5 ml of the enzyme preparation in uptake buffer per well. After 4-hour incubation, plates are washed 2 times with 0.5 ml Dulbecco's PBS. 100 µl of M-PER lysis buffer (Pierce) is added to the plates and shaken at room temperature for 10 minutes. Lysate is stored at −80° C. until ready to assay.

For the enzyme assay, 10 µl of each lysate is added in duplicate to the black 96-well plate (see above).

For the lysate protein assay, 10 µl of each lysate in duplicate are assayed using a Pierce BCA Protein Assay Kit according to manufacturer's instructions. Absorbance is read at 562 nm with a plate reader (BMG FluoStar Optima Plate reader) and µg/ml concentration determined using BSA as a standard.

For each enzyme load, uptake is expressed as nmoles of 4-MU liberated in 30 minutes. For saturation curves, enzyme concentrations ranging from 1.6-50 nM are used to generate a saturation curve using the assays described above.

Cellular stability of the Naglu fusion proteins was determined by monitoring intracellular Naglu activity over the period of ~8 days. Human MPS IIIB fibroblasts plated at a density of $1 \times 10^5$ cells per well in 24-well plates (VWR #62406-183) were treated with Naglu fusion protein at 20 nM final concentration for 4 hours. After 4-hour incubation, cells were switched to growth media without Naglu fusion protein. For each time point (4 hours, 28 hours, 4 days, 6 days & 8 days), cells were lysed in 100 µl of M-PER lysis buffer (Pierce) at room temperature for 10 minutes, and assayed for enzyme activity using a 4-MU labeled substrate. Reduction of Naglu activity over the 8-day sample period can be fit to first-order kinetics to approximate a cellular half-life of the protein.

Using this assay, exemplary Naglu fusion proteins, including Naglu-(GGGGS)$_4$GGGPS-IGF-II (SEQ ID NO: 568), Naglu-(GGGGA)$_4$GGGPS-IGF-II (SEQ ID NO: 569), Naglu-Rigid-IGF-II (SEQ ID NO: 566), Naglu-Helical-IGF-II (SEQ ID NO: 567), and Naglu-XTEN-IGF-II (SEQ ID NO: 565), were shown to be internalized into MPS IIIB fibroblasts with $K_{uptake}$ values of ~2.3-6.3 nM. Untagged Naglu protein, in contrast, was not taken up by the cells under these experimental conditions. Furthermore, the observed uptake of Naglu fusion protein was inhibited by IGF-II, but not by M6P. After uptake, exemplary Naglu fusion proteins were found to be stable with an estimated half-life of ~9.5 days, based on enzymatic activity (4-MU substrate) measured in cell lysates. Uptake and half-life data for exemplary Naglu fusion proteins is provided in Table 1.

EXAMPLE 6

In Vivo Naglu Fusion Protein Activity

To determine the activity of Naglu fusion proteins in vivo, the fusion proteins are administered to Naglu knock-out animals (see Li et al., Proc Natl Acad Sci USA 96:14505-510, 1999). Naglu knockouts present with large amounts of heparan sulfate in the brain, liver and kidney, increase of beta-hexosaminidase activity and lysosomal-associated membrane protein 2 (LAMP-2) staining in brain, and elevation of gangliosides in brain.

Activity and biodistribution of the exogenous enzyme are determined after 4 ICV (intracerebroventricular) injections over a two week period (100 µg/injection) of recombinant human (rh) Naglu-IGF2. A permanent cannulae is implanted in the mouse (n=12/gp, 8-12 wks old at start) and adjusted to cover those mice whose cannulae are not in the ventricle. Endpoint measurements include Naglu biodistribution, reduction of GAG, e.g., heparan sulfate, storage in the lysosomes of brain cells, and activation of astrocytes and microglia. Levels of various lysosomal or neuronal biomarkers (Ohmi et al., PLoS One 6:e27461, 2011) measured in treated and control groups levels include, but are not limited to, Lysosomal-associated membrane protein 1 (LAMP-1), LAMP-2, glypican 5, Naglu-specific non-reducing ends (NREs) of heparan sulfate, gangliosides, cholesterol, Subunit c of Mitochondrial ATP Synthase (SCMAS), ubiquitin, P-GSK3beta, beta amyloid, P-tau (phosphorylated-Tau), GFAP (astrocyte activation) and CD68 (microglial activation).

Additional experiments to determine survival and behavioral analysis are carried out using mice receiving 4 ICV injections over a two week period of rhNaglu-IGF2 (n=12/gp, 5 months old at start, 100 µg/injection). Endpoints to be measured include survival time, open field activity, Naglu biodistribution, reduction of GAG, e.g., heparan sulfate, storage in lysosomes, levels of lysosomal or neuronal biomarkers, such as LAMP-1, LAMP-2, glypican 5, gangliosides, cholesterol, SCMAS, ubiquitin, P-GSK3beta, beta amyloid, P-tau, GFAP and CD68.

Naglu knockout mice (Naglu −/−) having a mutation in exon 6 of the naglu gene have been developed (Li et al., Proc Natl Acad Sci USA. 96:14505-10, 1999). The exon 6 site was chosen because this is the site of many mutations in humans. No Naglu activity is detected in homozygous mice, and there is reduced Naglu activity in heterozygotes. Naglu −/− mice have reduced survival times (6-12 months), and may have other functional phenotypes like reduced activity levels. The effects of Naglu fusion proteins on the Naglu −/− mice are assayed.

Naglu−/− mice (n=8) and 8 vehicle control Naglu−/− mice (n=8 littermate heterozygotes) are administered 4 ICV doses (100 µg Naglu-IGF2/dose) over 2 weeks. At day −2, mice are anesthetized and the left lateral ventricle cannulated. The mice are allowed to recover. At days 1, 5, 10 and 14, mice are anesthetized (Benedryl, 5 mg/kg IP) 15 minutes prior to ICV dose. The ICV dose is infused via cannula, 5 µl volume over 15 minutes, and mice are allowed to recover. On day 15, mice are sacrificed, exsanguinated and serum frozen. Brains are harvested and IR dye is injected into the cannula and the cannula imaged.

The following assays are carried out to determine the effects of Naglu fusion proteins: body weight assessment, NIR imaging for cannula placement, assessment of Naglu-IGF2, GFAP, LAMP-1 and LAMP-2 levels in brain using immunohistochemistry, biochemical assay for Naglu activity, β-hexosaminadase levels and activity, SensiPro assay to detect non-reducing ends of accumulated glycosaminoglycans (GAGs) specific for Mucopolysaccharidosis IIIb (MPS-IIIb) (WO 2010/078511A2), GM3 ganglioside levels as measured by biochemical assay, as well as immunostain for SCMAS, A-beta, glypican 5, CD68, GFAP and Naglu in medial entorrhinal cortex (Li et al., supra).

Effective treatment with Naglu-IGF2 is expected to result in a decrease in levels of LAMP-1, LAMP-2, GFAP, CD68, SCMAS, A-beta, glypican 5, β-hexosaminidase, GM3 ganglioside, and MPS-IIIb-specific GAGs.

In Vivo Efficacy of Exemplary Naglu Fusion Proteins in a Mouse Model of MPS IIIb.

Four ICV doses (100 µg/dose) of Naglu-IGF-II fusion protein, either Naglu-(GGGGS)$_4$GGGPS-IGF-II (SEQ ID NO: 568) or Naglu-Rigid-IGF-II (SEQ ID NO: 566), were administered over a two week period to Naglu −/− mice (n=8). Naglu −/− mice (n=8) and eight heterozygous or wild-type littermates (n=8) were given vehicle alone as a control. At day −5, mice were anesthetized; the left lateral ventricle of the brain was cannulated. The mice were allowed to recover. On days 1, 5, 10 and 14, mice were anesthetized with inhaled isoflourane. Benadryl (5 mg/kg IP) was administered to each mouse 15 minutes prior to ICV dose to reduce any potential histamine release in response to the Naglu-IGF-II treatment. The ICV dose was infused via the implanted cannula, 5 µl volume over 15-20 minutes, and the mice were allowed to recover. At 1, 7, 14, and 28 days following the final dose, mice were sacrificed. Brains were harvested and divided sagittally into 5 sections for distribution to various assays.

The following assays were carried out to determine the effects of Naglu-IGF-II fusion protein: immunohisochemical assessment of Naglu, LAMP-2, GFAP and CD68 levels in brain, biochemical assays for Naglu and beta-hexosaminadase activity, SensiPro assay (Deakin et al., Glycobiology 18:483, 2008; Lawrence et al., Nat Chem. Biol. 8:197, 2012; Lawrence et al., J Biol. Chem. 283:33674, 2008) to detect total heparan sulfate and NREs of heparan sulfate specific for Mucopolysaccharidosis IIIB (MPS-IIIB) (WO 2010/078511A2), and immunoflourescent staining for SCMAS, beta-amyloid (A-beta), p-Tau, P-GSK3beta, glypican 5, GFAP and CD68 in medial entorrhinal cortex (Li et al., supra).

When evaluated 24 hours after the final dose, treatment with either Naglu-(GGGGS)$_4$GGGPS-IGF-II (SEQ ID NO: 568) or Naglu-Rigid-IGF-II (SEQ ID NO: 566) fusion protein resulted in a marked increase in Naglu enzyme activity, with a concomitant decrease in beta-hexosaminadase activity and levels of total heparan sulfate, Naglu-specific NREs of heparan sulfate, and LAMP-2. Naglu enzyme was easily detectable in brain tissues, not only in cortex, hippocampus, dentate gyrus and thalamus, but also in remote distal geographic locations, including amygdyla, perirhinal cortex and hypothalamus. Significant decreases in the levels of CD68, SCMAS, beta-amyloid (A-beta), p-Tau, P-GSK3beta, and glypican 5 were also observed in Naglu −/− brains upon treatment with Naglu-IGF-II. GFAP staining did not change by 24 hours post-last-dose. Immunohistochemistry demonstrated the presence of Naglu enzyme in many areas of the brain, inside neurons and glial cells, co-localizing with LAMP-2.

Levels of heparan sulfate, Naglu-specific NREs, and beta-hexosaminidase activity continued to decrease over the 7, 14, and 28 days-post-last-dose timepoints. At 28 days, all analytes were at or near the normal mouse control values.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all, of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

All publications and patent documents cited in this application are incorporated by reference in their entirety to the same extent as if the contents of each individual publication or patent document were incorporated herein.

What is claimed:

1. A targeted therapeutic fusion protein comprising (i) a human α-N-acetylglucosaminidase (Naglu) protein comprising amino acids 1-743 or 24-743 of SEQ ID NO:1, (ii) a peptide tag comprising SEQ ID NO: 2 or amino acids 8-67 of SEQ ID NO:5and (iii) a spacer peptide located between the Naglu protein and the peptide tag, wherein the spacer peptide comprises the amino acid sequence GAPGGGSPAPAPTPAPAPTPAPAGGGPSGAP (SEQ ID NO: 51).

2. The targeted therapeutic fusion protein of claim 1, wherein the peptide tag is an N-terminal tag or a C-terminal tag.

3. The targeted therapeutic fusion protein of claim 1, wherein the peptide tag comprises amino acids 8-67 of SEQ ID NO:5.

4. The targeted therapeutic fusion protein of claim 1, wherein the peptide tag comprises SEQ ID NO:2.

5. A pharmaceutical composition suitable for treating a lysosomal storage disease comprising the targeted therapeutic fusion protein of claim 1 and a pharmaceutically acceptable carrier, diluent or excipient.

6. The targeted therapeutic fusion protein of claim 1, wherein the peptide tag consists of amino acids 8-67 of SEQ ID NO:5.

7. The targeted therapeutic fusion protein of claim 1, wherein the spacer peptide consists of the amino acid sequence of SEQ ID NO:51.

8. A targeted therapeutic fusion protein comprising (i) a human α-N-acetylglucosaminidase (Naglu) protein consisting of amino acids 1-743 or 24-743 of SEQ ID NO:1, (ii) a peptide tag consisting of SEQ ID NO:2 or amino acids 8-67 of SEQ ID NO:5 and (iii) a spacer peptide located between the Naglu protein and the peptide tag, wherein the spacer peptide consists of the amino acid sequence GAPGGGSPAPAPTPAPAPTPAPAGGGPSGAP (SEQ ID NO: 51).

9. The targeted therapeutic fusion protein of claim 8 that consists of (i) a human α-N-acetylglucosaminidase (Naglu) protein consisting of amino acids 24-743 of SEQ ID NO:1, (ii) a peptide tag consisting of amino acids 8-67 of SEQ ID NO:5 and (iii) a spacer peptide located between the Naglu protein and the peptide tag, wherein the spacer peptide consists of the amino acid sequence GAPGGGSPAPAPTPAPAPTPAPAGGGPS GAP (SEQ ID NO: 51).

10. The targeted therapeutic fusion protein of claim 8 that consists of (i) a human α-N-acetylglucosaminidase (Naglu) protein consisting of amino acids 24-743 of SEQ ID NO:1, (ii) a peptide tag consisting of SEQ ID NO:2 and (iii) a spacer peptide located between the Naglu protein and the peptide tag, wherein the spacer peptide consists of the amino acid sequence GAPGGGSPAPAPTPAPAPTPAPAGGGPSGAP (SEQ ID NO: 51).

11. A pharmaceutical composition suitable for treating a lysosomal storage disease comprising the targeted therapeutic fusion protein of claim 8 and a pharmaceutically acceptable carrier, diluent or excipient.

12. A pharmaceutical composition suitable for treating a lysosomal storage disease comprising the targeted therapeutic fusion protein of claim 9 and a pharmaceutically acceptable carrier, diluent or excipient.

13. A pharmaceutical composition suitable for treating a lysosomal storage disease comprising the targeted therapeutic fusion protein of claim 10 and a pharmaceutically acceptable carrier, diluent or excipient.

14. A method for treating Mucopolysaccharidosis Type IIIB (Sanfilippo B Syndrome) in a subject or reducing glycosaminoglycan levels in vivo comprising administering to the subject suffering from Sanfilippo B Syndrome a therapeutically effect amount of a pharmaceutical composition comprising a targeted therapeutic fusion protein comprising (i) a human α-N-acetylglucosaminidase (Naglu) protein comprising amino acids 1-743 or 24-743of SEQ ID NO: 1, (ii) a peptide tag comprising SEQ ID NO: 2 or amino acids 8-67 of SEQ ID NO: 5, and (iii) a spacer peptide located between the Naglu protein and the peptide tag, wherein the spacer peptide comprises the amino acid sequence GAPGGGSPAPAPTPAPAPTPAPAGGGPSGAP (SEQ ID NO: 51).

15. The method of claim 14, wherein the peptide tag is an N-terminal tag or a C-terminal tag.

16. The method of claim 14, wherein the peptide tag comprises amino acids 8-67 of SEQ ID NO: 5.

17. The method of claim 14, wherein the peptide tag comprises SEQ ID NO: 2.

18. The method of claim 14, wherein the effective amount is in the range of 2.5-20 mg per kilogram of body weight of the subject.

19. The method of claim 14, wherein the pharmaceutical composition is administered intrathecally and/or intravenously.

20. The method of claim 19, wherein the administering comprises introducing the pharmaceutical composition into a cerebral ventricle, lumbar area, or cisterna magna.

21. The method of claim 14, wherein the pharmaceutical composition is administered intravenously.

* * * * *